(12) United States Patent
Fish et al.

(10) Patent No.: US 11,634,391 B2
(45) Date of Patent: Apr. 25, 2023

(54) COMPOUNDS WHICH ARE INHIBITORS OF NOTUM

(71) Applicant: UCL BUSINESS LTD, London (GB)

(72) Inventors: Paul Vincent Fish, London (GB); William Mahy, London (GB); Nicky John Willis, London (GB); Hannah Woodward, London (GB); Benjamin N Atkinson, London (GB); Elliott D Bayle, London (GB); James Sipthorp, London (GB); Edith Yvonne Jones, Oxford (GB); Yuguang Zhao, Oxford (GB); Luca Vecchia, Oxford (GB); Reinis Reinholds Ruza, Oxford (GB)

(73) Assignee: UCL Business LTD, London (GB)

( * ) Notice: Subject to any disclaimer, the term of this patent is extended or adjusted under 35 U.S.C. 154(b) by 35 days.

(21) Appl. No.: 17/272,268

(22) PCT Filed: Aug. 30, 2019

(86) PCT No.: PCT/EP2019/073177
§ 371 (c)(1),
(2) Date: Feb. 26, 2021

(87) PCT Pub. No.: WO2020/043866
PCT Pub. Date: Mar. 5, 2020

(65) Prior Publication Data
US 2021/0171475 A1 Jun. 10, 2021

(30) Foreign Application Priority Data
Aug. 31, 2018 (GB) .................................. 1814151

(51) Int. Cl.
| | | |
|---|---|---|
| C07D 249/06 | (2006.01) |
| C07D 249/12 | (2006.01) |
| C07D 231/12 | (2006.01) |
| C07D 207/34 | (2006.01) |
| C07D 213/16 | (2006.01) |
| C07D 213/64 | (2006.01) |
| C07D 231/20 | (2006.01) |
| C07D 233/56 | (2006.01) |
| C07D 233/64 | (2006.01) |
| C07D 237/14 | (2006.01) |
| C07D 239/34 | (2006.01) |
| C07D 239/36 | (2006.01) |
| C07D 249/08 | (2006.01) |
| C07D 257/04 | (2006.01) |
| C07D 261/08 | (2006.01) |
| C07D 263/32 | (2006.01) |
| C07D 271/06 | (2006.01) |
| C07D 271/07 | (2006.01) |
| C07D 271/113 | (2006.01) |
| C07D 285/06 | (2006.01) |
| C07D 285/135 | (2006.01) |
| C07D 401/04 | (2006.01) |
| C07D 403/04 | (2006.01) |
| C07D 403/10 | (2006.01) |
| C07D 405/04 | (2006.01) |
| C07D 413/04 | (2006.01) |
| C07D 413/10 | (2006.01) |

(52) U.S. Cl.
CPC ......... *C07D 249/06* (2013.01); *C07D 207/34* (2013.01); *C07D 213/16* (2013.01); *C07D 213/64* (2013.01); *C07D 231/12* (2013.01); *C07D 231/20* (2013.01); *C07D 233/56* (2013.01); *C07D 233/64* (2013.01); *C07D 237/14* (2013.01); *C07D 239/34* (2013.01); *C07D 239/36* (2013.01); *C07D 249/08* (2013.01); *C07D 249/12* (2013.01); *C07D 257/04* (2013.01); *C07D 261/08* (2013.01); *C07D 263/32* (2013.01); *C07D 271/06* (2013.01); *C07D 271/07* (2013.01); *C07D 271/113* (2013.01); *C07D 285/06* (2013.01); *C07D 285/135* (2013.01); *C07D 401/04* (2013.01); *C07D 403/04* (2013.01); *C07D 403/10* (2013.01); *C07D 405/04* (2013.01); *C07D 413/04* (2013.01); *C07D 413/10* (2013.01); *C07B 2200/05* (2013.01)

(58) Field of Classification Search
CPC .. C07D 249/06; C07D 213/16; C07D 231/12; C07D 249/12; C07D 401/04
See application file for complete search history.

(56) References Cited

U.S. PATENT DOCUMENTS

| | | | |
|---|---|---|---|
| 4,212,867 A | 7/1980 | Boesch | |
| 4,298,602 A | 11/1981 | Pawloski | |
| 4,931,083 A | 6/1990 | Beck et al. | |
| 6,255,319 B1 | 7/2001 | Jegham et al. | |
| 2011/0215276 A1* | 9/2011 | Nazeeruddin | C07F 15/0033 252/301.16 |
| 2012/0065200 A1 | 3/2012 | Barbosa et al. | |
| 2012/0302562 A1 | 11/2012 | Barbosa et al. | |
| 2013/0158042 A1 | 6/2013 | Heimann et al. | |
| 2015/0250769 A1 | 9/2015 | Larsen et al. | |

FOREIGN PATENT DOCUMENTS

| | | |
|---|---|---|
| CN | 103980222 A | 8/2014 |
| CN | 107286110 A | 10/2017 |

(Continued)

OTHER PUBLICATIONS

Toriyabe, et al. JP 2000026421 (abstract) retrieved from STN; entered in STN on Jan. 26, 2000; Document Accession No. 2000:59978.*

(Continued)

*Primary Examiner* — Shawquia Jackson
(74) *Attorney, Agent, or Firm* — Stites & Harbison PLLC; Richard S. Myers, Jr.

(57) ABSTRACT

A compound for use in the treatment of a disease ameliorated by the inhibition of Notum of formula (I):

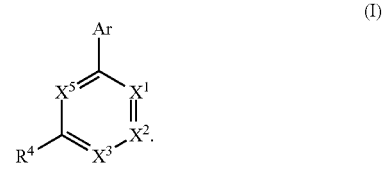

16 Claims, No Drawings

(56) References Cited

FOREIGN PATENT DOCUMENTS

| EP | 0655445 A1 | 5/1995 |
|---|---|---|
| EP | 3434674 A1 | 1/2019 |
| WO | WO 2009/130481 A1 | 10/2009 |
| WO | WO 2010/139966 A1 | 12/2010 |
| WO | WO 2015/031109 A8 | 3/2015 |
| WO | WO 2016/026772 A1 | 2/2016 |
| WO | WO 2016/108249 A1 | 7/2016 |
| WO | WO 2016/187521 A1 | 11/2016 |
| WO | WO 2017/162133 A1 | 9/2017 |

OTHER PUBLICATIONS

Mo, et al. Org. Biomol. Chem., 2013, 11, 2756-2760.*
Tarver, et al., Stimulation of cortical bone formation with thienopyrimidine based inhibitors of Notum Pectinacetylesterase Bioorganic & Medicinal Chemistry Letters 26 Feb. 10, 2016 1525-1528.
Han, et al., 4H-Thieno[3,2-c]chromene based inhibitors of Notum Pectinacetylesterase Bioorganic & Medicinal Chemistry Letters 26 Jan. 18, 2016 1184-1187.
Mahy, et al., The development of CNS penetrant small molecule inhibitors of Notum to potentiate Wnt signaling for the maintenance in synaptic function in Alzheimer's disease (poster for ARUK Conference 2018) Mar. 28, 2018.
Mahy, et al., The development of CNS penetrant small molecule inhibitors of Notum to potentiate Wnt signaling for the maintenance in synaptic function in Alzheimer's disease (abstract for ARUK Conference 2018) Mar. 28, 2018.
Collden, et al., Therapeutic Potential of Targeting the Ghrelin pathway International Journal of Molecular Sciences 18(4) Apr. 11, 2017 798 (1-29).
Fish, Development of Potent, Selective, CNS Penetrant Small Molecule Inhibitors of Notum to Potentiate Wnt Signalling (presentation at EFMC-ISMC Ljubljana, Solvenia) Sep. 5, 2018.
Mahy, et al., Development of Potent, Selective, CNS Penetrant Small Molecule Inhibitors of Notum to Potentiate Wnt Signalling (abstract for EFMC-ISMC Ljubljana, Solvenia) Sep. 5, 2018.
Ji, et al., Palladium-CatalyzedOxidative O—H/N—H Carbonylation of Hydrazides: Access to Substituted 1,3,4-Oxadiazole-2(3H)-ones The Journal of Organic Chemistry 80(11) May 14, 2015 5713-5718.
Boechat, et al., Novel 1,2,3-Triazole Derivatives for Use against Mycobacterium tuberculosis H37Rv (ATTC 27294) Strain Journal of Medicinal Chemistry 54(17) Jul. 21, 2011 5988-5999.
Indrasena, et al., Ethyl Imidazole-1-Carboxylate as a Novel Carbonylating agent for the Synthesis of 1,2,3-Oxadiazol-5(4H)-Ones and Evaluation of their Anti-Mycobacterial Activity Organic Chemistry: An Indian Journal 13(1) May 27, 2017 113(1-12).
Mallinger, et al., Discovery of Potent, Orally Bioavailable, Small-Molecule Inhibitors of WNT Signaling from a Cell-Based Pathway Screen Journal of Medicinal Chemistry 58(4) Feb. 13, 2015 1717-1735.
Gonzaga, et al., 1-Phenyl-1H- and 2-phenyl-2H-1,2,3-triazol derivatives: Design, synthesis and inhibitory effect on alpha-glycosidases European Journal of Medicinal Chemistry 74 Jan. 8, 2014 461-476.
Jia, et al., Click assembly of selective inhibitors for MAO-A 20(21) Bioorganic & Medicinal Chemistry Letters 20(21) Aug. 26, 2010 6222-6225.
Mazouz, et al., 5-[4-(Benzyloxy)phenyl]-1,3,4-oxadiazol-2(3H)-one Derivatives and Related Analogues: New Reversible, Highly Potent, and Selective Monoamine Oxidase Type B Inhibitors Journal of Medicinal Chemistry 36 Jan. 1993 1157-1167.
Katane, et al., Identification of Novel D-Amino Acid Oxidase Inhibitors by in Silico Screening and Their Functional Characterization in Vitro Journal of Medicinal Chemistry 56(5) Feb. 7, 2013 1894-1907.
Andersen, et al., The identification of novel acid isostere based inhibitors of the VPS10P family sorting receptor Sortilin Bioorganic & Medicinal Chemistry Letters 27(11) Feb. 20, 2017 2629-2633.
Khanam, et al., Inhibitory growth evaluation and apoptosis induction in MCF-7 cancer cells by new 5-aryl-2-butylthio-1,3,4-oxadiazole derivatives Cancer Chemotherapy and Pharmacology 80(5) Aug. 16, 2017 1027-1042.
Macaev, et al., Synthesis of novel 5-aryl-2-thio-1,3,4-oxadiazoles and the study of their structure-anti-mycobacterial activities Bioorganic & Medicinal Chemistry 13(16) Jun. 29, 2005 4842-4850.
Karabanovich, et al., S-substituted 3,5-dinitrophenyl 1,3,4-oxadiazole-2-thiols and tetrazole-5-thiols as highly efficient antitubercular agents European Journal of Medicinal Chemistry 126 Nov. 21, 2016 369-383.
Kumar, et al., Synthesis and biological activity of 5-substituted-2-amino-1,3,4-oxadiazole derivatives Turkish Journal of Chemistry 35 Jan. 2011 99-108.
Da Silva, et al., Synthesis of 1H-1,2,3-triazoles and Study of their Antifungal and Cytotoxicity Activities Medicinal Chemistry 9(8) Dec. 2013 1085-1090.
Lima-Neto, et al., Synthesis of 1,2,3-Triazole Derivatives and in Vitro Antifungal Evaluation on Candida Strains Molecules 17(12) May 16, 2012 5882-5892.
Zender, et al., Discovery and Biophysical Characterization of 2-Amino-oxadiazoles as Novel Antagonists of PqsR, an Important Regulator of Pseudomonas aeruginosa Virulence Journal of Medicinal Chemistry 56(17) Aug. 21, 2013 6961-6774.
Moura, et al., Synthesis, Anticlotting and Antiplatelet Effects of 1,2,3-Triazoles Derivatives Medicinal Chemistry 12(8) Oct. 28, 2016 733-741.
Rehman, et al., Synthesis, Characterization and Urease Inhibiting Derivatives of 5-(3,4-Methylenedioxyphenyl)-1,3,4-Oxadiazol-2-thiol Asian Journal of Chemistry 26(15) Jul. 16, 2014 4605-4609.
Xu, et al., Inhibition of Tobacco Bacterial Wilt with Sulfone Derivatives Containing an 1,3,4-Oxadiazole Moiety Journal of Agricultural and Food Chemistry 60(4) Dec. 29, 2011 1036-1041.
Kumar, et al., Synthesis of trifluoromethyl-substituted N-ary-poly-1,2,3-trizole derivatives Journal of Materials Chemistry A 2(21) Feb. 21, 2014 7917-7926 1036-1041.
Beck, et al., Synthesis of Ethyl 2-[(1-Aryl-1H-1,2,4-triazol-3-yl)oxy]propionates and Related Derivatives Journal of Heterocyclic Chemistry 25 Sep/Oct. 1988 1467-1470.
Puglisi, et al., Synthesis and biological evaluation of 2-alkoxyphenyl-6-(substituted phenyl)-1,3,4-thiadiazole-[3,2-a]-s-triazin-5,7-diones and 1-(alkyl and substituted phenyl)-3-[5-alkoxyphenyl-1,3,4-thia-and oxadiazol-2-yl]-ureas European Journal of Medicinal Chemistry 24(3) May 1989 277-286.
Niu, et al., Synthesis of 2-Amino-1,3,4-oxadiazoles and 2-Amino-1,3,4-thiadiazoles via Sequential Condensation and I2-Mediated Oxidatives C—O/C—S Bond Formation The Journal of Organic Chemistry 80(2) Dec. 15, 2014 1018-1024.
Flanagan, et al., Preparation, Gram-Negative Antibacterial Activity, And Hydrolytic Stability of Novel Siderophore-Conjugated Monocarbom Diols ACS Medicinal Chemistry Letters 2(5) Mar. 2, 2011 385-390.
Suciu, et al., Selective Irreversible inhibitors of the Wnt-Deacylating Enzyme NOTUM Developed by Activity-Based Protein Profiling ACS Medicinal Chemistry Letters 9(6) May 26, 2018 563-568.
Nusse, et al., Wnt/B-Catenin Signaling, Disease and Emerging Therapeutic Modalities Cell 169 Jun. 1, 2017 985-999.
Niehrs, The complex world of WNT receptor signalling Nature Reviews Molecular Cell Biology 13 Nov. 15, 2012 767-779.
Malinauskas, et al., Extracellular modulators of Wnt signalling Current Opinion in Structural Biology 29 Oct. 20, 2004 77-84.
Kinzler, et al., Identification of FAP Locus Genes from Chromosome 5q21 Science 253(5020) Aug. 9, 1991 661-665.
Rubinfeld, et al., Association of the APC gene product with B-catenin Science 262(5140) Dec. 10, 1993 1731-1734.
Korinek, et al., Constitutive Transcriptional Activation by a B-Catenin-Tcf Complex in APC-/- Colon Carcinoma Science 275(5307) Mar. 21, 1997 1784-1787.
Boulter, et al., WNT signaling drives cholangiocarcinoma growth and can be pharmacologically inhibited The Journal of Clinical Investigation 125(3) Feb. 17, 2015 1269-1285.

(56) References Cited

OTHER PUBLICATIONS

Lento, et al., Wnt Signaling in Normal and Malignant Hematopoiesis (doi:10.1101/cshperspect.a008011) Cold Spring Harbor Perspectives in Biology Feb. 1, 2013.

Delmas, et al., B-Catenin induces immortalization of melanocytes by suppressing p16INK4a expression and cooperates with N-Ras in melanoma development Genes and Development 21 2007 2923-2935.

Howe, et al., Wnt Signaling and Breast Cancer Cancer Biology & Therapy 3(1) Jan. 14, 2004 36-41.

Reya, et al., Wnt signalling in stem cells and cancer Nature 434 Apr. 14, 2005 843-850.

Wu, et al., Canonical Wnt signaling regulates Slug activity and links epithelial-mesenchymal transition with epigenetic Breast Cancer 1, Early Onset (BRCA1) repression PNAS 109(41) Oct. 9, 2012 16654-16659.

Inestrosa, et al., Wnt signaling in the nervous system and in Alzheimer's disease Journal of Molecular Cell Biology 6(1) Feb. 2014 64-74.

Mucke, et al., Neurotoxicity of amyloid B-protein: synaptic and network dysfunction Cold Spring Harbor Perspectives in Medicine 2(7) Jul. 2012 a006338.

Wan, et al., The Role of Wnt Signaling in the Development of Alzheimer's Disease: A Potential Therapeutic Target? BioMed Research International 2014 May 4, 2014 301575(1-9).

De Ferrari, et al., Common genetic variation within the Low-Density Lipoprotein Receptor-Related Protein 6 and late-onset Alzheimer's disease PNAS 104(22) May 29, 2007 9434-9439.

Liu, et al., Deficiency in LRP6-Mediated Wnt Signaling Contributes to Synaptic Abnormalities and Amyloid Pathology in Alzheimer's Disease Neuron 84(1) Oct. 1, 2014 63-77.

Purro, et al., The Secreted Wnt Antagonist Dickkopf-1 Is Required for Amyloid B-Mediated Synaptic Loss The Journal of Neuroscience 32(10) Mar. 7, 2012 3492-3498.

Galli, et al., Deficient Wnt signalling triggers striatal synaptic degeneration and impaired motor behaviour in adult mice Nature Communications 5 Oct. 16, 2014 4992(1-13).

Kakugawa, et al., Notum deacylates Wnt proteins to suppress signalling activity Nature 519(7542) Mar. 12, 2015 187-192.

Canal, et al., Generation of Mice with Hepatocyte-Specific Conditional Deletion of Notum Plos One 11(3) Mar. 14, 2016 e0150997.

Gerlitz, et al., Wingful, an extracellular feedback inhibitor of Wingless Genes & Development 16 Mar. 28, 2002 1055-1059.

Giraldez, et al., HSPG Modification by the Secreted Enzyme Notum Shapes the Wingless Morphogen Gradient Developmental Cell 2(5) May 2002 667-676.

Oshima, et al., Loss of Ape heterozygosity and abnormal tissue building in nascent intestinal polyps in mice carrying a truncated Apc gene PNAS 92(10) May 9, 1995 4482-4486.

Lazarov, et al., Of mice and men: neurogenesis, cognition and Alzheimer's disease Frontiers in Aging Neuroscience 5(43) Aug. 27, 2013 1-8.

Spalding, et al., Dynamics of Hippocampal Neurogenesis in Adult Humans Cell 153 Jun. 6, 2013 1219-1227.

Lazarov, et al., When neurogenesis encounters aging and disease Trends in Neuroscience 33(12) Dec. 2010 569-579.

Snyder, et al., Could adult hippocampal neurogenesis be relevant for human behavior? Behavioural Brain Research 227 Jun. 28, 2011 384-390.

Ming, et al., Adult Neurogenesis in the Mammalian Brain: Significant Answers and Significant Questions Neuron 70(4) May 26, 2011 687-702.

Seib, et al. Loss of Dickkopf-1 Restores Neurogenesis in Old Age and Counteracts Cognitive Decline Cell Stem Cell 12(2) Feb. 7, 2013 204-214.

Vargas, et al., In vivo Activation of Wnt Signaling Pathway Enhances Cognitive Function of Adult Mice and Reverses Cognitive Deficits in an Alzheimer's Disease Model Journal of Neuroscience 34(6) Feb. 5, 2014 2191-2202.

Cho, et al., Reck and Gpr124 Are Essential Receptor Cofactors for Wnt7a/Wnt7b-Specific Signaling in Mammalian CNS Angiogenesis and Blood-Brain Barrier Regulation Neuron 95(5) Aug. 30, 2017 1056-1073.

Liu, et al., Dysfunctional Wnt/B-catenin signaling contributes to blood-brain barrier breakdown in Alzheimer's disease Neurochemistry International 75 May 22, 2014 19-25.

Fuchs, Chapter Nineteen—Epithelial Skin Biology: Three Decades of Developmental Biology, a Hundred Questions Answered and a Thousand New Ones to Address Current Topics in Developmental Biology 116 2016 357-374.

Lien, et al., In vivo transcriptional governance of hair follicle stem cells by canonical Wnt regulators Nature Cell Biology 16 Jan. 26, 2014 179-190.

Ma, et al., Wnt agonist stimulates liver regeneration after small-for-size liver transplantation in rats Hepatology Research 46(3) Jul. 14, 2015 E154-E164.

Kawakami, et al., Wnt signalling in kidney diseases: dual roles in renal injury and repair Journal of Pathology 229 2013 221-231.

Petersen, et al., Polarized notum Activation at Wounds Inhibits Wnt Function to Promote Planarian Head Regeneration Science 332(6031) May 13, 2011 852-855.

Resh, Covalent lipid modifications of proteins Current Biology 23(10) May 20, 2013 R431-5.

Yanagi, et al., The Homeostatic Force of Ghrelin Cell Metabolism 27(4) Apr. 3, 2018 786-804.

De Ferrari, et al., Activation of Wnt signaling rescues neurodegeneration and behavioural impairments induced in B-amyloid fibrils Molecular Psychiatry 8 Feb. 27, 2003 195-208.

Cerpa, et al., Wnt-5aoccludes AB oligomer-induced depression of glutamatergic transmission in hippocampal neurons Molecular Neurodegeneration 5(3) Jan. 18, 2010 1-13.

Torisu, et al., Human homolog of NOTUM, overexpressed in hepatocellular carcinoma, is regulated transcriptionally by B-catenin/TCF Cancer Science 99(6) Apr. 21, 2008 1139-1146.

Pentinmikko, et al., Notum produced by Paneth cells ettenuates regeneration of ages intestinal epithelium Nature 571(7765)Jul. 10, 2019 398-402.

Marzo, et al., Reversal of Synapse Degeneration by Restoring Wnt Signaling in the Adult Hippocampus Current Biology 26 Oct. 10, 2016 2551-2561.

* cited by examiner

COMPOUNDS WHICH ARE INHIBITORS OF NOTUM

CROSS REFERENCE TO RELATED APPLICATIONS

This application is a § 371 National State Application of PCT/EP2019/073177 filed Aug. 30, 2019, which claims priority to GB 1814151.5 filed Aug. 31, 2018.

The present application provides compounds which are inhibitors of Notum, and which may be used to treat diseases ameliorated by the inhibition of Notum.

BACKGROUND

Wnt Signalling Pathways

Members of the Wnt family are secreted signalling proteins that play key roles in adult stem cell biology as well as in embryonic development. Wnt signalling is required for stem cell maintenance, for example in the brain, gut and skin (reviewed in Nusse R. et al., Cell. 169, 985-999. (2017).

Wnts initiate signalling by binding to cell surface receptors. Two main pathways have been identified downstream of Wnts: the so-called 'canonical' and 'planar cell polarity' pathways.

The both pathways are triggered by the binding of Wnt to a member of the Frizzled family of cell surface receptors and, for the canonical pathway, a member of the LDL-receptor-related protein (LRP) family of cell surface receptors (typically LRP5 or LRP6). This binding elicits an intracellular signalling cascade that results in both biochemical and transcriptional changes within the cell, with the canonical pathway involving the accumulation and translocation of β-catenin within the cell. Both pathways are tightly regulated by a sophisticated network of modulators and feedbacks (reviewed in Niehrs C., Nat Rev Mol Cell Biol. 13, 767-779, 2012; Malinauskas T. et al., Curr. Opin. Struct. Biol. 29, 77-84, 2014).

Role of Wnt in Disease

Conversely, dysregulation of Wnt signalling is frequently associated with growth-related pathologies and cancers, particularly those of tissues for which Wnts normally stimulate self-renewal and repair.

For example, one of the first findings establishing a link between Wnt signalling and cancer was the discovery that mutations of the adenomatous polyposis coli (APC) gene were the underlying cause of the hereditary colon cancer syndrome termed familial adenomatous polyposis (Kinzler K. et al, Science 1991; 253: 661-665). The APC gene was found to interact with β-catenin (Rubinfeld B et al., Science 1993; 262: 1731-1734) and loss of function of APC resulted in overactive T-cell factor (TCF)4/β-catenin signalling (Korinek V et al. Science 1997; 275: 1784-1787). Since then, accumulating evidence has implicated Wnt pathways in other gastrointestinal tumours (Boulter L et al., J Clin Invest 2015; 125: 1269-1285), Leukaemias (Lento W et al. Cold Spring Harb Perspect Biol, 1 Feb. 2013 doi:10.1101/cshperspect.a008011), melanoma (Delmas V et al., Genes Dev 2007; 21: 2923-2935), breast cancer (Howe L R et al., Cancer Biol Ther 2004; 3: 36-41), cancer stem cells (Reya T et al., Nature 2005; 434: 843-850), and metastasis (Wu Z-Q et al., Proc Natl Acad Sci USA 2012; 109: 16654-16659).

Wnt signalling is also implicated to have a role in neurodegenerative diseases such as Alzheimer's disease (AD; Inestrosa N C. et al., J Mol Cell Biol. 2014 February; 6(1):64-74). AD is characterized by the accumulation of amyloid-β (Aβ) plaques, the formation of neurofibrillary tangles (NFT), synaptic loss, and memory deficits. Cognitive impairments, characteristic of AD, correlate closely with the loss of synapses (Mucke L., et al., Cold Spring Harb Perspect Med. 2012 July; 2(7):a006338). Current knowledge suggests that excess Aβ causes synapse dysfunction by impairing synapse maintenance.

Although multiple factors contribute to synapse maintenance, several lines of evidence have highlighted the relevance of Wnt signalling (reviewed in Inestrosa N C. et al., J Mol Cell Biol. 2014 February; 6(1):64-74; Wan et al., Biomed Res Int. 2014; 2014:301575. doi: 10.1155/2014/301575). For example, a variant LRP6, a receptor that mediates canonical Wnt signalling has been associated with late-onset AD in humans (De Ferrari et al., Proc Natl Acad Sci USA. 2007 May 29; 104(22):9434-9), with conditional removal of LRP6 in mice leads to a range of phenotypes resembling those seen in AD (Liu et al., Neuron. 2014 Oct. 1; 84(1):63-77). In addition, Aβ increases the levels of Dickkopf-1, a secreted Wnt antagonist that prevents canonical signaling and triggers synapse degeneration in mature hippocampal neurons (Purro et al., J Neurosci. 2012 Mar. 7; 32(10):3492-8) as well as in the adult striatum (Galli et al., Nat Commun. 2014 Oct. 16; 5:4992). These studies highlight the role of sustained Wnt signalling in synapse maintenance.

SUMMARY

The present authors have developed a range of potent inhibitors of the secreted carboxy esterase, Notum. Through its esterase activity, Notum removes the palmitoleate group from Wnt proteins, thereby inactivating them and inhibiting Wnt signalling. The Notum inhibitors described herein therefore lead to increased levels of Wnt signalling, so allowing for the treatment of disorders characterized by abnormal Wnt signalling.

Accordingly, in a first aspect the present disclosure provides a compound for use in the treatment of a disease ameliorated by the inhibition of Notum of formula (I):

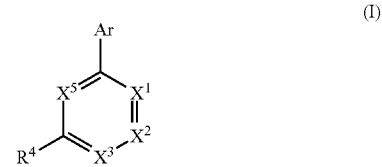

where Ar is $C_5$ heteroaryl or a $C_6$ N-containing heteroaryl, optionally substituted by a group selected from a) OH, SH, $NH_2$, OMe, SMe, NHMe, $NMe_2$, OEt, NHCN, Me;

b) CN, $CO_2H$;

c) $SO_2Me$, $SO_3^-Na^+$;

d) $CH_2Q^1$, where $Q^1$ is selected from OH, OMe, Cl, CN, NHCOMe, $SO_3H$, $NR^{N1}R^{N2}$, where $R^{N1}$ and $R^{N2}$ are either H or Me;

e) $C_{2-3}$ alkyl substituted by OH;

where a N-ring heteroatom may additional bear a methyl group; and $X^1$ is selected from $CR^1$ and N;

$X^2$ is selected from $CR^2$ and N;

$X^3$ is selected from $CR^3$ and N;

$X^5$ is selected from $CR^5$ and N, where only 1 of $X^1$, $X^2$, $X^3$ and $X^5$ may be N;

$R^1$, $R^2$, $R^3$, $R^4$ and $R^5$ (if present) are independently selected from:
i) H;
ii) halo;
iii) $C_{1-4}$ alkyl, optionally substituted by one or more F atoms;
iv) $C_{3-6}$ cycloalkyl, with an optional O ring atom;
v) CN, $NMe_2$, $NO_2$;
vi) O—$C_{1-4}$ alkyl, optionally substituted by one or more F atoms;
vii) $OCH_2Q^2$, where $Q^2$ is selected from $C_{3-6}$ cycloalkyl and phenyl;
viii) $CH_2OH$;
ix) $NR^{N6}R^{N7}$, where $R^{N6}$ and $R^{N7}$ together form a $C_{4-6}$heterocyclyl group optionally substituted with 1 to 2 groups selected from halo, $C_{1-3}$alkyl, cyano and oxetanyl;
or two adjacent groups of $R^1$ to $R^4$ together form a group -$Q^3$-$(CR^C_2)_n$-$Q^4$-, where $Q^3$ is selected from $NR^{N3}$ and O, where $R^{N3}$ is selected from H, $C_{1-3}$ alkyl, cyclopropylmethyl and COMe; $Q^4$ is $NR^{N4}$, O or a single bond, where $R^{N4}$ is selected from H, $C_{1-3}$ alkyl, cyclopropylmethyl and COMe; each Re is independently H, F or Me or two $R^c$ which are attached to the same atom can be linked together to form a $C_{3-5}$cycloalkyl; and n is 1, 2 or 3; or two adjacent groups of $R^1$ to $R^4$ form a fused benzene or $C_{5-6}$ heteroaromatic ring with the phenyl group, which itself is optionally substituted by a $C_{1-2}$ alkyl group.

The first aspect of the present invention also provides a method of treatment of a disease ameliorated by the inhibition of Notum, comprising administering to a patient in need of treatment, a compound as defined, and the use of a compound as defined in the manufacture of a medicament for treating a disease ameliorated by the inhibition of Notum.

A second aspect of the present invention provides a compound as defined in the first aspect for use in a method of therapy and a pharmaceutical composition comprising a compound as defined in the first aspect and a pharmaceutically acceptable excipient.

A third aspect of the present invention provides a compound as defined in the first aspect, wherein:
(i) Ar is

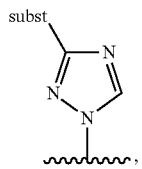

where subst represents the optional substituent;
(ii) Ar is

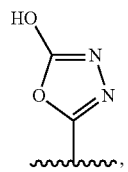

and:
a. at least 2 of $R^1$ to $R^5$ are not H and one of $R^1$ to $R^5$ is not Me; and $R^1$, $R^2$, $R^3$, $R^4$ and $R^5$ (if present) are independently selected from:
i) H;
ii) $C_{3-6}$ cycloalkyl, with an optional O ring atom;
ii) CN, $NMe_2$, $NO_2$;
iv) $OCH_2Q^2$, where $Q^2$ is selected from $C_{3-6}$ cycloalkyl and phenyl;
v) $CH_2OH$;
vi) $NR^{N6}R^{N7}$, where $R^{N6}$ and $R^{N7}$ together form a $C_{4-6}$heterocyclyl group optionally substituted with 1 to 2 groups selected from halo, $C_{1-3}$alkyl, cyano and oxetanyl;
or two adjacent groups of $R^1$ to $R^4$ together form a group -$Q^3$-$(CR^C_2)_n$-$Q^4$-, where $Q^3$ is selected from $NR^{N3}$ and O, where $R^{N3}$ is selected from H, $C_{1-3}$ alkyl, cyclopropylmethyl and COMe; $Q^4$ is $NR^{N4}$, O or a single bond, where $R^{N4}$ is selected from H, $C_{1-3}$ alkyl, cyclopropylmethyl and COMe; each $R^C$ is independently H, F or Me or two $R^c$ which are attached to the same atom can be linked together to form a $C_{3-5}$cycloalkyl; and n is 1, 2 or 3;
or two adjacent groups of $R^1$ to $R^5$ form a fused benzene or $C_{5-6}$ heteroaromatic ring with the phenyl group, which itself is optionally substituted by a $C_{1-2}$ alkyl group;
b. at least 1 of $R^1$ to $R^4$ (if present) is $C_{3-6}$ cycloalkyl;
c. two adjacent groups of $R^1$ to $R^4$ together form a group -$Q^3$-$(CH_2)_n$-$Q^4$-, where $Q^3$ is selected from $NR^{N3}$ and O, where $R^{N3}$ is selected from H, Me and COMe; $Q^4$ is a single bond; and n is 1 or 2;
(iii) Ar is

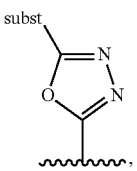

subst is selected from:
a) H;
b) $NH_2$, SH, OMe, SMe;
c) CN, $CO_2H$, COmorph;
d) $SO_2Me$;
e) $C_{2-3}$ alkyl substituted by OH;
and at least 2 of $R^1$ to $R^4$ are not H;
(iv) Ar is

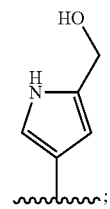 [SMILES: *c1c[nH]c(CO)c1]

or
(v) Ar is

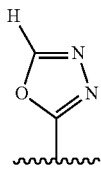

and $R^3$ is iPr;
(vi)

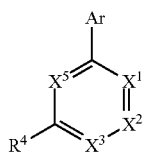

is

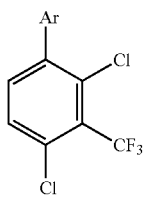

and Ar is a $C_5$heteroaryl group.

DESCRIPTION

Definitions $C_{1-4}$ alkyl: The term "$C_{1-4}$ alkyl" as used herein, pertains to a monovalent moiety obtained by removing a hydrogen atom from a carbon atom of a hydrocarbon compound having from 1 to 4 carbon atoms. The term "$C_{2-3}$ alkyl" as used herein, pertains to a monovalent moiety obtained by removing a hydrogen atom from a carbon atom of a hydrocarbon compound having from 2 to 3 carbon atoms. Examples of alkyl groups include, but are not limited to, methyl ($C_1$), ethyl ($C_2$), propyl ($C_3$) and butyl ($C_4$).

Examples of linear alkyl groups include, but are not limited to, methyl ($C_1$), ethyl ($C_2$), n-propyl ($C_3$) and n-butyl ($C_4$).

Examples of branched alkyl groups include iso-propyl ($C_3$), iso-butyl ($C_4$), sec-butyl ($C_4$) and tert-butyl ($C_4$).

$C_{3-6}$ cycloalkyl, with an optional O ring atom: The term "$C_{3-6}$ cycloalkyl" as used herein, pertains to a monovalent moiety obtained by removing a hydrogen atom from an alicyclic ring atom of a cyclic hydrocarbon (carbocyclic) compound, which moiety has from 3 to 6 carbon atoms, including from 3 to 6 ring atoms.

Examples of cycloalkyl groups include, but are not limited to, those derived from: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$) and methylcyclopentane ($C_6$).

If the optional O ring atom is present, the group may have 4 to 7 ring atoms in total. Examples of cycloalkyl groups with a O ring atom include, but are not limited to, those derived from: oxetane ($OC_3$), tetrahydrofuran ($OC_4$), tetrahydropyran ($OC_5$) and oxepane ($OC_6$).

$C_5$ heteroaryl: The term "$C_5$ heteroaryl", as used herein, pertains to a monovalent moiety obtained by removing a hydrogen atom from an aromatic ring atom of a heteroaromatic compound, which moiety has from 5 ring atoms. At least one ring atom must be a heteroatom, which may be selected from N, O and S. The groups may also have an oxo (=O) substituent.

Examples of C heteroaryl groups include, but are not limited to, those derived from:
$N_1$: pyrrole (azole) ($C_5$);
$O_1$: furan (oxole) ($C_5$);
$S_1$: thiophene (thiole) ($C_5$);
$N_1O_1$: oxazole ($C_5$), isoxazole ($C_5$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$);
$N_2S_1$: thiadiazole ($C_5$)
$N_3$: triazole ($C_5$); and,
$N_4$: tetrazole ($C_5$).

C heteroaryl: The term "C heteroaryl", as used herein, pertains to a monovalent moiety obtained by removing a hydrogen atom from an aromatic ring atom of a heteroaromatic compound, which moiety has from 6 ring atoms. At least one ring atom must be a heteroatom, which may be selected from N, O and S. If the group is a C N-containing heteroaryl, at least one ring atom must be N. The groups may also have an oxo (=O) substituent.

Examples of C heteroaryl groups include, but are not limited to, those derived from:
$N_1$: pyridine (azine) ($C_6$);
$N_1O_1$: isoxazine ($C_6$);
$N_2$: pyridazine (1,2-diazine) ($C_6$), pyrimidine (1,3-diazine) ($C_6$) (e.g., cytosine, thymine,
uracil), pyrazine (1,4-diazine) ($C_6$); and
$N_3$: triazine ($C_6$).

$C_{4-6}$heterocyclyl: The term "$C_{4-6}$heterocylyl", as used herein, pertains to a monovalent moiety obtained by removing a hydrogen atom from a ring atom of a monocyclic heterocyclic compound, which has from 4 to 6 ring atoms; of which at least one ring atom is N and up to 1 additional ring atoms may be chosen from N, O and S.

In this context, the prefixes (e.g. $C_{4-6}$) denote the number of ring atoms, or range of number of ring atoms, whether carbon atoms or heteroatoms.

Examples of $C_{4-6}$heterocyclyl groups include, but are not limited to, those derived from:
$N_1$: azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), pyrrole ($C_5$), piperidine ($C_6$), dihydropyridine ($C_6$), tetrahydropyridine ($C_6$), pyridine ($C_6$);
$N_2$: diazetidine ($C_4$), imidazolidine ($C_5$), pyrazolidine (diazolidine) ($C_5$), imidazoline ($C_5$), pyrazoline (dihydropyrazole) ($C_5$), imidazole ($C_5$), pyrazole ($C_5$), piperazine ($C_6$), pyrazine ($C_6$), pyrimidine ($C_6$), pyridazine ($C_6$);
$N_1O_1$: tetrahydrooxazole ($C_5$), dihydrooxazole ($C_5$), tetrahydroisoxazole ($C_5$), dihydroisoxazole ($C_5$), isoxazole ($C_5$), oxazole ($C_5$), morpholine ($C_6$), tetrahydrooxazine ($C_6$), dihydrooxazine ($C_6$), oxazine ($C_6$);

$N_1S_1$: thiazetidine ($C_4$), thiazolidine ($C_5$), isothiazolidine ($C_5$), thiomorpholine ($C_6$), thiazinane ($C_6$).

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N*HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge 1977.

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^3$. Examples of suitable organic cations include, but are not limited to, ammonium ion (i.e. NH$_4^+$) and substituted ammonium ions (e.g. NH$_3$R$^+$, NH$_2$R$^{2+}$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

In the present invention, the carbon atom to which R$^1$ and Cy are bound may be a stereochemical centre, i.e. when R$^1$ is not H and R$^1$ and Cy are different. The compounds of the present invention may be a racemic mixture, or may be in enantiomeric excess or substantially enantiomerically pure.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

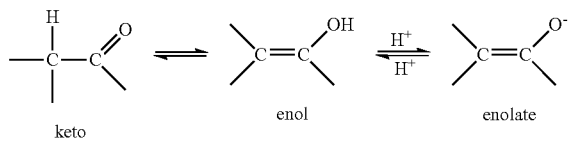

keto          enol          enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Methods of Treatment

The compounds of the present invention may be used in a method of therapy. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, and Lactated Ringer's Injection. Preservatives, stabilisers, buffers, antioxidants and/or other additives may be included, as required.

Notum

The secreted carboxy esterase, Notum, is a member of the sophisticated network of modulators and feedbacks that control the levels of Wnt signalling. Notum is a highly conserved and specific secreted inhibitor of Wnt signalling.

It has recently been demonstrated that Notum exerts its inhibitory activity on Wnt signalling through enzymatic modification of Wnt itself (Kakugawa et al., Nature. 2015 Mar. 12; 519(7542):187-192). Specifically, it was found that Notum acts as a carboxylesterase to remove a palmitoleate moiety from Wnt proteins, a post-translational modification known to be essential for Wnt's signalling activity. Notum is therefore the first identified extracellular protein deacylase.

Notum is not a major component of Wnt signal transduction; genetic removal of Notum leads to increased signalling but still within a physiological range (Canal, F. et al., PLoS ONE 11, e0150997; Gerlitz, O. et al., Genes & Development 16, 1055-1059; Giraldez, A. J. et al. Dev. cell 2, 667-676). This is in contrast with removal of APC or Axin, which leads to maximal signalling activity and rapid tumour formation in various tissues, including the gut and the liver (Oshima et al., Proc Natl Acad Sci USA. 1995 May 9; 92(10):4482-6). The present authors therefore identified Notum as a target with the potential to boost Wnt signalling in vivo. With this in mind, the present authors assessed whether Notum may be amenable to pharmacological inhibition.

In some embodiments, Notum polypeptide corresponds to Genbank accession no. AAH36872, version no. AAH36872.2, record update date: Sep. 23, 2014 03:00 PM. In one embodiment, the nucleic acid encoding Notum polypeptide corresponds to Genbank accession no. BC036872, version no. BC036872.1, record update date: Sep. 23, 2014 03:00 PM. In some embodiments, Notum polypeptide corresponds to Uniprot/Swiss-Prot accession No. Q6P988-1.

Substrate Binding by Notum

The crystal structure of human Notum (hNotum) has been published, revealing a canonical $\alpha/\beta$-hydrolase fold with catalytic triad comprising Ser232, Asp340 and His389 (Kakugawa et al., Nature. 2015 Mar. 12; 519(7542):187-192).

Through study of this structure, the present authors noted a ~380 $Å^3$ hydrophobic pocket positioned adjacent to the catalytic triad. Co-crystallization of inactive hNotum (S232A) with a palmitoleoylated (C16) disulfide-bonded peptide that mimics the palmitoleoylated loop in Wnt showed well-ordered electron density for the palmitoleoyl group occupying the active site pocket and the ester bond, but not for the peptide. A similar binding mode was observed for a hNotum-myristoleate (C14) crystal structure. These results indicate that the Notum hydrophobic pocket can accommodate long-chain fatty acids of up to 16 carbon atoms, with the authors noting that the shape of the hydrophobic pocket optimally accommodated the cis-unsaturated fatty acids myristoleate and palmitoleate.

These observations suggested that Notum was suitable for targeted inhibition via the hydrophobic pocket, allowing for the development of inhibitors with novel pharmokinetics properties, improved efficacy, and new clinical applications (c.f. Tarver J., et al., Bioorg. Med. Chem. Lett. 2016, 26, 1525; Suciu et al., ACS Med. Chem. Lett. 2018, 9, 563). Accordingly, the present authors set out to exploit a high resolution crystal form of hNotum for an XCHEM fragment screen at the UK synchrotron light source, Diamond, to identify molecular fragments that bind to the hydrophobic pocket as part of a process of guided Notum inhibitor design by structure based drug design (SBDD) with iterative cycles of Notum-inhibitor structure determinations on preferred compounds.

Therapeutic Roles for Modulators of Wnt Signalling

The Notum inhibitors described herein have numerous applications in clinical context where sustaining and/or stimulating Wnt signalling is expected to have therapeutic value. Examples include:

Hippocampal Neurogenesis

The dentate gyrus of the hippocampus is one of two main sites of neurogenesis in the adult mammalian brain, including that of humans. Adult-born neurons in the dentate gyrus contribute to spatial learning and memory. Neuronal production in the hippocampus declines with age in both rodents and humans, and this age-related decrease has been associated with the reduced performance of older rodents in cognitive and affective behavioural assays. Crucially, reduced hippocampal neurogenesis is also seen in aging humans, likely contributing to cognitive decline (Lazarov, O. et al., Front. aging neuroscience 5, 43; Spalding, K. L. et al., Cell 153, 1219-1227; Lazarov, O. et al., Trends in neurosciences 33, 569-579; Snyder, J. S. et al., Behavioural brain research 227, 384-390; Ming, G.-l. et al., Neuron 70, 687-702).

Stem cells and amplifying progenitors are located in the subgranular zone of the dentate gyrus where they are exposed to several signalling proteins, including Wnts, which stimulate their self-renewal and proliferation. Indeed, inhibition of Wnt signalling reduces neurogenesis in the developing hippocampus and, conversely, tissue-specific removal of Dkk1, a Wnt antagonist, leads to enhanced self-renewal and increased generation of immature neurons in both young and old animals. Importantly, such Wnt-induced neurogenesis is associated with improved cognitive functions (Seib, D. R. M. et al., Stem Cell 12, 204-214).

These results highlight an important role for Wnt signalling in adult neurogenesis and suggest that boosting Wnt signalling could help alleviate the symptoms of age-related neurogenesis decline and neurodegeneration in humans (Seib, D. R. M. et al., Stem Cell 12, 204-214).

Synapse Maintenance

Synapses, the structures through which nerve cells communicate and "encode" learning and memory, are critically modulated by Wnt signalling. Wnt signalling is required for synapse integrity in the adult hippocampus, and a decrease in Wnt signalling causes synapse loss and dysfunction, resulting in impaired long-term memory. Thus, enhancing Wnt signalling is an approach with potential to maintain synapse structure and function, and memory (Liu, C.-C. et al., Neuron, 1-45; Marzo, A. et al., Current Biology, 1-12; Vargas, J. Y. et al., J. Neuroscience 34, 2191-2202).

Blood Brain Barrier (BBB) Maintenance

The BBB is the cellular structure that controls the access of small and large molecules, circulating cells and infectious agents from the periphery to the brain and spinal cord. Wnt signalling is essential for maintenance of the BBB in the adult animal; loss leads to BBB dysfunction and leakage, and subsequent brain pathology. BBB dysfunction is well-documented in a number of neurodegenerative diseases, including Alzheimer's disease; as such enhancing Wnt signalling may be an approach to help maintain BBB structure function (Cho, C. et al., Neuron 95, 1056-1073; Liu, L. et al., Neurochemistry Int. 75, 19-25).

Hair Cell Regeneration

Maintenance of follicle stem cells in the skin require high Wnt signalling activity. Enhancing Wnt signalling could overcome natural or pathological hair loss (Fuchs, E., Current topics in dev. biology 116, 357-374; Lien, W.-H. et al., Nature cell biology 16, 179-190).

Regeneration of the Liver or Other Organs

Sustained Wnt signalling contributes to the development and growth of the liver and kidneys. An appropriate regimen of Notum inhibitor treatment could therefore contribute to organ regeneration (Ma, Y. et al., Hepatology Research 46, E154-E164; Kawakami, T. et al. J. Pathology 229, 221-231; Petersen, C. P. et al., Science 332, 852-855).

Other Notum Substrates

Although Notum is thought to act mostly through modulating Wnt proteins, its enzyme activity in principle allows it to catalyse the removal of other lipids on extracellular proteins or peptides. Considering potential substrates, only three families of secreted proteins have been reported to be acylated, namely Wnts, Hedgehogs and Ghrelins (Resh, Curr Biol. 2013 May 20; 23(10):R431-5).

Whilst it appears that Notum does not act on Hedgehog, the present authors have demonstrated that Notum can deacylate Ghrelin, an acylated (n-octanoyl modified) gastric-derived peptide involved in the regulation of energy homeostasis (reviewed Yanagi et al, Cell Metab. 2018 Apr. 3; 27(4):786-804). Consistent with this, a hNotum/n-octanoyl (C8) modified Ghrelin structure revealed well-ordered electron density in the Notum hydrophobic binding pocket. Accordingly, the Notum inhibitors described herein also offer the possibility of modulating Ghrelin signalling and, consequently, metabolic activity.

Treated Disorders

The multiple roles of Wnt signalling in brain health and disease are described herein. Accordingly, the Notum inhibitors described herein are believed to have particular utility in the treatment of a number of disorders of the central nervous system.

For example, evidence suggests that boosting Wnt signalling could alleviate Aβ-mediated synaptic loss and memory deficits in Alzheimer's Disease (AD; reviewed in Inestrosa NC. et al., J Mol Cell Biol. 2014 February; 6(1):64-74; Wan et al., Biomed Res Int. 2014; 2014:301575. doi: 10.1155/2014/301575). It has been reported that a variant LRP6 is associated with late-onset AD in humans (De Ferrari et al., Proc Natl Acad Sci USA. 2007 May 29; 104(22):9434-9), suggesting that impaired Wnt signalling could contribute to the disease. Furthermore, removal of LRP6 in mice leads to a range of phenotypes resembling those seen in AD (Liu et al., Neuron. 2014 Oct. 1; 84(1): 63-77), further supporting a role of sustained Wnt signalling in synapse maintenance. This is consistent with the observation that in cultured hippocampal neurons exogenous Wnt3A (a canonical Wnt) has a neuroprotective effect against Aβ (De Ferrari et al., Mol Psychiatry. 2003 February; 8(2):195-208; Cerpa et al., Mol Neurodegener. 2010 Jan. 18; 5:3).

Accordingly, the Notum inhibitors described herein may be used in methods of treating both:

(1) Neurodegenerative disorders such as Alzheimer's disease, multiple sclerosis, vascular dementia, small vessel disease, Ataxia-telangiectasia, Baggio-Yoshinari syndrome, neuronal ceroid lipofuscinoses such as Batten disease or Kufs disease, Corticobasal degeneration, Corticobasal syndrome, Prion disease such as Creutzfeldt-Jakob disease, Fatal insomnia, Huntington's disease, Refsum disease, Kufor-Rakeb syndrome, Machado-Joseph disease, Motor Neurone disease, Niemann-Pick disease, Parkinson's disease, Pontocerebellar hypoplasia, Sandhoff disease, Shy-Drager syndrome, Spinocerebellar ataxia, Spinal muscular atrophy, Tabes dorsalis, and Tay-Sachs disease; and (2) Other central nervous system disorders such as stroke, ischemia, and traumatic brain damage.

Other uses of the Notum inhibitors described herein arise from the therapeutic roles for modulators of Wnt signalling described herein. These include use in methods of treating:

(A) Proliferative disorders, such as cancer, for example colorectal cancer, hepatocellular carcinoma (Torisu, Y. et al., Cancer science 99, 1139-1146), melanoma, breast cancer such as triple-negative breast cancer, gastrointestinal cancer, leukaemia, and lymphoma;

(B) Bone disorders, such as osteoporosis pseudoglioma syndrome, sclerosteosis, van Buchem's disease, and osteopenia (see Tarver J., et al., Bioorg. Med. Chem. Lett. 2016, 26, 1525);

(C) Liver disorders, such liver fibrosis, liver cirrhosis, non-alcoholic steatohepatitis, alcoholic liver disease, cholangiopathies such as Primary Sclerosing Cholangitis (PSC), Focal nodular hyperplasia, Polycystic liver disease (PCLD), hepatocellular adenomas, hepatocellular cancers, and hepatoblastomas;

(D) Hair disorders, such as:
  (a) alopecia including male-pattern hair loss, female-pattern hair loss, alopecia areata, and telogen effluvium; and
  (b) hypertrichosis;

(E) Metabolic disorders, such as Type 2 diabetes, insulin resistance, metabolic syndrome, obesity, cachexia, Prader-Willi Syndrome, and Anorexia Nervosa; and (F) Metabolic complications, such as chronic inflammation, gastroparesis, cardiopathy, renal and pulmonary disease, gastrointestinal (GI) disorders, inflammatory disorders (see Collden G. et al., Int. J. Mol. Sci. 2017, 18, 798).

Notum inhibitors may also have utility for promoting the regeneration of aging tissues, including the intestine (Pentinmikko N., et al., Nature 2019, 571(7765):398-402; doi: 10.1038/s41586-019-1383-0).

More generally, the Notum inhibitors described herein are expected to have utility in the treatment of any disorder characterised by abnormal levels of Wnt or Ghrelin signalling.

Further Preferences

The following preferences may apply to all aspects of the invention as described above, or may relate to a single aspect. The preferences may be combined together in any combination.

Ar

In some embodiments, Ar is C heteroaryl, with an optional substituent.

In some of these embodiments, there is one heteroatom in the ring. In these embodiments, Ar may be:

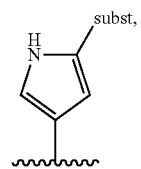

where subst represents the optional substituent.

In others of these embodiments, there are two heteroatoms in the ring. In these embodiments, Ar may be selected from:

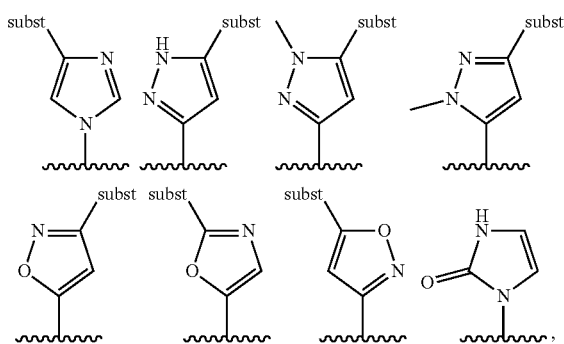

where subst represents the optional substituent. Where there is more than one available position for the optional substituent group, the substituent group may also be in those positions.

In others of these embodiments, there are three heteroatoms in the ring. In these embodiments Ar may be selected from:

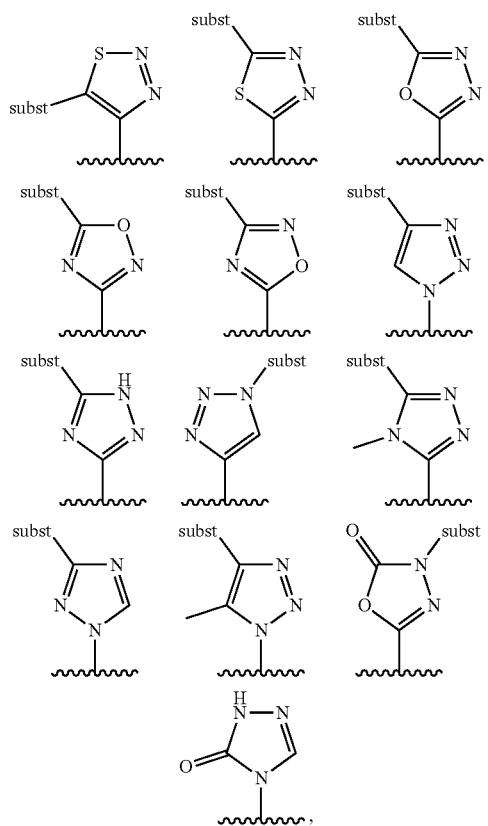

where subst represents the optional substituent. Where there is more than one available position for the optional substituent group, the substituent group may also be in those positions.

In others of these embodiments, there are four heteroatoms in the ring. In these embodiments, Ar may be selected from:

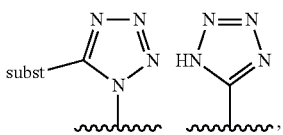

where subst represents the optional substituent. Where there is more than one available position for the optional substituent group, the substituent group may also be in those positions.

In some embodiments, it may be preferred that Ar is selected from:

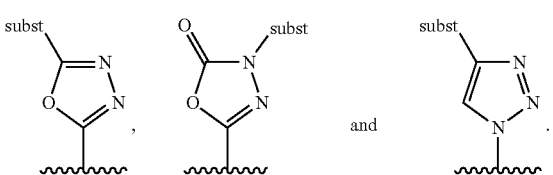

In some embodiments, it may be preferred that Ar is:

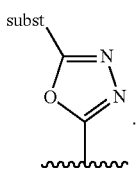

In other embodiments, it may be preferred that Ar is:

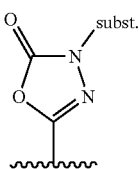

In other embodiments, it may be preferred that Ar is:

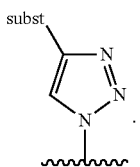

In some embodiments, Ar is C N-containing heteroaryl, with an optional substituent.

In some of these embodiments, there is one heteroatom in the ring. In these embodiments, Ar may be selected from:

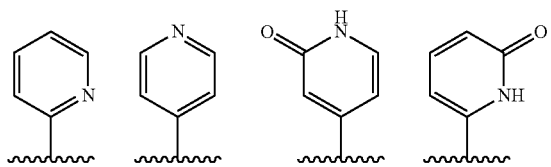

In others of these embodiments, there are two heteroatoms in the ring. In these embodiments, Ar may be selected from:

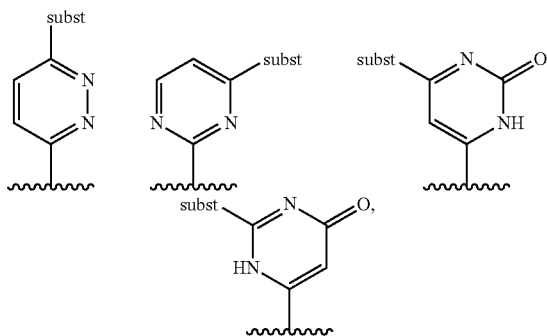

where subst represents the optional substituent. Where there is more than one available position for the optional substituent group, the substituent group may also be in those positions.

In some embodiments, Ar is selected from:

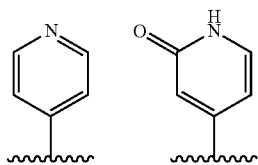

In some of these embodiments, Ar is:

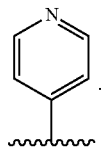

Substituent on Ar

In some embodiments, the substituent on Ar is selected from OH, SH, $NH_2$, OMe, SMe, NHMe, $NMe_2$, OEt, NHCN and Me. In some embodiments, the substituent on Ar is selected from OH, SH, $NH_2$, OMe and SMe. In some of these embodiments, the substituent is OH. In other of these embodiments, the substituent is SH. In other of these embodiments, the substituent is $NH_2$. In other of these embodiments, the substituent is OMe. In other of these embodiments, the substituent is SMe. It may be preferred that the substituent is OH In other embodiments, the substituent on Ar is selected from CN and $CO_2H$. In some of these embodiments, the substituent is CN. In other of these embodiments, the substituent is $CO_2H$.

In other embodiments, the substituent on Ar is selected from $SO_2Me$ and $SO_3^-Na^+$. In some of these embodiments, the substituent is $SO_2Me$. In other of these embodiments, the substituent is $SO_3^-Na^+$.

In other embodiments, the substituent on Ar is selected from $CH_2Q^1$, where $Q^1$ is selected from OH, OMe, Cl, CN, NHCOMe, $SO_3H$ and $NR^{N1}R^{N2}$, where $R^{N1}$ and $R^{N2}$ are either H or Me. In these embodiments, the substituent may be $CH_2OH$, $CH_2OMe$, $CH_2Cl$, $CH_2NH_2$, $CH_2NHMe$, $CH_2NMe_2$, $CH_2CN$, $CH_2NHCOMe$ and $CH_2SO_3H$. In some of these embodiments, the substituent may preferably be $CH_2OH$.

In other embodiments, the substituent on Ar is selected from $C_{2-3}$ alkyl substituted by OH. In these embodiments, the substituent may be $C(CH_3)_2OH$ or $CH(CH_3)OH$. In other of these embodiments, the substituent may be $CH_2CH_2CH_2OH$, $CH_2CH_2OH$ or $CH_2CH(CH_3)OH$.

In some embodiments, there is no substituent on Ar.

$X^1$, $X^2$, $X^3$ and $X^5$ $X^1$ is selected from $CR^1$ and N, $X^2$ is selected from $CR^2$ and N, $X^3$ is selected from $CR^3$ and N and $X^5$ is selected from $CR^5$ and N, where only 1 of $X^1$, $X^2$, $X^3$ and $X^5$ may be N.

In some embodiments, none of $X^1$, $X^2$, $X^3$ and $X^5$ are N.

In other embodiments, one of $X^1$, $X^2$, $X^3$ and $X^5$ is N. In some of these embodiments, $X^1$ is N. In other of these embodiments $X^2$ is N. In other of these embodiments $X^3$ is N. In other of these embodiments $X^5$ is N.

In some embodiments $X^5$ is CH.

$R^1$ to $R^5$

In some embodiments, $R^1$ to $R^5$ (if present) are all H.

In other embodiments, one of $R^1$ to $R^5$ (if present) is not H.

In other embodiments, two of $R^1$ to $R^5$ (if present) are not H.

In other embodiments, three of $R^1$ to $R^5$ (if present) are not H.

In some embodiments, those of $R^1$ to $R^5$ which are not H may be halo. In some of these embodiments, the halo group is Cl or F.

In some embodiments, those of $R^1$ to $R^5$ which are not H may be $C_{1-4}$ alkyl, optionally substituted by one or more F atoms. In some of these embodiments, the $C_{1-4}$ alkyl group is methyl, ethyl, iso-propyl or tert-butyl. If the $C_{1-4}$ alkyl group is substituted by F atoms, it may be perfluorinated, such as $CF_3$, or partially fluorinated, e.g. $CF_2H$.

In some embodiments, those of $R^1$ to $R^5$ which are not H may be $C_{3-6}$ cycloalkyl, which group may have an O ring atom. In some embodiments, there is no additional O ring atom, such that group may be selected from cyclopropyl, cyclopentyl and cyclohexyl. In other embodiments, where there is an O ring atom, the group may be oxetanyl.

In some embodiments, those of $R^1$ to $R^5$ which are not H may be CN, $NMe_2$ or $NO_2$. In some of these embodiments, the group is CN. In other of these embodiments, the group is $NMe_2$. In other of these embodiments, the group is $NO_2$.

In some embodiments, those of $R^1$ to $R^5$ which are not H may be O—$C_{1-4}$ alkyl, optionally substituted by one or more F atoms. In some of these embodiments, the O—$C_{1-4}$ alkyl group is methoxy, ethoxy or propyloxy (e.g. iso-propyloxy). If the O—$C_{1-4}$ alkyl group is substituted by F atoms, it may be perfluorinated, such as $OCF_3$.

In some embodiments, those of $R^1$ to $R^5$ which are not H may be $OCH_2Q^2$, where $Q^2$ is selected from $C_{3-6}$ cycloalkyl and phenyl. In some of these embodiment, the group is $OCH_2$-cycloalkyl, for example $OCH_2$-cyclopropyl. In other of these embodiments, the group is $OCH_2Ph$.

In some embodiments, those of $R^1$ to $R^5$ which are not H may be $CH_2OH$.

In some embodiments, those of $R^1$ to $R^5$ which are not H may be $NR^{N6}R^{N7}$, where $R^{N6}$ and $R^{N7}$ together form a $C_{4-6}$ heterocyclyl group optionally substituted with 1 to 2 groups selected from halo, $C_{1-3}$ alkyl, cyano and oxetanyl. In some of these embodiments, the group is azetidinyl, pyrrolidinyl or morpholinyl. In some of these embodiment, the group is azetidinyl substituted with one or two F atoms.

Fused Groups

In some embodiments, two adjacent groups of $R^1$ to $R^5$ together form a group $-Q^3-(CR^C_2)_n-Q^4-$, where $Q^3$ is selected from $NR^{N3}$ and O, where $R^{N3}$ is selected from H, $C_{1-3}$ alkyl, cyclopropylmethyl and COMe; $Q^4$ is $NR^{N4}$, O or a single bond, where $R^{N4}$ is selected from H, $C_{1-3}$alkyl cyclopropylmethyl and COMe; each Re is independently H, F or Me or two $R^c$ which are attached to the same atom can be linked together to form a $C_{3-5}$cycloalkyl; and n is 1, 2 or 3.

The two adjacent groups may be $R^1$ and $R^2$; $R^2$ and $R^3$; $R^3$ and $R^4$, or $R^4$ and $R^5$.

In some embodiments, when $Q^3$ is $NR^{N3}$, $Q^4$ is a single bond.

In some embodiments, when $Q^3$ is $NR^{N3}$, $Q^4$ is $NR^{N4}$.
In some embodiments, when $Q^3$ is $NR^{N3}$, $Q^4$ is O.
In some embodiments, when $Q^3$ is O, $Q^4$ is O.
In some embodiments, when $Q^3$ is O, $Q^4$ is O.
In some embodiments, when $Q^3$ is O, $Q^4$ is a single bond.
In some embodiments, $R^{N3}$ is H.
In other embodiments, $R^{N3}$ is $C_{1-3}$ alkyl, for example methyl or iso-propyl.
In other embodiments, $R^{N3}$ is cyclopropylmethyl.
In other embodiments, $R^{N3}$ is COMe.
In some embodiments, $R^{N4}$ is $C_{1-3}$alkyl, for example methyl or iso-propyl.
When $Q^3$ is $NR^{N3}$, in some embodiments each Re is H.
When $Q^3$ is O, in some embodiments each Re is selected from H and F.

In some embodiments, two adjacent groups of $R^1$ to $R^5$ together form a group selected from $-OC_3H_6-$; $-OCH_2C(Me)_2-$; $-N(Me)CH_2C(CH_2CH_2)-$; $-N(Me)CH_2C(CH_2CH_2)O-$; $-N(Me)C_2H_4N(Me)-$ and $-N(Me)C_2H_4O-$.

In some embodiments, two adjacent groups of $R^1$ to $R^4$ together form a group selected from $-NHC_2H_4-$; $-NMeC_2H_4-$; $-N(COMe)C_2H_4-$; and $-N\text{-}iPr\text{-}C_2H_4-$.

In some embodiments, two adjacent groups of $R^1$ to $R^4$ together form a group selected from $-OCH_2O-$; $-OCF_2O-$; and $-OC_2H_4O-$.

In some embodiments, two adjacent groups of $R^1$ to $R^4$ form a fused benzene or $C_{5-6}$ heteroaromatic ring with the phenyl group, which itself is optionally substituted by a $C_{1-2}$ alkyl group.

The two adjacent groups may be $R^1$ and $R^2$; $R^2$ and $R^3$; or $R^3$ and $R^4$.

In some of these embodiments, the fused ring is benzene.
In others of these embodiments, the fused ring is a C heteroaromatic ring, for example imadazoline. If the C heteroaromatic ring comprises a N-ring atom, this N-ring atom, may bear a methyl or ethyl group.
In others of these embodiments, the fused ring is a C heteroaromatic ring, for example pyridine or piperazine.

Combinations

In some embodiments, two of $R^1$ to $R^5$ are: both Cl; both F; both Me; or both $CF_3$.

In some embodiments, one of $R^1$ to $R^5$ is Cl and another is selected from $CF_3$; $OCF_3$; CN; OMe; and Br. In some of these embodiments, one of $R^1$ to $R^4$ is Cl and another is $CF_3$.

In some embodiments, one of $R^1$ to $R^5$ is $CF_3$ and another is selected from Cl, Me and cyclo-propyl.

In some embodiments where two of $R^1$ to $R^5$ are not H, the substituents may be in the 3,4; 2,3; or 2,4 positions. In some of these embodiments, the substituents may be in the 3,4 positions.

In some embodiments, where three of $R^1$ to $R^5$ are not H, the substituents may be OH and two F groups, for example 2-OH, 3,5-F.

In some embodiments, where three of $R^1$ to $R^5$ are not H, the substituents may be $CF_3$ and two Cl groups m for example, 2-Cl, 3-$CF_3$ and 4-Cl.

Further Embodiments

Further embodiments of the present invention include a compound as defined in the first aspect, wherein:

(i) Ar is

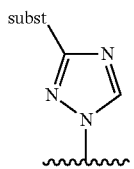

where subst represents the optional substituent;

(ii) Ar is

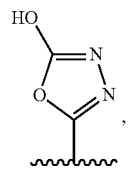

and:

a. at least 2 of $R^1$ to $R^5$ are not H and one of $R^1$ to $R^5$ is not Me; and $R^1$, $R^2$, $R^3$, $R^4$ and $R^5$ (if present) are independently selected from:

i) H;

ii) $C_{3-6}$ cycloalkyl, with an optional O ring atom;

ii) CN, $NMe_2$, $NO_2$;

iv) $OCH_2Q^2$, where $Q^2$ is selected from $C_{3-6}$ cycloalkyl and phenyl;

v) $CH_2OH$;

vi) $NR^{N6}R^{N7}$, where $R^{N6}$ and $R^{N7}$ together form a $C_{4-6}$heterocyclyl group optionally substituted with 1 to 2 groups selected from halo, $C_{1-3}$alkyl, cyano and oxetanyl;

or two adjacent groups of $R^1$ to $R^4$ together form a group $-Q^3-(CR^C_2)_n-Q^4-$, where $Q^3$ is selected from $NR^{N3}$ and O, where $R^{N3}$ is selected from H, $C_{1-3}$ alkyl, cyclopropylmethyl and COMe; $Q^4$ is $NR^{N4}$, O or a single bond, where $R^{N4}$ is selected from H, $C_{1-3}$ alkyl, cyclopropylmethyl and COMe; each R is independently H, F or Me or two $R^c$ which are attached to the same atom can be linked together to form a $C_{3-5}$cycloalkyl; and n is 1, 2 or 3;

or two adjacent groups of $R^1$ to $R^5$ form a fused benzene or $C_{5-6}$ heteroaromatic ring with the phenyl group, which itself is optionally substituted by a $C_{1-2}$ alkyl group;

b. at least 1 of $R^1$ to $R^4$ (if present) is $C_{3-6}$ cycloalkyl;

c. two adjacent groups of $R^1$ to $R^4$ together form a group $-Q^3-(CH_2)_n-Q^4-$, where $Q^3$ is selected from $NR^{N3}$ and O, where $R^{N3}$ is selected from H, Me and COMe; $Q^4$ is a single bond; and n is 1 or 2;

(iii) Ar is

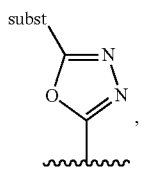

subst is selected from:
a) H;
b) $NH_2$, SH, OMe, SMe;
c) CN, $CO_2H$, COmorph;
d) $SO_2Me$;
e) $C_{2-3}$ alkyl substituted by OH
and at least 2 of $R^1$ to $R^4$ are not H;
(iv) Ar is

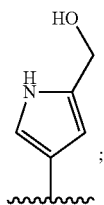 [SMILES: *c1c[nH]c(CO)c1]

or
(v) Ar is

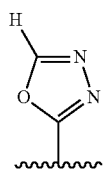

and $R^3$ is iPr;
(vi)

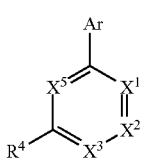

is

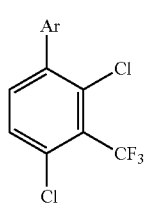

and Ar is a $C_5$heteroaryl group.

A compound of particular interest is:

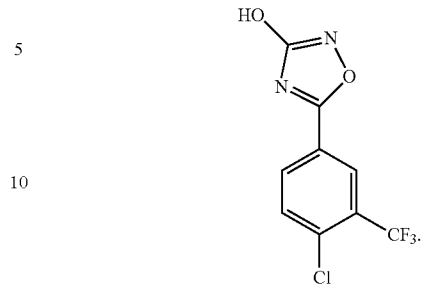

Other compounds of interest include:
5-(4-chloro-3-(trifluoromethyl)phenyl)-1,3,4-oxadiazol-2-ol (67);
5-[4-chloro-3-(trifluoromethyl)phenyl]-1,3,4-thiadiazol-2-ol (183);
5-(1-methylindolin-5-yl)-1,3,4-oxadiazol-2-ol (81);
2-[4-chloro-3-(trifluoromethyl)phenyl]-1,3,4-oxadiazole (196);
1-[4-chloro-3-(trifluoromethyl)phenyl]triazole (175);
5-(7-chloro-1,3,3-trimethyl-indolin-5-yl)-1,3,4-oxadiazol-2-ol (179);
4-[2,4-dichloro-3-(trifluoromethyl)phenyl]-1H-triazole (306);
2-(2,4-dichloro-3-(trifluoromethyl)phenyl)-5-(methoxy-d3)-1,3,4-oxadiazole (241);
2-(2,4-dichloro-3-(trifluoromethyl)phenyl)-5-ethoxy-1,3,4-oxadiazole (242);
4,5-dideuterio-1-[2,4-dichloro-3-(trifluoromethyl)phenyl]triazole (308);
5-[2,4-dichloro-3-(trifluoromethyl)phenyl]-1,3,4-oxadiazol-2-ol (261);
2-(2,4-dichloro-3-(trifluoromethyl)phenyl)-5-methoxy-1,3,4-oxadiazole (243);
1-[2,4-dichloro-3-(trifluoromethyl)phenyl]triazole (295);
N-(5-(2,4-dichloro-3-(trifluoromethyl)phenyl)-1,3,4-oxadiazol-2-yl)cyanamide, ammonia salt (246); and
3,5-dichloro-2-(triazol-1-yl)-4-(trifluoromethyl)pyridine (307).

EXAMPLES

General Experimental

Unless preparative details are provided, all reagents were purchased from commercial suppliers and used without further purification. All solvents were of ACS reagent grade or higher and purchased from commercial suppliers without further purification. Any anhydrous solvents were purchased as such from Acros Organics or Sigma Aldrich. Thin layer chromatography (TLC) was carried out on aluminium backed silica plates. The plates were visualized under UV (254 nm) light, followed by staining with phosphomolybdic acid dip or potassium permanganate and gentle heating. During compound separations, column chromatography was carried out using a Biotage Isolera using prepacked Biotage SNAP KP-Sil silica cartridges or Biotage SNAP Ultra C18 reverse phase cartridges. Organic layers were routinely dried with anhydrous $MgSO_4$ and concentrated using a Büchi rotary evaporator.

Melting points were determined using Stuart SMP20 melting point equipment using closed end glass capillary tubes and are uncorrected. $^1H$ NMR/$^{13}C$ NMR spectra were run in deuterated (≥99.5%) solvents, on either a Bruker Avance 400 (400 MHz), a Bruker Avance 600 (600 MHz) or a Bruker Avance Neo 700 (700 MHz). Chemical shifts (δ) are reported as parts per million (ppm). The coupling constants (J) are reported in Hz and signal multiplicities are reported as singlet (s), doublet (d), triplet (t), quartet (q), pentet (p), quintet (qu), sextet (sext), doublet of doublets (dd), doublet of triplets (dt), triplet of triplets (tt), multiplet (m), or broad singlet (br. s) etc. For mass spectrometry data, LCMS analysis was performed on a Waters Acquity H-Class UPLC system with either an acidic (HSS C18 column, $H_2O$-acetonitrile, 0.1% TFA) or basic (BEH C18 column, $H_2O$:acetonitrile, 10 mM $NH_4OH$) mobile phase. The observed mass and isotope pattern matched the corresponding theoretical values as calculated from the expected elemental formula.

Generic Route 1—Preparation of (1-(4-ethoxyphenyl)-1H-1,2,3-triazol-4-yl)methanol

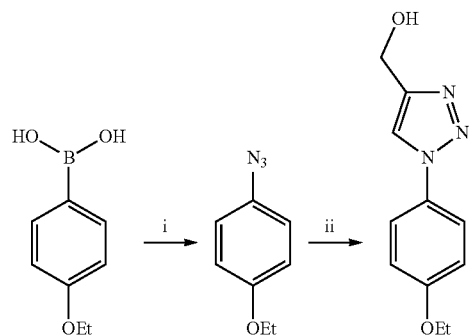

Reagents and conditions: i) Sodium azide, copper (II) sulfate pentahydrate, methanol, 40° C.; ii) copper (II) sulfate pentahydrate, sodium L-ascorbate, propargyl alchohol, isopropanol, water.

Step 1:

Sodium azide (260 mg, 4.0 mmol, 2.0 equiv.) and copper (II) sulfate pentahydrate (100 mg, 0.4 mmol, 0.2 equiv.) was added to a solution of 4-ethoxyphenylboronic acid (332 mg, 2.0 mmol, 1.0 equiv.) in methanol (10 mL). The resultant solution was then stirred at 40° C. for 5 hours, before concentrating to approximately 50% volume under reduced pressure. The mixture was then diluted with water and extracted with ethyl acetate. The organic layer was then cautiously concentrated under reduced pressure at 25° C., to provide crude 1-azido-4-ethoxybenzene, which was used without further purification.

Step 2:

Copper(II) sulfate pentahydrate (100 mg, 0.4 mmol, 0.22 equiv.), sodium L-ascorbate (56 mg, 0.28 mmol, 0.15 equiv.) and propargyl alcohol (0.1 mL, 1.8 mmol, 1.0 equiv.) was added to a solution of crude 1-azido-4-ethoxybenzene in isopropanol (1.7 mL) and water (1.7 mL). The reaction vessel was stirred at 40° C. overnight, after this time the reaction was diluted with water, extracted with ethyl acetate and the organic phase was washed with water and brine. The organic phase was then dried over anhydrous $MgSO_4$, filtered and concentrated under reduced pressure. Purification by column chromatography (0-5% methanol in dichloromethane) gave (1-(4-ethoxyphenyl)-1H-1,2,3-triazol-4-yl)methanol (224 mg, 1.02 mmol, 57%) as a white solid.

Generic Route 2—Preparation of (1-(isoquinolin-6-yl)-1H-1,2,3-triazol-4-yl)methanol

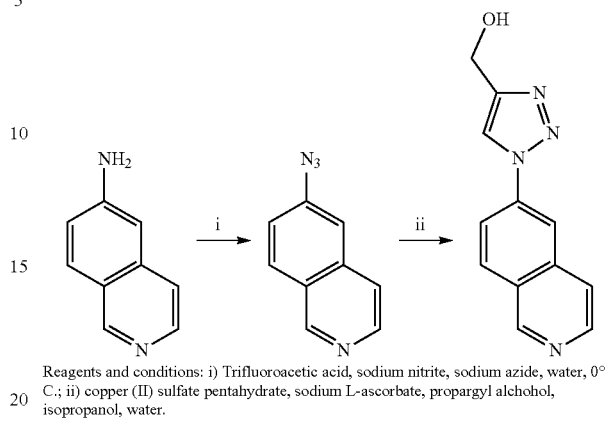

Reagents and conditions: i) Trifluoroacetic acid, sodium nitrite, sodium azide, water, 0° C.; ii) copper (II) sulfate pentahydrate, sodium L-ascorbate, propargyl alchohol, isopropanol, water.

Step 1:

Sodium nitrite (115 mg, 1.66 mmol, 1.2 equiv.) was added portionwise to a solution of isoquinolin-6-amine (200 mg, 1.39 mmol, 1.0 equiv.) in trifluoroacetic acid (1.0 mL) at 0° C. over a period of 30 minutes. The reaction mixture was then allowed to warm to room temperature for 1.5 hours, water (100 µL) was then added and the mixture was then re-cooled to 0° C. Sodium azide (90 mg, 1.39 mmol, 1.0 equiv.) was then added portionwise over 30 minutes, the reaction mixture was then allowed to warm to room temperature over 1 hour. The mixture was basified to pH 8-9 by dropwise addition of saturated aqueous sodium bicarbonate, and extracted with dichloromethane. The organic phase was dried over anhydrous $MgSO_4$, filtered and cautiously concentrated under reduced pressure at 25° C., to provide crude 6-azidoisoquinoline, which was used without further purification.

Step 2:

Copper(II) sulfate pentahydrate (64 mg, 0.28 mmol, 0.2 equiv.) sodium L-ascorbate (110 mg, 0.55 mmol, 0.4 equiv.) and propargyl alcohol (80 µL, 1.39 mmol, 1.0 equiv.) was added to a solution of crude 6-azidoisoquinoline in isopropanol (2.0 mL) and water (2.0 mL). The reaction vessel was stirred at 40° C. overnight, after this time the reaction was diluted with water, extracted with ethyl acetate and the organic phase was washed with water and brine. The organic phase was then dried over anhydrous $MgSO_4$, filtered and concentrated under reduced pressure. Purification by column chromatography (0-5% methanol in dichloromethane) gave (1-(isoquinolin-6-yl)-1H-1,2,3-triazol-4-yl)methanol (46 mg, 0.2 mmol, 15%) as a white solid.

Generic Route 3—Preparation of 5-(4-chloro-3-(trifluoromethyl)phenyl)-1,3,4-oxadiazol-2-ol

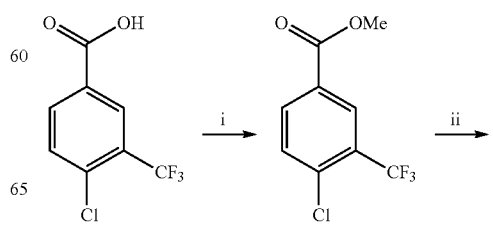

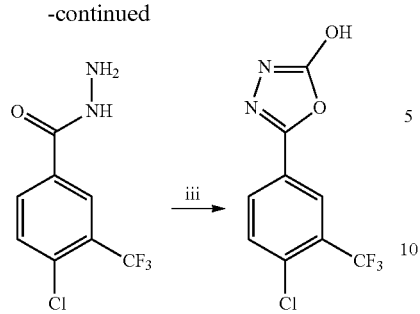

Reagants and conditions: i) Sulfuric acid, methanol; ii) hydrazine monohydrate, ethanol, toluene; iii) triphosgene, N,N-diisopropylethylamine, dichloromethane.

Step 1:
Sulfuric acid (60 µL, 1.11 mmol, 0.5 equiv.) was added to a solution of 4-chloro-3-(trifluoromethyl)benzoic acid (500 mg, 2.23 mmol, 1.0 equiv.) in methanol (10 mL) and heated to 85° C. for 3 days. The reaction mixture was then cooled to room temperature, concentrated to approximately one third volume then diluted with ethyl acetate and saturated aqueous sodium bicarbonate. The organic phase was dried over anhydrous $MgSO_4$, filtered and concentrated under reduced pressure to give crude methyl 4-chloro-3-(trifluoromethyl)benzoate as a white solid, which was used without further purification.

Step 2:
Hydrazine monohydrate (355 mg, 7.09 mmol, 3.2 equiv.) was added to a solution of crude methyl 4-chloro-3-(trifluoromethyl)benzoate in ethanol (4 mL) and toluene (2 mL). The mixture was heated to 40° C. for 16 hours, cooled to room temperature and concentrated under reduced pressure. The crude residue was azeotroped with ethanol and toluene to provide crude 4-chloro-3-(trifluoromethyl)benzohydrazide as an off-white solid, which was used without further purification.

Step 3:
A solution of triphosgene (208 mg, 0.70 mmol, 1.0 equiv.) in dichloromethane (3 mL), was added dropwise to a cloudy suspension of crude 4-chloro-3-(trifluoromethyl)benzohydrazide and N,N-diisopropylethylamine (0.61 mL, 3.5 mmol, 5.0 equiv.) in dichloromethane (40 mL) at 0° C. (external). The reaction was then allowed to warm to room temperature over 2 hours and the reaction mixture was diluted with saturated aqueous sodium bicarbonate. The organic phase was dried over anhydrous $MgSO_4$, filtered and concentrated under reduced pressure. Purification by column chromatography (10-60% ethyl acetate in cyclohexane) gave 5-(4-chloro-3-(trifluoromethyl)phenyl)-1,3,4-oxadiazol-2-ol (229 mg, 0.87 mmol, 41%, over 3 steps) as a white solid.

Generic Route 4—Preparation of 5-(4-chloro-3-(trifluoromethyl)phenyl)-1,3,4-oxadiazol-2-ol

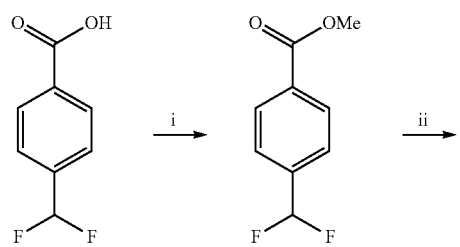

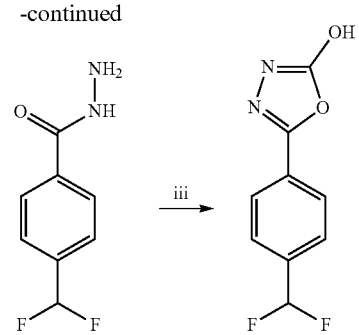

Reagants and conditions: i) Thionyl chloride, methanol; ii) Hydrazine monohydrate, ethanol, toluene; iii) triphosgene, N,N-diisopropylethylamine, dichloromethane.

Step 1:
Thionyl chloride (0.83 mL, 7.26 mmol, 5.0 equiv.), was added dropwise to a solution of 4-(difluoromethyl)benzoic acid (250 mg, 1.45 mmol, 1.0 equiv.) in methanol (8 mL) at 0° C. (external). The reaction mixture was heated to reflux for 2 hours, cooled to room temperature and concentrated under reduced pressure. The crude residue was then passed through a short pad of silica (0-20% ethyl acetate in cyclohexane) to provide crude methyl 4-(difluoromethyl)benzoate, which was used without further purification.

Step 2:
Hydrazine monohydrate (582 mg, 11.6 mmol, 8.0 equiv.) was added to a solution of crude methyl 4-(difluoromethyl)benzoate in ethanol (2.5 mL) and toluene (2.5 mL). The mixture was heated to 70° C. for 16 hours, cooled to room temperature and concentrated under reduced pressure. The crude residue was azeotroped with ethanol and toluene to provide crude 4-(difluoromethyl)benzohydrazide as an off-white solid, which was used without further purification.

Step 3:
A solution of triphosgene (172 mg, 0.58 mmol, 0.4 equiv.) in dichloromethane (15 mL) was added dropwise to a solution of crude 4-(difluoromethyl)benzohydrazide and N,N-diisopropylethylamine (0.51 mL, 2.9 mmol, 2.0 equiv.) in dichloromethane (5 mL) at 0° C. (external). The reaction was stirred at 0° C. for 20 minutes, then warmed to room temperature and stirred for a further 40 minutes. The reaction mixture was diluted with dichloromethane, and cautiously diluted with saturated aqueous sodium bicarbonate. The organic phase was dried over anhydrous $MgSO_4$, filtered and concentrated under reduced pressure. Purification by column chromatography (0-2% methanol in dichloromethane) gave 5-(4-(difluoromethyl)phenyl)-1,3,4-oxadiazol-2-ol (165 mg, 0.78 mmol, 54%, over 3 steps) as a white solid.

Generic Route 5—Preparation of 3-(1,3,4-oxadiazol-2-yl)benzonitrile

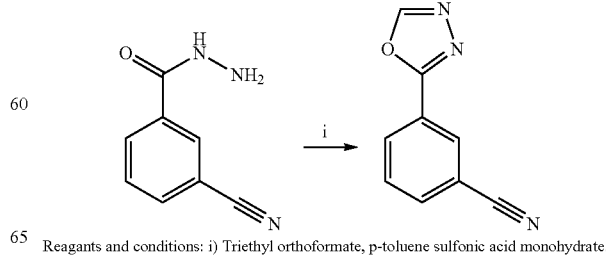

Reagants and conditions: i) Triethyl orthoformate, p-toluene sulfonic acid monohydrate.

Step 1:

Triethyl orthoformate (0.44 mL, 2.85 mmol, 4.5 equiv) was added cautiously to a 20 mL microwave vial containing 3-cyanobenzohydrazide (103 mg, 0.64 mmol, 1.0 equiv) and p-toluenesulfonic acid monohydrate (12 mg, 0.06 mmol, 0.1 equiv) under a nitrogen atmosphere and then cautiously warmed to 60° C. The mixture was then stirred at that temperature for 30 minutes. The reaction was cooled to room temperature and sat. aq. NaHCO$_3$ (20 mL) added dropwise. The mixture was diluted with dichloromethane (50 mL), the organics were separated, dried over anhydrous MgSO$_4$ and concentrated under reduced pressure. Purification by column chromatography (0-40% ethyl acetate in cyclohexane) gave 3-(1,3,4-oxadiazol-2-yl)benzonitrile (66 mg, 0.39 mmol, 61% yield) as a white solid.

Generic Route 6—Preparation of (1-(2-chlorophenyl)-1H-1,2,3-triazol-4-yl)methanamine hydrochloride

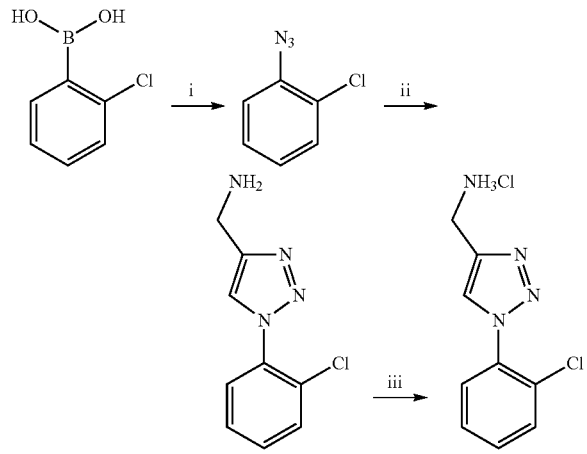

Reagents and conditions: i) Sodium azide, copper (II) sulfate pentahydrate, methanol, 40° C.; ii) copper (II) sulfate pentahydrate, sodium L-ascorbate, propargylamine, isopropanol, water. iii) 7 N HCl in dioxane, ethyl acetate.

Step 1:

Sodium Azide (260 mg, 4.0 mmol, 2.0 equiv.) and copper (II) sulfate pentahydrate (100 mg, 0.4 mmol, 0.2 equiv.) was added to a solution of 2-chorophenylboronic acid (313 mg, 2.0 mmol, 1.0 equiv.) in methanol (10 mL). The resultant solution was stirred at 40° C. for 5 hours, before concentrating to approximately 50% volume under reduced pressure. The mixture was diluted with water and extracted with ethyl acetate. The organic layer was then cautiously concentrated under reduced pressure at 25° C., to provide crude 1-azido-4-ethoxybenzene, which was used without further purification.

Step 2:

Copper(II) sulfate pentahydrate (100 mg, 0.4 mmol, 0.22 equiv.), sodium L-ascorbate (55.5 mg, 0.28 mmol, 0.15 equiv.) and propargylamine (0.15 mL, 2.4 mmol, 1.2 equiv.) was added to a solution of crude 1-azido-4-ethoxybenzene in isopropanol (1.7 mL) and water (1.7 mL). The reaction vessel was stirred at 40° C. overnight, after this time the reaction was diluted with water, extracted with ethyl acetate and the organic phase was washed with water and brine. The organic phase was then dried over anhydrous MgSO$_4$, filtered and concentrated under reduced pressure. Purification by column chromatography (0-5% methanol in dichloromethane) gave [1-(2-chlorophenyl)triazol-4-yl]methanamine as a colourless oil.

Step 3:

[1-(2-chlorophenyl)triazol-4-yl]methanamine was dissolved in ethyl acetate (2 mL) and charged with 0.4 mL of 7 N HCl in dioxane. The resulting precipitate was removed via filtration and dried under a continuous flow of air to give (1-(2-chlorophenyl)-1H-1,2,3-triazol-4-yl)methanamine hydrochloride (205 mg, 0.84 mmol, 42%) as a white solid.

Generic Route 7—Preparation of 3-(4-chloro-3-(trifluoromethyl)phenyl)-1H-pyrazole

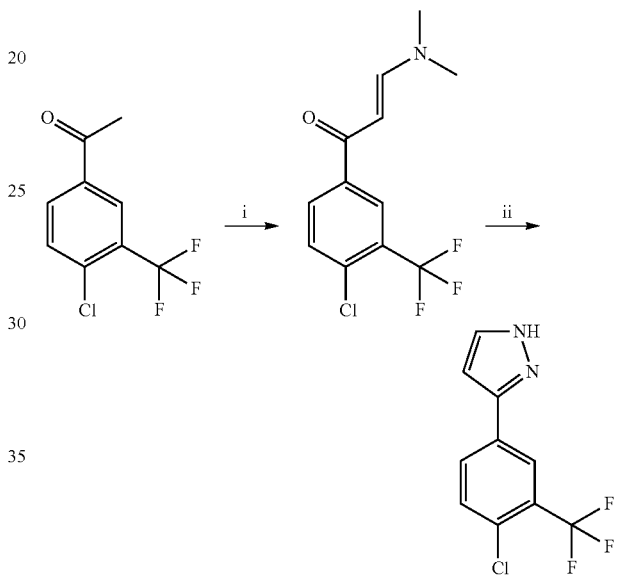

Reagents and conditions: i) N,N-Dimethylformamide dimethyl acetal, N,N-dimethylformamide, 90° C.; ii) hydrazine monohydrate, methanol, 68° C.

Step 1:

A solution of 4'-chloro-3'-(trifluoromethyl)acetophenone (200 mg, 0.90 mmol, 1.0 equiv.) and N,N-dimethylformamide dimethyl acetal (0.4 mL, 2.70 mmol, 3.0 equiv.) in anhydrous N,N-dimethylformamide (5 mL) was purged with N$_2$ and heated to 90° C. for 2 hours. The solution was cooled to room temperature and the solvent removed under reduced pressure. The brown residue [(E)-1-[4-chloro-3-(trifluoromethyl)phenyl]-3-(dimethylamino)prop-2-en-1-one] was dried under high vacuum for 18 hours and used without further purification in the next stage. (LCMS: MS m/z 278.1 [M+H]$^+$)

Step 2:

To a solution of (E)-1-[4-chloro-3-(trifluoromethyl)phenyl]-3-(dimethylamino)prop-2-en-1-one (240 mg, 0.86 mmol, 1.0 equiv.) in methanol (8 mL) was added hydrazine monohydrate (0.42 mL, 8.64 mmol, 10 equiv.). The solution was heated to 68° C. for 2.5 hours. The solution was cooled to room temperature and the solvent removed under reduced pressure. Purified by column chromatography (0-50% ethyl acetate in cyclohexane) gave 3-[4-chloro-3-(trifluoromethyl)phenyl]-1H-pyrazole (200 mg, 0.81 mmol, 94% yield) as an off-white solid.

Generic Route 8—Preparation of
1-(4-isopropylphenyl)-1H-1,2,3-triazole

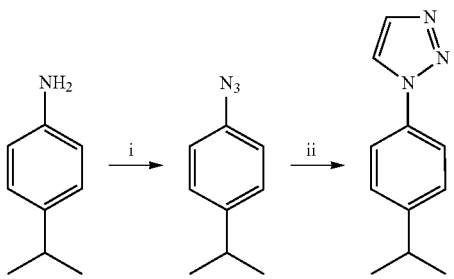

Reagents and conditions: i) Sodium nitrite, hydrochloric acid, sodium azide, water, acetonitrile; ii) copper (II) sulfate pentahydrate, sodium L-ascorbate, trimethylsilylacetylene, potassium carbonate, methanol, water.

Step 1:

4-Isopropylaniline (0.2 mL, 1.87 mmol, 1.0 equiv.) was dissolved in water (0.9 mL) and acetonitrile (6.2 mL). >37% Hydrochloric Acid (3.7 mL, 120.14 mmol, 64 equiv.) was added and the solution stirred vigorously at room temperature for 10 minutes. Sodium nitrite (257 mg, 3.73 mmol, 2.0 equiv.) was then added portion-wise and the solution stirred for an additional 1 hour. The solution was cooled to 0° C. and sodium azide (242 mg, 3.73 mmol, 2.0 equiv.) was added. After 1 hour, the solution was diluted with water (30 mL) then extracted with diethyl ether. tert-butyl alcohol (2 mL) was added and the organic layer was concentrated under reduced pressure to around 2 mL and the resulting solution of 1-azido-4-isopropyl-benzene in tert-butyl alcohol taken through to the next step without further purification.

Step 2:

A suspension of 1-azido-4-isopropyl-benzene (300 mg, 1.86 mmol, 1.0 equiv.) as a solution in tert-butyl alcohol (2 mL), trimethylsilylacetylene (0.4 mL, 2.79 mmol, 1.5 equiv.), copper(II) sulfate pentahydrate (47 mg, 0.19 mmol, 0.1 equiv.), potassium carbonate (514 mg, 3.72 mmol, 2.0 equiv.) and sodium L-ascorbate (73.7 mg, 0.37 mmol, 0.2 equiv.) in methanol (1 mL) and water (2.5 mL) was stirred in a sealed microwave vial for 18 hours. LCMS showed presence of product as well as TMS-product. Further potassium carbonate (514 mg, 3.72 mmol, 2.0 equiv.) was added and the suspension heated to 60° C. for 4 hours. The reaction mixture was diluted with ethyl acetate and washed with water and brine. The organic phase was dried over anhydrous MgSO₄, filtered and concentrated under reduced pressure. Purification by column chromatography (0-40% ethyl acetate in cyclohexane) gave 1-(4-isopropylphenyl)-1H-1,2,3-triazole (57 mg, 0.31 mmol, 16%) as an off-white solid.

Generic Route 9—Preparation of
5-(3,5-dimethylphenyl)-1H-tetrazole

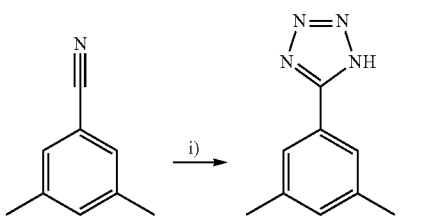

Reagants and conditions: i) Sodium azide, triethylamine hydrochloride, toluene, 100° C.

To a solution of 3,5-dimethylbenzonitrile (75 mg, 0.57 mmol, 1.0 equiv.) in toluene (20 mL) was added sodium azide (112 mg, 1.72 mmol, 3.0 equiv.) and triethylamine hydrochloride (236 mg, 1.72 mmol, 3.0 equiv.). The reaction mixture was heated to 100° C. for 36 hours. The residue was purified by PE-AX cartridge (MeOH-2 M HCl in dioxane/MeOH). The solvent was concentrated under reduced pressure to give 5-(3,5-dimethylphenyl)-1H-tetrazole (10 mg, 0.057 mmol, 10%) as a colourless gum.

Generic Route 10—Preparation of
1-(4-chlorophenyl)tetrazole

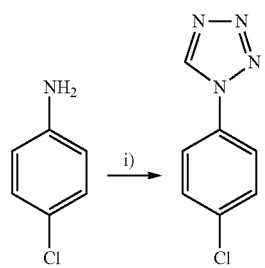

Reagents and conditions: i) Sodium azide, triethyl orthoformate, acetic acid, toluene, 76° C.

To a suspension of 4-chloroaniline (65 mg, 0.51 mmol, 1.0 equiv.) in acetic acid (2 mL, 35 mmol, 68.3 equiv.) was added triethyl orthoformate (0.14 mL, 0.82 mmol, 1.6 equiv.) and sodium azide (50 mg, 0.77 mmol, 1.5 equiv.). The reaction mixture was heated to 76° C. under $N_2$ in a MW vial (turns into pale yellow solution) for 18 hours. The reaction mixture was concentrated under reduced pressure. The resulting residue was washed with 1 M HCl, aq. sat. NaHCO₃ and hexane and dried under vacuum to give 1-(4-chlorophenyl)tetrazole (54.8 mg, 0.30 mmol, 59%) as an off-white solid.

Generic Route 11—Preparation of
5-(1-methylindolin-5-yl)-1,3,4-oxadiazol-2-ol

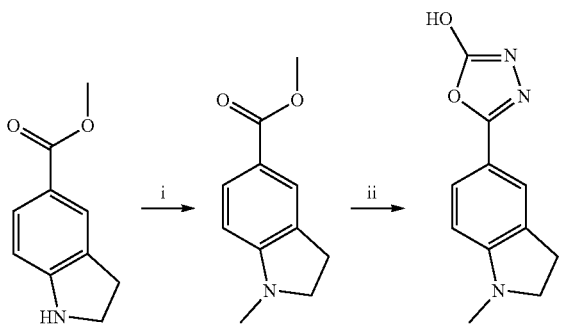

Reagents and conditions: i) Methyl iodide, sodium hydride 60% wt on mineral oil, tetrahydrofuran; ii) Generic route 4.

Step 1:

A solution of methyl indoline-5-carboxylate (200 mg, 1.13 mmol, 1.0 equiv.) in tetrahydrofuran (10 mL) was cooled in an ice-water bath for 5 minutes. Sodium hydride (45 mg, 1.13 mmol, 1.0 equiv.) in tetrahydrofuran (2 mL) was added dropwise and the reaction was stirred for 20 minutes before the dropwise addition of iodomethane (0.07 mL, 1.13 mmol, 1.0 equiv.). The reaction mixture was stirred for 30 minutes before warming to 60° C. for 24 hours. Additional sodium hydride (23 mg, 0.57 mmol, 0.5 equiv.) in tetrahydrofuran (1 mL) was added followed by iodomethane (0.04 mL, 0.57 mmol, 0.5 equiv.) in tetrahydrofuran (1 mL) and the reaction was stirred for a further 24 hours at 60° C. The reaction was cooled to room temperature and added dropwise to a saturated solution of $NH_4Cl$ solution and extracted with ethyl acetate three times. The organics were combined, dried over anhydrous $MgSO_4$, filtered to remove the solids, and adsorbed onto silica. Purification by column chromatography (0-70% ethyl acetate in cyclohexane) gave methyl 1-methylindoline-5-carboxylate (61 mg, 0.32 mmol, 28%) as a white solid.
Step 2:
Following generic route 4, using methyl 1-methylindoline-5-carboxylate, to afford 5-(1-methylindolin-5-yl)-1,3,4-oxadiazol-2-ol (60 mg, 0.28 mmol, 87%) as a white solid.

Generic Route 12—Preparation of 5-(3-cyclopropylphenyl)-1,3,4-oxadiazol-2-ol

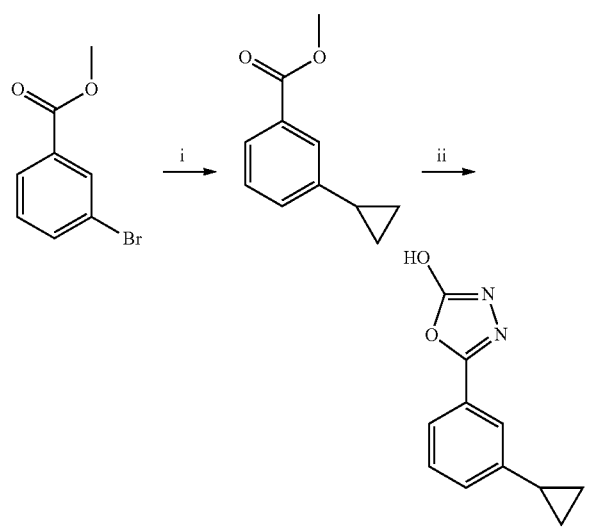

Reagents and conditions: i) Pd(dppf)Cl$_2$·dichloromethane, cyclopropylboronic acid, 1 N NaHCO$_3$, 1,4-dioxane, Ar, 110° C. (ii) Generic route 4

Step 1:
A microwave vial was charged with Pd(dppf)Cl$_2$.dichloromethane (142 mg, 0.17 mmol, 0.05 equiv.), cyclopropylboronic acid (599 mg, 6.98 mmol, 2.0 equiv.) and methyl 3-bromobenzoate (750 mg, 3.49 mmol, 1.0 equiv.). The vial was sealed, evacuated and purged with argon 3 times. Anhydrous 1,4-dioxane (10 mL) was added, followed by disodium carbonate aqueous solution (1 N, 10.5 mL, 10.5 mmol). The vial was evacuated and purged with argon a further 3 times. The vial was placed into a preheated aluminium heating block at 110° C. and stirred for 24 hours. The vial was cooled to room temperature and the pressure in the vial was carefully released by means of a syringe. The reaction was added to water and the aqueous solution acidified using 1 N HCl solution. The resulting precipitate was extracted with ethyl acetate. The organics were separated and washed with 20 mL of NaOH solution and water (30 mL). The organics were discarded and the aqueous layer was re-acidified with 1 N HC. The precipitate was extracted with ethyl acetate, the organic layer was isolated, dried over anhydrous $MgSO_4$ and the solids removed via filtration. The organics were removed under reduced pressure to give 3-cyclopropylbenzoic acid (435 mg, 2.68 mmol, 77%) as a pale brown solid, containing approximately 7% benzoic acid
Step 2:
Following generic route 4, using 3-cyclopropylbenzoic acid, to afford 5-(3-cyclopropylphenyl)-1,3,4-oxadiazol-2-ol (160 mg, 0.79 mmol, 30%) as a white solid.

Generic Route 13—Preparation of 1-(3-(pyrrolidin-1-yl)-4-(trifluoromethyl)phenyl)-1H-1,2,3-triazole (287)

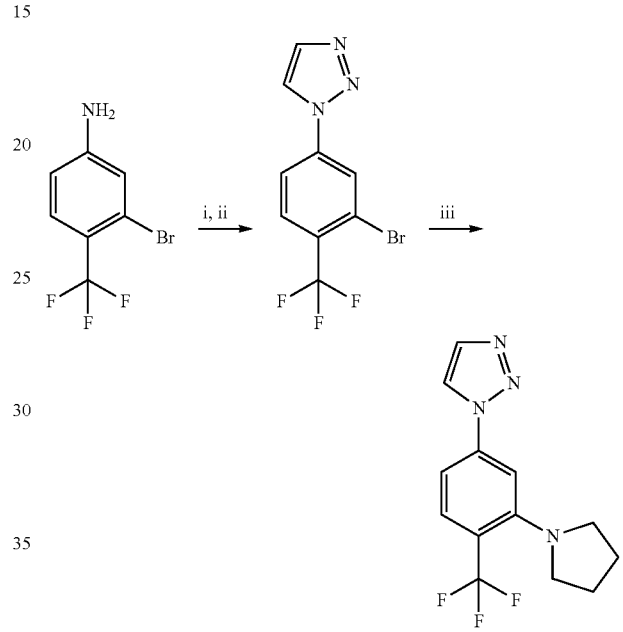

Reagents and conditions: i) Sodium nitrite, hydrochloric acid, sodium azide, water, acetonitrile; ii) copper (II) sulfate pentahydrate, sodium L-ascorbate, trimethylsilylacetylene, potassium carbonate, methanol, water; iii) pyrrolidine, cesium carbonate, Pd$_2$(dba)$_3$, (±)-2,2'-bis(diphenylphosphino)-1,1-binaphthalene, toluene.

Step 1 & 2:
Following Generic route 9, using 3-bromo-4-(trifluoromethyl)aniline to afford 1-[3-bromo-4-(trifluoromethyl)phenyl]triazole (827 mg, 2.83 mmol, 69% yield) as a pale yellow oil.
Step 3:
To a solution of 1-[3-bromo-4-(trifluoromethyl)phenyl]triazole (100 mg, 0.34 mmol) in toluene (3 mL) was added pyrrolidine (0.04 mL, 0.51 mmol) and cesium carbonate (167 mg, 0.51 mmol). The reaction mixture was sealed in a microwave tube. After 10 mins at r.t. tris(dibenzylideneacetone)dipalladium (0) (16 mg, 0.02 mmol) and (±)-2,2'-bis (diphenylphosphino)-1,1-binaphthalene (21 mg, 0.03 mmol) was added and the reaction stirred for a further 20 mins at r.t. The reaction mixture was then heated to 115° C. and stirred for 18 hrs. The reaction mixture was filtered and concentrated under reduced pressure. The residue was purified by column chromatography (25 g, 0-100% dichloromethane in cyclohexane) to give 1-(3-(pyrrolidin-1-yl)-4-(trifluoromethyl)phenyl)-1H-1,2,3-triazole (287) (88 mg, 0.313 mmol, 91% yield) as a colourless oil.
LCMS: MS m/z 283.1 [M+H]$^+$; $^1$H NMR (600 MHz, CDCl$_3$) δ 8.00 (d, J=1.1 Hz, 1H), 7.85 (d, J=1.1 Hz, 1H), 7.69 (d, J=8.5 Hz, 1H), 7.40 (d, J=1.9 Hz, 1H), 7.01 (dd, J=8.5, 1.9 Hz, 1H), 3.47-3.44 (m, 4H), 2.02-1.97 (m, 4H).

Generic Route 14—Preparation of 2-(2,4-dichloro-3-(trifluoromethyl)phenyl)-5-(methoxy-d3)-1,3,4-oxadiazole (241)

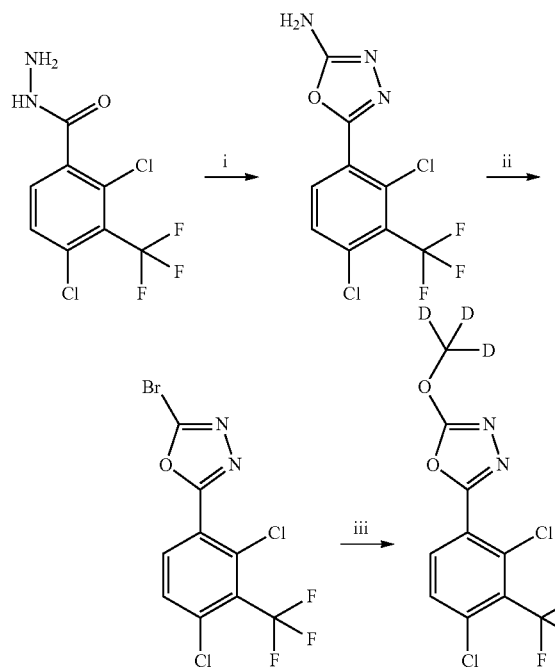

Reagents and conditions: i) Trimethylsilylisothiocyanate, 5N sodium hydroxide, 5% iodine in 10% potassium iodide, ethanol, reflux; ii) copper (II) bromide, tert-butyl nitrite, acetonitrile iii) methanol-d4, sodium hydride, tetrahydrofuran, 0° C. to room temperature.

Step 1:
2,4-dichloro-3-(trifluoromethyl)benzohydrazide (100 mg, 0.37 mmol) and trimethylsilylisothiocyanate (0.05 mL, 0.37 mmol) in ethanol (5 mL) was refluxed for 4 hours. An additional trimethylsilylisothiocyanate (0.05 mL, 0.37 mmol) was added and the reaction was heated at reflux overnight. Sodium hydroxide 5N in water (0.37 mL, 1.83 mmol) was added resulting in the formation of a clear solution. To this 5% iodine in 10% potassium iodide solution was added dropwise with stirring until the colour of iodine persisted (approx. 3.5 mL added). The reaction mixture was refluxed for an additional 2 hours, cooled and poured on to ice-water. The solid was separated via Buchner filtration. The solid was dried under a continuous flow of air. $^1$H NMR showed residual impurities. The crude material was dissolved in the minimum volume of DMSO and chromatographed via reverse phase (eluent 0-100% acetonitrile in water, 0.1% ammonium hydroxide modifier) to 5-[2,4-dichloro-3-(trifluoromethyl)phenyl]-1,3,4-oxadiazol-2-amine (248) (34 mg, 0.11 mmol, 31%) as a white solid.

LCMS: MS m/z 296.0 [M−H]$^-$; $^1$H NMR (700 MHz, DMSO) δ 8.02 (d, J=8.6 Hz, 1H), 7.86 (d, J=8.6 Hz, 1H), 7.45 (s, 2H).

Step 2:
To 5-[2,4-dichloro-3-(trifluoromethyl)phenyl]-1,3,4-oxadiazol-2-amine (100 mg, 0.34 mmol) in acetonitrile (2 mL) was added copper (II) bromide (95 mg, 0.43 mmol). The dark green solution was stirred for 15 min at room temperature. tert-Butyl nitrite (0.09 mL, 0.67 mmol) was added and stirred at room temperature for 2 hours. The crude material was adsorbed on to silica and chromatographed (SNAP KP Sil 12 g, eluent 0-100% dichloromethane in cyclohexane) to give 2-bromo-5-[2,4-dichloro-3-(trifluoromethyl)phenyl]-1,3,4-oxadiazole (75 mg, 0.21 mmol, 62%) as an off-white solid. LCMS: MS m/z no mass ion detected; $^1$H NMR (700 MHz, DMSO) δ 8.16 (d, J=8.6 Hz, 1H), 7.96 (d, J=8.6 Hz, 1H).

Step 3:
To an ice-cooled solution of 2-bromo-5-[2,4-dichloro-3-(trifluoromethyl)phenyl]-1,3,4-oxadiazole (200 mg, 0.55 mmol) in tetrahydrofuran (2 mL) was added sodium hydride 60 wt. % on mineral oil (44 mg, 1.1 mmol). Following complete addition, methanol-d4 (0.02 mL, 0.61 mmol) was added. The reaction was warmed to room temperature and stirred for 1 hour. The contents of the reaction vial were condensed under a continuous flow of air and dissolved in the minimum volume of dimethyl sulfoxide. The crude material was chromatographed via reverse phase (13 g column, eluent 0-100% acetonitrile in water, 0.1% ammonium hydroxide modifier) to give 2-(2,4-dichloro-3-(trifluoromethyl)phenyl)-5-(methoxy-d3)-1,3,4-oxadiazole (241) (54 mg, 0.17 mmol, 31%) as a white solid. LCMS: MS m/z 316.0 [M+H]$^+$; $^1$H NMR (700 MHz, DMSO) δ 8.08 (dd, J=8.6, 0.6 Hz, 1H), 7.89 (dd, J=8.6, 0.7 Hz, 1H).

Generic Route 15—Preparation of 5-(3-(pyrrolidin-1-yl)-4-(trifluoromethyl)phenyl)-1,3,4-oxadiazol-2-ol (259)

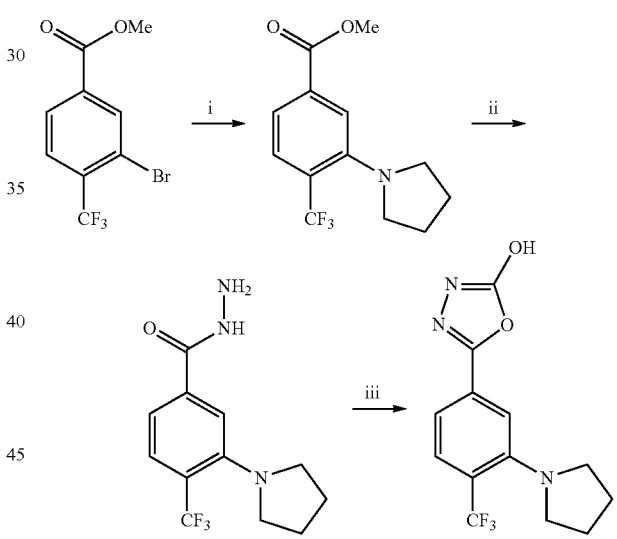

Reagents and conditions: i) Pyrrolidine, cesium carbonate, Pd$_2$(dba)$_3$, (±)-2,2'-bis (diphenylphosphino)-1,1-binaphthalene, toluene; ii) hydrazine monohydrate, ethanol, toluene; iii) triphosgene, N,N-diisopropylethylamine, dichloromethane.

Step 1:
To a solution of methyl 3-bromo-4-(trifluoromethyl)benzoate (0.31 mL, 1.77 mmol) in toluene (10 mL) was added pyrrolidine (0.19 mL, 2.65 mmol) and cesium carbonate (864 mg, 2.65 mmol). The reaction mixture was sealed in a microwave tube and placed under nitrogen. After 10 mins at room temperature. (±)-2,2'-bis(diphenylphosphino)-1,1-binaphthalene (110 mg, 0.18 mmol) and tris(dibenzylideneacetone)dipalladium (0) (81 mg, 0.09 mmol) was added and the reaction stirred for a further 20 mins at r.t. The reaction mixture was then heated to 115° C. and stirred for 18 hours. The reaction mixture was filtered and concentrated under reduced pressure. The reaction mixture was purified by column chromatography (50 g, 0-100% dichloromethane in cyclohexane) to afford methyl 3-pyrrolidin-1-yl-4-(trifluoromethyl)benzoate (600 mg, 2.2 mmol, quantitative) as a colourless oil.

Step 2 & 3:

Following generic route 4, using methyl 3-pyrrolidin-1-yl-4-(trifluoromethyl)benzoate, to give 5-(3-(pyrrolidin-1-yl)-4-(trifluoromethyl)phenyl)-1,3,4-oxadiazol-2-ol (259) (102 mg, 0.34 mmol, 93% yield) as a white solid.

LCMS: MS m/z 300.0 [M+H]⁺; ¹H NMR (700 MHz, CDCl₃) δ 9.15 (br s, 1H), 7.65 (d, J=8.3 Hz, 1H), 7.36 (app s, 1H), 7.25 (d, J=8.3 Hz, 1H), 3.42-3.41 (m, 4H), 2.00-1.98 (m, 2H).

Generic Route 16—Preparation of 5-(2,4-dichloro-3-(trifluoromethyl)phenyl)-N,N-dimethyl-1,3,4-oxadiazol-2-amine (247)

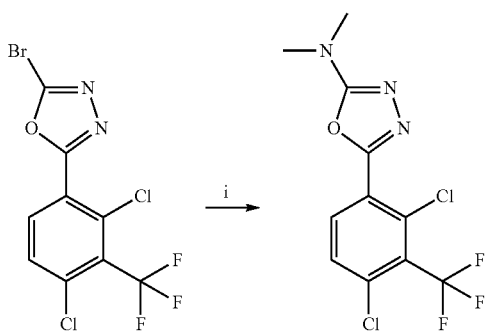

Reagents and conditions: i) Dimethylamine 2N in tetrahydrofuran, tetrahydrofuran.

Step 1:

To a solution of 2-bromo-5-[2,4-dichloro-3-(trifluoromethyl)phenyl]-1,3,4-oxadiazole (40 mg, 0.11 mmol) in tetrahydrofuran (1 mL) was added dimethylamine 2N in tetrahydrofuran (0.11 mL, 0.22 mmol). The reaction was stirred at room temperature for 1 hour. The contents of the reaction vessel were condensed under a continuous flow of air and dissolved in the minimum volume of dimethyl sulfoxide. The crude material was chromatographed via reverse phase (13 g column, eluent 0-100% acetonitrile in water, 0.1% ammonium hydroxide modifier) to give 5-(2,4-dichloro-3-(trifluoromethyl)phenyl)-N,N-dimethyl-1,3,4-oxadiazol-2-amine (247) (33 mg, 0.10 mmol, 92%) as a white solid.

LCMS: MS m/z 326.1 [M+H]⁺; ¹H NMR (700 MHz, DMSO) δ 8.10 (d, J=8.6 Hz, 1H), 7.86 (d, J=8.6 Hz, 1H), 3.08 (s, 6H).

Generic Route 17—Preparation of 5-(2,4-dichloro-3-(trifluoromethyl)phenyl)-3-methyl-1,3,4-oxadiazol-2(3H)-one (245)

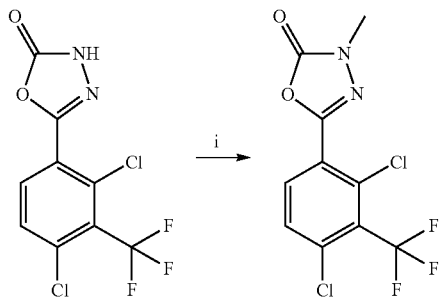

Reagents and conditions: i) Iodomethane, potassium carbonate, N,N-dimethylformamide.

Step 1:

To a solution of 5-[2,4-dichloro-3-(trifluoromethyl)phenyl]-3H-1,3,4-oxadiazol-2-one (100 mg, 0.33 mmol) and potassium carbonate (116 mg, 0.84 mmol) in N,N-dimethylformamide (2 mL) was added iodomethane (0.02 mL, 0.40 mmol). The reaction mixture was stirred at room temperature overnight. The crude material was loaded directly on to a reverse phase cartridge and chromatographed (0-100% acetonitrile in water, 0.1% ammonium hydroxide modifier) to give 5-(2,4-dichloro-3-(trifluoromethyl)phenyl)-3-methyl-1,3,4-oxadiazol-2(3H)-one (245) (85 mg, 0.27 mmol, 81%) as a white solid. LCMS: MS m/z no mass ion; ¹H NMR (700 MHz, DMSO) δ 8.03 (dd, J=8.6, 0.6 Hz, 1H), 7.89 (dd, J=8.6, 0.7 Hz, 1H), 3.45 (s, 3H).

Generic Route 18—Preparation of 4-(4-(1,3,4-oxadiazol-2-yl)-2-(trifluoromethyl)phenyl)morpholine (279)

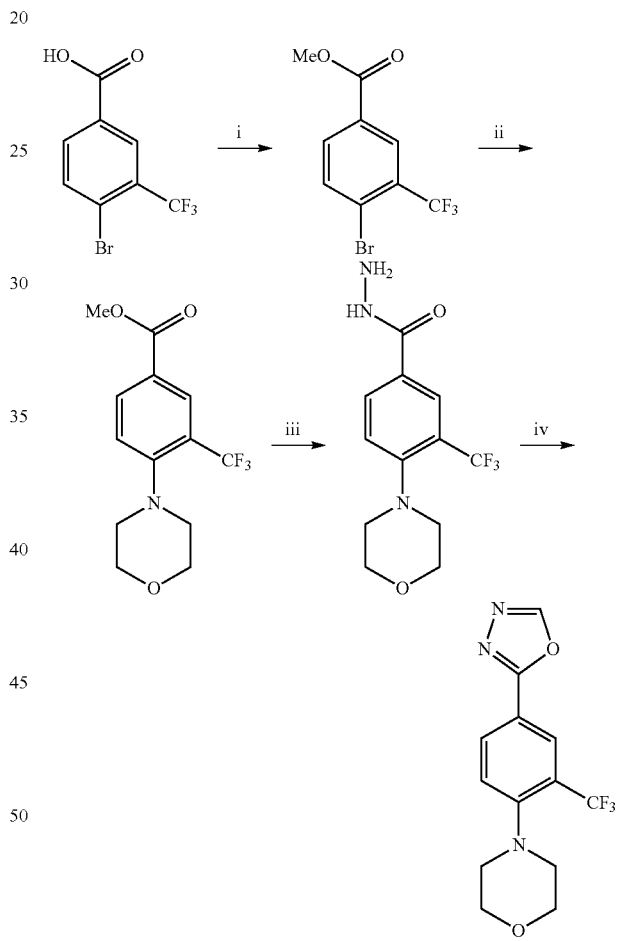

Reagents and conditions: i) Thionyl chloride, methanol, 65° C.; ii) morpholine, Pd₂(dba)₃, (±)-2,2'-bis(diphenylphosphino)-1,1-binaphthalene, cesium carbonate, toluene; iii) hydrazine monohydrate, ethanol, toluene; iv) generic route 5

Step 1:

Thionyl chloride (1.63 mL, 22.3 mmol, 6.0 equiv.) was added dropwise to a solution of 4-bromo-3-(trifluoromethyl) benzoic acid (1000 mg, 3.72 mmol, 1.0 equiv.) in methanol (15 mL) at 0° C. (external). The reaction mixture was heated to reflux for 3 hours, cooled to room temperature and concentrated under reduced pressure. The reaction mixture was carefully diluted with water and saturated aqueous sodium hydrogen carbonate and product extracted with dichloromethane. Organic layer was separated, washed with brine, and then dried over magnesium sulfate, filtered and concentrated to give methyl 4-bromo-3-(trifluoromethyl)benzoate as an off-white solid. The product was carried through without further purification.

Step 2:

To a 20 mL microwave vial was added successively methyl 4-bromo-3-(trifluoromethyl)benzoate (500 mg, 1.77 mmol), (±)-2,2'-bis(diphenylphosphino)-1,1-binaphthalene (110 mg, 0.18 mmol), cesium carbonate (806 mg, 2.47 mmol) and tris(dibenzylideneacetone)dipalladium (0) (81 mg, 0.09 mmol) and the reaction was sealed and purged with nitrogen for 5 minutes. After this toluene (10 mL) and morpholine (0.17 mL, 1.94 mmol) were added and the reaction was stirred under nitrogen at 100° C. for 18 hours. After this time the reaction was filtered through a plug of Celite®, washing with ethyl acetate (100 mL). The organics were washed with water (30 mL) and the mixture was separated. The aqueous was washed with ethyl acetate (2×30 ml). The combined organics were then washed with brine (10 mL), separated and dried (magnesium sulfate) before concentration to dryness. Purification by column chromatography (0-40% ethyl acetate in cyclohexane) gave methyl 4-morpholino-3-(trifluoromethyl)benzoate (264 mg, 0.91 mmol, 52% yield) as an off-white solid.

LCMS: MS m/z 290.1 [M+H]$^+$; $^1$H NMR (700 MHz, CDCl$_3$) δ 8.31 (d, J=2.0 Hz, 1H), 8.17 (dd, J=8.4, 2.0 Hz, 1H), 7.31 (d, J=8.4 Hz, 1H), 3.93 (s, 3H), 3.85 (dd, J=5.4, 3.7 Hz, 4H), 3.04-3.00 (m, 4H).

Step 3:

Hydrazine monohydrate (0.8 mL, 16.4 mmol, 18.6 equiv.) was added to a solution of crude methyl 4-morpholino-3-(trifluoromethyl)benzoate (254 mg, 0.88 mmol) in ethanol (2.5 mL) and toluene (2.5 mL). The mixture was heated to 40° C. for 16 hours, cooled to room temperature and concentrated under reduced pressure. The crude residue was azeotroped with ethanol and toluene to provide crude 4-morpholino-3-(trifluoromethyl)benzohydrazide as an off-white solid, which was used without further purification.

Step 4:

Following generic route 5, using 4-morpholino-3-(trifluoromethyl)benzohydrazide, to give 4-(4-(1,3,4-oxadiazol-2-yl)-2-(trifluoromethyl)phenyl)morpholine (279) (63 mg, 0.21 mmol, 68%) as a white solid.

LCMS: MS m/z 300.1 [M+H]$^+$; $^1$H NMR (600 MHz, CDCl$_3$) δ 8.48 (d, J=2.7 Hz, 1H), 8.34 (d, J=2.1 Hz, 1H), 8.24 (dd, J=8.5, 2.0 Hz, 1H), 7.43 (d, J=8.5 Hz, 1H), 3.90-3.81 (m, 4H), 3.06-3.00 (m, 4H).

Generic Route 19—Preparation of (1-(2-Fluorophenyl)-1H-1,2,3-triazol-4-yl)methanol (273)

Step 1:

Sodium nitrite (155 mg, 2.25 mmol) was added to a solution of 2-fluoroaniline (0.21 g, 1.87 mmol) in trifluoroacetic acid (2 mL, 3.75 mmol) at 0° C. over a period of 30 minutes. The reaction mixture was then allowed to warm to room temperature for 1.5 hours, before the mixture was re-cooled to 0° C. A solution of sodium azide (134 mg, 2.06 mmol) in water (20 mL) was then added dropwise over 30 minutes, the reaction mixture was then allowed to warm to room temperature over 16 hours. The mixture was basified to pH 8-9 by dropwise addition of 5N sodium hydroxide. The reaction mixture was diluted with tert-butanol (2.5 mL), to provide a solution of crude azide, which was used without further purification.

Step 2:

Copper(II)sulfate pentahydrate (93 mg, 0.38 mmol), sodium L-ascorbate (149 mg, 0.75 mmol), water (2.5 mL), then propargyl alcohol (105 mg, 1.88 mmol) were added to the solution from step 1. The reaction vessel was stirred at 50° C. for 16 hours, after this time the reaction was diluted with brine, then extracted with ethyl acetate. The organic phase was dried over anhydrous magnesium sulfate, filtered and concentrated under reduced pressure. Purification via reverse phase chromatography (0-100% acetonitrile in water, 0.1% formic acid modifier), then silica gel chromatography, eluting with 0-70% ethyl acetate in cyclohexane gave [1-(3-cyclopropylphenyl)triazol-4-yl]methanol (273) (11 mg, 0.05 mmol, 3% yield) as a light brown oil.

LCMS: MS m/z 194.1 [M+H]$^+$; $^1$H NMR (400 MHz, MeOD) δ 8.31 (d, J=2.4 Hz, 1H), 7.89-7.77 (m, 1H), 7.63-7.51 (m, 1H), 7.47-7.35 (m, 2H), 4.80-4.78 (m, 2H).

Generic Route 20—Preparation of 1-[3,4-dichloro-5-(trifluoromethyl)phenyl]triazole (309)

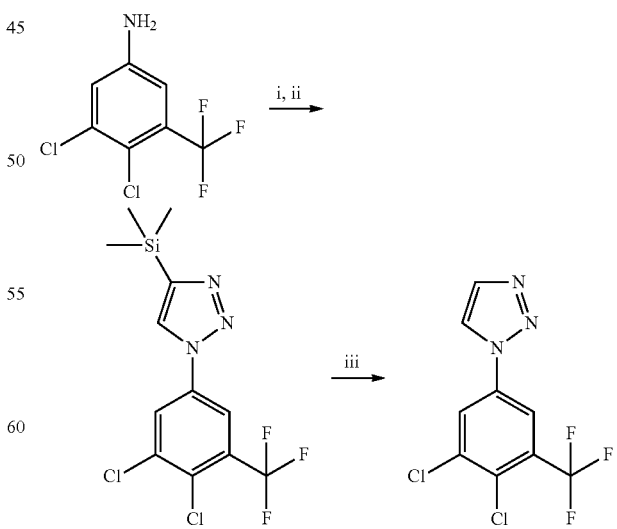

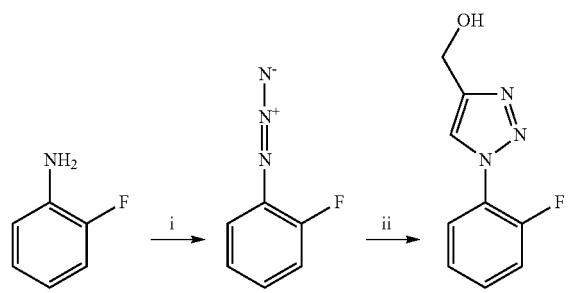

Reagents and conditions: i) Sodium nitrite, trifluoroacetic acid, water, sodium azide; ii) copper(II) sulfate pentahydrate, sodium L-ascorbate, propargyl alcohol, tert-butanol, water.

Reagents and conditions: i) Sodium nitrite, trifluoroacetic acid, water, sodium azide; ii) copper(II)sulfate pentahydrate, sodium L-ascorbate, water, methanol, tert-butanol trimethylsilylacetylene; iii) sodium carbonate, methanol.

Step 1:

Sodium nitrite (144 mg, 2.09 mmol) was added portion-wise to a solution of 3,4-dichloro-5-(trifluoromethyl)aniline (400 mg, 1.74 mmol) in trifluoroacetic acid (3 mL, 3.5 mmol) at 0° C. over a period of 30 minutes. The reaction mixture was allowed to warm to room temperature for 1.5 hours, water (300 µL) was then added and the mixture was re-cooled to 0° C.

Sodium azide (124 mg, 1.91 mmol) was added portion-wise over 30 minutes, the reaction mixture was then allowed to warm to room temperature over 16 hours. The mixture was basified to pH 8-9 by dropwise addition of saturated aqueous sodium bicarbonate, and extracted with dichloromethane.

The organic phase was diluted with 2-methyl-2-propanol (2 mL), then cautiously concentrated under reduced pressure at 25° C., to provide a solution of crude azide, which was used without further purification.

Step 2:

Copper(II)sulfate pentahydrate (87 mg, 0.35 mmol), sodium L-ascorbate (138 mg, 0.70 mmol), water (2 mL), methanol (1 mL), then trimethylsilylacetylene (171 mg, 1.74 mmol) were then added to a solution of crude azide from step 1. The reaction vessel was stirred at 50° C. for 2 hours, after this time the reaction was diluted with brine, extracted with dichloromethane. The organics were separated, dried over sodium sulfate and concentrated under reduced pressure.

Step 3:

The crude residue was then dissolved in methanol (5 mL) and stirred vigorously overnight with sodium carbonate (2 g). The carbonate was cautiously quenched by addition of 2N aqueous hydrochloric acid. Once gas evolution had ceased the organics were then removed under reduced pressure and the aqueous layer was extracted with dichloromethane. The organics were separated, dried over sodium sulfate and concentrated under reduced pressure.

The crude material was purified by reverse phase chromatography (0-100% MeCN in $H_2O$, 0.1% formic acid modifier) to give 1-[3,4-dichloro-5-(trifluoromethyl)phenyl] triazole (309) (158 mg, 0.56 mmol, 32% yield) as a pale yellow solid.

LCMS: MS 282.1 m/z [M+H]$^+$; $^1$H NMR (700 MHz, DMSO) δ 9.07 (s, 1H), 8.65 (d, J=2.4 Hz, 1H), 8.40 (d, J=2.4 Hz, 1H), 8.06 (s, 1H).

Generic Route 21—Preparation of 1-[1-[2,4-dichloro-3-(trifluoromethyl)phenyl]triazol-4-yl]ethanol (310)

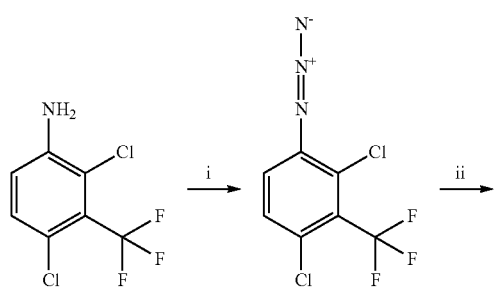

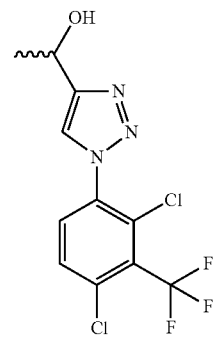

Reagents and conditions: i) Sodium nitrite, water, aq. HCl (37%), sodium azide; ii) copper(II) sulfate pentahydrate, sodium L-ascorbate, water, methanol, 3-butyn-2-ol Step 1:

2,4-dichloro-3-(trifluoromethyl)aniline (150 mg, 0.65 mmol) was dissolved in water (0.5 mL) and acetonitrile (3 mL). Aqueous hydrochloric acid (37%, 7.3 mL, 32.6 mmol) was added and the solution stirred vigorously at room temperature for 10 minutes. Sodium nitrite (90 mg, 1.3 mmol) was added portion-wise and the solution stirred for 1 hour. The solution was cooled to 0° C., sodium azide (85 mg, 1.3 mmol) was added. After 1 hour, the solution was diluted with water then extracted with diethyl ether. 2-Methyl-2-propanol (2 mL) was added and the organic layer was concentrated under reduced pressure to around 2 mL and the resulting solution of azide in was used without further purification.

Step 2:

Sodium L-ascorbate (52 mg, 0.26 mmol), 3-butyn-2-ol (46 mg, 0.65 mmol), copper(II) sulfate pentahydrate (33 mg, 0.13 mmol), methanol (1 mL) and water (2 mL) were then added, and the reaction vessel was stirred at 40° C. overnight. After this time the reaction was diluted with water, extracted with ethyl acetate and the organic phase was washed with water and brine. The organic phase was dried over anhydrous magnesium sulfate, filtered and concentrated under reduced pressure, before purification by column chromatography (0-5% methanol in dichloromethane) gave 1-[1-[2,4-dichloro-3-(trifluoromethyl)phenyl]triazol-4-yl] ethanol (310) (40 mg, 0.12 mmol, 19% yield) as a white solid.

LCMS: MS m/z 326.1 [M+H]$^+$; $^1$H NMR (400 MHz, CDCl$_3$) δ 7.87 (d, J=0.6 Hz, 1H), 7.67-7.61 (m, 2H), 5.20 (q, J=6.6 Hz, 1H), 2.51 (broad s, 1H), 1.68 (d, J=6.6 Hz, 3H).

TABLE 1

Substituted (1-phenyl-1H-1,2,3-triazol-4-yl)methanol

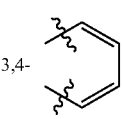

| Compound Number | R group | Generic Route | IUPAC Name |
|---|---|---|---|
| 1 | 4-OEt | 1 | (1-(4-ethoxyphenyl)-1H-1,2,3-triazol-4-yl)methanol |
| 2 | 3-OEt | 1 | (1-(3-ethoxyphenyl)-1H-1,2,3-triazol-4-yl)methanol |
| 3 | 3,4- 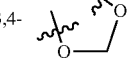 | 1 | (1-(naphthalen-2-yl)-1H-1,2,3-triazol-4-yl)methanol |
| 4 | 3,4- 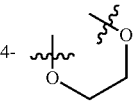 | 1 | (1-(benzo[d][1,3]dioxol-5-yl)-1H-1,2,3-triazol-4-yl)methanol |
| 5 | 3,4-Me | 1 | (1-(3,4-dimethylphenyl)-1H-1,2,3-triazol-4-yl)methanol |
| 6 | 3,4- 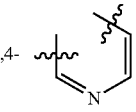 | 1 | (1-(2,3-dihydrobenzo[b][1,4]dioxin-6-yl)-1H-1,2,3-triazol-4-yl)methanol |
| 7 | 2,3-Cl | 1 | (1-(2,3-dichlorophenyl)-1H-1,2,3-triazol-4-yl)methanol |
| 8 | 2,4-Cl | 1 | (1-(2,4-dichlorophenyl)-1H-1,2,3-triazol-4-yl)methanol |
| 9 | 3-CF$_3$, 4-Cl | 1 | (1-(4-chloro-3-(trifluoromethyl)phenyl)-1H-1,2,3-triazol-4-yl)methanol |
| 10 | 3-CN, 4-Cl | 1 | 2-chloro-5-(4-(hydroxymethyl)-1H-1,2,3-triazol-1-yl)benzonitrile |
| 11 | 3,4- 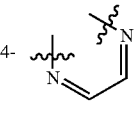 | 2 | (1-(isoquinolin-6-yl)-1H-1,2,3-triazol-4-yl)methanol |
| 12 | 3,4-  | 2 | (1-(quinoxalin-6-yl)-1H-1,2,3-triazol-4-yl)methanol |
| 13 | 3-Cl, 4-CF$_3$ | 2 | (1-(3-chloro-4-(trifluoromethyl)phenyl)-1H-1,2,3-triazol-4-yl)methanol |
| 14 | 3,4- | 2 | (1-(2-ethyl-2H-indazol-6-yl)-1H-1,2,3-triazol-4-yl)methanol |

TABLE 1-continued

Substituted (1-phenyl-1H-1,2,3-triazol-4-yl)methanol

| Compound Number | R group | Generic Route | IUPAC Name |
|---|---|---|---|
| 15 | 3,4- (1-methyl-indazol-6-yl) | 2 | (1-(1-methyl-1H-indazol-6-yl)-1H-1,2,3-triazol-4-yl)methanol |
| 16 | 3,4- (quinolin-7-yl) | 2 | (1-(quinolin-7-yl)-1H-1,2,3-triazol-4-yl)methanol |
| 17 | 3-OCH$_2$C$_6$H$_5$, 4-Cl | — | (1-(3-(benzyloxy)-4-chlorophenyl)-1H-1,2,3-triazol-4-yl)methanol |
| 18 | 3-OCH$_2$$^c$Pr, 4-Cl | — | (1-(4-chloro-3-(cyclopropylmethoxy)phenyl)-1H-1,2,3-triazol-4-yl)methanol |
| 19 | 3,4-Cl | 1 | (1-(3,4-dichlorophenyl)-1H-1,2,3-triazol-4-yl)methanol |
| 20 | 2-Cl | 1 | (1-(2-chlorophenyl)-1H-1,2,3-triazol-4-yl)methanol |
| 21 | 3-Cl | 1 | (1-(3-chlorophenyl)-1H-1,2,3-triazol-4-yl)methanol |
| 22 | H | 1 | (1-phenyl-1H-1,2,3-triazol-4-yl)methanol |
| 23 | 4-CN | 1 | 4-(4-(hydroxymethyl)-1H-1,2,3-triazol-1-yl)benzonitrile |
| 24 | 3-CN | 1 | 3-(4-(hydroxymethyl)-1H-1,2,3-triazol-1-yl)benzonitrile |
| 25 | 2,3- (naphthalen-1-yl) | 1 | (1-(naphthalen-1-yl)-1H-1,2,3-triazol-4-yl)methanol |
| 26 | 2,5-Cl | 1 | (1-(2,5-dichlorophenyl)-1H-1,2,3-triazol-4-yl)methanol |
| 27 | 3,5-Cl | 1 | (1-(3,5-dichlorophenyl)-1H-1,2,3-triazol-4-yl)methanol |
| 28 | 3-Br, 4-Cl | 1 | (1-(3-bromo-4-chlorophenyl)-1H-1,2,3-triazol-4-yl)methanol |
| 29 | 4-Cl | — | (1-(4-chlorophenyl)-1H-1,2,3-triazol-4-yl)methanol |
| 30 | 3-OMe, 4-Cl | — | (1-(4-chloro-3-methoxyphenyl)-1H-1,2,3-triazol-4-yl)methanol |

Compound 1: (1-(4-ethoxyphenyl)-1H-1,2,3-triazol-4-yl)methanol

Following generic route 1, using 4-ethoxyphenylboronic acid, yield=51% (white solid). LCMS: MS m/z 220.2 [M+H]$^+$; $^1$H NMR (400 MHz, DMSO) δ 8.55 (s, 1H), 7.83-7.71 (m, 2H), 7.19-7.01 (m, 2H), 5.27 (t, J=5.6 Hz, 1H), 4.59 (d, J=5.4 Hz, 2H), 4.10 (q, J=7.0 Hz, 2H), 1.35 (t, J=7.0 Hz, 3H).

Compound 2: (1-(3-ethoxyphenyl)-1H-1,2,3-triazol-4-yl)methanol

Following generic route 1, using 3-ethoxyphenylboronic acid, yield=48% (white solid). LCMS: MS m/z 220.2 [M+H]$^+$; $^1$H NMR (600 MHz, DMSO) δ 8.70 (s, 1H), 7.52-7.41 (m, 3H), 7.09-6.95 (m, 1H), 5.31 (t, J=5.6 Hz, 1H), 4.60 (d, J=5.5 Hz, 2H), 4.13 (q, J=7.0 Hz, 2H), 1.36 (t, J=7.0 Hz, 3H).

Compound 3: (1-(naphthalen-2-yl)-1H-1,2,3-triazol-4-yl)methanol

Following generic route 1, using 2-naphthylboronic acid, yield=42% (white solid). LCMS: MS m/z 226.1 [M+H]$^+$; $^1$H NMR (400 MHz, DMSO) δ 8.81 (s, 1H), 8.49 (d, J=2.1 Hz, 1H), 8.18-7.99 (m, 4H), 7.68-7.57 (m, 2H), 5.35 (t, J=5.6 Hz, 1H), 4.72-4.58 (m, 2H).

Compound 4: (1-(benzo[d][1,3]dioxol-5-yl)-1H-1,2,3-triazol-4-yl)methanol

Following generic route 1, using 1,3-benzodioxol-5-ylboronic acid, yield=40% (white solid). LCMS: MS m/z 220.1 [M+H]+; 1H NMR (400 MHz, DMSO) δ 8.55 (s, 1H), 7.49 (d, J=2.2 Hz, 1H), 7.36 (dd, J=8.4, 2.2 Hz, 1H), 7.09 (d, J=8.4 Hz, 1H), 6.14 (s, 2H), 5.28 (t, J=5.6 Hz, 1H), 4.59 (d, J=5.5 Hz, 2H).

Compound 5: (1-(3,4-dimethylphenyl)-1H-1,2,3-triazol-4-yl)methanol

Following generic route 1, using (3,4-dimethylphenyl)boronic acid, yield=32% (white solid). LCMS: MS m/z 204.2 [M+H]+; 1H NMR (400 MHz, DMSO) δ 8.58 (s, 1H), 7.70 (d, J=2.1 Hz, 1H), 7.59 (dd, J=8.1, 2.4 Hz, 1H), 7.33 (d, J=8.2 Hz, 1H), 5.28 (t, J=5.6 Hz, 1H), 4.69-4.51 (m, 2H), 2.32 (s, 3H), 2.28 (s, 3H).

Compound 6: (1-(2,3-dihydrobenzo[b][1,4]dioxin-6-yl)-1H-1,2,3-triazol-4-yl)methanol Following generic route 1, using 2,3-dihydro-1,4-benzodioxin-6-ylboronic acid, yield=27% (white solid). LCMS: MS m/z 234.2 [M+H]+; 1H NMR (600 MHz, DMSO) δ 8.56 (s, 1H), 7.41 (d, J=2.6 Hz, 1H), 7.35 (dd, J=8.7, 2.6 Hz, 1H), 7.04 (d, J=8.7 Hz, 1H), 5.27 (t, J=5.6 Hz, 1H), 4.58 (d, J=5.5 Hz, 2H), 4.34-4.27 (m, 4H).

Compound 7: (1-(2,3-dichlorophenyl)-1H-1,2,3-triazol-4-yl)methanol

Following generic route 1, using (2,3-dichlorophenyl)boronic acid, yield=20% (white solid). LCMS: MS m/z 244.1 [M+H]+; 1H NMR (600 MHz, DMSO) δ 8.46 (s, 1H), 7.92 (dd, J=8.1, 1.5 Hz, 1H), 7.67 (dd, J=8.0, 1.5 Hz, 1H), 7.61 (apparent t, J=8.0 Hz, 1H), 5.38 (t, J=5.6 Hz, 1H), 4.63 (d, J=5.6 Hz, 2H).

Compound 8: (1-(2,4-dichlorophenyl)-1H-1,2,3-triazol-4-yl)methanol

Following generic route 1, using (2,4-dichlorophenyl)boronic acid, yield=17% (white solid). LCMS: MS m/z 244.1 [M+H]+; 1H NMR (600 MHz, DMSO) δ 8.42 (s, 1H), 8.00 (d, J=2.1 Hz, 1H), 7.71 (d, J=8.5 Hz, 1H), 7.68 (dd, J=8.5, 2.2 Hz, 1H), 5.37 (t, J=5.6 Hz, 1H), 4.62 (d, J=5.6 Hz, 2H).

Compound 9: (1-(4-chloro-3-(trifluoromethyl)phenyl)-1H-1,2,3-triazol-4-yl)methanol Following generic route 1, using 4-chloro-3-(trifluoromethyl)phenylboronic acid, yield=6% (white solid). LCMS: MS m/z 278.1 [M+H]+; 1H NMR (600 MHz, DMSO) δ 8.91 (s, 1H), 8.37 (d, J=2.5 Hz, 1H), 8.28 (dd, J=8.7, 2.5 Hz, 1H), 7.98 (d, J=8.7 Hz, 1H), 5.39 (t, J=5.6 Hz, 1H), 4.63 (d, J=5.5 Hz, 2H).

Compound 10: 2-chloro-5-(4-(hydroxymethyl)-1H-1,2,3-triazol-1-yl)benzonitrile Following generic route 1, using (4-chloro-3-cyanophenyl)boronic acid, yield=9% (white solid). LCMS: MS m/z 235.1 [M+H]+; 1H NMR (400 MHz, DMSO) δ 8.81 (s, 1H), 8.61 (d, J=2.6 Hz, 1H), 8.32 (dd, J=8.9, 2.7 Hz, 1H), 7.98 (d, J=8.9 Hz, 1H), 5.41 (t, J=5.5 Hz, 1H), 4.62 (d, J=5.4 Hz, 2H).

Compound 11: (1-(isoquinolin-6-yl)-1H-1,2,3-triazol-4-yl)methanol

Following generic route 2, using isoquinolin-6-amine, yield=15% (white solid). LCMS: MS m/z 227.2 [M+H]+; 1H NMR (600 MHz, DMSO) δ 9.42 (s, 1H), 8.91 (s, 1H), 8.60 (d, J=5.7 Hz, 1H), 8.58 (d, J=1.9 Hz, 1H), 8.38 (d, J=8.9 Hz, 1H), 8.29 (dd, J=8.8, 2.1 Hz, 1H), 7.96 (d, J=5.8 Hz, 1H), 5.43 (t, J=5.3 Hz, 1H), 4.66 (d, J=4.8 Hz, 2H).

Compound 12: (1-(quinoxalin-6-yl)-1H-1,2,3-triazol-4-yl)methanol

Following generic route 2, using quinoxalin-6-amine, yield=10% (orange solid). LCMS: MS m/z 228.1 [M+H]+; 1H NMR (600 MHz, DMSO) δ 9.06 (d, J=1.8 Hz, 1H), 9.04 (s, 1H), 9.03 (d, J=1.8 Hz, 1H), 8.65 (d, J=2.4 Hz, 1H), 8.52 (dd, J=9.1, 2.5 Hz, 1H), 8.33 (d, J=9.1 Hz, 1H), 5.42 (t, J=5.6 Hz, 1H), 4.66 (d, J=5.5 Hz, 2H).

Compound 13: (1-(3-chloro-4-(trifluoromethyl)phenyl)-1H-1,2,3-triazol-4-yl)methanol Following generic route 2, using 3-chloro-4-(trifluoromethyl)aniline, yield=65% (white solid). LCMS: MS m/z 278.1 [M+H]+; 1H NMR (400 MHz, DMSO) δ 8.92 (s, 1H), 8.38 (d, J=1.9 Hz, 1H), 8.16 (dd, J=8.6, 1.4 Hz, 1H), 8.08 (d, J=8.7 Hz, 1H), 5.41 (t, J=5.6 Hz, 1H), 4.63 (d, J=5.4 Hz, 2H).

Compound 14: (1-(2-ethyl-2H-indazol-6-yl)-1H-1,2,3-triazol-4-yl)methanol

Following generic route 2, using 2-ethylindazol-6-amine, yield=49% (white solid). LCMS: MS m/z 244.2 [M+H]+; 1H NMR (600 MHz, DMSO) δ 8.75 (s, 1H), 8.53 (s, 1H), 8.10 (s, 1H), 7.92 (d, J=8.9 Hz, 1H), 7.63 (dd, J=8.9, 1.7 Hz, 1H), 5.35 (t, J=5.6 Hz, 1H), 4.62 (d, J=5.6 Hz, 2H), 4.50 (q, J=7.3 Hz, 2H), 1.53 (t, J=7.3 Hz, 3H).

Compound 15: (1-(1-methyl-1H-indazol-6-yl)-1H-1,2,3-triazol-4-yl)methanol

Following generic route 2, using 1-methylindazol-6-amine, yield=46% (white solid). LCMS: MS m/z 230.2 [M+H]+; 1H NMR (600 MHz, DMSO) δ 8.79 (s, 1H), 8.26 (s, 1H), 8.16 (s, 1H), 7.96 (d, J=8.6 Hz, 1H), 7.72 (dd, J=8.6, 1.6 Hz, 1H), 5.39 (t, J=5.6 Hz, 1H), 4.65 (d, J=5.6 Hz, 2H), 4.12 (s, 3H).

Compound 16: (1-(quinolin-7-yl)-1H-1,2,3-triazol-4-yl)methanol

Following generic route 2, using 7-aminoquinoline, yield=34% (white solid). LCMS: MS m/z 227.2 [M+H]+; 1H NMR (600 MHz, DMSO) δ 9.01 (dd, J=4.2, 1.7 Hz, 1H), 8.98 (s, 1H), 8.53 (d, J=2.0 Hz, 1H), 8.49 (dd, J=8.3, 0.9 Hz, 1H), 8.29-8.20 (m, 2H), 7.63 (dd, J=8.3, 4.2 Hz, 1H), 5.40 (t, J=5.6 Hz, 1H), 4.65 (d, J=5.6 Hz, 2H).

Compound 17: (1-(3-(benzyloxy)-4-chlorophenyl)-1H-1,2,3-triazol-4-yl)methanol

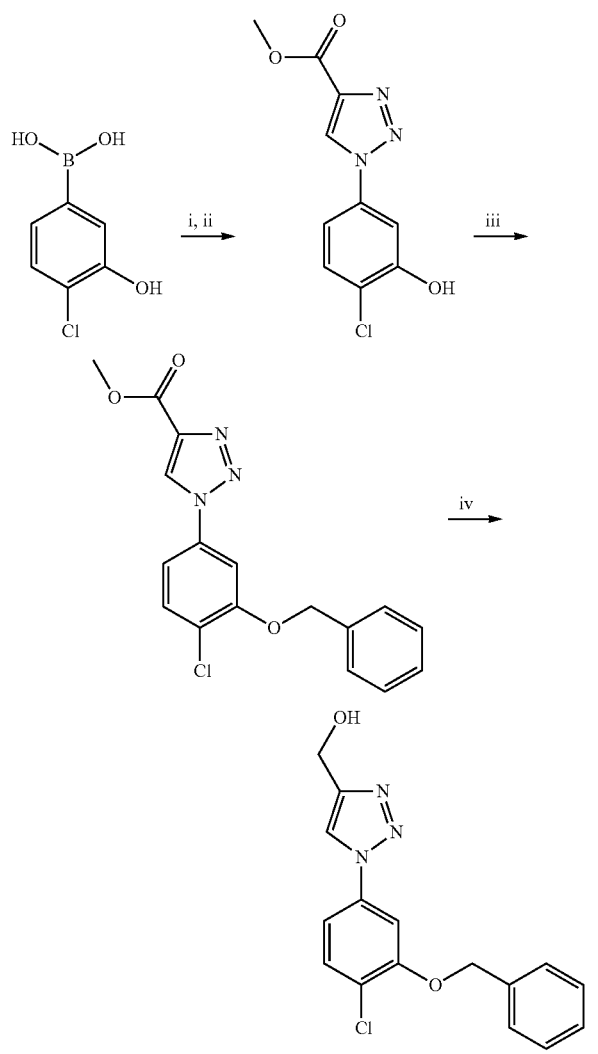

Reagents and conditions: i) Sodium azide, copper (II) sulfate pentahydrate, methanol, 40° C.; (ii) copper (II) sulfate pentahydrate, sodium L-ascorbate, methyl propiolate, isopropanol, water; iii) benzyl bromide, cesium carbonate, acetonitrile; iv.) lithium aluminium hydride, tetrahydrofuran.

Step 1 & 2:

Following generic route 1, using (4-chloro-3-hydroxyphenyl)boronic acid and methyl prop-2-ynoate.

Step 3:

Benzyl bromide (50 μL, 0.41 mmol) was added to a suspension of methyl 1-(4-chloro-3-hydroxy-phenyl)triazole-4-carboxylate (70 mg, 0.28 mmol) and cesium carbonate (180 mg, 0.55 mmol) in acetonitrile (2 mL). The suspension was heated at 60° C. for 4 hours, cooled to room temperature, partitioned between ethyl acetate (20 mL) and brine (5 mL). The organic phase was dried over anhydrous MgSO₄, filtered and concentrated under reduced pressure to give crude methyl 1-(3-(benzyloxy)-4-chlorophenyl)-1H-1,2,3-triazole-4-carboxylate, which was used without further purification.

Step 4:

Lithium aluminium hydride (1 M in tetrahydrofuran, 1.1 mL, 1.1 mmol) was added dropwise to a solution of crude methyl 1-(3-(benzyloxy)-4-chlorophenyl)-1H-1,2,3-triazole-4-carboxylate in anhydrous tetrahydrofuran (2 mL) at 0° C. (external). After 15 minutes, water (0.5 mL), then 2 M NaOH (0.5 mL) were added, and the mixture was warmed to room temperature. MgSO₄ (100 mg) was then added and the mixture was stirred at room temperature for 15 minutes, then filtered and washed with diethyl ether (10 mL). The mother liquors were concentrated under reduced pressure and purified via reverse phase chromatography (0-100% acetonitrile in water, 10 mM ammonium hydroxide modifier). The desired fractions were concentrated under reduced pressure to give (1-(3-(benzyloxy)-4-chlorophenyl)-1H-1,2,3-triazol-4-yl)methanol (4.5 mg, 0.01 mmol, 1%) as a glassy solid. LCMS: MS m/z 316.0 [M+H]⁺; ¹H NMR (600 MHz, MeOD) δ 8.48 (s, 1H), 7.68 (d, J=2.4 Hz, 1H), 7.60-7.57 (m, 1H), 7.53-7.50 (m, 2H), 7.43 (dd, J=8.5, 2.4 Hz, 1H), 7.42-7.38 (m, 2H), 7.35-7.31 (m, 1H), 5.29 (s, 2H), 4.76 (s, 2H).

Compound 18: (1-(4-chloro-3-(cyclopropylmethoxy)phenyl)-1H-1,2,3-triazol-4-yl)methanol

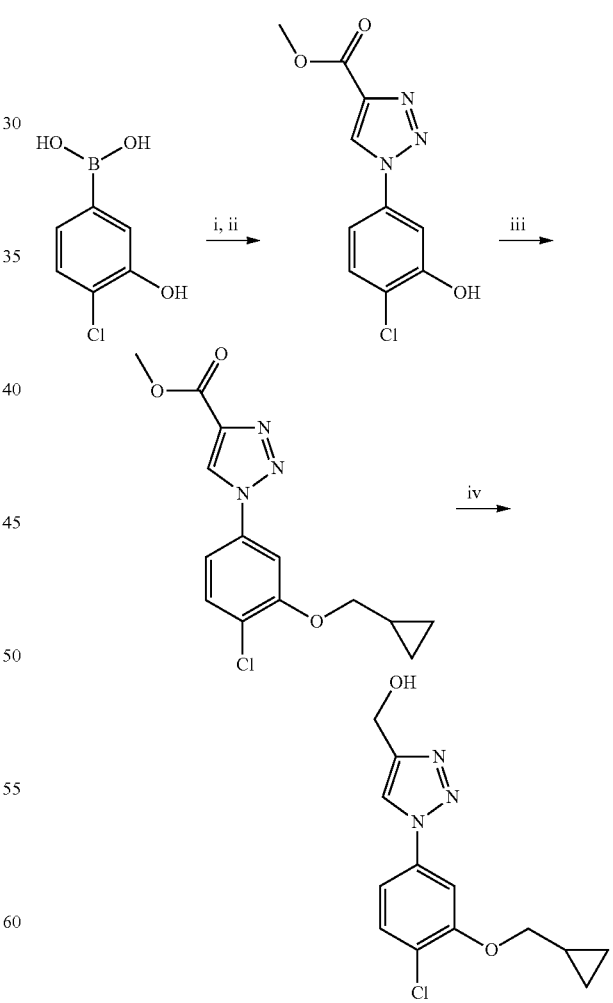

Reagents and conditions: i) Sodium azide, copper (II) sulfate pentahydrate, methanol, 40° C.; (ii) copper (II) sulfate pentahydrate, sodium L-ascorbate, methyl propiolate, isopropanol, water; iii) 1-(bromomethyl)cyclopropane, cesium carbonate, acetonitrile; iv.) lithium aluminium hydride, tetrahydrofuran.

Step 1 & 2:

Following generic route 1, using (4-chloro-3-hydroxyphenyl)boronic acid and methyl prop-2-ynoate.

Step 3:

1-(Bromomethyl)cyclopropane (27 µL, 0.28 mmol) was added to a suspension of methyl 1-(4-chloro-3-hydroxyphenyl)triazole-4-carboxylate (70 mg, 0.28 mmol) and cesium carbonate (180 mg, 0.55 mmol) in acetonitrile (2 mL). The suspension was heated at 60° C. for 4 hours, cooled to room temperature, partitioned between ethyl acetate (20 mL) and brine (5 mL). The organic phase was dried over anhydrous MgSO$_4$, filtered and concentrated under reduced pressure to give crude methyl 1-(4-chloro-3-(cyclopropylmethoxy)phenyl)-1H-1,2,3-triazole-4-carboxylate, which was used without further purification.

Step 4:

Lithium aluminium hydride (1 M in tetrahydrofuran, 1.1 mL, 1.1 mmol) was added dropwise to a solution of crude methyl 1-(4-chloro-3-(cyclopropylmethoxy)phenyl)-1H-1,2,3-triazole-4-carboxylate in anhydrous tetrahydrofuran (2 mL) at 0° C. (external). After 15 minutes, water (0.5 mL), then 2 M NaOH (0.5 mL) were added, and the mixture was warmed to room temperature. Na$_2$SO$_4$ (100 mg) was added and the mixture was stirred at room temperature for 15 minutes, then filtered and washed with diethyl ether (10 mL). The mother liquors were concentrated under reduced pressure and purified via reverse phase chromatography (0-100% acetonitrile in water, 10 mM ammonium hydroxide modifier). The desired fractions were then concentrated under reduced pressure to give (1-(4-chloro-3-(cyclopropylmethoxy)phenyl)-1H-1,2,3-triazol-4-yl)methanol (7 mg, 0.03 mmol, 1%) as a glassy solid. LCMS: MS m/z 280.2 [M+H]$^+$; $^1$H NMR (600 MHz, MeOD) δ 8.49 (s, 1H), 7.57-7.53 (m, 2H), 7.39 (dd, J=8.5 Hz, 2.4 Hz, 1H), 4.75 (s, 2H), 4.03 (d, J=6.8 Hz, 2H), 1.37-1.34 (m, 1H), 0.68-0.65 (m, 2H), 0.45-0.42 (m, 2H).

Compound 19: (1-(3,4-dichlorophenyl)-1H-1,2,3-triazol-4-yl)methanol

Following generic route 1, using (3,4-dichlorophenyl)boronic acid, yield=4% (white solid). LCMS: MS m/z 244.1 [M+H]$^+$; $^1$H NMR (600 MHz, DMSO) δ 8.79 (s, 1H), 8.27 (d, J=2.5 Hz, 1H), 7.97 (dd, J=8.8, 2.5 Hz, 1H), 7.87 (d, J=8.8 Hz, 1H), 5.36 (t, J=5.6 Hz, 1H), 4.61 (d, J=5.5 Hz, 2H). Compound also purchased from a commercial supplier, namely Key Organics.

Compound 20: (1-(2-chlorophenyl)-1H-1,2,3-triazol-4-yl)methanol

Following generic route 1, using (2-chlorophenyl)boronic acid, yield=7% (white solid). LCMS: MS m/z 210.1 [M+H]$^+$; $^1$H NMR (600 MHz, DMSO) δ 8.39 (s, 1H), 7.77 (dd, J=8.0, 1.3 Hz, 1H), 7.62 (dddd, J=26.9, 15.2, 7.6, 1.6 Hz, 3H), 5.32 (t, J=5.6 Hz, 1H), 4.63 (d, J=5.6 Hz, 2H).

Compound 21: (1-(3-chlorophenyl)-1H-1,2,3-triazol-4-yl)methanol

Following generic route 1, using (3-chlorophenyl)boronic acid, yield=27% (white solid). LCMS: MS m/z 210.1 [M+H]$^+$; $^1$H NMR (600 MHz, DMSO) δ 8.77 (s, 1H), 8.05 (apparent t, J=2.0 Hz, 1H), 7.93 (ddd, J=8.1, 2.1, 0.9 Hz, 1H), 7.62 (t, J=8.1 Hz, 1H), 7.55 (ddd, J=8.1, 2.0, 0.9 Hz, 1H), 5.34 (t, J=5.6 Hz, 1H), 4.61 (d, J=5.6 Hz, 2H).

Compound 22: (1-phenyl-1H-1,2,3-triazol-4-yl)methanol

Following generic route 1, using phenylboronic acid, yield=28% (white solid). LCMS: MS m/z 176.1 [M+H]$^+$; $^1$H NMR (400 MHz, DMSO) δ 8.67 (s, 1H), 7.95-7.82 (m, 2H), 7.65-7.53 (m, 2H), 7.53-7.42 (m, 1H), 5.30 (t, J=5.6 Hz, 1H), 4.67-4.54 (m, 2H).

Compound 23: 4-(4-(hydroxymethyl)-1H-1,2,3-triazol-1-yl)benzonitrile

Following generic route 1, using (4-cyanophenyl)boronic acid, yield=13% (white solid). LCMS: MS m/z 201.2 [M+H]$^+$; $^1$H NMR (600 MHz, DMSO) δ 8.85 (s, 1H), 8.21-8.12 (m, 2H), 8.12-8.03 (m, 2H), 5.38 (t, J=5.6 Hz, 1H), 4.63 (d, J=5.5 Hz, 2H).

Compound 24: 3-(4-(hydroxymethyl)-1H-1,2,3-triazol-1-yl)benzonitrile

Following generic route 1, using (3-cyanophenyl)boronic acid, yield=25% (white solid). LCMS: MS m/z 201.1 [M+H]$^+$; $^1$H NMR (600 MHz, DMSO) δ 8.80 (s, 1H), 8.48-8.38 (m, 1H), 8.30 (ddd, J=8.3, 2.2, 0.8 Hz, 1H), 7.95 (dd, J=6.7, 1.1 Hz, 1H), 7.81 (t, J=8.0 Hz, 1H), 5.38 (t, J=5.6 Hz, 1H), 4.63 (d, J=5.5 Hz, 2H).

Compound 25: (1-(naphthalen-1-yl)-1H-1,2,3-triazol-4-yl)methanol

Following generic route 1, using 1-naphthylboronic acid, yield=9% (white solid). LCMS: MS m/z 226.2 [M+H]$^+$; $^1$H NMR (600 MHz, DMSO) δ 8.50 (s, 1H), 8.22-8.17 (m, 1H), 8.13 (d, J=8.0 Hz, 1H), 7.71 (dd, J=6.3, 2.3 Hz, 2H), 7.69-7.65 (m, 1H), 7.63 (ddd, J=8.2, 6.8, 1.3 Hz, 1H), 7.52-7.46 (m, 1H), 5.37 (t, J=5.6 Hz, 1H), 4.68 (d, J=5.5 Hz, 2H).

Compound 26: (1-(2,5-dichlorophenyl)-1H-1,2,3-triazol-4-yl)methanol

Following generic route 1, using (2,5-dichlorophenyl)boronic acid, yield=18% (white solid). LCMS: MS m/z 244.1 [M+H]$^+$; $^1$H NMR (600 MHz, DMSO) δ 8.44 (s, 1H), 7.88 (d, J=2.5 Hz, 1H), 7.81 (d, J=8.7 Hz, 1H), 7.73 (dd, J=8.7, 2.5 Hz, 1H), 5.38 (t, J=5.6 Hz, 1H), 4.62 (d, J=5.6 Hz, 2H).

Compound 27: (1-(3,5-dichlorophenyl)-1H-1,2,3-triazol-4-yl)methanol

Following generic route 1, using (3,5-dichlorophenyl)boronic acid, yield=22% (white solid). LCMS: MS m/z 244.1 [M+H]$^+$; $^1$H NMR (600 MHz, DMSO) δ 8.85 (s, 1H), 8.09 (d, J=1.8 Hz, 2H), 7.76 (t, J=1.8 Hz, 1H), 5.41 (t, J=5.5 Hz, 1H), 4.61 (d, J=5.4 Hz, 2H).

Compound 28: (1-(3-bromo-4-chlorophenyl)-1H-1,2,3-triazol-4-yl)methanol

Following generic route 1, using (3-bromo-4-chlorophenyl)boronic acid, yield=23% (pale yellow solid). LCMS: MS m/z 288.1 [M+H]$^+$; $^1$H NMR (600 MHz, DMSO) δ 8.38 (s, 1H), 8.11 (d, J=2.2 Hz, 1H), 7.71 (dd, J=8.5 Hz, J=2.2 Hz, 1H), 7.65 (d, J=8.5 Hz, 1H), 5.37 (t, J=5.5 Hz, 1H), 4.62 (d, J=5.5 Hz, 2H).

Compound 29: (1-(4-chlorophenyl)-1H-1,2,3-triazol-4-yl)methanol

Compound purchased from a commercial supplier, namely Key Organics.

Compound 30: (1-(4-chloro-3-methoxyphenyl)-1H-1,2,3-triazol-4-yl)methanol

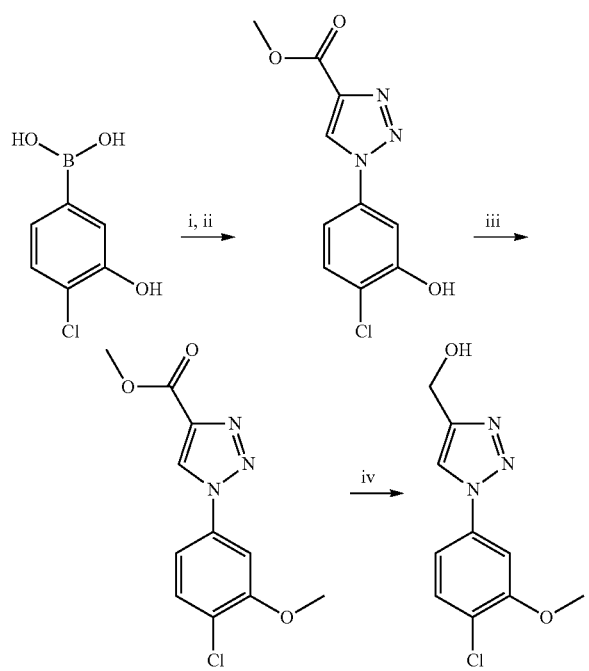

Reagents and conditions: i) Sodium azide, copper (II) sulfate pentahydrate, methanol, 40° C.; (ii) copper (II) sulfate pentahydrate, sodium L-ascorbate, methyl propiolate, isopropanol, water; iii) 1-(Bromomethyl)cyclopropane, cesium carbonate, acetonitrile; iv) Lithium aluminium hydride, tetrahydrofuran.

Step 1 & 2:

Following generic route 1, using (4-chloro-3-hydroxyphenyl)boronic acid and methyl prop-2-ynoate.

Step 3:

Iodomethane (20 µL, 0.39 mmol) was added to a suspension of methyl 1-(4-chloro-3-hydroxy-phenyl)triazole-4-carboxylate (100 mg, 0.39 mmol) and Cesium carbonate (128 mg, 0.39 mmol) in acetonitrile (2 mL) at room temperature, then heated to 40° C. for 3 hours. The mixture was concentrated under reduced pressure, diluted with brine and ethyl acetate, the organic phase was dried over anhydrous $MgSO_4$, filtered and concentrated under reduced pressure to give crude methyl 1-(4-chloro-3-methoxy-phenyl)triazole-4-carboxylate (67 mg, 0.25 mmol, 64%) as an off white solid, which was used without further purification.

Step 4:

Lithium aluminium hydride (1 M in tetrahydrofuran, 1.6 mL, 1.6 mmol) was added dropwise to a solution of crude methyl 1-(4-chloro-3-methoxy-phenyl)triazole-4-carboxylate in anhydrous tetrahydrofuran (2 mL) at 0° C. (external). After 30 minutes, 2 M NaOH (0.5 mL) was added and the mixture was warmed to room temperature. $Na_2SO_4$ (100 mg) was then added and the mixture was stirred at room temperature for 15 minutes, then filtered. The mother liquors were concentrated under reduced pressure, then purified via reverse phase chromatography (0-100% acetonitrile in water, 10 mM ammonium hydroxide modifier). The desired fractions were then concentrated under reduced pressure to give (1-(4-chloro-3-methoxyphenyl)-1H-1,2,3-triazol-4-yl)methanol (11 mg, 0.05 mmol, 2%) as an off-white solid. LCMS: MS m/z 240.2 $[M+H]^+$; $^1H$ NMR (600 MHz, MeOD) δ 7.71 (s, 1H), 6.79 (d, J=2.3 Hz, 1H), 6.75 (d, J=8.5 Hz, 1H), 6.61 (dd, J=8.5 Hz, J=2.4 Hz, 1H), 3.95 (s, 2H), 3.19 (s, 3H).

TABLE 2

Substituted (1-phenyl-1H-1,2,3-triazol-4-yl)methanamine

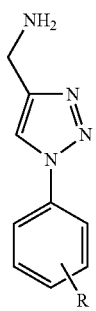

| Compound Number | R group | Generic Route | IUPAC Name |
|---|---|---|---|
| 31 | 3,4-Cl | 1 | (1-(3,4-dichlorophenyl)-1H-1,2,3-triazol-4-yl)methanamine |
| 32 | 2-Cl | 6 | (1-(2-chlorophenyl)-1H-1,2,3-triazol-4-yl)methanamine hydrochloride |
| 33 | 3-Cl | 6 | (1-(3-chlorophenyl)-1H-1,2,3-triazol-4-yl)methanamine hydrochloride |
| 34 | 2,3-Cl | 6 | (1-(2,3-dichlorophenyl)-1H-1,2,3-triazol-4-yl)methanamine hydrochloride |

TABLE 2-continued

Substituted (1-phenyl-1H-1,2,3-triazol-4-yl)methanamine

| Compound Number | R group | Generic Route | IUPAC Name |
|---|---|---|---|
| 35 | 2,5-Cl | 6 | (1-(2,5-dichlorophenyl)-1H-1,2,3-triazol-4-yl)methanamine hydrochloride |
| 36 | 3,5-Cl | 6 | (1-(3,5-dichlorophenyl)-1H-1,2,3-triazol-4-yl)methanamine hydrochloride |
| 37 | 2,3- (fused ring) | 6 | (1-(naphthalen-1-yl)-1H-1,2,3-triazol-4-yl)methanamine hydrochloride |
| 38 | 3-CF$_3$ | 6 | (1-(3-(trifluoromethyl)phenyl)-1H-1,2,3-triazol-4-yl)methanamine hydrochloride |
| 39 | H | — | (1-phenyl-1H-1,2,3-triazol-4-yl)methanamine |

Compound 31: (1-(3,4-dichlorophenyl)-1H-1,2,3-triazol-4-yl)methanamine

Following generic route 1, using (3,4-dichlorophenyl)boronic acid and propargylamine, yield=4% (white solid). LCMS: MS m/z 243.1 [M+H]$^+$; $^1$H NMR (600 MHz, DMSO) δ 8.71 (s, 1H), 8.24 (d, J=2.5 Hz, 1H), 7.94 (dd, J=8.8, 2.5 Hz, 1H), 7.87 (d, J=8.7 Hz, 1H), 3.85 (s, 2H), 1.85 (s, 2H).

Compound 32: (1-(2-chlorophenyl)-1H-1,2,3-triazol-4-yl)methanamine hydrochloride Following generic route 6, using 2-chlorophenylboronic acid, yield=42% (white solid). LCMS: MS m/z 209.1 [M+H]$^+$; $^1$H NMR (600 MHz, DMSO) δ 8.66 (s, 1H), 8.62 (s, 3H), 7.85-7.75 (m, 1H), 7.67 (dtd, J=5.7, 4.1, 1.8 Hz, 2H), 7.64-7.59 (m, 1H), 4.23 (d, J=2.9 Hz, 2H).

Compound 33: (1-(3-chlorophenyl)-1H-1,2,3-triazol-4-yl)methanamine hydrochloride Following generic route 6, using 3-chlorophenylboronic acid, yield=40% (white solid). LCMS: MS m/z 209.1 [M+H]$^+$; $^1$H NMR (600 MHz, DMSO) δ 8.98 (s, 1H), 8.65 (s, 3H), 8.03 (t, J=2.0 Hz, 1H), 7.90 (ddd, J=8.1, 2.1, 0.9 Hz, 1H), 7.67 (t, J=8.1 Hz, 1H), 7.61 (ddd, J=8.1, 1.9, 0.9 Hz, 1H), 4.20 (s, 2H).

Compound 34: (1-(2,3-dichlorophenyl)-1H-1,2,3-triazol-4-yl)methanamine hydrochloride Following generic route 6, using 2,3-dichlorophenylboronic acid, yield=33% (white solid). LCMS: MS m/z 243.1 [M+H]$^+$; $^1$H NMR (600 MHz, DMSO) δ 8.71 (s, 1H), 8.67 (s, 3H), 7.95 (dd, J=7.8, 1.8 Hz, 1H), 7.70-7.58 (m, 2H), 4.23 (s, 2H).

Compound 35: (1-(2,5-dichlorophenyl)-1H-1,2,3-triazol-4-yl)methanamine hydrochloride Following generic route 6, using 2,5-dichlorophenylboronic acid, yield=27% (white solid). LCMS: MS m/z 243.1 [M+H]$^+$; $^1$H NMR (600 MHz, DMSO) δ 8.70 (s, 1H), 8.63 (s, 3H), 7.88 (d, J=2.5 Hz, 1H), 7.85 (d, J=8.7 Hz, 1H), 7.77 (dd, J=8.7, 2.5 Hz, 1H), 4.23 (s, 2H).

Compound 36: (1-(3,5-dichlorophenyl)-1H-1,2,3-triazol-4-yl)methanamine hydrochloride Following generic route 6, using 3,5-dichlorophenylboronic acid, yield=41% (white solid). LCMS: MS m/z 243.1 [M+H]$^+$; $^1$H NMR (600 MHz, DMSO) δ 9.04 (s, 1H), 8.65 (s, 3H), 8.08 (d, J=1.8 Hz, 2H), 7.83 (t, J=1.8 Hz, 1H), 4.20 (s, 2H).

Compound 37: (1-(naphthalen-1-yl)-1H-1,2,3-triazol-4-yl)methanamine hydrochloride Following generic route 6, using naphthalene-1-boronic acid, yield=51% (white solid). LCMS: MS m/z 225.2 [M+H]$^+$; $^1$H NMR (600 MHz, DMSO) δ 8.73 (s, 1H), 8.67 (s, 3H), 8.24 (dd, J=7.4, 1.7 Hz, 1H), 8.16 (d, J=8.1 Hz, 1H), 7.76-7.71 (m, 2H), 7.71-7.67 (m, 1H), 7.64 (ddd, J=8.1, 6.9, 1.2 Hz, 1H), 7.50 (d, J=8.3 Hz, 1H), 4.28 (s, 2H).

Compound 38: (1-(3-(trifluoromethyl)phenyl)-1H-1,2,3-triazol-4-yl)methanamine hydrochloride Following generic route 6, using 3-(trifluoromethyl)phenylboronic acid, yield=48% (white solid). LCMS: MS m/z 243.1 [M+H]$^+$; $^1$H NMR (600 MHz, DMSO) δ 9.08 (s, 1H), 8.67 (s, 3H), 8.25 (d, J=12.0 Hz, 2H), 7.90 (dt, J=15.5, 7.8 Hz, 2H), 4.21 (s, 2H).

Compound 39:
(1-phenyl-1H-1,2,3-triazol-4-yl)methanamine

Compound purchased from a commercial supplier, namely Key Organics.

TABLE 3

Substituted 1-(3,4-dichlorophenyl)-1H-1,2,3-triazole

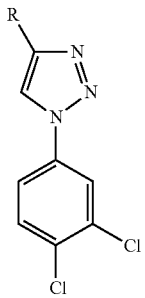

| Compound Number | R group | Generic Route | IUPAC Name |
|---|---|---|---|
| 40 | (HO-CH(CH₃)-) | 1 | 1-(1-(3,4-dichlorophenyl)-1H-1,2,3-triazol-4-yl)ethan-1-ol |
| 41 | (HO-C(CH₃)₂-) | 1 | 2-(1-(3,4-dichlorophenyl)-1H-1,2,3-triazol-4-yl)propan-2-ol |
| 42 | $CH_2NHAc$ | — | N-((1-(3,4-dichlorophenyl)-1H-1,2,3-triazol-4-yl)methyl)acetamide |
| 43 | $CH_2OMe$ | — | 1-(3,4-dichlorophenyl)-4-(methoxymethyl)-1H-1,2,3-triazole |
| 44 | $CH_2N(CH_3)_2$ | — | 1-(1-(3,4-dichlorophenyl)-1H-1,2,3-triazol-4-yl)-N,N-dimethylmethanamine hydrochloride |
| 46 | $CH_2SO_3H$ | — | (1-(3,4-dichlorophenyl)-1H-1,2,3-triazol-4-yl)methanesulfonate |

Compound 40: 1-(1-(3,4-dichlorophenyl)-1H-1,2,3-triazol-4-yl)ethan-1-ol

Following generic route 1, using (3,4-dichlorophenyl)boronic acid and 3-butyn-2-ol, yield=22% (waxy solid). LCMS: MS m/z 258.1 [M+H]⁺; ¹H NMR (400 MHz, MeOD) δ 8.50-8.47 (m, 1H), 8.14 (d, J=2.5 Hz, 1H), 7.85 (dd, J=8.7, 2.5 Hz, 1H), 7.74 (d, J=8.7 Hz, 1H), 5.05 (q, J=6.6 Hz, 1H), 1.59 (d, J=6.6 Hz, 3H).

Compound 41: 2-(1-(3,4-dichlorophenyl)-1H-1,2,3-triazol-4-yl)propan-2-ol

Following generic route 1, using (3,4-dichlorophenyl)boronic acid and 2-methyl-3-butyn-2-ol, yield=21% (waxy solid). LCMS: MS m/z 272.1 [M+H]⁺; ¹H NMR (600 MHz, MeOD) δ 8.45 (s, 1H), 8.14 (d, J=2.5 Hz, 1H), 7.85 (dd, J=8.7, 2.5 Hz, 1H), 7.74 (d, J=8.7 Hz, 1H), 1.64 (s, 6H).

Compound 42: N-((1-(3,4-dichlorophenyl)-1H-1,2,3-triazol-4-yl)methyl)acetamide

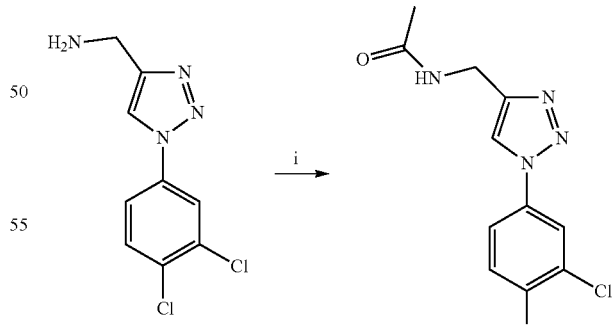

Reagents and conditions: i) Acetyl chloride, trimethylamine, dichloromethane, 0° C.

To a solution of (1-(3,4-dichlorophenyl)-1H-1,2,3-triazol-4-yl)methanamine (100 mg, 0.41 mmol) in dichloromethane (10 mL) was added triethylamine (0.06 mL, 0.45 mmol). The reaction mixture was cooled in an ice-water bath before the dropwise addition of acetyl chloride (0.03 mL, 0.45 mmol). The reaction was allowed to warm to room temperature and stirred for 1 hour. After this time methanol was added and the reaction mixture was allowed to stir for a further 10 minutes. The crude reaction mixture was adsorbed on to silica. Purification by column chromatography (1-100% ethyl acetate in cyclohexane) gave N-((1-(3,4-dichlorophenyl)-1H-1,2,3-triazol-4-yl)methyl)acetamide (95 mg, 0.33 mmol, 81%) as a white solid. LCMS: MS m/z 285.1 [M+H]+; $^1$H NMR (600 MHz, DMSO) δ 8.74 (s, 1H), 8.42 (t, J=5.2 Hz, 1H), 8.27 (d, J=2.5 Hz, 1H), 7.96 (dd, J=8.8, 2.6 Hz, 1H), 7.87 (d, J=8.8 Hz, 1H), 4.37 (d, J=5.7 Hz, 2H), 1.86 (s, 3H).

Compound 43: 1-(3,4-dichlorophenyl)-4-(methoxymethyl)-1H-1,2,3-triazole

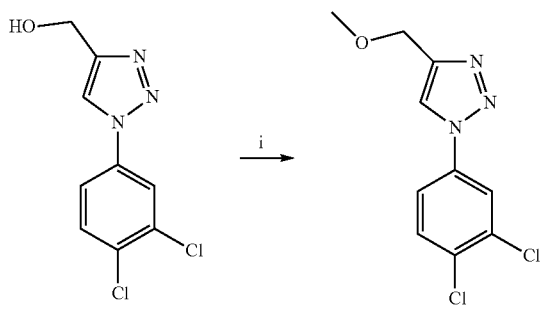

Reagents and conditions: i) Iodomethane, sodium hydride 60% wt. on mineral oil, tetrahydrofuran, 0° C.

To a solution of (1-(3,4-dichlorophenyl)-1H-1,2,3-triazol-4-yl)methanol (100 mg, 0.41 mmol) in tetrahydrofuran (10 mL) was added sodium hydride (18 mg, 0.45 mmol). The reaction mixture was stirred for 10 minutes before iodomethane (0.03 mL, 0.49 mmol) was added. The reaction was stirred at room temperature for 2 hours. After this time the reaction was quenched with water (20 mL) and extracted with dichloromethane (20 mL). The organics were separated, washed with water and brine, dried over anhydrous MgSO$_4$, filtered and adsorbed on to silica. Purification by column chromatography (1-100% ethyl acetate in cyclohexane) gave 1-(3,4-dichlorophenyl)-4-(methoxymethyl)-1H-1,2,3-triazole (85 mg, 0.33 mmol, 80%) as a white solid. LCMS: MS m/z 258.1 [M+H]+; $^1$H NMR (400 MHz, DMSO) δ 8.92 (s, 1H), 8.28 (d, J=2.5 Hz, 1H), 7.97 (dd, J=8.8, 2.5 Hz, 1H), 7.88 (d, J=8.8 Hz, 1H), 4.55 (s, 2H), 3.32 (s, 3H).

Compound 44: 1-(1-(3,4-dichlorophenyl)-1H-1,2,3-triazol-4-yl)-N,N-dimethylmethanamine hydrochloride

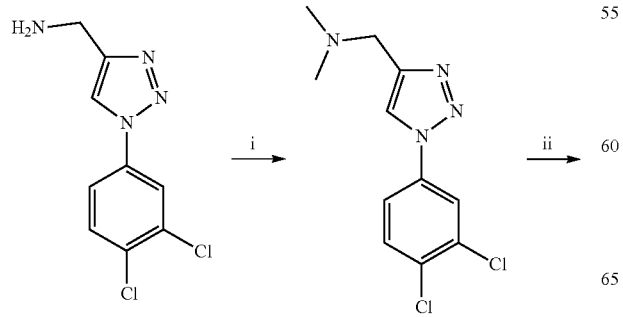

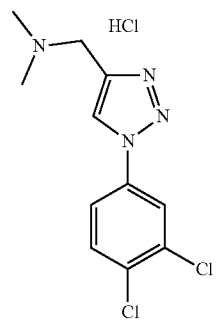

Reagents and conditions: i) Formic acid, formaldehyde, acetonitrile, 40° C. ii) 7N HCl in 1,4-dioxane, ethyl acetate.

To a solution of (1-(3,4-dichlorophenyl)-1H-1,2,3-triazol-4-yl)methanamine (50 mg, 0.21 mmol) in acetonitrile (5 mL) was added formic acid (0.04 mL, 1.03 mmol) and formaldehyde solution (0.1 mL, 0.45 mmol). The reaction mixture was warmed to 40° C. and allowed to stir for 2 hours. After this time the reaction mixture was added to aq. sat. NaHCO$_3$(20 mL). The aqueous phase was extracted with dichloromethane. The organics were washed with water and brine, dried over anhydrous MgSO$_4$, filtered and adsorbed on to silica. Purification by column chromatography (0-25% ammonia methanol solution in dichloromethane) gave 1-[1-(3,4-dichlorophenyl)triazol-4-yl]-N,N-dimethyl-methanamine as a colourless gum. The gum was dissolved in ethyl acetate (2 mL) and treated with 7 N HCl in dioxane (0.32 mmol). The resulting precipitate was isolated via buchner filtration to give 1-(1-(3,4-dichlorophenyl)-1H-1,2,3-triazol-4-yl)-N,N-dimethylmethanamine hydrochloride (29 mg, 0.094 mmol, 46%) as a white solid. LCMS: MS m/z 271.1 [M+H]+; $^1$H NMR (600 MHz, DMSO) δ 8.83 (s, 1H), 8.28 (d, J=2.5 Hz, 1H), 8.16 (s, 1H), 7.98 (dd, J=8.8, 2.5 Hz, 1H), 7.87 (d, J=8.8 Hz, 1H), 3.63 (s, 2H), 2.23 (s, 6H).

Compound 46: (1-(3,4-dichlorophenyl)-1H-1,2,3-triazol-4-yl)methanesulfonate

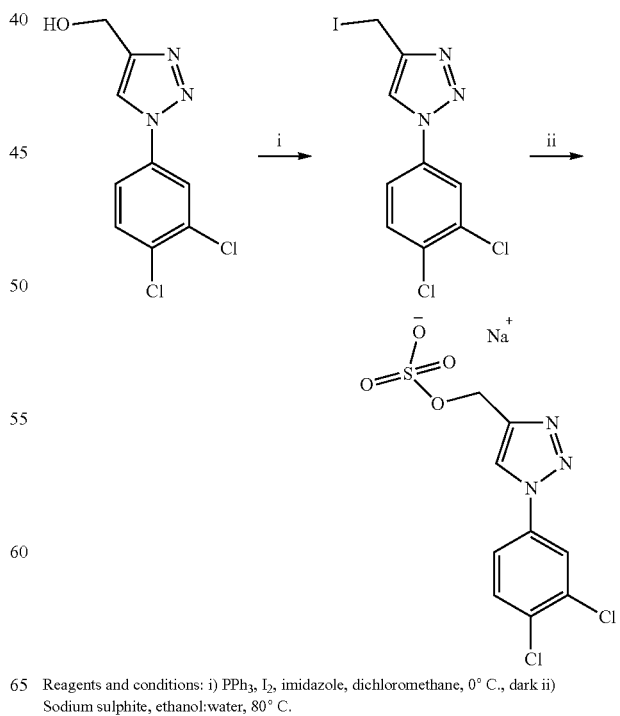

Reagents and conditions: i) PPh$_3$, I$_2$, imidazole, dichloromethane, 0° C., dark ii) Sodium sulphite, ethanol:water, 80° C.

Step 1:

To a cooled (0° C.) solution of triphenylphosphine (322 mg, 1.23 mmol, 1.2 eq.), iodine (312 mg, 1.23 mmol, 1.2 eq.) and imidazole (84 mg, 1.23 mmol, 1.2 eq.) in dichloromethane (5 mL) was added [1-(3,4-dichlorophenyl)triazol-4-yl]methanol (250 mg, 1.02 mmol). The solution was stirred at 0° C. for a further 6 hours in the dark. The solution was diluted in dichloromethane (30 mL), washed with aq. sat. sodium metabisulfate (20 mL), water and brine. The organic phase was dried over anhydrous MgSO$_4$ (avoiding light as much as possible), filtered and concentrated under reduced pressure. The residue was purified by column chromatography (1-20% ethyl acetate in cyclohexane) to give 1-(3,4-dichlorophenyl)-4-(iodomethyl)triazole (288 mg, 0.81 mmol, 79%) as a white solid. LCMS: MS m/z 353.9 [M+H]$^+$; $^1$H NMR (600 MHz, CDCl$_3$) δ 7.99 (s, 1H), 7.89 (dd, J=2.1, 0.5 Hz, 1H), 7.63-7.59 (m, 2H), 4.54 (s, 2H).

Step 2:

A suspension of 1-(3,4-dichlorophenyl)-4-(iodomethyl)triazole (197 mg, 0.56 mmol) and sodium sulfite (281 mg, 2.23 mmol) in ethanol (2 mL) and water (1 mL) was sealed and heated to 80° C. for 1 hour. The reaction was cooled to room temperature and the suspension was diluted with ethyl acetate and the solvent removed under reduced pressure. The material was then dissolved in dimethyl sulfoxide and purified by reverse phase chromatography (Water 0.1% Formic and acetonitrile 0.1% formic from 0-100% acetonitrile) to give (1-(3,4-dichlorophenyl)-1H-1,2,3-triazol-4-yl)methanesulfonate (119 mg, 0.36 mmol, 65%) as a white crystalline solid. LCMS: MS m/z 308.0 [M+H]$^+$; $^1$H NMR (600 MHz, DMSO) δ 8.74 (s, 1H), 8.31 (d, J=2.4 Hz, 1H), 8.00 (dd, J=8.8, 2.5 Hz, 1H), 7.85 (d, J=8.8 Hz, 1H), 3.88 (d, J=3.7 Hz, 2H).

TABLE 4

(1-(3,4-dichlorophenyl)-1H-1,2,4-triazol-3-yl)methanol

| Compound Number | R group | IUPAC Name |
|---|---|---|
| 47 | OH | (1-(3,4-dichlorophenyl)-1H-1,2,4-triazol-3-yl)methanol |

Compound 47: (1-(3,4-dichlorophenyl)-1H-1,2,4-triazol-3-yl)methanol

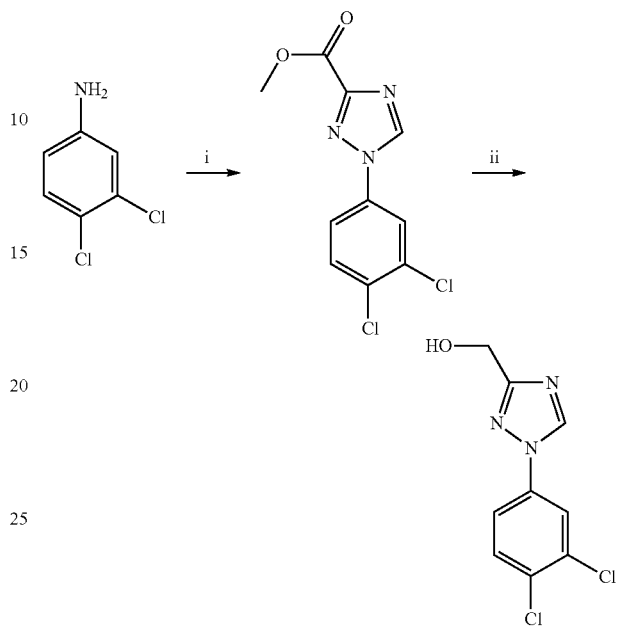

Reagents and conditions: i) 37% hydrochloric acid, sodium nitrite, water, 0° C.; ii) Methyl 2-isocyanoacetate, sodium acetate, methanol:water, 0° C.; iii) Lithium aluminum hydride, tetrahydrofuran, 0° C.

Step 1: A 10 mL microwave vial was charged with 3,4-dichloroaniline (500 mg, 3.09 mmol) and diluted with >37% hydrochloric acid (5.22 mL, 5.22 mmol) to give a suspension. The solution was cooled in an ice-water bath for 5 minutes before sodium nitrite (212 mg, 3.09 mmol) and water (0.87 mL, 48.3 mmol) was added. The vial was capped and the reaction was stirred at 0° C. for 20 minutes. To a cooled (0° C.) solution of methyl 2-isocyanoacetate (0.22 mL, 2.47 mmol) in methanol (13 mL, 3.09 mmol) and water (0.87 mL, 48.3 mmol) was added sodium acetate (1620 mg, 19.8 mmol). The resulting solution was added dropwise to the diazonium solution and the reaction mixture was stirred for an hour at 0° C. The reaction was allowed to warm to room temperature and stirred overnight.

The reaction was diluted with water, and extracted with ethyl acetate. The organics were washed with water and brine. The organics were dried over anhydrous MgSO$_4$, filtered and adsorbed on to silica. Purification by column chromatography (1-100% ethyl acetate in cyclohexane) gave methyl 1-(3,4-dichlorophenyl)-1,2,4-triazole-3-carboxylate (144 mg, 0.53 mmol, 17%) as a white solid. LCMS: MS m/z 272.1 [M+H]$^+$; $^1$H NMR (600 MHz, DMSO) δ 8.41 (s, 1H), 8.04 (d, J=2.4 Hz, 1H), 7.84 (t, J=5.3 Hz, 1H), 7.64 (dd, J=8.6, 2.4 Hz, 1H), 3.82 (s, 3H).

Step 2:

To a solution of methyl 1-(3,4-dichlorophenyl)-1,2,4-triazole-3-carboxylate (144 mg, 0.53 mmol) in tetrahydrofuran (5 mL) cooled in an ice-water bath, was added lithium aluminium hydride (20 mg, 0.53 mmol) portion wise. After complete addition the reaction mixture was allowed to warm to room temperature. The reaction was stirred at room temperature for 1 hour before cooling in an ice-water bath and quenching with water dropwise. Further water (10 mL) was added and the aqueous solution was extracted with ethyl acetate. The organics were washed with water and brine, dried over anhydrous MgSO$_4$, filtered and adsorbed on to silica. Purification by column chromatography (0-10% methanol in dichloromethane) gave [1-(3,4-dichlorophenyl)-1,2,4-triazol-3-yl]methanol (82 mg, 0.34 mmol, 64%) as a white solid. LCMS: MS m/z 244.1 [M+H]$^+$; $^1$H NMR (400 MHz, DMSO) δ 9.30 (s, 1H), 8.24-8.12 (m, 1H), 7.93-7.77 (m, 2H), 5.42 (t, J=6.0 Hz, 1H), 4.53 (d, J=6.0 Hz, 2H).

TABLE 5

5-(3-ethoxyphenyl)-1,3,4-thiadiazol-2-amine

| Compound Number | R group | IUPAC Name |
|---|---|---|
| 48 | NH$_2$ | 5-(3-ethoxyphenyl)-1,3,4-thiadiazol-2-amine |

Compound 48:
5-(3-ethoxyphenyl)-1,3,4-thiadiazol-2-amine

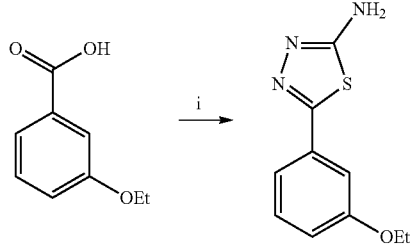

Reagents and conditions: i) Phosphorous(V) oxychloride, thiosemicarbazide.

Phosphorus(V) oxychloride (5 mL, 5.0 mmol) was cautiously added to a stirring mixture of 3-ethoxybenzoic acid (831 mg, 5.0 mmol) and thiosemicarbazide (456 mg, 5.0 mmol) at room temperature. The mixture was heated to 75° C. for 30 minutes, cooled to 0° C., then water (5 mL) was cautiously added dropwise. The reaction mixture was then heated to reflux for 4 hours. After cooling to room temperature, the mixture was basified to pH 8 by dropwise addition of 50% aqueous NaOH solution under rapid stirring. The precipitate was filtered and recrystallized from ethanol, then dried under reduced pressure to give 5-(3-ethoxyphenyl)-1,3,4-thiadiazol-2-amine (75 mg, 0.34 mmol, 7%) as an off-white solid. LCMS: MS m/z 222.2 [M+H]$^+$; $^1$H NMR (600 MHz, DMSO) δ 7.44 (s, 2H), 7.38-7.34 (m, 1H), 7.29-7.25 (m, 2H), 7.01-6.97 (m, 1H), 4.08 (q, J=7.0 Hz, 2H), 1.34 (t, J=7.0 Hz, 3H).

TABLE 6

Substituted 4-phenyl-2H-1,2,3-triazole

| Compound Number | R group | IUPAC Name |
|---|---|---|
| 49 | 3,4-CF$_3$ | 4-(3,4-bis(trifluoromethyl)phenyl)-1H-1,2,3-triazole |
| 50 | 3-CF$_3$, 4-Cl | 4-(4-chloro-3-(trifluoromethyl)phenyl)-1H-1,2,3-triazole |

Compound 49: 4-(3,4-bis(trifluoromethyl)phenyl)-1H-1,2,3-triazole

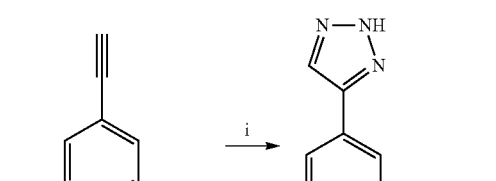

Reagents and conditions: i) Copper (I) iodide, azotrimethylsilane, N,N-dimethylformamide:methanol, 100° C.

Copper (I) iodide (4.8 mg, 0.03 mmol) was dissolved in anhydrous N,N-dimethylformamide (1.5 mL) and anhydrous methanol (0.75 mL) under an atmosphere of nitrogen. 4-ethynyl-1,2-bis(trifluoromethyl)benzene (120 mg, 0.5 mmol) was added to this dropwise, followed by azidotrimethylsilane (0.1 mL, 0.76 mmol). This was heated to 100° C. for 15 hours. The crude pale green solution was diluted with methanol (20 mL) and ethyl acetate (20 mL) then concentrated under reduced pressure. Purification by column chromatography (0-50% ethyl acetate in cyclohexane) gave a residue which contained N,N-dimethylformamide, therefore it was re-dissolved in ethyl acetate (30 mL) then washed with 5% LiCl solution (2×20 mL) then with brine (20 mL) and dried over MgSO$_4$ and concentrated under reduced pressure to give 4-(3,4-bis(trifluoromethyl)phenyl)-1H-1,2,3-triazole (73 mg, 0.26 mmol, 52%) as a white solid. LCMS: MS m/z 282.1 [M+H]$^+$; $^1$H NMR (600 MHz, MeOD) δ 8.42 (s, 1H), 8.41 (s, 1H), 8.26 (d, J=8.2 Hz, 1H), 8.00 (d, J=8.2 Hz, 1H).

Compound 50: 4-(4-chloro-3-(trifluoromethyl)phenyl)-1H-1,2,3-triazole

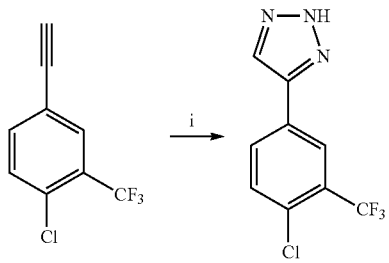

Reagents and conditions: i) Copper (I) iodide, azotrimethylsilane, N,N-dimethylformamide:methanol, 100° C.

Copper (I) iodide (23 mg, 0.12 mmol) was dissolved in anhydrous N,N-dimethylformamide (6 mL) and anhydrous methanol (3 mL) under an atmosphere of nitrogen. 1-chloro-4-ethynyl-2-(trifluoromethyl)benzene (492 mg, 2.4 mmol) was added to this dropwise, followed by azidotrimethylsilane (0.48 mL, 3.6 mmol). This was heated to 100° C. for 15 hours. The crude pale green solution was diluted with methanol (20 mL) and ethyl acetate (20 mL) then concentrated under reduced pressure Purification by column chromatography (0-50% ethyl acetate in cyclohexane) gave a residue which contained N,N-dimethylformamide, therefore it was re-dissolved in ethyl acetate (30 mL) then washed with 5% LiCl solution (2×20 mL) then with brine (20 mL) and dried over MgSO$_4$ and concentrated under reduced pressure to give 4-(4-chloro-3-(trifluoromethyl)phenyl)-1H-1,2,3-triazole (480 mg, 1.94 mmol, 81% yield) as an off white solid. LCMS: MS m/z 248.0 [M+H]$^+$; $^1$H NMR (600 MHz, MeOD) δ 8.31 (s, 1H), 8.26 (s, 1H), 8.07 (d, J=7.8 Hz, 1H), 7.69 (dd, J=8.3, 3.6 Hz, 1H).

TABLE 7

Substituted 3-phenyl-1H-pyrazole

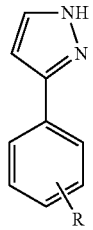

| Compound Number | R group | Generic Route | IUPAC Name |
|---|---|---|---|
| 51 | 3-CF3, 4-Cl | 7 | 3-(4-chloro-3-(trifluoromethyl)phenyl)-1H-pyrazole |
| 52 | 2-OH, 3,5-F | 7 | 2,4-difluoro-6-(1H-pyrazol-3-yl)phenol |
| 53 | 3,4-F | 7 | 3-(3,4-difluorophenyl)-1H-pyrazole |
| 54 | 3-Cl | 7 | 3-(3-chlorophenyl)-1H-pyrazole |
| 55 | 3,4-Cl | 7 | 3-(3,4-dichlorophenyl)-1H-pyrazole |
| 56 | 3,5-F | 7 | 3-(3,5-difluorophenyl)-1H-pyrazole |
| 57 | 2-OH, 4-OMe | 7 | 5-methoxy-2-(1H-pyrazol-3-yl)phenol |

Compound 51: 3-(4-chloro-3-(trifluoromethyl)phenyl)-1H-pyrazole

Following generic route 7, using 4'-chloro-3'-(trifluoromethyl)acetophenone, yield=94% (off-white solid). LCMS: MS m/z 247.1 [M+H]$^+$; $^1$H NMR (600 MHz, CDCl$_3$) δ 10.36 (br s, 1H), 8.14 (d, J=1.9 Hz, 1H), 7.91 (dd, J=8.4, 1.9 Hz, 1H), 7.66 (d, J=2.4 Hz, 1H), 7.55 (d, J=8.4 Hz, 1H), 6.67 (d, J=2.4 Hz, 1H).

Compound 52: 2,4-difluoro-6-(1H-pyrazol-3-yl)phenol

Following generic route 7, using 3',5'-difluoro-2'-hydroxyacetophenone, yield=42% (white solid). LCMS: MS m/z 197.1 [M+H]$^+$; $^1$H NMR (600 MHz, CDCl$_3$) δ 10.85 (br s, 1H), 10.37 (br s, 1H), 7.70 (d, J=2.6 Hz, 1H), 7.10 (ddd, J=9.2, 3.0, 1.9 Hz, 1H), 6.84 (ddd, J=10.7, 8.0, 3.0 Hz, 1H), 6.69 (d, J=2.6 Hz, 1H).

Compound 53: 3-(3,4-difluorophenyl)-1H-pyrazole

Following generic route 7, using 3',4'-difluoroacetophenone, yield=64% (white solid). LCMS: MS m/z 181.1 [M+H]$^+$; $^1$H NMR (600 MHz, CDCl$_3$) δ 10.27 (br s, 1H), 7.64-7.60 (m, 2H), 7.51 (m, 1H), 7.20 (dt, J=10.0, 8.4 Hz, 1H), 6.59 (d, J=2.4 Hz, 1H).

Compound 54: 3-(3-chlorophenyl)-1H-pyrazole

Following generic route 7, using 3'-chloroacetophenone, yield=99% (white solid). LCMS: MS m/z 179.1 [M+H]$^+$; $^1$H NMR (600 MHz, CDCl$_3$) δ 10.29 (br s, 1H), 7.79 (m, 1H), 7.67 (apparent dt, J=7.7, 1.4 Hz, 1H), 7.64 (d, J=2.2 Hz, 1H), 7.35 (apparent t, J=7.8 Hz, 1H), 7.30 (ddd, J=8.0, 2.2, 1.2 Hz, 1H), 6.64 (d, J=2.3 Hz, 1H).

Compound 55: 3-(3,4-dichlorophenyl)-1H-pyrazole

Following generic route 7, using 3',4'-dichloroacetophenone, yield=97% (white solid). LCMS: MS m/z 213.1 [M+H]$^+$; $^1$H NMR (600 MHz, CDCl$_3$) δ 10.48 (br s, 1H), 7.90 (d, J=1.9 Hz, 1H), 7.64-7.62 (m, 2H), 7.48 (d, J=8.3 Hz, 1H), 6.63 (d, J=2.4 Hz, 1H).

Compound 56: 3-(3,5-difluorophenyl)-1H-pyrazole

Following generic route 7, using 3,5-difluoroacetophenone, yield=63% (white solid). LCMS: MS m/z 181.1 [M+H]$^+$; $^1$H NMR (600 MHz, CDCl$_3$) δ 10.30 (br s, 1H), 7.64 (d, J=2.4 Hz, 1H), 7.35-7.31 (m, 2H), 6.77 (apparent tt, J=8.9, 2.3 Hz, 1H), 6.63 (d, J=2.4 Hz, 1H).

Compound 57: 5-methoxy-2-(1H-pyrazol-3-yl)phenol

Following generic route 7, using 2'-hydroxy-4'-methoxyacetophenone, yield=69% (white solid). LCMS: MS m/z 191.2 [M+H]$^+$; $^1$H NMR (600 MHz, DMSO) δ 11.15 (s, 1H), 7.88 (s, 1H), 7.63 (d, J=8.21 Hz, 1H), 6.77 (s, 1H), 6.40-6.56 (m, 2H), 3.74 (s, 3H).

TABLE 8

Substituted 1-(4-chloro-3-(trifluoromethyl)phenyl)-1H-1,2,3-triazole

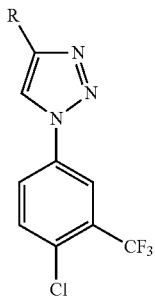

| Compound Number | R group | IUPAC Name |
|---|---|---|
| 58 | COOH | 1-(4-chloro-3-(trifluoromethyl)phenyl)-1H-1,2,3-triazole-4-carboxylic acid |
| 59 | CN | 1-(4-chloro-3-(trifluoromethyl)phenyl)-1H-1,2,3-triazole-4-carbonitrile |

Compound 58: 1-(4-chloro-3-(trifluoromethyl)phenyl)-1H-1,2,3-triazole-4-carboxylic acid

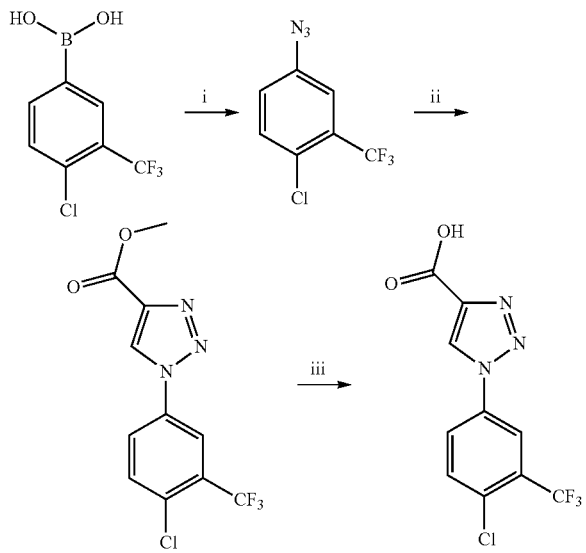

Reagents and conditions: i) Sodium azide, copper (II) sulfate pentahydrate, methanol, 40° C.; ii) copper (II) sulfate pentahydrate, sodium L-ascorbate, methyl propiolate, isopropanol, water; iii) lithium hydroxide monohydrate, tetrahydrofuran.

Step 1:
Following generic route 1, with 4-chloro-3-(trifluoromethyl)phenylboronic acid and sodium-L-ascorbate
Step 2:
Following generic route 1 using methyl propiolate.
Step 3:
Lithium hydroxide monohydrate (16.5 mg, 0.39 mmol) and methyl 1-[4-chloro-3-(trifluoromethyl)phenyl]triazole-4-carboxylate (40.0 mg, 0.13 mmol) were added to a vial and dissolved in tetrahydrofuran (0.5 mL) and heated to 50° C. for 1 hour in a microwave. The solution was then acidified with 1 M HCl (5 mL), diluted with water (5 mL) and extracted with ethyl acetate (3×20 mL). This was then dried over MgSO$_4$ and concentrated under reduced pressure before being purified using reverse phase biotage 12 g column eluting with water:acetonitrile (0.1% formic Acid) to give 1-(4-chloro-3-(trifluoromethyl)phenyl)-1H-1,2,3-triazole-4-carboxylic acid (28 mg, 0.10 mmol, 6%) as a white solid. LCMS: MS m/z 292.0 [M+H]$^+$; $^1$H NMR (600 MHz, MeOH-d$_4$) δ 9.22 (s, 1H), 8.37 (d, J=2.5 Hz, 1H), 8.20 (dd, J=8.7, 2.5 Hz, 1H), 7.87 (d, J=8.7 Hz, 1H).

Compound 59: 1-(4-chloro-3-(trifluoromethyl)phenyl)-1H-1,2,3-triazole-4-carbonitrile

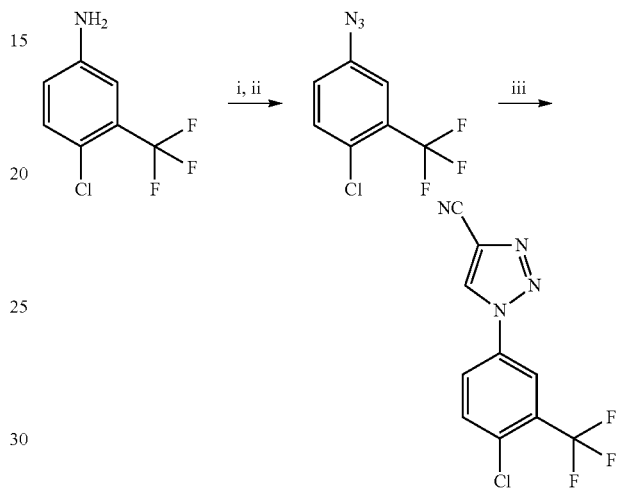

Reagents and conditions: i) Sodium nitrite, >37% aqueous hydrochloric acid, acetonitrile, water, room temperature; ii) sodium azide, 0° C.

Step 1:
Aqueous hydrochloric acid (37%, 13.2 mL, 435.8 mmol) was added to a solution of 4-chloro-3-trifluoromethylaniline (1.32 g, 6.77 mmol) in water (3.75 mL) and acetonitrile (26.3 mL). The reaction mixture was stirred at room temperature for 2 minutes before portionwise addition of sodium nitrite (935 mg, 13.5 mmol). The mixture was then stirred for one hour, cooled to 0° C. and sodium azide (880 mg, 13.5 mmol) was added. The reaction mixture was then allowed to warm to room temperature over 1 hour, before stirring for an additional 2 hours. The reaction was diluted with water (30 mL), then extracted with diethyl ether (2×40 mL) to provide 4-azido-1-chloro-2-(trifluoromethyl)benzene as a stock solution (assumed 84.6 mM, 80 mL), which was used without further purification.
Step 2:
Water (3 mL) was added to a solution of 4-azido-1-chloro-2-(trifluoromethyl)benzene (750 mg, 3.4 mmol) in diethyl ether (40 mL). The organics were then removed under reduced pressure at room temperature and 2-chloroacrylonitrile (180 μL, 2.2 mmol) was then added. The reaction vessel was sealed and stirred at 80° C. overnight, after this time the reaction was diluted with saturated brine, extracted with dichloromethane. The organic phase was then dried over anhydrous MgSO$_4$, filtered and concentrated under reduced pressure. Purification by column chromatography (0-10% ethyl acetate in cyclohexane) gave 1-(4-chloro-3-(trifluoromethyl)phenyl)-1H-1,2,3-triazole-4-carbonitrile (17 mg, 0.06 mmol, 2%) as a pale yellow solid. LCMS: MS m/z not found; $^1$H NMR (600 MHz, DMSO) δ 9.91 (s, 1H), 8.40 (d, J=1.0 Hz, 1H), 8.22-8.14 (m, 2H).

TABLE 9

Substituted 1-phenyl-1H-1,2,3-triazole

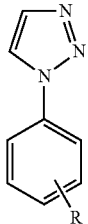

| Compound Number | R group | Generic Route | IUPAC Name |
|---|---|---|---|
| 60 | 4-iPr | 8 | 1-(4-isopropylphenyl)-1H-1,2,3-triazole |
| 61 | 3-F | 8 | 1-(3-fluorophenyl)triazole |
| 62 | 3-OMe | 8 | 1-(3-methoxyphenyl)triazole |
| 63 | 4-Me | 8 | 1-(p-tolyl)triazole |
| 64 | 4-F | 8 | 1-(4-fluorophenyl)triazole |
| 65 | 3-CF$_3$ | 8 | 1-[3-(trifluoromethyl)phenyl]triazole |
| 66 | 3-Cl | 8 | 1-(3-chlorophenyl)triazole |

Compound 60: 1-(4-isopropylphenyl)-1H-1,2,3-triazole

Following generic route 8, using 4-isopropylaniline, yield=16% (off-white solid). LCMS: MS m/z 188.1 [M+H]$^+$; $^1$H NMR (600 MHz, CDCl$_3$) δ 7.96 (d, J=0.8 Hz, 1H), 7.84 (d, J=0.8 Hz, 1H), 7.67-7.65 (m, 2H), 7.40-7.38 (m, 2H), 3.00 (m, 1H), 1.30 (d, J=7.1 Hz, 6H).

Compound 61: 1-(3-fluorophenyl)triazole

Following generic route 8, using 3-fluoroaniline, yield=23% (white solid). LCMS: MS m/z 164.1 [M+H]$^+$; $^1$H NMR (600 MHz, CDCl$_3$) δ 8.01 (d, J=0.8 Hz, 1H), 7.87 (d, J=0.8 Hz, 1H), 7.57-7.50 (m, 3H), 7.17 (m, 1H).

Compound 62: 1-(3-methoxyphenyl)triazole

Following generic route 8, using m-anisidine, yield=67% (yellow oil). LCMS: MS m/z 176.1 [M+H]$^+$; $^1$H NMR (600 MHz, CDCl$_3$) δ 7.99 (d, J=1.0 Hz, 1H), 7.85 (d, J=1.0 Hz, 1H), 7.42 (apparent t, J=8.3 Hz, 1H), 7.37 (apparent t, J=2.3 Hz, 1H), 7.27 (ddd, J=8.3, 2.4, 0.8 Hz, 1H), 6.98 (ddd, J=8.3, 2.4, 0.8 Hz, 1H), 3.89 (s, 3H).

Compound 63: 1-(p-tolyl)triazole

Following generic route 8, using p-toluidine, yield=11% (white solid). LCMS: MS m/z 160.1 [M+H]$^+$; $^1$H NMR (600 MHz, CDCl$_3$) δ 7.96 (d, J=1.0 Hz, 1H), 7.84 (d, J=1.0 Hz, 1H), 7.64-7.62 (m, 2H), 7.33 (br d, J=8.2 Hz, 2H), 2.44 (s, 3H).

Compound 64: 1-(4-fluorophenyl)triazole

Following generic route 8, using 4-fluoroaniline, yield=15% (white solid). LCMS: MS m/z 164.1 [M+H]$^+$; $^1$H NMR (600 MHz, DMSO) δ 8.81 (d, J=1.1 Hz, 1H), 8.01-7.91 (m, 3H), 7.53-7.40 (m, 2H).

Compound 65: 1-[3-(trifluoromethyl)phenyl]triazole

Following generic route 8, using 1-azido-3-(trifluoromethyl)benzene, yield=53% (white solid). LCMS: MS m/z 214.1 [M+H]$^+$; $^1$H NMR (600 MHz, DMSO) δ 9.01 (d, J=1.1 Hz, 1H), 8.33-8.25 (m, 2H), 8.03 (d, J=1.1 Hz, 1H), 7.91-7.83 (m, 2H).

Compound 66: 1-(3-chlorophenyl)triazole

Following generic route 8, using 1-azido-3-chloro-benzene, yield=29% (white solid). LCMS: MS m/z 180.0 [M+H]$^+$; $^1$H NMR (600 MHz, DMSO) δ 8.91 (d, J=1.1 Hz, 1H), 8.06 (apparent t, J=2.0 Hz, 1H), 8.00 (d, J=1.1 Hz, 1H), 7.94 (ddd, J=8.1, 2.1, 0.9 Hz, 1H), 7.64 (apparent t, J=8.1 Hz, 1H), 7.57 (ddd, J=8.1, 2.0, 0.9 Hz, 1H).

TABLE 10

Substituted 5-phenyl-1,3,4-oxadiazol-2-ols

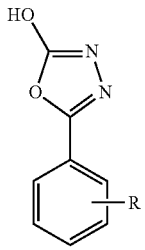

| Compound Number | R group | Generic Route | IUPAC Name |
|---|---|---|---|
| 67 | 3-CF$_3$, 4-Cl | 3 | 5-(4-chloro-3-(trifluoromethyl)phenyl)-1,3,4-oxadiazol-2-ol |
| 68 | 3-OCF$_3$, 4-Cl | 4 | 5-(4-chloro-3-(trifluoromethoxy)phenyl)-1,3,4-oxadiazol-2-ol |
| 69 | 3-CHF$_2$ | 3 | 5-(3-(difluoromethyl)phenyl)-1,3,4-oxadiazol-2-ol |
| 70 | 3-Et | 3 | 5-(3-ethylphenyl)-1,3,4-oxadiazol-2-ol |

TABLE 10-continued

Substituted 5-phenyl-1,3,4-oxadiazol-2-ols

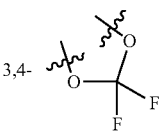 [SMILES: *OC(F)(F)O*]

| Compound Number | R group | Generic Route | IUPAC Name |
| --- | --- | --- | --- |
| 71 | 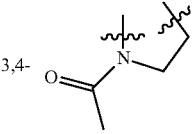 [SMILES: *CCN(*)C(C)=O] | 3 | 5-(2,2-difluorobenzo[d][1,3]dioxol-5-yl)-1,3,4-oxadiazol-2-ol |
| 72 | 3-OCHF$_2$ | 3 | 5-(3-(difluoromethoxy)phenyl)-1,3,4-oxadiazol-2-ol |
| 73 | 4-cyclopentyl | 3 | 5-(4-cyclopentylphenyl)-1,3,4-oxadiazol-2-ol |
| 74 | 3,4-Me | 3 | 5-(3,4-dimethylphenyl)-1,3,4-oxadiazol-2-ol |
| 75 | 4-CHF$_2$ | 4 | 5-(4-(difluoromethyl)phenyl)-1,3,4-oxadiazol-2-ol |
| 76 | 4-O$^i$Pr | 4 | 5-(4-isopropoxyphenyl)-1,3,4-oxadiazol-2-ol |
| 77 | 4-Et | 4 | 5-(4-ethylphenyl)-1,3,4-oxadiazol-2-ol |
| 78 | 3-cyclopropyl | 4 | 5-(3-cyclopropylphenyl)-1,3,4-oxadiazol-2-ol |
| 79 | 3-OCF$_3$, 4-Me | 4 | 5-(4-methyl-3-(trifluoromethoxy)phenyl)-1,3,4-oxadiazol-2-ol |
| 80 | 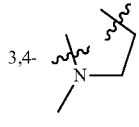 | 4 | 1-(5-(5-hydroxy-1,3,4-oxadiazol-2-yl)indolin-1-yl)ethan-1-one |
| 81 | 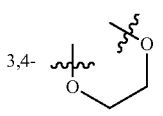 | 11 | 5-(1-methylindolin-5-yl)-1,3,4-oxadiazol-2-ol |
| 82 | 5-Cl, 3,4- (HN cyclic) | 4 | 5-(7-chloroindolin-5-yl)-1,3,4-oxadiazol-2-ol |
| 83 | 3,4-Cl | 3 | 5-(3,4-dichlorophenyl)-1,3,4-oxadiazol-2-ol |
| 84 | 4-F | 3 | 5-(4-fluorophenyl)-1,3,4-oxadiazol-2-ol |
| 85 | 4-CF$_3$ | 3 | 5-(4-(trifluoromethyl)phenyl)-1,3,4-oxadiazol-2-ol |
| 86 | 3-Me, 5-CF$_3$ | 3 | 5-(3-methyl-5-(trifluoromethyl)phenyl)-1,3,4-oxadiazol-2-ol |
| 87 | 3-CF$_3$, 4-Me | 3 | 5-(4-methyl-3-(trifluoromethyl)phenyl)-1,3,4-oxadiazol-2-ol |
| 88 | 3-Cl, 5-CF$_3$ | 3 | 5-(3-chloro-5-(trifluoromethyl)phenyl)-1,3,4-oxadiazol-2-ol |
| 89 | 3,5-Me | 3 | 5-(3,5-dimethylphenyl)-1,3,4-oxadiazol-2-ol |
| 90 | 3-Cl | 3 | 5-(3-chlorophenyl)-1,3,4-oxadiazol-2-ol |
| 91 | 3,4- (OCH$_2$CH$_2$O) | 3 | 5-(2,3-dihydrobenzo[b][1,4]dioxin-6-yl)-1,3,4-oxadiazol-2-ol |
| 92 | 4-OMe | 4 | 5-(4-methoxyphenyl)-1,3,4-oxadiazol-2-ol |

TABLE 10-continued

Substituted 5-phenyl-1,3,4-oxadiazol-2-ols

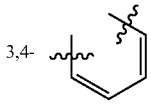

| Compound Number | R group | Generic Route | IUPAC Name |
|---|---|---|---|
| 93 | 3,4- (fused ring) | 4 | 5-(naphthalen-2-yl)-1,3,4-oxadiazol-2-ol |
| 94 | 3-F | 4 | 5-(3-fluorophenyl)-1,3,4-oxadiazol-2-ol |
| 95 | 3-OMe | 4 | 5-(3-methoxyphenyl)-1,3,4-oxadiazol-2-ol |
| 96 | 4-OCF$_3$ | 4 | 5-[4-(trifluoromethoxy)phenyl]-1,3,4-oxadiazol-2-ol |
| 97 | 4-$^t$Bu | 4 | 5-(4-tert-butylphenyl)-1,3,4-oxadiazol-2-ol |
| 98 | 4-CN | 4 | 4-(5-hydroxy-1,3,4-oxadiazol-2-yl)benzonitrile |
| 99 | 4-$^i$Pr | 4 | 5-(4-isopropylphenyl)-1,3,4-oxadiazol-2-ol |
| 100 | 4-NMe$_2$ | 4 | 5-[4-(dimethylamino)phenyl]-1,3,4-oxadiazol-2-ol |
| 101 | 4-$^c$Pr | 12 | 5-(4-cyclopropylphenyl)-1,3,4-oxadiazol-2-ol |
| 102 | 4-Cl | — | 5-(4-chlorophenyl)-1,3,4-oxadiazol-2-ol |
| 103 | 4-Me | — | 5-(4-methylphenyl)-1,3,4-oxadiazol-2-ol |
| 104 | 3-CF$_3$ | — | 5-(3-(trifluoromethyl)phenyl)-1,3,4-oxadiazol-2-ol |
| 105 | 3-Me | — | 5-(3-methylphenyl)-1,3,4-oxadiazol-2-ol |
| 106 | — | — | 5-phenyl-1,3,4-oxadiazol-2-ol |
| 107 | 4-NO$_2$ | — | 5-(4-nitrophenyl)-1,3,4-oxadiazol-2-ol |
| 108 | 2-Me | — | 5-(2-methylphenyl)-1,3,4-oxadiazol-2-ol |
| 179 | 5-Cl, 3,4- (indoline) | — | 5-(7-chloro-1,3,3-trimethyl-indolin-5-yl)-1,3,4-oxadiazol-2-ol |
| 180 | 3,4- (indoline) | — | 5-(1,3,3-trimethylindolin-5-yl)-1,3,4-oxadiazol-2-ol |
| 191 | 3-CF$_3$, 4-cyclopropyl | 12 | 5-[4-cyclopropyl-3-(trifluoromethyl)phenyl]-1,3,4-oxadiazol-2-ol |
| 193 | 3-cyclopropyl, 4-CF$_3$ | 12 | 5-[3-cyclopropyl-4-(trifluoromethyl)phenyl]-1,3,4-oxadiazol-2-ol |

TABLE 10-continued

Substituted 5-phenyl-1,3,4-oxadiazol-2-ols

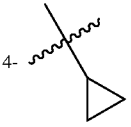 [SMILES: *C1CC1]

| Compound Number | R group | Generic Route | IUPAC Name |
|---|---|---|---|
| 195 | 3-Me, 4- 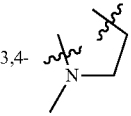 | 12 | 5-(4-cyclopropyl-3-methyl-phenyl)-1,3,4-oxadiazol-2-ol |
| 197 | 5-Cl, 3,4- 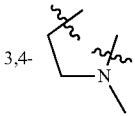 [SMILES: *CCN(*)C] | — | 5-(7-chloro-1-methyl-indolin-5-yl)-1,3,4-oxadiazol-2-ol |
| 198 | 3,4- 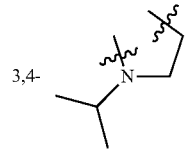 [SMILES: *CCN(*)C(C)C] | — | 5-(1-methylindolin-6-yl)-1,3,4-oxadiazol-2-ol |
| 199 | 2,3-Cl | — | 5-(2,3-dichlorophenyl)-1,3,4-oxadiazol-2-ol |
| 200 | 2-F | — | 5-(2-fluorophenyl)-1,3,4-oxadiazol-2-ol |
| 201 | 2-CF$_3$ | — | 5-[2-(trifluoromethyl)phenyl]-1,3,4-oxadiazol-2-ol |
| 202 | 3,4- 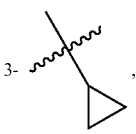 | — | 5-(1-isopropylindolin-5-yl)-1,3,4-oxadiazol-2-ol |
| 211 | 3- [cyclopropyl], 5-CF$_3$, | — | 5-[3-cyclopropyl-5-(trifluoromethyl)phenyl]-1,3,4-oxadiazol-2-ol |
| 218 | 3-NMe$_2$ | 3 | 5-[3-(dimethylamino)phenyl]-1,3,4-oxadiazol-2-ol |
| 223 | 2-Me, 4-Cl | 3 | 5-(4-chloro-2-methyl-phenyl)-1,3,4-oxadiazol-2-ol |

TABLE 10-continued

Substituted 5-phenyl-1,3,4-oxadiazol-2-ols

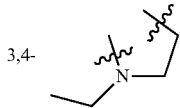

| Compound Number | R group | Generic Route | IUPAC Name |
|---|---|---|---|
| 227 | 3,4- 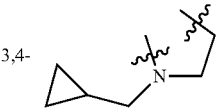 [SMILES: *CCN(*)CC1CC1] | 11 | 5-(1-ethylindolin-5-yl)-1,3,4-oxadiazol-2-ol |
| 228 | 3,4- (cyclopropylmethyl-N-pyrrolidinyl) | 11 | 5-[1-(cyclopropylmethyl)indolin-5-yl]-1,3,4-oxadiazol-2-ol |
| 230 | 2-Cl | 3 | 5-(2-chlorophenyl)-1,3,4-oxadiazol-2-ol |

Compound 67: 5-(4-chloro-3-(trifluoromethyl)phenyl)-1,3,4-oxadiazol-2-ol

Following generic route 3, using 4-chloro-3-(trifluoromethyl)benzoic acid yield=40% (white solid). LCMS: MS m/z 263.0 [M−H]⁻; $^1$H NMR (600 MHz, DMSO) δ 12.86 (s, 1H), 8.14-8.04 (m, 2H), 7.93 (d, J=8.1 Hz, 1H).

Compound 68: 5-(4-chloro-3-(trifluoromethoxy)phenyl)-1,3,4-oxadiazol-2-ol

Following generic route 4, using 4-chloro-3-(trifluoromethoxy)benzoic acid, yield=50% (white solid). LCMS: MS m/z 279.0 [M−H]−; $^1$H NMR (600 MHz, DMSO) δ 12.82 (s, 1H), 7.90 (d, J=8.9 Hz, 1H), 7.86-7.80 (m, 2H).

Compound 69: 5-(3-(difluoromethyl)phenyl)-1,3,4-oxadiazol-2-ol

Following generic route 3, using 3-(difluoromethyl)benzoic acid yield=15% (white solid). LCMS: MS m/z 211.1 [M−H]⁻; $^1$H NMR (600 MHz, DMSO) δ 12.70 (s, 1H), 7.95 (d, J=6.9 Hz, 2H), 7.77 (d, J=7.6 Hz, 1H), 7.71 (t, J=7.9 Hz, 1H), 7.15 (t, J=55.6 Hz, 1H).

Compound 70: 5-(3-ethylphenyl)-1,3,4-oxadiazol-2-ol

Following generic route 3, using 3-ethyl-benzoic acid yield=59% (white solid). LCMS: MS m/z 189.1 [M−H]⁻; $^1$H NMR (600 MHz, DMSO) δ 12.56 (s, 1H), 7.65-7.59 (m, 2H), 7.48-7.41 (m, 2H), 2.68 (q, J=7.6 Hz, 2H), 1.20 (t, J=7.6 Hz, 3H).

Compound 71: 5-(2,2-difluorobenzo[d][1,3]dioxol-5-yl)-1,3,4-oxadiazol-2-ol

Following generic route 3, using 2,2-difluoro-benzo[1,3]dioxole-5-carboxylic acid methyl ester yield=8% (white solid). LCMS: MS m/z 241.0 [M−H]⁻; $^1$H NMR (600 MHz, DMSO) δ 12.67 (s, 1H), 7.83 (d, J=1.5 Hz, 1H), 7.67 (dd, J=8.4, 1.7 Hz, 1H), 7.59 (d, J=8.5 Hz, 1H).

Compound 72: 5-(3-(difluoromethoxy)phenyl)-1,3,4-oxadiazol-2-ol

Following generic route 3, using 3-(difluoromethoxy)benzohydrazide yield=29% (white solid). LCMS: MS m/z 227.0 [M−H]⁻; $^1$H NMR (600 MHz, DMSO) δ 12.98-12.33 (m, 1H), 7.69-7.65 (m, 1H), 7.64-7.58 (m, 1H), 7.53 (s, 1H), 7.42-7.37 (m, 1H), 7.37 (t, J=73.6 Hz, 1H).

Compound 73: 5-(4-cyclopentylphenyl)-1,3,4-oxadiazol-2-ol

Following generic route 3, using methyl 4-cyclopentylbenzoate yield=12% (white solid). LCMS: MS m/z not found; $^1$H NMR (600 MHz, DMSO) δ 12.74-12.33 (m, 1H), 7.69 (d, J=8.3 Hz, 2H), 7.40 (d, J=8.2 Hz, 2H), 3.09-2.97 (m, 1H), 2.08-2.00 (m, 2H), 1.83-1.73 (m, 2H), 1.73-1.60 (m, 2H), 1.61-1.49 (m, 2H).

Compound 74: 5-(3,4-dimethylphenyl)-1,3,4-oxadiazol-2-ol

Following generic route 3, using 3,4-dimethylbenzohydrazide, yield=18% (white solid). LCMS: MS m/z 191.1 [M+H]⁺; $^1$H NMR (600 MHz, DMSO) δ 12.47 (s, 1H), 7.57 (apparent s, 1H), 7.51 (dd, J=7.9 Hz, J=1.7 Hz, 1H), 7.30 (d, J=7.9 Hz, 1H), 2.30-2.26 (m, 6H).

Compound 75: 5-(4-(difluoromethyl)phenyl)-1,3,4-oxadiazol-2-ol

Following generic route 4, using 4-(difluoromethyl)benzoic acid, yield=54% (white solid). LCMS: MS m/z 211.1 [M−H]⁻; $^1$H NMR (600 MHz, DMSO) δ 12.71 (s, 1H), 7.93 (d, J=8.1 Hz, 2H), 7.74 (d, J=8.1 Hz, 2H), 7.13 (t, J=55.6 Hz, 1H).

Compound 76: 5-(4-isopropoxyphenyl)-1,3,4-oxadiazol-2-ol

Following generic route 4, using 4-(propan-2-yloxy)benzohydrazide, yield=89% (white solid). LCMS: MS m/z 221.1 [M+H]$^+$; $^1$H NMR (600 MHz, DMSO) δ 12.41 (s, 1H), 7.74-7.61 (m, 2H), 7.12-6.97 (m, 2H), 4.71 (hept, J=6.0 Hz, 1H), 1.29 (d, J=6.0 Hz, 6H).

Compound 77: 5-(4-ethylphenyl)-1,3,4-oxadiazol-2-ol

Following generic route 4, using 4-ethylbenzene-1-carbohydrazide, yield=82% (white solid). LCMS: MS m/z 191.2 [M+H]$^+$; $^1$H NMR (600 MHz, DMSO) δ 12.51 (s, 1H), 7.75-7.64 (m, 2H), 7.38 (d, J=8.4 Hz, 2H), 2.67 (q, J=7.6 Hz, 2H), 1.20 (t, J=7.6 Hz, 3H).

Compound 78: 5-(3-cyclopropylphenyl)-1,3,4-oxadiazol-2-ol

Following generic route 4, using methyl 3-bromobenzoate, yield=23% over 2 steps (white solid). LCMS: MS m/z 201.1 [M−H]$^-$; $^1$H NMR (600 MHz, DMSO) δ 12.56 (s, 1H), 7.58-7.52 (m, 1H), 7.48 (t, J=1.7 Hz, 1H), 7.41 (apparent t, J=7.8 Hz, 1H), 7.29-7.24 (m, 1H), 2.03 (apparent tt, J=8.4, 5.1 Hz, 1H), 1.05-0.95 (m, 2H), 0.77-0.68 (m, 2H).

Compound 79: 5-(4-methyl-3-(trifluoromethoxy)phenyl)-1,3,4-oxadiazol-2-ol

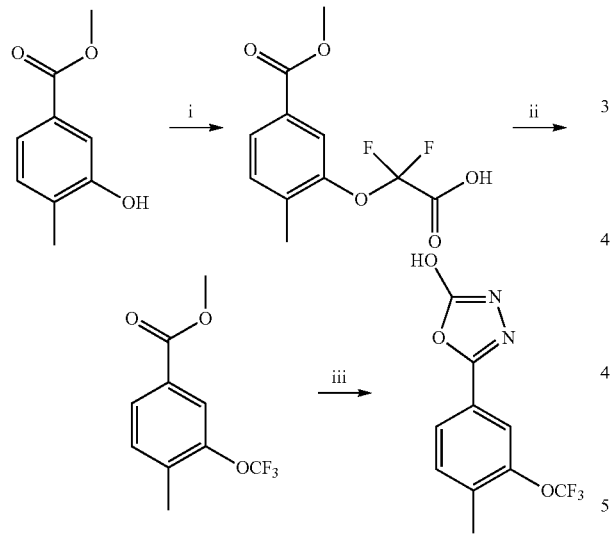

Reagents and conditions: i) Sodium 2-bromo-2,2-difluoro-acetate, sodium hydride 60% wt on mineral oil, dioxane; ii) silver nitrate, Selectfluor(II), trifluoromethanesulfonic acid, trifluoromethylbenzene:water; iii) Generic route 4.

Step 1:
To a suspension of methyl 3-hydroxy-4-methyl-benzoate (332 mg, 2 mmol) in 1,4-dioxane (7 mL) was added sodium hydride 60% wt on mineral oil (96 mg, 2.4 mmol). The reaction mixture was stirred at room temperature for 30 minutes. After this time sodium 2-bromo-2,2-difluoro-acetate (590 mg, 3 mmol) in 1,4-dioxane (2 mL) was added. Upon addition the reaction mixture formed a thick suspension. Upon efficient stirring the reaction flask was fitted with a reflux condenser and heated to 80° C. overnight. The reaction mixture was cooled to room temperature and concentrated to half its original volume. The solution was acidified with 2 N HCl aq. solution and was extracted with ethyl acetate. The organics were combined, dried over anhydrous MgSO$_4$ and the solids were removed via filtration. Purification by reverse phase column chromatography (5-100% water in acetonitrile, 0.1% formic acid) gave 2,2-difluoro-2-(5-methoxycarbonyl-2-methyl-phenoxy)acetic acid as a white solid (150 mg, 0.58 mmol, 29%). LCMS: MS m/z 259.1 [M−H]$^-$; $^1$H NMR (600 MHz, DMSO) δ 7.81 (dd, J=7.9, 1.6 Hz, 1H), 7.71 (s, 1H), 7.51 (d, J=8.0 Hz, 1H), 3.86 (s, 3H), 2.31 (s, 3H).

Step 2:
A vial was charged with Selectfluor(II) (645 mg, 2.02 mmol), silver nitrate (19 mg, 0.12 mmol) and 2,2-difluoro-2-(5-methoxycarbonyl-2-methyl-phenoxy)acetic acid (150 mg, 0.58 mmol). The vial was capped and the contents were evacuated and purged with argon three times. Trifluoromethylbenzene (5.8 mL, 0.5800 mmol) and water (0.58 mL) was added via syringe. Trifluoromethanesulfonic acid (0.15 mL, 1.73 mmol) was then added via syringe. The vial was heated to 80° C. overnight. The reaction was cooled to room temperature and diluted with water (5 mL) and sat. NaHCO$_3$aq. solution (5 mL). The aqueous layer was extracted with dichloromethane three times. The organics were combined, dried over anhydrous MgSO$_4$ and the solids were removed via filtration. Purification by column chromatography (0-20% ethyl acetate in cyclohexane) gave methyl 4-methyl-3-(trifluoromethoxy)benzoate as a colourless oil (35 mg, 0.162 mmol, 28%).

Step 3:
Following generic route 4, using methyl 4-methyl-3-(trifluoromethoxy)benzoate, yield=41% (white solid). LCMS: MS m/z 259.1 [M−H]$^-$; $^1$H NMR (600 MHz, DMSO) δ 12.68 (s, 1H), 7.73 (dd, J=8.0, 1.6 Hz, 1H), 7.62 (s, 1H), 7.59 (d, J=8.0 Hz, 1H), 2.35 (s, 3H).

Compound 80: 1-(5-(5-hydroxy-1,3,4-oxadiazol-2-yl)indolin-1-yl)ethan-1-one

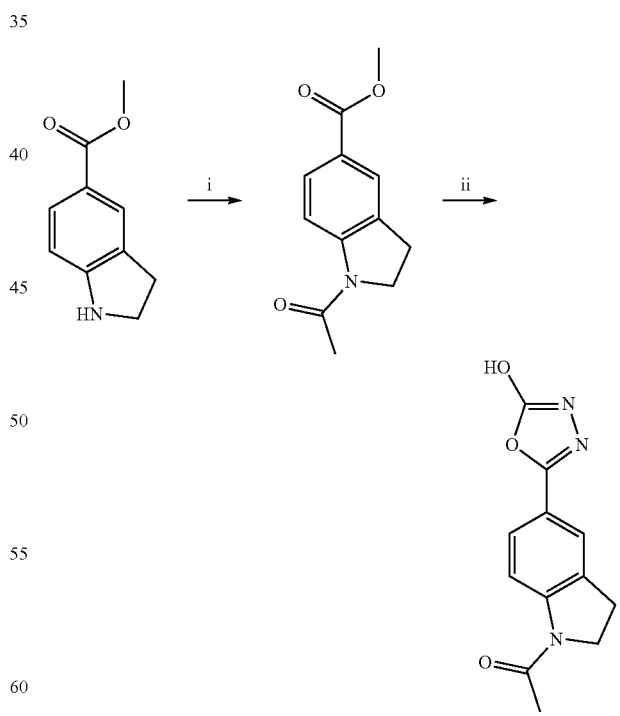

Reagents and conditions: i) Acetyl chloride, sodium hydride 60% wt on mineral oil, tetrahydrofuran; ii) Generic route 4.

Step 1:
A solution of methyl indoline-5-carboxylate (200 mg, 1.13 mmol) in tetrahydrofuran (10 mL) was cooled in an ice-water bath for 5 minutes. Sodium hydride (45.15 mg, 1.13 mmol) in tetrahydrofuran (2 mL) was added drop wise and the reaction was allowed to stir under cooling for 20 minutes before the dropwise addition of acetyl chloride (0.08 mL, 1.13 mmol). The reaction mixture was stirred for 30 minutes. The reaction mixture was removed from the ice-water bath and allowed to warm to ambient temperature. After 1 hour the reaction was added dropwise to a saturated NH$_4$Cl solution and extracted with ethyl acetate three times. The organics were combined, dried over anhydrous MgSO$_4$, filtered to remove the solids, and concentrated under reduced pressure to give methyl 1-acetylindoline-5-carboxylate as an off-white solid (235 mg, 1.07 mmol, 95%). LCMS: MS m/z 220.1 [M+H]$^+$; $^1$H NMR (400 MHz, DMSO) δ 8.09 (d, J=8.9 Hz, 1H), 7.79 (d, J=7.6 Hz, 2H), 4.14 (t, J=8.6 Hz, 2H), 3.81 (s, 3H), 3.17 (t, J=8.6 Hz, 2H), 2.18 (s, 3H).

Step 2:

Following generic route 4, using methyl 1-acetylindoline-5-carboxylate, yield=17% (white solid). LCMS: MS m/z 246.1 [M+H]$^+$; $^1$H NMR (600 MHz, DMSO) δ 12.45 (s, 1H), 8.13 (d, J=8.4 Hz, 1H), 7.63 (s, 1H), 7.60 (d, J=8.4 Hz, 1H), 4.15 (t, J=8.6 Hz, 2H), 3.20 (t, J=8.5 Hz, 2H), 2.19 (s, 3H).

Compound 81:
5-(1-methylindolin-5-yl)-1,3,4-oxadiazol-2-ol

Following generic route 11, using iodomethane, yield=24% over 2 steps (white solid). LCMS: MS m/z 218.1 [M+H]$^+$; $^1$H NMR (600 MHz, DMSO) δ 12.19 (s, 1H), 7.44 (dd, J=8.2, 1.7 Hz, 1H), 7.40 (d, J=1.3 Hz, 1H), 6.53 (d, J=8.3 Hz, 1H), 3.41 (t, J=8.4 Hz, 2H), 2.95 (t, J=8.4 Hz, 2H), 2.78 (s, 3H).

Compound 82:
5-(7-chloroindolin-5-yl)-1,3,4-oxadiazol-2-ol

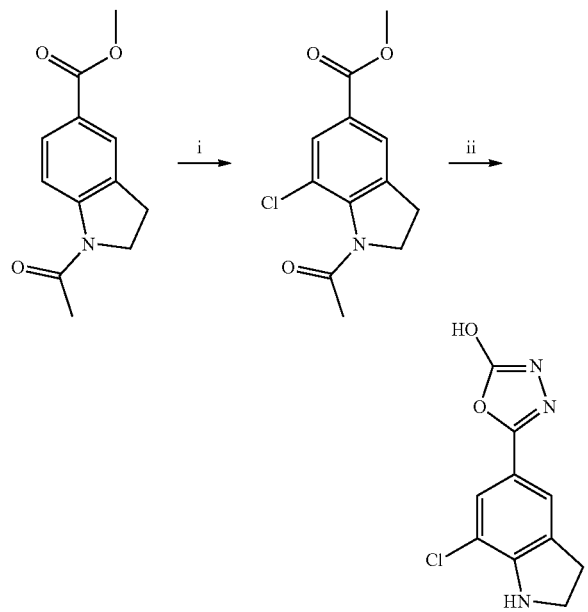

Reagents and conditions: i) N-Chlorosuccinimide, acetic acid; ii) Generic route 4.

Step 1:

A solution of methyl 1-acetylindoline-5-carboxylate (135 mg, 0.62 mmol) in acetic acid (0.25 mL) was cooled in an ice bath before portion wise addition of N-chlorosuccinimide (123 mg, 0.92 mmol). The reaction was warmed to 50° C. and stirred overnight. The reaction mixture was cooled to room temperature and diluted with water (10 mL). The suspension was then extracted with ethyl acetate (×3). The organics were combined, dried over anhydrous MgSO$_4$, filtered to remove the solids and concentrated under reduced pressure. Purification by column chromatography (0-60% ethyl acetate in cyclohexane) gave methyl 7-chloroindoline-5-carboxylate as a pale orange solid (46 mg, 0.18 mmol, 29%). LCMS: MS m/z 254.1 [M+H]$^+$.

Step 2:

Following generic route 4, using methyl 7-chloroindoline-5-carboxylate, yield=33% (white solid). LCMS: MS m/z 238.1 [M+H]$^+$; $^1$H NMR (600 MHz, DMSO) δ 12.29 (s, 1H), 7.35 (dd, J=6.9, 1.4 Hz, 2H), 6.47 (s, 1H), 3.59 (t, J=8.8 Hz, 2H), 3.09 (t, J=8.8 Hz, 2H).

Compound 83:
5-(3,4-dichlorophenyl)-1,3,4-oxadiazol-2-ol

Following generic route 3, using 3,4-dichlorobenzene-1-carbohydrazide, yield=24% (white solid). LCMS: MS m/z 229.0 [M–H]$^-$; $^1$H NMR (600 MHz, DMSO) δ 12.79 (s, 1H), 7.97 (d, J=2.0 Hz, 1H), 7.83 (d, J=8.4 Hz, 1H), 7.76 (dd, J=8.4, 2.0 Hz, 1H).

Compound 84:
5-(4-fluorophenyl)-1,3,4-oxadiazol-2-ol

Following generic route 3, using 4-fluorobenzhydrazide, yield=10% (white solid). LCMS: MS m/z 179.1 [M–H]$^-$; $^1$H NMR (600 MHz, DMSO) δ 12.58 (s, 1H), 7.89-7.80 (m, 2H), 7.44-7.34 (m, 2H).

Compound 85:
5-(4-(trifluoromethyl)phenyl)-1,3,4-oxadiazol-2-ol

Following generic route 3, using ethyl 4-(trifluoromethyl)benzoate, yield=30% (white solid). LCMS: MS m/z 229.1 [M–H]$^-$; $^1$H NMR (600 MHz, DMSO) δ 12.92-12.59 (m, 1H), 8.00 (d, J=8.6 Hz, 2H), 7.91 (d, J=8.6 Hz, 2H).

Compound 86: 5-(3-methyl-5-(trifluoromethyl)phenyl)-1,3,4-oxadiazol-2-ol

Following generic route 3, using 3-methyl-5-(trifluoromethyl)benzoic acid, yield=24% (white solid). LCMS: MS m/z 243.1 [M–H]$^-$; $^1$H NMR (600 MHz, DMSO) δ 13.02-12.48 (m, 1H), 7.91 (s, 1H), 7.81 (s, 1H), 7.78 (s, 1H), 2.47 (s, 3H).

Compound 87: 5-(4-methyl-3-(trifluoromethyl)phenyl)-1,3,4-oxadiazol-2-ol

Following generic route 3, using methyl 4-methyl-3-(trifluoromethyl)benzoate, yield=16% (white solid). LCMS: MS m/z 243.1 [M–H]$^-$; $^1$H NMR (600 MHz, DMSO) δ 12.69 (s, 1H), 8.00-7.94 (m, 2H), 7.64 (d, J=8.1 Hz, 1H), 2.52 (s, 3H).

Compound 88: 5-(3-chloro-5-(trifluoromethyl)phenyl)-1,3,4-oxadiazol-2-ol

Following generic route 3, using 3-chloro-5-(trifluoromethyl)benzoic acid, yield=61% (white solid). LCMS: MS m/z 263.0 [M–H]⁻; ¹H NMR (600 MHz, DMSO) δ 12.90 (s, 1H), 8.12 (s, 1H), 8.09 (s, 1H), 7.98 (s, 1H).

Compound 89:
5-(3,5-dimethylphenyl)-1,3,4-oxadiazol-2-ol

Following generic route 3, using 3,5-dimethylbenzohydrazide, yield=8% (white solid). LCMS: MS m/z not found; ¹H NMR (600 MHz, DMSO) δ 12.52 (s, 1H), 7.41 (s, 2H), 7.20 (s, 1H), 2.33 (s, 6H).

Compound 90:
5-(3-chlorophenyl)-1,3,4-oxadiazol-2-ol

Following generic route 3, using 3-chlorobenzohydrazide, yield=35% (white solid). LCMS: MS m/z 195.0 [M–H]⁻; ¹H NMR (600 MHz, DMSO) δ 12.79-12.48 (m, 1H), 7.79-7.72 (m, 2H), 7.64 (d, J=7.8 Hz, 1H), 7.57 (dd, J=17.5, 9.7 Hz, 1H).

Compound 91: 5-(2,3-dihydrobenzo[b][1,4]dioxin-6-yl)-1,3,4-oxadiazol-2-ol

Following generic route 3, using 2,3-dihydro-1,4-benzodioxine-6-carbohydrazide, yield=50% (white solid). LCMS: MS m/z 221.1 [M+H]⁺, ¹H NMR (600 MHz, DMSO) δ 12.44 (s, 1H), 7.25 (dd, J=8.4, 2.0 Hz, 1H), 7.20 (d, J=2.0 Hz, 1H), 7.00 (d, J=8.4 Hz, 1H), 4.32-4.27 (m, 4H).

Compound 92:
5-(4-methoxyphenyl)-1,3,4-oxadiazol-2-ol

Following generic route 4, using 4-methoxybenzhydrazide, yield=60% (white solid). LCMS: MS m/z 193.1 [M+H]⁺; ¹H NMR (600 MHz, DMSO) δ 12.42 (s, 1H), 7.90-7.52 (m, 2H), 7.32-6.95 (m, 2H), 3.83 (s, 3H).

Compound 93: 5-(2-naphthyl)-1,3,4-oxadiazol-2-ol

Following generic route 4, using naphthalene-2-carbohydrazide, yield=53% (white solid). LCMS: MS m/z not found; ¹H NMR (600 MHz, DMSO) δ 12.66 (s, 1H), 8.39 (s, 1H), 8.14-8.09 (m, 1H), 8.07 (d, J=8.7 Hz, 1H), 8.03-7.97 (m, 1H), 7.88 (dd, J=8.6, 1.7 Hz, 1H), 7.67-7.59 (m, 2H).

Compound 94:
5-(3-fluorophenyl)-1,3,4-oxadiazol-2-ol

Following generic route 4, using 3-fluorobenzohydrazide, yield=77% (white solid). LCMS: MS m/z 179.1 [M–H]⁻; ¹H NMR (400 MHz, DMSO) δ 12.72 (s, 1H), 7.60 (qdd, J=9.4, 2.5, 1.3 Hz, 3H), 7.48-7.39 (m, 1H).

Compound 95:
5-(3-methoxyphenyl)-1,3,4-oxadiazol-2-ol

Following generic route 4, using 3-methoxybenzohydrazide, yield=82% (white solid). LCMS: MS m/z not found; ¹H NMR (400 MHz, DMSO) δ 12.61 (s, 1H), 7.46 (t, J=8.0 Hz, 1H), 7.39-7.33 (m, 1H), 7.26 (dd, J=2.5, 1.6 Hz, 1H), 7.14 (ddd, J=8.3, 2.6, 1.0 Hz, 1H), 3.82 (s, 3H).

Compound 96: 5-[4-(trifluoromethoxy)phenyl]-1,3,4-oxadiazol-2-ol

Following generic route 4, using 4-(trifluoromethoxy)benzohydrazide, yield=80% (white solid). LCMS: MS m/z 245.1 [M–H]⁻; ¹H NMR (400 MHz, DMSO) δ 12.69 (s, 1H), 7.98-7.85 (m, 2H), 7.55 (dd, J=8.9, 0.9 Hz, 2H).

Compound 97:
5-(4-tert-butylphenyl)-1,3,4-oxadiazol-2-ol

Following generic route 4, using 4-(tert-butyl)benzenecarbohydrazide, yield=91% (white solid). LCMS: MS m/z not found; ¹H NMR (600 MHz, DMSO) δ 12.52 (s, 1H), 7.75-7.68 (m, 2H), 7.59-7.52 (m, 2H), 1.30 (s, 9H).

Compound 98:
4-(5-hydroxy-1,3,4-oxadiazol-2-yl)benzonitrile

Following generic route 4, using 4-cyanobenzohydrazide, yield=68% (white solid). LCMS: MS m/z 186.0 [M–H]⁻; ¹H NMR (600 MHz, DMSO) δ 12.85 (s, 1H), 8.03-7.98 (m, 2H), 7.97-7.92 (m, 2H).

Compound 99:
5-(4-isopropylphenyl)-1,3,4-oxadiazol-2-ol

Following generic route 4, using methyl 4-isopropylbenzoate, yield=33% (white solid). LCMS: MS m/z not found; ¹H NMR (600 MHz, DMSO) δ 12.51 (s, 1H), 7.76-7.66 (m, 2H), 7.41 (d, J=8.3 Hz, 2H), 2.95 (hept, J=6.9 Hz, 1H), 1.22 (d, J=6.9 Hz, 6H).

Compound 100: 5-[4-(dimethylamino)phenyl]-1,3,4-oxadiazol-2-ol

Following generic route 4, using ethyl 4-(dimethylamino)benzoate, yield=8% (white solid). LCMS: MS m/z 206.2 [M+H]⁺ ¹H NMR (600 MHz, DMSO) δ 12.22 (s, 1H), 7.65-7.48 (m, 2H), 6.87-6.65 (m, 2H), 2.99 (s, 6H).

Compound 101:
5-(4-cyclopropylphenyl)-1,3,4-oxadiazol-2-ol

Following generic route 12, using methyl 4-bromobenzoate, yield=27% over 2 steps (white solid). LCMS: MS m/z not found; ¹H NMR (400 MHz, DMSO) δ 12.50 (s, 1H), 7.68-7.59 (m, 2H), 7.26-7.17 (m, 2H), 2.04-1.94 (m, 1H), 1.08-0.96 (m, 2H), 0.80-0.69 (m, 2H).

Compound 102:
5-(4-chlorophenyl)-1,3,4-oxadiazol-2-ol

Compound purchased from a commercial supplier, namely Sigma Aldrich.

Compound 103:
5-(4-methylphenyl)-1,3,4-oxadiazol-2-ol

Compound purchased from a commercial supplier, namely Key Organics.

Compound 104:
5-(3-(trifluoromethyl)phenyl)-1,3,4-oxadiazol-2-ol

Compound purchased from a commercial supplier, namely Combi-Blocks.

Compound 105: 5-(3-methylphenyl)-1,3,4-oxadiazol-2-ol

Compound purchased from a commercial supplier, namely Combi-Blocks.

Compound 106: 5-phenyl-1,3,4-oxadiazol-2-ol

Compound purchased from a commercial supplier, namely Key Organics.

Compound 107: 5-(4-nitrophenyl)-1,3,4-oxadiazol-2-ol

Compound purchased from a commercial supplier, namely Key Organics.

Compound 108: 5-(2-methylphenyl)-1,3,4-oxadiazol-2-ol

Compound purchased from a commercial supplier, namely Combi-Blocks.

Compound 179: 5-(7-chloro-1,3,3-trimethyl-indolin-5-yl)-1,3,4-oxadiazol-2-ol

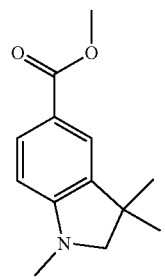
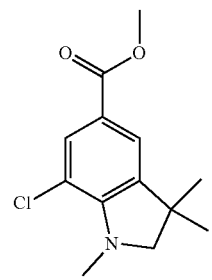
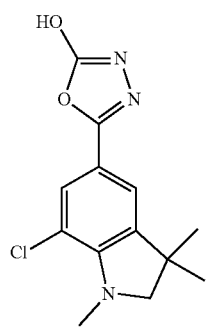

Reagents and conditions: i) N-chlorosuccinimide, acetic acid; ii) Generic route 4

Step 1:

A solution of methyl methyl 1,3,3-trimethylindoline-5-carboxylate (100 mg, 0.46 mmol) in acetic acid (0.5 mL) was cooled to 0° C. in an ice-water bath before the addition of N-chlorosuccinimide (73 mg, 0.55 mmol). The reaction was warmed to room temperature and stirred overnight. The reaction mixture was diluted with water and extracted with ethyl acetate (×3). The organics were combined, dried over anhydrous MgSO$_4$, filtered to remove the solids and concentrated under reduced pressure. Purification by column chromatography (0-50% ethyl acetate in cyclohexane) gave methyl 7-chloro-1,3,3-trimethylindoline-5-carboxylate as a white solid. LCMS: MS m/z 254.1 [M+H]$^+$.

Step 2:

Following generic route 4, using methyl 7-chloro-1,3,3-trimethylindoline-5-carboxylate, to afford 5-(7-chloro-1,3,3-trimethyl-indolin-5-yl)-1,3,4-oxadiazol-2-ol (23 mg, 0.08 mmol, 18%) as a white solid over all steps. LCMS: MS m/z 280.1 [M+H]$^+$; $^1$H NMR (600 MHz, DMSO) δ 12.36 (s, 1H), 7.36 (d, J=1.7 Hz, 1H), 7.33 (d, J=1.7 Hz, 1H), 3.27 (s, 2H), 3.15 (s, 3H), 1.26 (s, 6H).

Compound 180: 5-(1,3,3-trimethylindolin-5-yl)-1,3,4-oxadiazol-2-ol

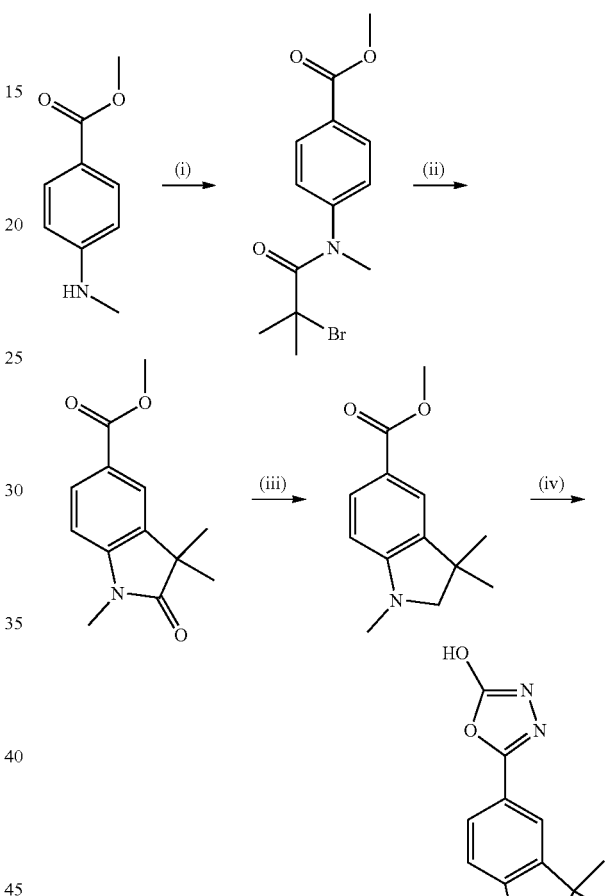

Reagents and conditions: i) 2-bromo-2-methyl-propanoyl bromide, 4-dimethylaminopyridine, trimethylamine, chloroform; ii) Cu(acac)$_2$, 1,10-phenanthroline, acetonitrile; iii) sodium borohydride, iodide, tetrahydrofuran; iv) Generic route 4

Step 1:

To a solution of methyl 4-(methylamino)benzoate (1000 mg, 6.05 mmol), 2-bromo-2-methyl-propanoyl bromide (1.12 mL, 9.08 mmol) and 4-dimethylaminopyridine (74 mg, 0.61 mmol) in chloroform (30 mL) at 0° C. was added triethylamine (1.27 mL, 9.08 mmol) slowly. The reaction mixture was stirred at room temperature for 30 minutes. The reaction mixture was diluted with ethyl acetate (100 mL), washed with water (3×50 mL), dried over anhydrous MgSO$_4$, filtered and concentrated under reduced pressure. Purification by column chromatography (0-40% ethyl acetate in cyclohexane) gave methyl 4-[(2-bromo-2-methyl-propanoyl)-methyl-amino]benzoate (1860 mg, 5.92 mmol, 98%) as a white solid. LCMS: MS m/z 314.0 [M+H]$^+$.

Step 2:

A mixture of methyl 4-[(2-bromo-2-methyl-propanoyl)-methyl-amino]benzoate (500 mg, 1.59 mmol), copper (Z)-4-oxopent-2-en-2-olate (833 mg, 3.18 mmol) and 1,10-phenanthroline (574 mg, 3.18 mmol) in acetonitrile (12 mL) was stirred at 90° C. for 6 hours under an argon atmosphere. The reaction mixture was then diluted with ethyl acetate (20 mL), washed with water (3×10 mL), dried over anhydrous MgSO$_4$, filtered and concentrated under reduced pressure. Purification by column chromatography (0-30% ethyl acetate in cyclohexane) gave methyl 1,3,3-trimethyl-2-oxo-indoline-5-carboxylate (310 mg, 1.33 mmol, 84%) as a white solid. LCMS: MS m/z 234.2 [M+H]$^+$; $^1$H NMR (600 MHz, DMSO) δ 7.94 (dd, J=8.1, 1.8 Hz, 1H), 7.93-7.90 (m, 1H), 7.14 (d, J=8.2 Hz, 1H), 3.83 (s, 3H), 3.18 (s, 3H), 1.30 (s, 6H).

Step 3:

To a stirred solution of sodium borohydride (402 mg, 10.6 mmol) in dry tetrahydrofuran (25 mL) under argon was added a solution of iodine (2.024 g, 7.97 mmol) in dry tetrahydrofuran (6 mL) at 0° C. Following complete addition, a solution of methyl 1,3,3-trimethyl-2-oxo-indoline-5-carboxylate (620 mg, 2.66 mmol) in dry tetrahydrofuran (6 mL) was added. The reaction mixture was warmed to 50° C. and stirred overnight. After this time the reaction was diluted with water (50 mL) and extracted with ethyl acetate. The organics were combined and dried over anhydrous MgSO$_4$. The solids were removed via filtration and purification by column chromatography (0-40% ethyl acetate in cyclohexane) gave methyl 1,3,3-trimethylindoline-5-carboxylate (385 mg, 1.76 mmol, 66%) as a white solid. LCMS: MS m/z 220.1 [M+H]$^+$; $^1$H NMR (400 MHz, DMSO) δ 7.69 (dd, J=8.3, 1.8 Hz, 1H), 7.52 (d, J=1.7 Hz, 1H), 6.50 (d, J=8.3 Hz, 1H), 3.75 (s, 3H), 3.21 (s, 2H), 2.80 (s, 3H), 1.25 (s, 6H).

Step 4:

Following generic route 4, using methyl 1,3,3-trimethyl-indoline-5-carboxylate, to afford 5-(1,3,3-trimethylindolin-5-yl)-1,3,4-oxadiazol-2-ol (17 mg, 0.07 mmol, 19%) as a white solid. LCMS: MS m/z 246.2 [M+H]$^+$; $^1$H NMR (400 MHz, MeOD) δ 12.21 (s, 1H), 7.45 (dd, J=8.3, 1.8 Hz, 1H), 7.37 (d, J=1.7 Hz, 1H), 6.56 (d, J=8.3 Hz, 1H), 3.18 (s, 2H), 2.79 (s, 3H), 1.25 (d, J=6.7 Hz, 6H).

Compound 191: 5-[4-cyclopropyl-3-(trifluoromethyl)phenyl]-1,3,4-oxadiazol-2-ol

Following generic route 12, using methyl 4-bromo-3-(trifluoromethyl)benzoate, yield=42% over 2 steps (white solid). LCMS: MS m/z 269.1 [M−H]$^−$; $^1$H NMR (600 MHz, DMSO) δ 12.68 (s, 1H), 7.92 (m, 2H), 7.31 (d, J=8.2 Hz, 1H), 2.16 (m, 1H), 1.17-1.10 (m, 2H), 0.93-0.86 (m, 2H).

Compound 193: 5-[3-cyclopropyl-4-(trifluoromethyl)phenyl]-1,3,4-oxadiazol-2-ol

Following generic route 12, using methyl 3-bromo-4-(trifluoromethyl)benzoate, yield=52% over 2 steps (white solid). LCMS: MS m/z 269.2 [M−H]$^−$; $^1$H NMR (600 MHz, DMSO) δ 12.78 (s, 1H), 7.84 (d, J=8.3 Hz, 1H), 7.75 (d, J=8.3 Hz, 1H), 7.43 (s, 1H), 2.22-2.11 (m, 1H), 1.16-1.04 (m, 2H), 0.92-0.79 (m, 2H).

Compound 195: 5-(4-cyclopropyl-3-methyl-phenyl)-1,3,4-oxadiazol-2-ol

Following generic route 12, using methyl 4-bromo-3-methyl-benzoate, yield=30% over 2 steps (white solid).

LCMS: MS m/z not found; $^1$H NMR (400 MHz, DMSO) δ 12.50 (s, 1H), 7.57 (s, 1H), 7.50 (dd, J=8.1, 1.6 Hz, 1H), 7.05 (d, J=8.1 Hz, 1H), 2.43 (s, 3H), 1.97 (tt, J=8.4, 5.4 Hz, 1H), 1.03-0.91 (m, 2H), 0.72-0.61 (m, 2H).

Compound 197: 5-(7-chloro-1-methyl-indolin-5-yl)-1,3,4-oxadiazol-2-ol

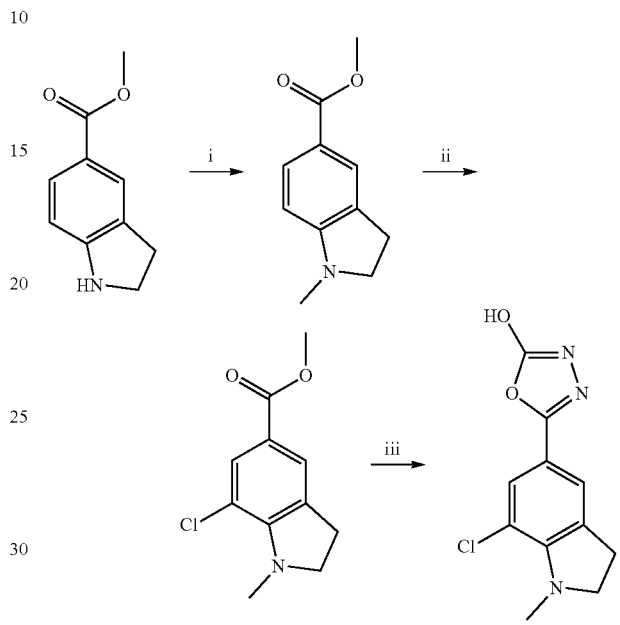

Reagents and conditions: i) Methyl iodide, sodium hydride 60% wt on mineral oil, tetrahydrofuran; ii) N-chlorosuccinimide, acetic acid, 50° C.; iii) Generic route 4

Step 1:

A solution of methyl indoline-5-carboxylate (200 mg, 1.13 mmol) in tetrahydrofuran (10 mL) was cooled in an ice-water bath for 5 minutes. Sodium hydride (45 mg, 1.13 mmol) in tetrahydrofuran (2 mL) was added dropwise and the reaction was stirred for 20 minutes before the dropwise addition of iodomethane (0.07 mL, 1.13 mmol). The reaction mixture was stirred for 30 minutes before warming to 60° C. for 24 hours. Additional sodium hydride (23 mg) in tetrahydrofuran (1 mL) was added followed by iodomethane (0.04 mL) in tetrahydrofuran (1 mL) and the reaction was stirred for a further 24 hours at 60° C. The reaction was cooled to room temperature and added dropwise to a saturated solution of NH$_4$Cl solution and extracted with ethyl acetate three times. The organics were combined, dried over anhydrous MgSO$_4$, filtered to remove the solids, and adsorbed on to silica. Purification by column chromatography (0-70% ethyl acetate in cyclohexane) gave methyl 1-methylindoline-5-carboxylate as a white solid (61 mg, 0.32 mmol, 28%). LCMS: MS m/z 192.1 [M+H]$^+$; $^1$H NMR (400 MHz, DMSO) δ 7.67 (dd, J=8.3, 1.8 Hz, 1H), 7.55 (d, J=1.4 Hz, 1H), 6.47 (d, J=8.3 Hz, 1H), 3.74 (s, 3H), 3.43 (t, J=8.5 Hz, 2H), 2.93 (t, J=8.5 Hz, 2H), 2.79 (s, 3H).

Step 2:

A solution of methyl 1-methylindoline-5-carboxylate (147 mg, 0.77 mmol) in acetic acid (1 mL) was cooled to 0° C. in an ice-water bath before the addition of N-chlorosuccinimide (154 mg, 1.15 mmol). The reaction was warmed to 50° C. and stirred overnight. The reaction mixture was cooled to room temperature and diluted with water. The suspension was extracted with ethyl acetate (×3). The organics were combined, dried over anhydrous MgSO$_4$, filtered to remove the solids and concentrated under reduced pressure. Purification by column chromatography (0-60% ethyl acetate in cyclohexane) gave methyl 7-chloro-1-methylindoline-5-carboxylate as a white solid (71 mg, 0.31 mmol, 41%). LCMS: MS m/z 224.1 [M+H]$^+$; $^1$H NMR (600 MHz, DMSO) δ 7.56-7.53 (m, 1H), 7.48 (dd, J=2.9, 1.3 Hz, 1H), 3.76 (s, 3H), 3.51 (t, J=8.9 Hz, 2H), 3.15 (s, 3H), 2.97 (t, J=8.9 Hz, 2H).

Step 3:

Following generic route 4, using methyl 7-chloro-1-methyl-indoline-5-carboxylate, to afford 5-(7-chloro-1-methyl-indolin-5-yl)-1,3,4-oxadiazol-2-ol (22 mg, 0.09 mmol, 28%) as a white solid. LCMS: MS m/z 252.1 [M+H]$^+$; $^1$H NMR (600 MHz, DMSO) δ 12.35 (s, 1H), 7.34 (apparent dt, J=9.2, 1.5 Hz, 2H), 3.48 (t, J=8.8 Hz, 2H), 3.13 (s, 3H), 2.98 (t, J=8.8 Hz, 2H).

Compound 198:
5-(1-methylindolin-6-yl)-1,3,4-oxadiazol-2-ol

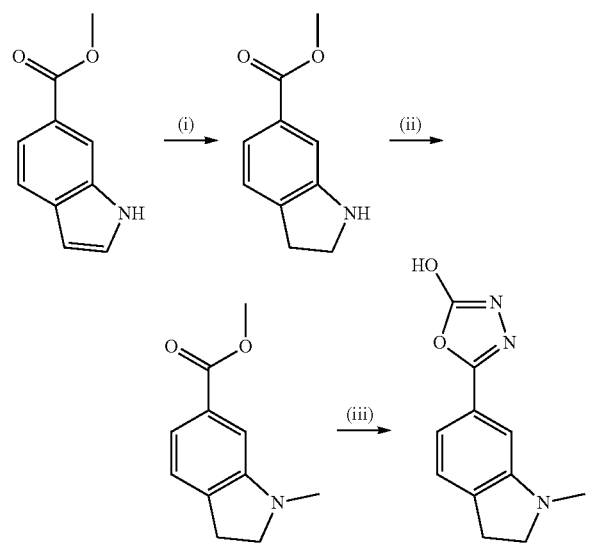

Reagents and conditions: i) sodium cyanoborohydride, acetic acid; ii) Methyl iodide, sodium hydride 60% wt on mineral oil, N,N-dimethylformamide; iii) Generic route 4

Step 1:

A solution of 1H-Indole-5-carboxylic acid methyl ester (1 g, 5.71 mmol) in acetic acid was cooled in an ice-water bath before the addition of sodium cyanoborohydride (1.08 g, 17.18 mmol). The mixture was stirred at room temperature for 1 hour. Water (3 mL) was added and all the solvents were removed under vacuum. The residue was dissolved in ethyl acetate (150 mL) and washed with saturated NaHCO$_3$ (150 mL). The layers were separated and the aqueous layer was extracted with ethyl acetate (3×75 mL). The combined extracts were washed with brine (150 mL), dried over anhydrous MgSO$_4$, filtered and evaporated. Purification by column chromatography (0-50% ethyl acetate in cyclohexane) gave methyl indoline-6-carboxylate (653 mg, 3.7 mmol, 65%) as a white solid. LCMS: MS m/z 178.1 [M+H]$^+$; $^1$H NMR (600 MHz, DMSO) δ 7.16 (dd, J=7.5, 1.5 Hz, 1H), 7.11 (d, J=7.6 Hz, 1H), 7.02 (d, J=1.4 Hz, 1H), 5.74 (s, 1H), 3.46 (td, J=8.6, 1.9 Hz, 2H), 2.96 (dd, J=12.8, 4.6 Hz, 2H).

Step 2:

A solution of methyl indoline-6-carboxylate (200 mg, 1.13 mmol) in N,N-dimethylformamide (3 mL) was cooled to 0° C. in an ice-water bath before the addition of sodium hydride (50 mg, 1.24 mmol). The reaction mixture was stirred for 10 minutes before iodomethane (0.08 mL, 1.24 mmol) was added dropwise. The reaction mixture was warmed to room temperature and stirred for 1 hour. After this time the reaction mixture was diluted with saturated NaHCO$_3$ solution and extracted with ethyl acetate. The organics were dried over anhydrous MgSO$_4$, filtered and concentrated under reduced pressure. Purification by column chromatography (0-50% ethyl acetate in cyclohexane) gave methyl 1-methylindoline-6-carboxylate (102 mg, 0.53 mmol, 47%) as a pale yellow oil. LCMS: MS m/z 192.1 [M+H]$^+$.

Step 3:

Following generic route 4, using methyl 1-methylindoline-6-carboxylate, to afford 5-(1-methylindolin-6-yl)-1,3,4-oxadiazol-2-ol (63 mg, 0.29 mmol, 56% yield) as a white solid. LCMS: MS m/z 218.1 [M+H]$^+$; $^1$H NMR (400 MHz, DMSO) δ 12.46 (s, 1H), 7.16 (d, J=7.6 Hz, 1H), 7.02 (dd, J=7.5, 1.5 Hz, 1H), 6.79 (d, J=1.3 Hz, 1H), 3.35-3.30 (m, 2H), 2.93 (t, J=8.3 Hz, 2H), 2.75 (s, 3H).

Compound 199:
5-(2,3-dichlorophenyl)-1,3,4-oxadiazol-2-ol

Following generic route 3, using 2,3-Dichlorobenzhydrazide, yield=75% (white solid). LCMS: MS m/z 229.0 [M−H]$^-$; $^1$H NMR (600 MHz, DMSO) δ 12.85 (s, 1H), 7.88 (dd, J=8.1, 1.5 Hz, 1H), 7.81 (dd, J=7.9, 1.5 Hz, 1H), 7.55 (apparent t, J=8.0 Hz, 1H).

Compound 200:
5-(2-fluorophenyl)-1,3,4-oxadiazol-2-ol

Following generic route 3, using 2-fluorobenzhydrazide, yield=84% (white solid). LCMS: MS m/z 181.0 [M+H]$^+$; $^1$H NMR (600 MHz, DMSO) δ 12.71 (s, 1H), 7.81 (td, J=7.6, 1.7 Hz, 1H), 7.63 (dddd, J=8.4, 7.2, 5.1, 1.8 Hz, 1H), 7.43 (ddd, J=11.2, 8.4, 0.9 Hz, 1H), 7.38 (td, J=7.7, 1.1 Hz, 1H).

Compound 201: 5-[2-(trifluoromethyl)phenyl]-1,3,4-oxadiazol-2-ol

Following generic route 3, using 2-(trifluoromethyl)benzoic acid hydrazide, yield=82% (white solid). LCMS: MS m/z 229.1 [M−H]$^-$; $^1$H NMR (400 MHz, DMSO) δ 12.85 (s, 1H), 7.97 (dd, J=10.8, 4.5 Hz, 2H), 7.91-7.79 (m, 2H).

Compound 202:
5-(1-isopropylindolin-5-yl)-1,3,4-oxadiazol-2-ol

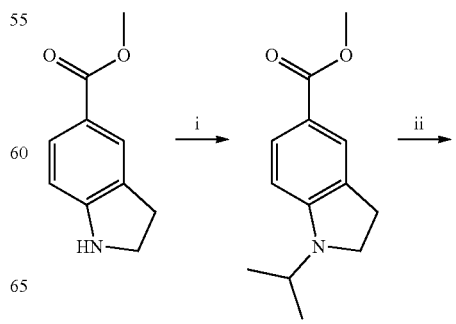

-continued

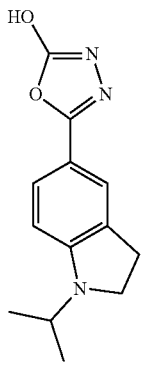

Reagents and conditions: i) acetone, sodium cyanoborohydride, dichloromethane, acetic acid; ii) Generic route 4

Step 1:

To a solution of methyl indoline-5-carboxylate (200 mg, 1.13 mmol) and acetone (0.17 mL, 2.2 6 mmol) in dichloromethane (10 mL) was added acetic acid (0.39 mL, 6.77 mmol). The reaction mixture was stirred at room temperature for 30 minutes before cooling to 0° C. in an ice-water bath. Sodium cyanoborohydride (213 mg, 3.39 mmol) was added in 3 portions. The reaction mixture was stirred at room temperature overnight. The reaction mixture was diluted with dichloromethane (30 mL), washed with saturated solution of NaHCO$_3$(3×30 mL) followed by brine (30 mL) and then dried over anhydrous MgSO$_4$. Purification by column chromatography (0-70% ethyl acetate in cyclohexane) gave methyl 1-isopropylindoline-5-carboxylate (45 mg, 0.21 mmol, 18% yield) as a colourless oil. LCMS: MS m/z 220.1 [M+H]$^+$; $^1$H NMR (400 MHz, DMSO) δ 7.64 (dd, J=8.4, 1.8 Hz, 1H), 7.52 (d, J=1.5 Hz, 1H), 6.44 (d, J=8.4 Hz, 1H), 3.96-3.84 (m, 1H), 3.45 (t, J=8.7 Hz, 2H), 2.93 (t, J=8.6 Hz, 2H), 1.11 (d, J=6.6 Hz, 6H).

Step 2:

Following generic route 4, using methyl 1-isopropylindoline-5-carboxylate, to afford 5-(1-isopropylindolin-5-yl)-1,3,4-oxadiazol-2-ol (26 mg, 0.11 mmol, 52%) as a white solid. LCMS: MS m/z 246.2 [M+H]$^+$; $^1$H NMR (600 MHz, DMSO) δ 12.16 (s, 1H), 7.41 (dd, J=8.3, 1.8 Hz, 1H), 7.37 (d, J=1.4 Hz, 1H), 6.50 (d, J=8.4 Hz, 1H), 3.89 (dq, J=13.3, 6.7 Hz, 1H), 3.43 (t, J=8.6 Hz, 2H), 2.94 (t, J=8.6 Hz, 2H), 1.12 (d, J=6.6 Hz, 6H).

Compound 211: 5-[3-cyclopropyl-5-(trifluoromethyl)phenyl]-1,3,4-oxadiazol-2-ol

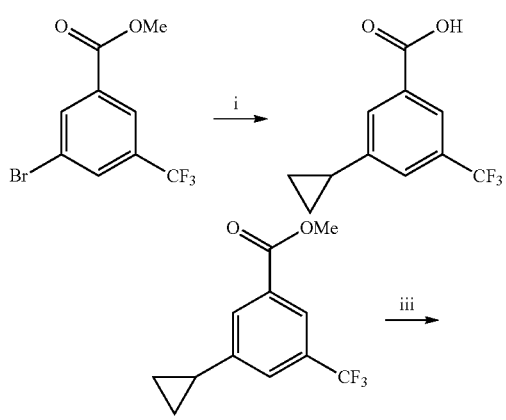

-continued

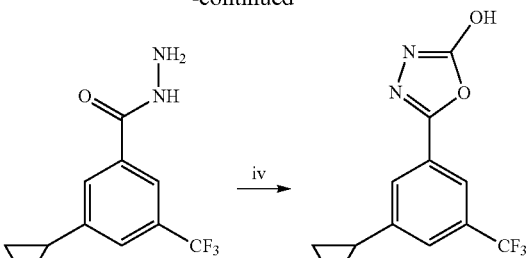

Reagents and conditions: i) Pd(dppf)Cl$_2$·CH$_2$Cl$_2$, cyclopropylboronic acid, 1,4-dioxane, sodium carbonate; ii) thionyl chloride, methanol; iii) hydrazine monohydrate, ethanol, toluene; iv) triphosgene, N,N-diisopropylethylamine, dichloromethane.

Step 1: To a 20 mL microwave vial was added [1,1'-Bis(diphenylphosphino)ferrocene]dichloropalladium(II), complex with dichloromethane (136 mg, 0.17 mmol), methyl 3-bromo-5-(trifluoromethyl)benzoate (943 mg, 3.33 mmol) and cyclopropylboronic acid (572 mg, 6.66 mmol). The vial was capped and evacuated and purged with argon 3 times, then degassed 1,4-dioxane (10 mL) and sodium carbonate (1 M, 10 mL, 10 mmol) were then added. The contents were mixed briefly via magnetic stirrer and evacuated and purged with argon. The vial was placed on to a preheated aluminium heating block at 110° C. and stirred for 3 days. The contents of the vial were then transferred to a round bottomed flask and concentrated under reduced pressure.

Step 2: The crude 3-cyclopropyl-5-(trifluoromethyl)benzoic from step 1, was dissolved in methyl alcohol (30 mL) and cooled in an ice-water bath. The solution was charged with thionyl chloride (0.81 mL, 11.2 mmol) dropwise. After complete addition the reaction was warmed to reflux for 2 hours. After this time the reaction was cooled to room temperature and concentrated under reduced pressure, and the crude material was then purified via silica gel chromatography, eluting with 20% ethyl acetate in cyclohexane to give the methyl ester intermediate as a waxy solid (530 mg, 2.17 mmol, 65%). LCMS: MS m/z not found; $^1$H NMR (600 MHz, MeOD) δ 8.02 (s, 1H), 7.93 (s, 1H), 7.61 (s, 1H), 4.85 (s, 3H), 2.13-2.04 (m, 1H), 1.14-1.04 (m, 2H), 0.83-0.77 (m, 2H).

Step 3:

Following generic route 4, using methyl 3-cyclopropyl-5-(trifluoromethyl)benzoate, yield=30% (white solid). LCMS: MS m/z 269.1 [M−H]$^−$; $^1$H NMR (400 MHz, DMSO) δ 12.77 (s, 1H), 7.77 (s, 1H), 7.72 (s, 1H), 7.63 (s, 1H), 2.23-2.14 (m, 1H), 1.11-1.04 (m, 2H), 0.88-0.82 (m, 2H).

Compound 218: 5-[3-(dimethylamino)phenyl]-1,3,4-oxadiazol-2-ol

Following generic route 3, using 3-(dimethylamino)benzohydrazide, yield=71% (white solid). LCMS: MS m/z 206.1 [M+H]$^+$; $^1$H NMR (600 MHz, CDCl$_3$) δ 9.07 (br s, 1H), 7.31 (apparent t, J=8.3 Hz, 1H), 7.19 (dt, J=7.7, 1.3 Hz, 1H), 7.14 (dd, J=2.7, 1.3 Hz, 1H), 6.85 (br dd, J=8.3, 2.7 Hz, 1H), 3.00 (s, 6H).

Compound 223: 5-(4-chloro-2-methyl-phenyl)-1,3,4-oxadiazol-2-ol

Following generic route 3, using 4-chloro-2-methylbenzhydrazide, yield=99% (white solid). LCMS: MS m/z 211.2

[M+H]⁺; ¹H NMR (600 MHz, CDCl₃) δ 8.62 (br s, 1H), 7.73 (d, J=8.3 Hz, 1H), 7.31-7.29 (m, 2H), 2.58 (s, 3H).

Compound 227: 5-(1-ethylindolin-5-yl)-1,3,4-oxadiazol-2-ol

Following generic route 11, using diethyl sulfate, yield=30% over 2 steps (white solid). LCMS: MS m/z 232.1 [M+H]⁺; ¹H NMR (600 MHz, DMSO) δ 12.16 (s, 1H), 7.42 (dd, J=8.2, 1.8 Hz, 1H), 7.38 (d, J=1.4 Hz, 1H), 6.52 (d, J=8.3 Hz, 1H), 3.45 (t, J=8.6 Hz, 2H), 3.21 (q, J=7.2 Hz, 2H), 2.96 (t, J=8.5 Hz, 2H), 1.10 (t, J=7.2 Hz, 3H).

Compound 228: 5-[1-(cyclopropylmethyl)indolin-5-yl]-1,3,4-oxadiazol-2-ol

Following generic route 11, using 1-(bromomethyl)cyclopropane, yield=24% over 2 steps (white solid). LCMS: MS m/z 258.2 [M+H]⁺; ¹H NMR (600 MHz, DMSO) δ 12.16 (s, 1H), 7.47-7.30 (m, 2H), 6.55 (d, J=8.3 Hz, 1H), 3.57 (t, J=8.6 Hz, 2H), 3.04 (d, J=6.8 Hz, 2H), 2.98 (t, J=8.5 Hz, 2H), 1.04-0.92 (m, 1H), 0.53-0.46 (m, 2H), 0.26-0.17 (m, 2H).

Compound 230: 5-(2-chlorophenyl)-1,3,4-oxadiazol-2-ol

Following generic route 3, using 2-chlorobenzhydrazide, yield=73% (white solid). LCMS: MS m/z 197.1 [M+H]⁺; ¹H NMR (600 MHz, CDCl₃) δ 9.11 (br s, 1H), 7.82 (dd, J=7.9, 1.8 Hz, 1H), 7.54 (dd, J=7.9, 1.4 Hz, 1H), 7.46 (td, J=7.6, 1.8 Hz, 1H), 7.40 (td, J=7.6, 1.4 Hz, 1H).

TABLE 11

Substituted 2-phenyl-1,3,4-oxadiazoles

| Compound Number | R group | Generic Route | IUPAC Name |
|---|---|---|---|
| 109 | 3-CN | 5 | 3-(1,3,4-oxadiazol-2-yl)benzonitrile |
| 110 | 4-ⁱPr | 5 | 2-(4-isopropylphenyl)-1,3,4-oxadiazole |
| 111 | 4-CN | 5 | 4-(1,3,4-oxadiazol-2-yl)benz-onitrile |
| 112 | 4-ᵗBu | 5 | 2-(4-tert-butylphenyl)-1,3,4-oxadiazole |
| 113 | 4-Me | 5 | 2-(p-tolyl)-1,3,4-oxadiazole |
| 114 | 4-F | 5 | 2-(4-fluorophenyl)-1,3,4-oxadiazole |
| 115 | 3-Cl | 5 | 2-(3-chlorophenyl)-1,3,4-oxadiazole |
| 116 | 3-F | 5 | 2-(3-fluorophenyl)-1,3,4-oxadiazole |
| 117 | 3-CF₃ | 5 | 2-[3-(trifluoromethyl)phenyl]-1,3,4-oxadiazole |
| 118 | 3-OMe | 5 | 2-(3-methoxyphenyl)-1,3,4-oxadiazole |
| 181 | 3-(oxetan-3-yl), 4-CF₃ | — | 2-[3-(oxetan-3-yl)-4-(trifluoromethyl)phenyl]-1,3,4-oxadiazole |
| 188 | 3-(oxetan-3-yl), 5-CF₃ | — | 2-[3-(oxetan-3-yl)-5-(trifluoromethyl)phenyl]-1,3,4-oxadiazole |
| 189 | 3-cyclopropyl, 4-CF₃ | 5 | 2-[3-cyclopropyl-4-(trifluoromethyl)phenyl]-1,3,4-oxadiazole |

TABLE 11-continued

Substituted 2-phenyl-1,3,4-oxadiazoles

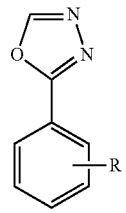

| Compound Number | R group | Generic Route | IUPAC Name |
|---|---|---|---|
| 192 | 3-CF3, 4-cyclopropyl | 5 | 2-[4-cyclopropyl-3-(trifluoromethyl)phenyl]-1,3,4-oxadiazole |
| 196 | 3-CF$_3$, 4-Cl | 5 | 2-[4-chloro-3-(trifluoromethyl)phenyl]-1,3,4-oxadiazole |
| 203 | 2-F | 5 | 2-(2-fluorophenyl)-1,3,4-oxadiazole |
| 204 | 2,3-Cl | 5 | 2-(2,3-dichlorophenyl)-1,3,4-oxadiazole |
| 210 | 3-cyclopropyl, 5-CF$_3$ | 5 | 2-[3-cyclopropyl-5-(trifluoromethyl)phenyl]-1,3,4-oxadiazole |
| 219 | 6-cyclohexyl | 5 | 2-(4-cyclohexylphenyl)-1,3,4-oxadiazole |
| 220 | 6-cyclopentyl | 5 | 2-(4-cyclopentylphenyl)-1,3,4-oxadiazole |
| 224 | 2-CF$_3$ | 5 | 2-[2-(trifluoromethyl)phenyl]-1,3,4-oxadiazole |
| 225 | 2-Cl | 5 | 2-(2-chlorophenyl)-1,3,4-oxadiazole |
| 231 | 2-Me, 4-Cl | 5 | 2-(4-chloro-2-methyl-phenyl)-1,3,4-oxadiazole |
| 232 | 3-NMe$_2$ | 5 | N,N-dimethyl-3-(1,3,4-oxadiazol-2-yl)aniline |

Compound 109: 3-(1,3,4-oxadiazol-2-yl)benzonitrile

Following generic route 5, using 3-cyanobenzohydrazide, yield=61% (white solid). LCMS: MS m/z 172.1 [M+H]$^+$; $^1$H NMR (600 MHz, CDCl$_3$) δ 8.54 (s, 1H), 8.38-8.35 (m, 2H), 7.86 (apparent dt, J=7.8, 1.4 Hz, 1H), 7.70 (apparent t, J=7.8 Hz, 1H).

Compound 110: 2-(4-isopropylphenyl)-1,3,4-oxadiazole

Following generic route 5, using 4-isopropylbenzohydrazide, yield=69% (white solid). LCMS: MS m/z 189.1 [M+H]$^+$; $^1$H NMR (600 MHz, DMSO) δ 9.31 (s, 1H), 8.01-7.87 (m, 2H), 7.48 (d, J=8.2 Hz, 2H), 2.99 (apparent dt, J=13.8, 6.9 Hz, 1H), 1.24 (d, J=6.9 Hz, 6H).

Compound 111: 4-(1,3,4-oxadiazol-2-yl)benzonitrile

Following generic route 5, using 4-cyanobenzohydrazide, yield=92% (white solid). LCMS: MS m/z 172.1 [M+H]$^+$; $^1$H NMR (600 MHz, CDCl$_3$) δ 8.55 (s, 1H), 8.24-8.22 (m, 2H), 7.85-7.83 (m, 2H).

Compound 112: 2-(4-tert-butylphenyl)-1,3,4-oxadiazole

Following generic route 5, using 4-(tert-butyl)benzenecarbohydrazide, yield=54% (colourless oil). LCMS: MS m/z 203.2 [M+H]⁺; ¹H NMR (600 MHz, CDCl₃) δ 8.45 (s, 1H), 8.03-8.01 (m, 2H), 7.56-7.54 (m, 2H), 1.37 (s, 9H).

Compound 113: 2-(p-tolyl)-1,3,4-oxadiazole

Following generic route 5, using p-toluic hydrazide, yield=85% (white solid). LCMS: MS m/z 161.1 [M+H]⁺; ¹H NMR (600 MHz, DMSO) δ 9.31 (s, 1H), 7.96-7.88 (m, 2H), 7.41 (d, J=7.9 Hz, 2H), 2.39 (s, 3H).

Compound 114: 2-(4-fluorophenyl)-1,3,4-oxadiazole

Following generic route 5, using 4-fluorobenzhydrazide, yield=80% (white solid). LCMS: MS m/z 165.0 [M+H]⁺; ¹H NMR (600 MHz, DMSO) δ 9.34 (s, 1H), 8.14-8.04 (m, 2H), 7.51-7.39 (m, 2H).

Compound 115 2-(3-chlorophenyl)-1,3,4-oxadiazole

Following generic route 5, using 3-chlorobenzohydrazide, yield=62% (white solid). LCMS: MS m/z 181.0 [M+H]⁺; ¹H NMR (600 MHz, DMSO) δ 9.41 (s, 1H), 8.02 (apparent t, J=4.7 Hz, 1H), 8.00 (dd, J=7.7, 1.0 Hz, 1H), 7.76-7.70 (m, 1H), 7.65 (apparent t, J=7.9 Hz, 1H).

Compound 116 2-(3-fluorophenyl)-1,3,4-oxadiazole

Following generic route 5, using 3-fluorobenzoic hydrazide, yield=50% (white solid). LCMS: MS m/z 165.0 [M+H]⁺; ¹H NMR (600 MHz, DMSO) δ 9.40 (s, 1H), 7.91-7.86 (m, 1H), 7.82 (ddd, J=9.4, 2.5, 1.5 Hz, 1H), 7.68 (td, J=8.1, 5.9 Hz, 1H), 7.54-7.49 (m, 1H).

Compound 117 2-[3-(trifluoromethyl)phenyl]-1,3,4-oxadiazole

Following generic route 5, using 3-trifluormethylbenzoic acid hydrazide, yield=72% (white solid). LCMS: MS m/z 215.1 [M+H]⁺; ¹H NMR (600 MHz, DMSO) δ 9.44 (s, 1H), 8.38-8.31 (m, 1H), 8.28 (s, 1H), 8.04 (d, J=7.9 Hz, 1H), 7.88 (apparent t, J=7.9 Hz, 1H).

Compound 118
2-(3-methoxyphenyl)-1,3,4-oxadiazole

Following generic route 5, using 3-methoxybenzohydrazide, yield=38% (white solid). LCMS: MS m/z 177.1 [M+H]⁺; ¹H NMR (600 MHz, DMSO) δ 9.35 (s, 1H), 7.61 (dd, J=7.6, 0.9 Hz, 1H), 7.55-7.50 (m, 2H), 7.30-7.14 (m, 1H), 3.86 (s, 3H).

Compound 181: 2-[3-(oxetan-3-yl)-4-(trifluoromethyl)phenyl]-1,3,4-oxadiazole

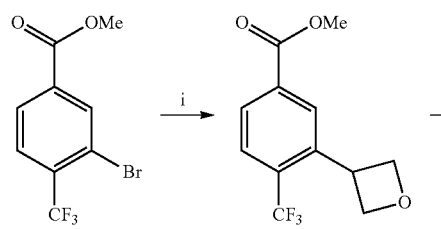

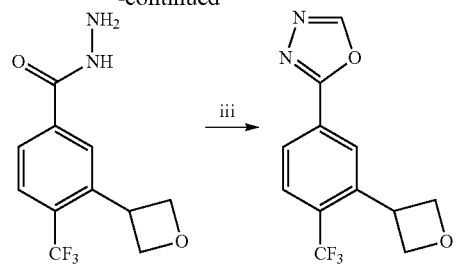

Reagents and conditions: i) Ir[dF(CF₃)ppy]₂(dtbbpy)PF₆, [(CH₃)₃Si]SiH, NiCl₂•glyme, 4,4'-di-tert-butyl-2,2'-bipyridine, sodium carbonate, 1,2-dimethoxyethane; ii) hydrazine monohydrate, ethanol, toluene; iii) triethyl orthoformate, p-toluene sulfonic acid monohydrate.

Step 1:
To a 10 mL microwave vial under an atmosphere of air was added photocatalyst [4,4'-bis(1,1-dimethylethyl)-2,2'-bipyridine-N¹,N¹']bis[3,5-difluoro-2-[5-(trifluoromethyl)-2-pyridinyl-N]phenyl-C]Iridium(III) hexafluorophosphate (2.8 mg, 25 μmol), methyl 3-bromo-4-(trifluoromethyl)benzoate (355 mg, 1.25 mmol), 3-bromooxetane (103 uL, 1.25 mmol), tris(trimethylsilyl)silane (386 uL, 1.25 mmol), disodium carbonate (265 mg, 2.50 mmol). A stirrer bar was then added and the vessel was sealed. The vessel was evacuated under vacuum, then back-filled with argon (process repeated three times), before addition of ethylene glycol dimethyl ether (10 mL). The mixture was then further deoxygenated by sparging with argon for 10 minutes. To a separate microwave vial under an atmosphere of air, was added nickel(II) chloride ethylene glycol dimethyl ether complex (6.0 mg, 30 μmol) and 4,4'-di-tert-butyl-2,2'-dipyridyl (7.8 mg, 30 μmol). A stirrer bar was then added and the vessel was sealed. The vessel was evacuated under vacuum, then back-filled with argon (process repeated three times), before addition of ethylene glycol dimethyl ether (12 mL). The mixture was then further deoxygenated by sparging with argon for 5 minutes under stirring to ensure catalyst dissolved. The nickel (II) precatalyst solution (2.5 mL) was then added to the iridium photocatalyst solution. The mixture was then further deoxygenated by sparging with argon for 5 minutes. The vessel was then stirred at room temperature and irradiated with blue strip LED lights for 5 hours at room temperature. The reaction mixture was then concentrated under reduced pressure and purified by silica gel chromatography, eluting with 0-20% ethyl acetate in cyclohexane. The desired fractions were then concentrated under reduced pressure to give methyl 3-(oxetan-3-yl)-4-(trifluoromethyl)benzoate (114 mg, 0.26 mmol, 21% yield, 59% purity) as a clear colourless oil. LCMS: MS m/z not found; ¹H NMR (400 MHz, CDCl₃) δ 8.51 (s, 1H), 8.04 (d, J=8.1 Hz, 1H), 7.73 (d, J=8.1 Hz, 1H), 5.08 (dd, J=8.2, 6.2 Hz, 2H), 4.83 (apparent t, J=6.5 Hz, 2H), 4.75-4.65 (m, 1H), 3.99 (s, 3H).

Step 2 & 3:
Following generic route 5, using methyl 3-(oxetan-3-yl)-4-(trifluoromethyl)benzoate yield=29% (white solid). LCMS: MS m/z 271.1[M+H]⁺; ¹H NMR (400 MHz, MeOD) δ 9.13 (s, 1H), 8.63 (s, 1H), 8.17 (d, J=8.1 Hz, 1H), 7.93 (d, J=8.1 Hz, 1H), 5.12 (dd, J=8.1, 6.2 Hz, 2H), 4.87-4.83 (m, 2H), 4.76 (s, 1H).

Compound 188: 2-[3-(oxetan-3-yl)-5-(trifluoromethyl)phenyl]-1,3,4-oxadiazole

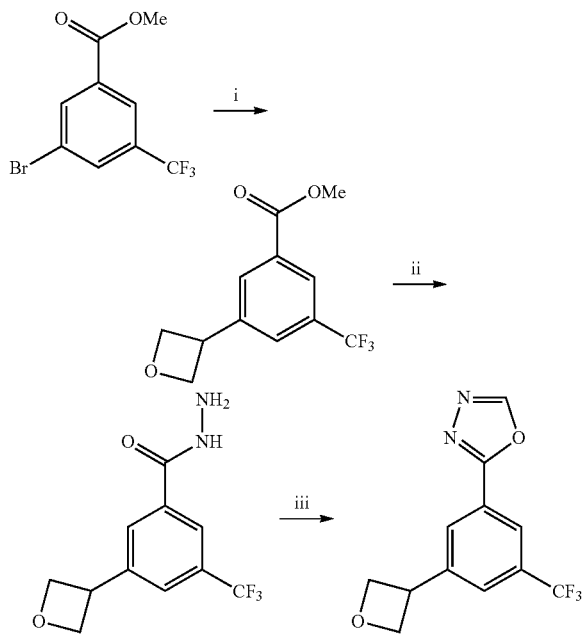

Reagents and conditions: i) Ir[dF(CF₃)ppy]₂(dtbbpy)PF₆, [(CH₃)₃Si]SiH, NiCl₂•glyme, 4,4'-di-tert-butyl-2,2'-bipyridine, sodium carbonate, 1,2-dimethoxyethane; ii) hydrazine monohydrate, ethanol, toluene; iii) triethyl orthoformate, p-toluene sulfonic acid monohydrate.

Step 1: To a 10 mL microwave vial under an atmosphere of air was added photocatalyst [4,4'-bis(1,1-dimethylethyl)-2,2'-bipyridine-N¹,N¹']bis[3,5-difluoro-2-[5-(trifluoromethyl)-2-pyridinyl-N]phenyl-C]Iridium(III) hexafluorophosphate (16.7 mg, 10 µmol), methyl 3-bromo-5-(trifluoromethyl)benzoate (425 mg, 1.50 mmol), 3-bromooxetane (124 uL, 1.5 mmol), tris(trimethylsilyl) silane (463 uL, 1.5 mmol), disodium carbonate (320 mg, 3.0 mmol). A stirrer bar was then added and the vessel was sealed. The vessel was evacuated under vacuum, then back-filled with argon (process repeated three times), before addition of ethylene glycol dimethyl ether (12 mL). The mixture was then further deoxygenated by sparging with argon for 10 minutes. To a separate microwave vial under an atmosphere of air, was added nickel(II) chloride ethylene glycol dimethyl ether complex (6.0 mg, 30 µmol) and 4,4'-di-tert-butyl-2,2'-dipyridyl (7.8 mg, 30 µmol). A stirrer bar was then added and the vessel was sealed. The vessel was evacuated under vacuum, then back-filled with argon (process repeated three times), before addition of ethylene glycol dimethyl ether (12 mL). The mixture was then further deoxygenated by sparging with argon for 5 minutes under stirring to ensure catalyst dissolved. The nickel (II) precatalyst solution (3.0 mL) was then added to the iridium photocatalyst solution. The mixture was then further deoxygenated by sparging with argon for 5 minutes. The vessel was then stirred at room temperature and irradiated with blue strip LED lights for 5 hours at room temperature. The reaction mixture was then concentrated under reduced pressure and purified by silica gel chromatography, eluting with 0-20% ethyl acetate in cyclohexane. The desired fractions were then concentrated under reduced pressure to give methyl 3-(oxetan-3-yl)-5-(trifluoromethyl)benzoate (153 mg, 0.53 mmol, 35% yield, 90% purity) as a clear colourless oil. LCMS: MS m/z not found; ¹H NMR (400 MHz, CDCl₃) δ 8.29 (s, 1H), 8.22 (s, 1H), 7.82 (s, 1H), 5.14 (dd, J=8.3, 6.3 Hz, 2H), 4.77 (d, J=6.4 Hz, 2H), 4.41-4.26 (m, 1H), 3.97 (s, 3H).

Step 2 & 3:
Following generic route 5, using methyl 3-(oxetan-3-yl)-5-(trifluoromethyl)benzoate yield=69% (white solid). LCMS: MS m/z 271.1 [M+H]⁺; ¹H NMR (600 MHz, DMSO) δ 10.27 (s, 1H), 9.17 (s, 1H), 8.99 (s, 1H), 8.84 (s, 1H), 5.82 (dd, J=8.3, 6.3 Hz, 2H), 5.50 (apparent t, J=6.3 Hz, 2H), 5.34-5.28 (m, 1H).

Compound 189: 2-[3-cyclopropyl-4-(trifluoromethyl)phenyl]-1,3,4-oxadiazole

Following generic route 5, using 3-cyclopropyl-4-(trifluoromethyl)benzohydrazide, yield=74% (white solid). LCMS: MS m/z 255.1 [M+H]⁺; ¹H NMR (600 MHz, DMSO) δ 9.43 (s, 1H), 7.99 (d, J=8.2 Hz, 1H), 7.90 (d, J=8.2 Hz, 1H), 7.69 (s, 1H), 2.28-2.15 (m, 1H), 1.16-1.09 (m, 2H), 0.94-0.86 (m, 2H).

Compound 192: 2-[4-cyclopropyl-3-(trifluoromethyl)phenyl]-1,3,4-oxadiazole

Following generic route 5, using 4-cyclopropyl-3-(trifluoromethyl)benzohydrazide, yield=64% (white solid). LCMS: MS m/z 255.1 [M+H]⁺; ¹H NMR (600 MHz, DMSO) δ 9.39 (s, 1H), 8.19 (d, J=1.6 Hz, 1H), 8.16 (dd, J=8.3, 1.7 Hz, 1H), 7.37 (d, J=8.3 Hz, 1H), 2.24-2.12 (m, 1H), 1.19-1.11 (m, 2H), 0.96-0.88 (m, 2H).

Compound 196: 2-[4-chloro-3-(trifluoromethyl)phenyl]-1,3,4-oxadiazole

Following generic route 5, using 4-chloro-3-(trifluoromethyl)benzohydrazide, yield=63% (white solid). LCMS: MS m/z 249.1 [M+H]⁺; ¹H NMR (600 MHz, DMSO) δ 9.46 (s, 1H), 8.34 (d, J=2.0 Hz, 1H), 8.31 (dd, J=8.4, 2.0 Hz, 1H), 8.00 (d, J=8.4 Hz, 1H).

Compound 203: 2-(2-fluorophenyl)-1,3,4-oxadiazole

Following generic route 5, using 2-fluorobenzhydrazide yield=73% (colourless oil). LCMS: MS m/z 165.0 [M+H]⁺; ¹H NMR (600 MHz, DMSO) δ 9.42 (s), 8.08-8.02 (m, 1H), 7.73-7.66 (m, 1H), 7.53-7.40 (m, 2H).

Compound 204: 2-(2,3-dichlorophenyl)-1,3,4-oxadiazole

Following generic route 5, using 2,3-dichlorobenzhydrazide yield=78% (white solid). LCMS: MS m/z 215.0 [M+H]⁺; ¹H NMR (600 MHz, DMSO) δ 9.50 (s, 1H), 7.97-7.90 (m, 2H), 7.60 (apparent t, J=8.0 Hz, 1H).

Compound 210: 2-[3-cyclopropyl-5-(trifluoromethyl)phenyl]-1,3,4-oxadiazole

Following generic route 5, using 3-cyclopropyl-5-(trifluoromethyl)benzohydrazide, yield=49% (white solid). LCMS: MS m/z 251.1 [M+H]⁺; ¹H NMR (400 MHz, DMSO) δ 9.43 (s, 1H), 8.02 (s, 1H), 7.97 (s, 1H), 7.71 (s, 1H), 2.27-2.19 (m, 1H), 1.13-1.06 (m, 2H), 0.91-0.86 (m, 2H).

Compound 219: 2-(4-cyclohexylphenyl)-1,3,4-oxadiazole

Following generic route 5, using 6-(trifluoromethyl)pyridine-2-carbohydrazide (prepared following generic route 3), yield=32% (white solid). LCMS: MS m/z 229.2 [M+H]⁺; ¹H NMR (600 MHz, DMSO) δ 9.31 (s, 1H), 7.97-7.92 (m, 2H), 7.49-7.43 (m, 2H), 2.64-2.58 (m, 1H), 1.84-1.69 (m, 5H), 1.48-1.34 (m, 4H), 1.29-1.22 (m, 1H).

Compound 220: 2-(4-cyclopentylphenyl)-1,3,4-oxadiazole

Following generic route 5, using 4-cyclopentylbenzohydrazide, yield=35% (white solid). LCMS: MS m/z 215.1 [M+H]+; 1H NMR (600 MHz, DMSO) δ 9.30 (s, 1H), 7.95-7.92 (m, 2H), 7.50-7.47 (m, 2H), 3.11-3.03 (m, 1H), 2.11-1.99 (m, 2H), 1.84-1.75 (m, 2H), 1.72-1.63 (m, 2H), 1.61-1.52 (m, 2H).

Compound 224: 2-[2-(trifluoromethyl)phenyl]-1,3,4-oxadiazole

Following generic route 5, using 2-(trifluoromethyl)benzoic acid hydrazide, yield=49% (colourless oil). LCMS: MS m/z 215.1 [M+H]+; 1H NMR (600 MHz, CDCl3) δ 8.57 (s, 1H), 8.04 (m, 1H), 7.87 (m, 1H), 7.74-7.69 (m, 2H).

Compound 225: 2-(2-chlorophenyl)-1,3,4-oxadiazole

Following generic route 5, using 2-chlorobenzhydrazide, yield=51% (colourless oil). LCMS: MS m/z 181.1 [M+H]+; 1H NMR (600 MHz, CDCl3) δ 8.55 (s, 1H), 7.99 (dd, J=7.8, 1.7 Hz, 1H), 7.56 (dd, J=7.8, 1.2 Hz, 1H), 7.48 (td, J=7.7, 1.6 Hz, 1H), 7.41 (td, J=7.7, 1.2 Hz, 1H).

Compound 231: 2-(4-chloro-2-methyl-phenyl)-1,3,4-oxadiazole

Following generic route 5, using 4-chloro-2-methylbenzhydrazide, yield=66% (white solid). LCMS: MS m/z 195.1 [M+H]+; 1H NMR (600 MHz, CDCl3) δ 8.49 (s, 1H), 7.89 (d, J=8.4 Hz, 1H), 7.37 (apparent d, J=2.0 Hz, 1H), 7.33 (apparent dd, J=8.4, 2.0 Hz, 1H), 2.72 (s, 3H).

Compound 232: N,N-dimethyl-3-(1,3,4-oxadiazol-2-yl)aniline

Following generic route 5, using 3-(dimethylamino)benzohydrazide, yield=58% (colourless gum). LCMS: MS m/z 190.1 [M+H]+; 1H NMR (600 MHz, CDCl3) δ 8.44 (s, 1H), 7.43 (m, 1H), 7.39-7.33 (m, 2H), 6.89 (m, 1H), 3.03 (s, 6H).

TABLE 12

Substituted (5-phenylisoxazol-3-yl)methanol

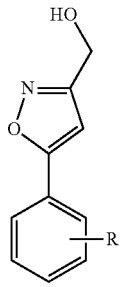

| Compound Number | R group | IUPAC Name |
|---|---|---|
| 121 | 3-CF3, 4-Cl | (5-(4-chloro-3-(trifluoromethyl)phenyl)isoxazol-3-yl)methanol |
| 122 | 3,4-Cl | (5-(3,4-dichlorophenyl)isoxazol-3-yl)methanol |

Compound 121: (5-(4-chloro-3-(trifluoromethyl)phenyl)isoxazol-3-yl)methanol

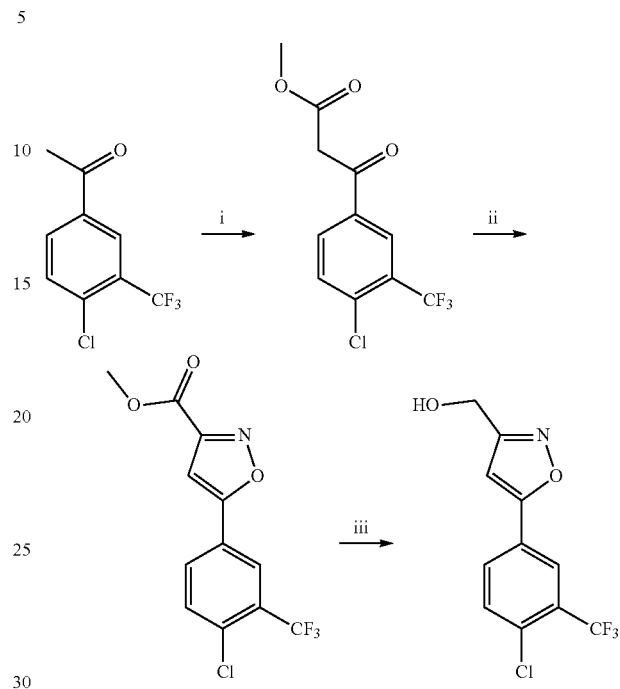

Reagents and conditions: i) Dimethyl oxalate, potassium tert-butoxide, toluene; ii) hydroxylamine hydrochloride, methanol; iii) sodium borohydride, methanol.

Step 1:

To a solution of dimethyl oxalate (292 mg, 2.47 mmol) and 1-[4-chloro-3-(trifluoromethyl)phenyl]ethanone (500 mg, 2.25 mmol) in toluene (9 mL) was added potassium tert-butoxide (302 mg, 2.7 mmol). The solution was stirred at room temperature overnight. The reaction was quenched with 1 N HCl and extracted with ethyl acetate (×3). The combined organic layers were dried over anhydrous MgSO4, filtered and concentrated under reduced pressure to provide crude methyl 3-(4-chloro-3-(trifluoromethyl)phenyl)-3-oxopropanoate, which was used without further purification.

Step 2:

Crude methyl 3-(4-chloro-3-(trifluoromethyl)phenyl)-3-oxopropanoate was dissolved in methanol (9 mL) and hydroxylamine hydrochloride (0.14 mL, 3.37 mmol) was added. The solution was heated to 50° C. for 6 hours. The solvent was removed under reduced pressure. Purification by column chromatography (0-20% ethyl acetate in cyclohexane) gave methyl 5-(4-chloro-3-(trifluoromethyl)phenyl)isoxazole-3-carboxylate as a white solid (436 mg, 1.43 mmol, 64% over 2 steps). LCMS: MS m/z not found; 1H NMR (600 MHz, DMSO) δ 8.39 (d, J=1.9 Hz, 1H), 8.26 (dd, J=8.4, 2.0 Hz, 1H), 7.94 (d, J=8.4 Hz, 1H), 7.83 (s, 1H), 3.94 (s, 3H).

Step 3:

To a solution of methyl 5-[4-chloro-3-(trifluoromethyl)phenyl]isoxazole-3-carboxylate (200 mg, 0.65 mmol) in methanol (3 mL) was added sodium borohydride (99 mg, 2.62 mmol). The reaction was warmed to 40° C. and stirred overnight. After this time the reaction was added dropwise to a saturated solution of NH4Cl and extracted with ethyl acetate(×3). The organics were combined, dried over anhydrous MgSO$_4$, filtered to remove the solids and adsorbed on to silica. Purification by column chromatography (0-40% ethyl acetate in cyclohexane) gave (5-(4-chloro-3-(trifluoromethyl)phenyl)isoxazol-3-yl)methanol as a white solid (160 mg, 0.58 mmol, 88%). LCMS: MS m/z 278.1 [M+H]$^+$; $^1$H NMR (600 MHz, DMSO) δ 8.28 (d, J=1.5 Hz, 1H), 8.19 (dd, J=8.4, 1.7 Hz, 1H), 7.91 (d, J=8.4 Hz, 1H), 7.31 (s, 1H), 5.61 (t, J=5.9 Hz, 1H), 4.57 (d, J=5.9 Hz, 2H).

Compound 122:
(5-(3,4-dichlorophenyl)isoxazol-3-yl)methanol

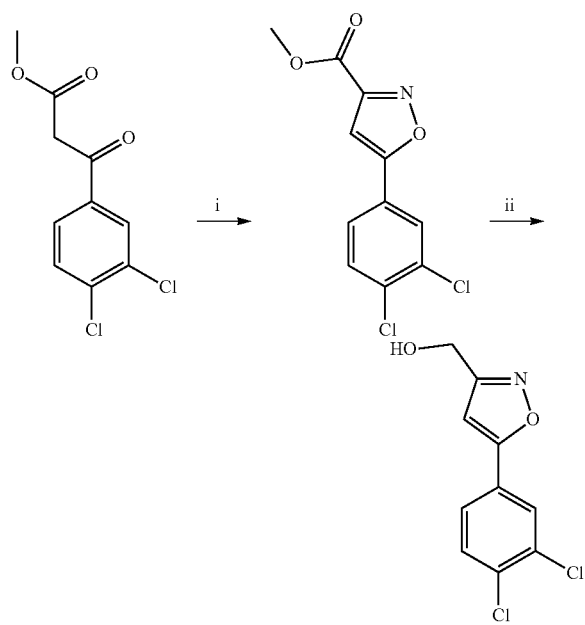

Reagents and conditions: i) Hydroxylamine hydrochloride, methanol; ii) Lithium aluminium hydride, tetrahydrofuran.

Step 1:
Methanol (50 mL) was added to a mixture of hydroxylamine hydrochloride (140 mg, 2.0 mmol) and methyl 4-(3,4-dichlorophenyl)-2,4-dioxobutanoate (557 mg, 2.0 mmol) and the resulting suspension was heated to 65° C. for 5 hours.

The reaction mixture was then cooled to room temperature, concentrated under reduced pressure then purified by column chromatography (40% ethyl acetate in cyclohexane) to give methyl 5-(3,4-dichlorophenyl)isoxazole-3-carboxylate (140 mg, 0.51 mmol, 25%) as a white solid. $^1$H NMR (600 MHz, DMSO) δ 8.30 (d, J=2.0 Hz, 1H), 7.96 (dd, J=8.5 Hz, J=2.0 Hz, 1H), 7.85 (d, J=8.5 Hz, 1H), 7.71 (s, 1H), 3.93 (s, 3H).

Step 2:
Lithium aluminium hydride (1 M in tetrahydrofuran, 200 μL, 0.2 mmol) was added dropwise to a solution of methyl 5-(3,4-dichlorophenyl)isoxazole-3-carboxylate (140 mg, 0.5 mmol) in anhydrous tetrahydrofuran (5 mL) at 0° C. (external). The solution was then stirred for 20 minutes, saturated aqueous ammonium chloride (5 mL) was then added dropwise, before acidifying to pH 1 with aqueous hydrochloric acid (2 N, 0.5 mL). The organics were then removed under reduced pressure, the mixture was then diluted with dichloromethane. The organic phase was then dried over anhydrous MgSO$_4$, filtered and concentrated under reduced pressure. Purification by column chromatography (10-40% ethyl acetate in cyclohexane) gave [5-(3,4-dichlorophenyl)isoxazol-3-yl]methanol as a white solid (85 mg, 0.4 mmol, 68%). LCMS: MS m/z 244.1 [M+H]$^+$; $^1$H NMR (600 MHz, DMSO) δ 8.19 (d, J=2.0 Hz, 1H), 7.87 (dd, J=8.4 Hz, 2.0 Hz, 1H), 7.81 (d, J=8.4 Hz, 1H), 7.19 (s, 1H), 5.59 (t, J=5.9 Hz, 1H), 4.55 (d, J=5.9 Hz, 2H).

TABLE 13

2-(6-chloropyridin-3-yl)-1,3,4-oxadiazole

| Compound Number | Generic Route | IUPAC Name |
|---|---|---|
| 124 | 5 | 2-(6-chloropyridin-3-yl)-1,3,4-oxadiazole |

Compound 124:
2-(6-chloropyridin-3-yl)-1,3,4-oxadiazole

Following generic route 5, using 6-chloronicotinohydrazide, yield=63% (white solid). LCMS: MS m/z 182.0 [M+H]$^+$; $^1$H NMR (600 MHz, DMSO) δ 9.47 (s, 1H), 9.04 (dd, J=2.5, 0.7 Hz, 1H), 8.45 (dd, J=8.4, 2.5 Hz, 1H), 7.82-7.75 (m, 1H).

TABLE 14

2-(chloromethyl)-5-(3,4-dichlorophenyl)-1,3,4-oxadiazole

| Compound Number | IUPAC Name |
|---|---|
| 125 | 2-(chloromethyl)-5-(3,4-dichlorophenyl)-1,3,4-oxadiazole |

Compound 125: 2-(chloromethyl)-5-(3,4-dichlorophenyl)-1,3,4-oxadiazole

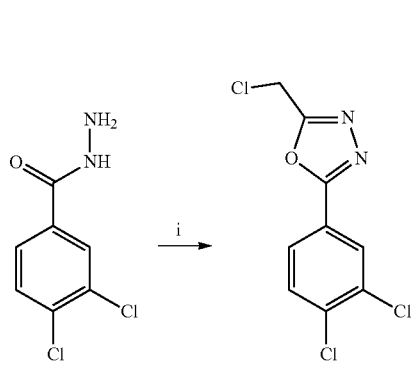

Reagents and conditions: (i) POCl₃, chloroacetyl chloride, reflux

A round bottomed flask was charged with 3,4-dichlorobenzohydrazide (500 mg, 2.44 mmol), phosphorus(V) oxychloride (1.71 mL, 18.3 mmol) and chloroacetyl chloride (0.19 mL, 2.44 mmol). The reaction mixture was heated at reflux overnight. After this time the reaction mixture was cooled to room temperature and concentrated under reduced pressure. The remaining residue was charged with crushed ice and water. The resulting suspension was then added to sat. NaHCO₃aq. solution and stirred for 10 minutes. The aqueous layer was extracted with dichloromethane. The organics were washed with water (×1) and brine (×1), dried over anhydrous MgSO₄, filtered and adsorbed on to silica. Purification by column chromatography (0-100% ethyl acetate in cyclohexane) gave 2-(chloromethyl)-5-(3,4-dichlorophenyl)-1,3,4-oxadiazole as a white solid (426 mg, 1.62 mmol, 66%). LCMS: MS m/z 265.0 [M+H]⁺; ¹H NMR (400 MHz, DMSO) δ 8.20 (d, J=2.0 Hz, 1H), 7.99 (dd, J=8.4, 2.0 Hz, 1H), 7.90 (d, J=8.4 Hz, 1H), 5.15 (s, 2H).

TABLE 157

| [5-(3,4-dichlorophenyl)-1,3,4-oxadiazol-2-yl]methanol |
|---|
| 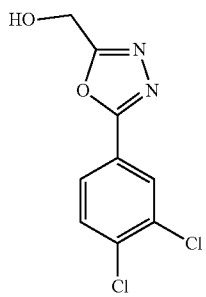 [SMILES: OCc1nnc(-c2ccc(Cl)c(Cl)c2)o1] |

| Compound Number | IUPAC Name |
|---|---|
| 126 | [5-(3,4-dichlorophenyl)-1,3,4-oxadiazol-2-yl]methanol |

Compound 126: [5-(3,4-dichlorophenyl)-1,3,4-oxadiazol-2-yl]methanol

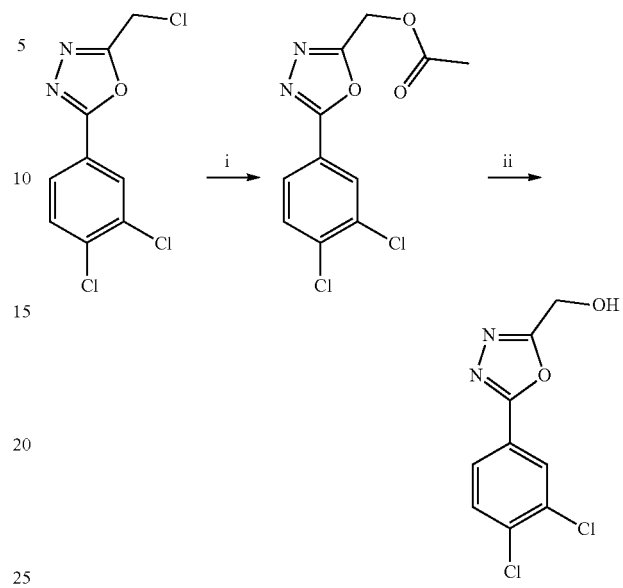

Reagents and conditions: i) Sodium acetate, acetonitrile, 80° C.; ii) K₂CO₃, methanol.

To a solution of 2-(chloromethyl)-5-(3,4-dichlorophenyl)-1,3,4-oxadiazole (100 mg, 0.38 mmol) in acetonitrile (3 mL) was added sodium acetate (62 mg, 0.76 mmol). The reaction was heated at 80° C. for 18 hours. The cooled mixture was concentrated under reduced pressure and the residue was partitioned between water and ethyl acetate. The organic phase was washed with brine, dried over anhydrous MgSO₄ and concentrated under reduced pressure. The residual oil was dissolved in methanol (3 mL), and potassium carbonate (105 mg, 0.76 mmol) and water (1 mL). The mixture was stirred at room temperature for 2 hours and then concentrated under reduced pressure. The residue was partitioned between ethyl acetate and water. The organics were washed with water (×1) and brine (×1), dried over anhydrous MgSO₄, filtered and adsorbed on to silica. Purification by column chromatography (0-10% methanol in dichloromethane) gave [5-(3,4-dichlorophenyl)-1,3,4-oxadiazol-2-yl]methanol as a white solid (66 mg, 0.27 mmol, 71%). LCMS: MS m/z 245.1 [M+H]⁺; ¹H NMR (600 MHz, DMSO) δ 8.18 (d, J=2.0 Hz, 1H), 7.97 (dd, J=8.4, 2.0 Hz, 1H), 7.89 (d, J=8.4 Hz, 1H), 5.97 (t, J=6.3 Hz, 1H), 4.73 (t, J=5.9 Hz, 2H).

TABLE 16

| [1-(3,4-dichlorophenyl)imidazol-4-yl]methanol |
|---|
| 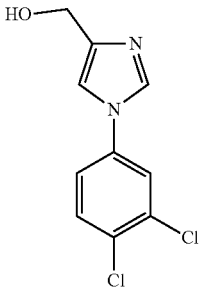 [SMILES: OCc1cn(-c2ccc(Cl)c(Cl)c2)cn1] |

| Compound Number | IUPAC Name |
|---|---|
| 127 | [1-(3,4-dichlorophenyl)imidazol-4-yl]methanol |

Compound 127: [1-(3,4-dichlorophenyl)imidazol-4-yl]methanol

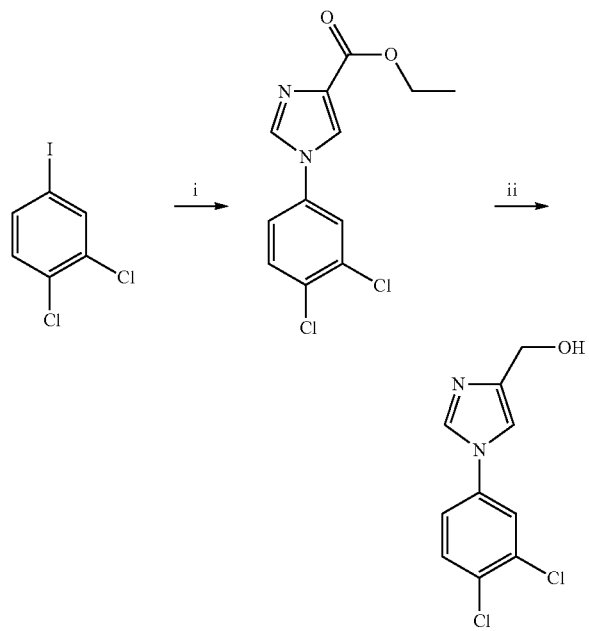

Reagents and conditions: (i) Ethyl imidazole-4-carboxylate, iodocopper, $K_2CO_3$, dimethyl sulfoxide, 110° C.; ii) Lithium aluminum hydride, tetrahydrofuran, 0° C.

Step 1:

A mixture of 1,2-dichloro-4-iodo-benzene (974 mg, 3.57 mmol), ethyl imidazole-4-carboxylate (500 mg, 3.57 mmol), iodocopper (136 mg, 0.71 mmol), and potassium carbonate (1479 mg, 10.7 mmol) in dimethyl sulfoxide (7 mL, 3.57 mmol) was evacuated and back-filled with nitrogen for three times, and heated to 110° C. for 16 hours. The cooled reaction mixture was diluted with ethyl acetate and water. The organics were separated, washed with water (×1), brine (×1), dried over anhydrous $MgSO_4$, filtered and adsorbed on to silica. Purification by column chromatography (0-100% ethyl acetate in cyclohexane) gave ethyl 1-(3,4-dichlorophenyl)imidazole-4-carboxylate as a white solid (176 mg, 0.62 mmol, 17%). $^1$H NMR (600 MHz, DMSO) δ 8.57 (d, J=1.3 Hz, 1H), 8.47 (d, J=1.3 Hz, 1H), 8.21 (d, J=2.0 Hz, 1H), 7.86-7.77 (m, 2H), 4.27 (q, J=7.1 Hz, 2H), 1.30 (t, J=7.1 Hz, 3H).

Step 2:

To a solution of ethyl 1-(3,4-dichlorophenyl)imidazole-4-carboxylate (150 mg, 0.53 mmol) in tetrahydrofuran (5 mL) cooled in an ice-water bath, was added lithium aluminium hydride (20 mg, 0.53 mmol) portion wise. After complete addition the reaction mixture was allowed to warm to room temperature. The reaction was stirred at room temperature for 1 hour before cooling in an ice-water bath. Water was added dropwise (10 mL) and the aqueous solution was extracted with ethyl acetate. The organics were washed with water (×1) and brine (×1), dried over anhydrous $MgSO_4$, filtered and adsorbed on to silica. Purification by column chromatography (0-10% methanol in dichloromethane) gave [1-(3,4-dichlorophenyl)imidazol-4-yl]methanol as a white solid (52 mg, 0.21 mmol, 41%). LCMS: MS m/z 243.1 [M+H]$^+$; $^1$H NMR (600 MHz, DMSO) δ 8.29 (d, J=1.3 Hz, 1H), 8.06 (d, J=2.6 Hz, 1H), 7.76 (d, J=8.7 Hz, 1H), 7.70 (dd, J=8.8, 2.6 Hz, 1H), 7.67 (s, 1H), 4.99 (t, J=5.5 Hz, 1H), 4.40 (d, J=5.2 Hz, 2H).

TABLE 17

Substituted 1-(4-chloro-3-(trifluoromethyl)phenyl)-1H-1,2,3-triazole

| Compound Number | R group | IUPAC Name |
|---|---|---|
| 129 | CN | 1-(4-chloro-3-(trifluoromethyl)phenyl)-1H-1,2,3-triazole-4-carbonitrile |
| 184 | SO$_2$Me | 2-[4-chloro-3-(trifluoromethyl)phenyl]-5-methylsulfonyl-1,3,4-oxadiazole |
| 185 | SMe | 2-[4-chloro-3-(trifluoromethyl)phenyl]-5-methylsulfanyl-1,3,4-oxadiazole |
| 186 | SH | 5-[4-chloro-3-(trifluoromethyl)phenyl]-1,3,4-oxadiazole-2-thiol |

Compound 129: 1-(4-chloro-3-(trifluoromethyl)phenyl)-1H-1,2,3-triazole-4-carbonitrile

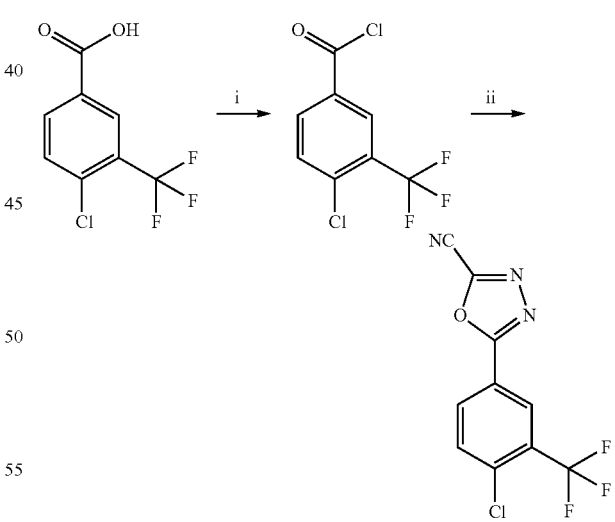

Reagents and conditions: i) Thionyl chloride, 80° C.; ii) oxamic hydrazide, sodium hydrogen carbonate, 1,4-dioxane, 110° C.

Step 1:

Thionyl chloride (4.9 mL, 66.8 mmol) was added to 4-chloro-3-(trifluoromethyl)benzoic acid (5.0 g, 22.3 mmol) and the mixture was heated to reflux for 16 hours. The reaction mixture was then concentrated under reduced pressure to provide crude 4-chloro-3-(trifluoromethyl)benzoyl chloride, which was used without further purification.

Step 2:

A solution of oxamic hydrazide (2.3 g, 22.3 mmol) in anhydrous 1,4-dioxane (20 mL) was added to a suspension of sodium hydrogen carbonate (2.1 g, 24.5 mmol) and crude 4-chloro-3-(trifluoromethyl)benzoyl chloride in 1,4-dioxane (200 mL). The mixture was then heated to reflux for 4 hours, before stirring at room temperature for 16 hours.

The solvent was removed under reduced pressure, then the residue was taken up in ethyl acetate (100 mL), then poured onto a stirred mixture of ice and saturated aqueous sodium bicarbonate (1:1, 200 mL). The mixture was stirred for 15 minutes until all the ice had melted, and diluted with brine. The organic phase was then dried over anhydrous MgSO$_4$, filtered and concentrated under reduced pressure. Purification by reverse phase chromatography (0-100% acetonitrile in water, 0.1% formic acid modifier) gave 5-[4-chloro-3-(trifluoromethyl)phenyl]-1,3,4-oxadiazole-2-carbonitrile (67 mg, 0.25 mmol, 1%) as a white solid. LCMS: MS m/z not found; $^1$H NMR (600 MHz, DMSO) δ 8.43-8.39 (m, 2H), 8.06 (d, J=9.1 Hz, 1H).

Compound 184: 2-[4-chloro-3-(trifluoromethyl)phenyl]-5-methylsulfonyl-1,3,4-oxadiazole

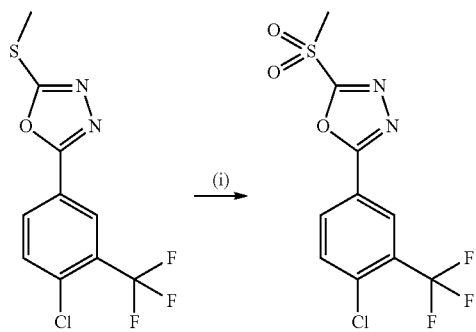

Reagents and conditions: i) Potassium permanganate 5% wt aqueous solution, acetic acid.

A solution of 2-[4-chloro-3-(trifluoromethyl)phenyl]-5-methylsulfanyl-1,3,4-oxadiazole (200 mg, 0.68 mmol) in acetic acid (1.7 mL) was cooled to 10° C. before potassium permanganate 5% wt aqueous solution (2.78 mL, 0.88 mmol) was added dropwise. The reaction was stirred for 2 hours and then quenched with 40% aqueous sodium hydrogen bisulphite solution (~10 mL) until the reaction mixture was decolorized. The reaction mixture was diluted with water, extracted with ethyl acetate, and the organics were dried over anhydrous MgSO$_4$, filtered and concentrated under reduced pressure. Purification by column chromatography (0-100% ethyl acetate in cyclohexane) gave 2-[4-chloro-3-(trifluoromethyl)phenyl]-5-methylsulfonyl-1,3,4-oxadiazole (62 mg, 0.19 mmol, 28%) as a white solid. LCMS: MS m/z 325.1 [M−H]$^-$; $^1$H NMR (600 MHz, DMSO) δ 8.43-8.37 (m, 2H), 8.05 (d, J=8.2 Hz, 1H), 3.74 (s, 3H).

Compound 185: 2-[4-chloro-3-(trifluoromethyl)phenyl]-5-methylsulfanyl-1,3,4-oxadiazole

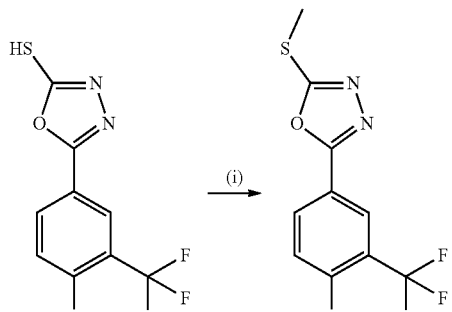

Reagents and conditions: i) Iodomethane, potassium carbonate, N,N-dimethylformamide.

A mixture of 5-[4-chloro-3-(trifluoromethyl)phenyl]-1,3,4-oxadiazole-2-thiol (250 mg, 0.89 mmol), potassium carbonate (185 mg, 1.34 mmol), iodomethane (0.06 mL, 0.98 mmol) and N,N-dimethylformamide (1.5 mL) was stirred for 16 hours at room temperature. The mixture was diluted with ethyl acetate, washed with water, 1 N HCl and brine. The organics were dried over anhydrous MgSO$_4$, filtered and concentrated under reduced pressure. Purification by column chromatography (0-70% ethyl acetate in cyclohexane) gave 2-[4-chloro-3-(trifluoromethyl)phenyl]-5-methylsulfanyl-1,3,4-oxadiazole (219 mg, 0.74 mmol, 83%) as a white solid. LCMS: MS m/z 294.9 [M+H]$^+$; $^1$H NMR (600 MHz, DMSO) δ 8.28 (d, J=2.0 Hz, 1H), 8.25 (dd, J=8.4, 2.1 Hz, 1H), 7.97 (d, J=8.4 Hz, 1H), 2.79 (s, 3H).

Compound 186: 5-[4-chloro-3-(trifluoromethyl)phenyl]-1,3,4-oxadiazole-2-thiol

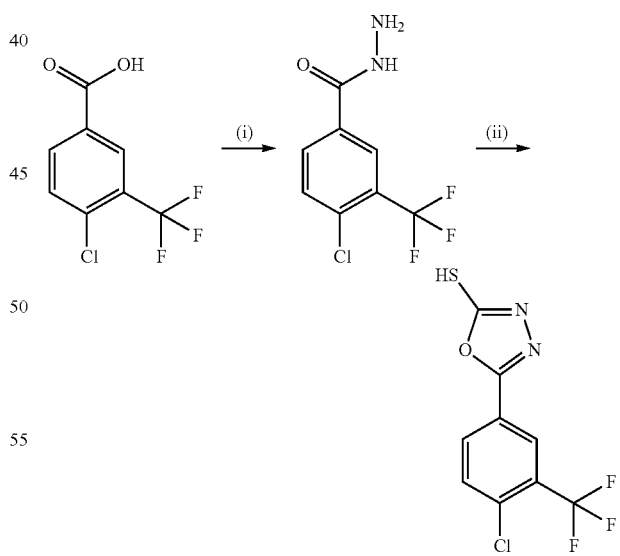

Reagents and conditions: i) Generic route 4; ii) C(S)Cl$_2$, N,N-diisopropylethylamine, dichloromethane.

Step 1:
Following generic route 4, using 4-chloro-3-(trifluoromethyl)benzoic acid, to afford 4-chloro-3-(trifluoromethyl)benzohydrazide as a white solid, which was used without further purification.

Step 2:

A solution of thiophosgene (0.34 mL, 4.4 mmol) in dichloromethane (10 mL), was added dropwise to a solution of crude 4-chloro-3-(trifluoromethyl)benzohydrazide (1000 mg, 4.19 mmol) and N,N-Diisopropylethylamine (1.46 mL, 8.38 mmol) in dichloromethane (10 mL) at 0° C. (external). The reaction was stirred at 0° C. for 20 minutes, then warmed to room temperature and stirred for a further 40 minutes. The reaction mixture was then diluted with dichloromethane, then cautiously diluted with saturated aqueous sodium bicarbonate. The organic phase was then dried over anhydrous MgSO$_4$, filtered and concentrated under reduced pressure. Purification by column chromatography (0-2% methanol in dichloromethane) gave 5-[4-chloro-3-(trifluoromethyl)phenyl]-1,3,4-oxadiazole-2-thiol (403 mg, 1.44 mmol, 34%) as a white solid. LCMS: MS m/z 279.0 [M−H]$^−$; $^1$H NMR (600 MHz, DMSO) δ 14.95 (s, 1H), 8.16 (m, 2H), 7.96 (d, J=9.0 Hz, 1H).

TABLE 18

2-(3-(3,4-dichlorophenyl)-1H-1,2,4-triazol-5-yl)pyridine

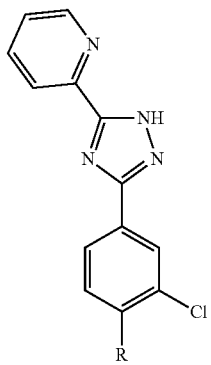

| Compound Number | R group | IUPAC Name |
|---|---|---|
| 130 | Cl | 2-(3-(3,4-dichlorophenyl)-1H-1,2,4-triazol-5-yl)pyridine |

Compound 130: 2-(3-(3,4-dichlorophenyl)-1H-1,2,4-triazol-5-yl)pyridine

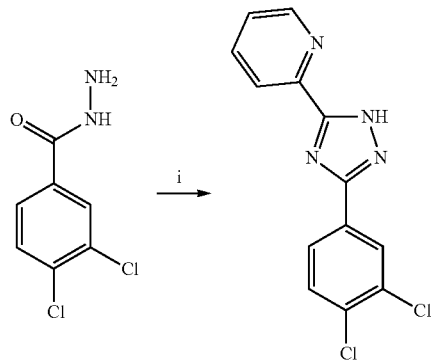

Reagents and conditions: i) methyl picolinimidate, ethanol, 85° C.

A solution of methyl picolinimidate (0.12 mL, 1 mmol) and 3,4-dichlorobenzene-1-carbohydrazide (205 mg, 1 mmol) in anhydrous ethanol (3 mL) was heated to 85° C. for 2 hours before the addition of acetic acid (0.5 mL). The reaction was heated at 85° C. for a further 6 hours. After this time the resulting suspension was cooled to room temperature and dissolved in acetonitrile (20 mL). The solution was heated at reflux for a further 9 hours. After this time the mixture was cooled to room temperature. The resulting precipitate was collected by filtration, washed with ethanol (5 mL) and dried in a drying oven to give 2-[3-(3,4-dichlorophenyl)-1H-1,2,4-triazol-5-yl]pyridine as a white solid (246 mg, 0.845 mmol, 85%). LCMS: MS m/z 291.0 [M+H]$^+$; $^1$H NMR (600 MHz, DMSO) δ 15.02 (br. s., 1H), 8.74 (d, J=4.45 Hz, 1H), 8.23 (s, 1H), 8.18 (d, J=7.81 Hz, 1H), 7.96-8.09 (m, 2H), 7.78 (d, J=8.33 Hz, 1H), 7.56 (dd, J=5.29, 6.73 Hz, 1H).

TABLE 19

Heteroaryl substituted benzenes

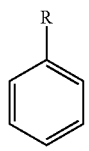

| Compound Number | R group | Supplier | IUPAC Name |
|---|---|---|---|
| 132 | ![N≡C-oxadiazole] | Enamine | 5-phenyl-1,3,4-oxadiazole-2-carbonitrile |
| 133 | ![triazole] | Enamine | 3-phenyl-1H-1,2,4-triazole |

TABLE 19-continued

Heteroaryl substituted benzenes

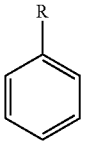

| Compound Number | R group | Supplier | IUPAC Name |
|---|---|---|---|
| 134 | 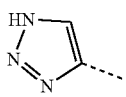 | Fluorochem | 1-phenyl-1H-tetrazole |
| 135 | 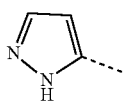 | Fluorochem | 4-phenyl-2H-1,2,3-triazole |
| 136 | 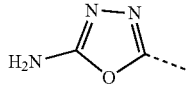 | Fluorochem | 3-phenyl-1H-pyrazole |
| 137 | 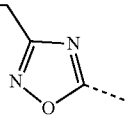 | Key Organics | 5-phenyl-1,3,4-oxadiazol-2-amine |
| 138 | 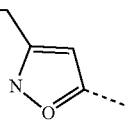 | Enamine | (5-phenyl-1,2,4-oxadiazol-3-yl)methanamine |
| 139 | 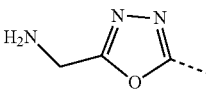 | Maybridge | (3-phenylisoxazol-5-yl)methanamine |
| 140 | 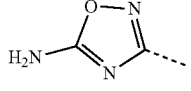 | Fluorochem | (5-phenyl-1,3,4-oxadiazol-2-yl)methanamine |
| 141 | 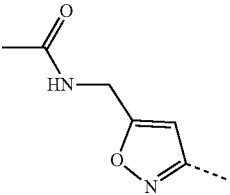 | Life Chemicals | 3-phenyl-1,2,4-oxadiazol-5-amine |
| 142 | 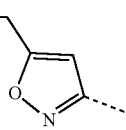 | Key Organics | N-((3-phenylisoxazol-5-yl)methyl)acetamide |
| 143 | 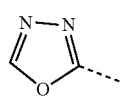 | Maybridge | (3-phenylisoxazol-5-yl)methanamine |
| 144 |  | Enamine | 2-phenyl-1,3,4-oxadiazole |

TABLE 19-continued
Heteroaryl substituted benzenes
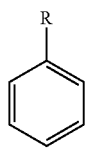
| Compound Number | R group | Supplier | IUPAC Name |
| --- | --- | --- | --- |
| 233 | | Sigma Aldrich | 4-phenylpyridine |
| 234 | | Sigma Aldrich | 2-phenylpyridine |
| 235 | | Key Organics | 3-phenyl-1H-pyrazol-5-ol |
| 236 | | Ark Pharm | 4-phenylpyridin-2(1H)-one |
| 237 | | Key Organics | 6-phenylpyridin-2(1H)-one |
| 238 | | Enamine | 6-phenylpyrimidin-4(3H)-one |
| 239 | | Enamine | 6-methylpyrimidin-2(1H)-one |
| 240 | | Enamine | 2-phenylpyrimidin-4-ol |

Compound 132: 5-phenyl-1,3,4-oxadiazole-2-carbonitrile

Compound purchased from a commercial supplier, namely Enamine.

Compound 133: 3-phenyl-1H-1,2,4-triazole

Compound purchased from a commercial supplier, namely Enamine.

Compound 134: 1-phenyl-1H-tetrazole

Compound purchased from a commercial supplier, namely Fluorochem.

Compound 135: 4-phenyl-2H-1,2,3-triazole

Compound purchased from a commercial supplier, namely Fluorochem.

Compound 136: 3-phenyl-1H-pyrazole

Compound purchased from a commercial supplier, namely Fluorochem.

Compound 137: 5-phenyl-1,3,4-oxadiazol-2-amine

Compound purchased from a commercial supplier, namely Key Organics.

Compound 138: (5-phenyl-1,2,4-oxadiazol-3-yl)methanamine

Compound purchased from a commercial supplier, namely Enamine.

Compound 139: (3-phenylisoxazol-5-yl)methanamine

Compound purchased from a commercial supplier, namely Maybridge.

Compound 140: (5-phenyl-1,3,4-oxadiazol-2-yl)methanamine

Compound purchased from a commercial supplier, namely Fluorochem.

Compound 141: 3-phenyl-1,2,4-oxadiazol-5-amine

Compound purchased from a commercial supplier, namely Life Chemicals.

Compound 142: N-((3-phenylisoxazol-5-yl)methyl)acetamide

Compound purchased from a commercial supplier, namely Key Organics.

Compound 143: (3-phenylisoxazol-5-yl)methanamine

Compound purchased from a commercial supplier, namely Maybridge.

Compound 144: 2-phenyl-1,3,4-oxadiazole

Compound purchased from a commercial supplier, namely Enamine.

Compound 233: 4-phenylpyridine

Compound purchased from a commercial supplier, namely Sigma Aldrich.

Compound 234: 2-phenylpyridine

Compound purchased from a commercial supplier, namely Sigma Aldrich.

Compound 235: 3-phenyl-1H-pyrazol-5-ol

Compound purchased from a commercial supplier, namely Key Organics.

Compound 236: 4-phenylpyridin-2(1H)-one

Compound purchased from a commercial supplier, namely Ark Pharm.

Compound 237: 6-phenylpyridin-2(1H)-one

Compound purchased from a commercial supplier, namely Key Organics.

Compound 238: 6-phenylpyrimidin-4(3H)-one

Compound purchased from a commercial supplier, namely Enamine.

Compound 239: 6-methylpyrimidin-2(1H)-one

Compound purchased from a commercial supplier, namely Enamine.

Compound 240: 2-phenylpyrimidin-4-ol

Compound purchased from a commercial supplier, namely Enamine.

TABLE 20

Heteroaryl substituted toluene

| Compound Number | R group | IUPAC Name |
|---|---|---|
| 145 | 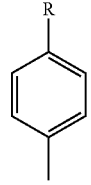 | 4-(p-tolyl)-1,2,3-thiadiazole |
| 146 | | 4-(p-tolyl)-2,4-dihydro-3H-1,2,4-triazol-3-one |

Compound 145: 4-(p-tolyl)-1,2,3-thiadiazole

Compound purchased from a commercial supplier, namely Key Organics.

Compound 146: 4-(p-tolyl)-2,4-dihydro-3H-1,2,4-triazol-3-one

Compound purchased from a commercial supplier, namely Key Organics.

TABLE 21

Substituted (3-phenylisoxazol-5-yl)methanamine

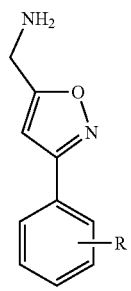

| Compound Number | R group | Salt | IUPAC Name |
|---|---|---|---|
| 147 | 3-Cl | — | (3-(3-chlorophenyl)isoxazol-5-yl)methanamine |
| 148 | 4-F | HCl | (3-(4-fluorophenyl)isoxazol-5-yl)methanamine hydrochloride |

Compound 147: (3-(3-chlorophenyl)isoxazol-5-yl)methanamine

Compound purchased from a commercial supplier, namely Chembridge.

Compound 148: (3-(4-fluorophenyl)isoxazol-5-yl)methanamine hydrochloride

Compound purchased from a commercial supplier, namely Manchester Organics.

TABLE 22

Heteroaryl substituted chlorobenzene

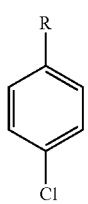

| Compound Number | R group | IUPAC Name |
|---|---|---|
| 149 | 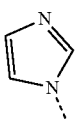 | 1-(4-chlorophenyl)imidazole |
| 150 | 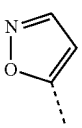 | 5-(4-chlorophenyl)isoxazole |

TABLE 22-continued

Heteroaryl substituted chlorobenzene

| Compound Number | R group | IUPAC Name |
|---|---|---|
| 151 | 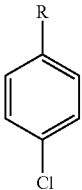 | 5-(4-chlorophenyl)oxazole |
| 152 | 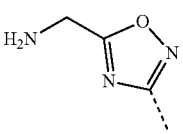 | [3-(4-chlorophenyl)-1,2,4-oxadiazol-5-yl]methanamine |
| 153 | 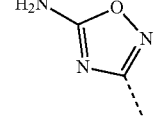 | 3-(4-chlorophenyl)-1,2,4-oxadiazol-5-amine |
| 154 | 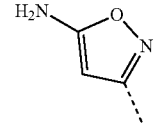 | 5-amino-3-(4-chlorophenyl)isoxazole |
| 155 | 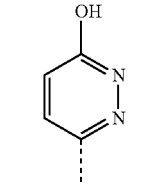 | 6-(4-chlorophenyl)pyridazin-3-ol |
| 156 | 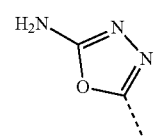 | 2-amino-5-(4-chlorophenyl)-1,3,4-oxadiazole |
| 157 | 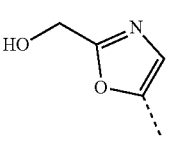 | [5-(4-chlorophenyl)oxazol-2-yl]methanol |
| 158 | 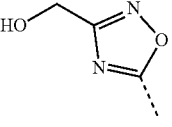 | [5-(4-chlorophenyl)-1,2,4-oxadiazol-3-yl]methanol |
| 159 | 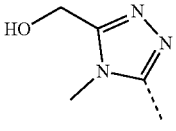 | [5-(4-chlorophenyl)-4-methyl-1,2,4-triazol-3-yl]methanol |

TABLE 22-continued

Heteroaryl substituted chlorobenzene

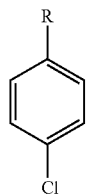

| Compound Number | R group | IUPAC Name |
|---|---|---|
| 160 | | 4-(4-chlorophenyl)-1H-pyrrole-2-carboxylic acid |
| 161 | | 3-(4-chlorophenyl)-1-methyl-1H-pyrazol-5-ol |
| 162 | | (1-(4-chlorobenzyl)-1H-1,2,3-triazol-4-yl)methanol |
| 163 | | (1-(4-chlorophenyl)-5-methyl-1H-1,2,3-triazol-4-yl)methanol |
| 164 | | (3-(4-chlorophenyl)-1,2,4-oxadiazol-5-yl)methanol |
| 165 | | (3-(4-chlorophenyl)isoxazol-5-yl)methanol |
| 166 | | (5-(4-chlorophenyl)isoxazol-3-yl)methanol |
| 167 | | (3-(4-chlorophenyl)isoxazol-5-yl)methanamine |

TABLE 22-continued

Heteroaryl substituted chlorobenzene

| Compound Number | R group | IUPAC Name |
|---|---|---|
| 168 | H₂N-[1,3,4-thiadiazol-2-yl] | 5-(4-chlorophenyl)-1,3,4-thiadiazol-2-amine |
| 169 | HO-CH₂-[1-methyl-pyrazol-3-yl] | [5-(4-chlorophenyl)-1-methyl-pyrazol-3-yl]methanol |
| 170 | HO-[1,2,4-oxadiazol-3-yl] | 3-(4-chlorophenyl)-1,2,4-oxadiazol-5-ol |
| 171 | HO-CH₂-[1H-pyrazol-3-yl] | [5-(4-chlorophenyl)-1H-pyrazol-3-yl]methanol |
| 229 | [3-methyl-1,3,4-oxadiazol-2(3H)-one-5-yl] | 5-(4-chlorophenyl)-3-methyl-1,3,4-oxadiazol-2(3H)-one |

Compound 149: 1-(4-chlorophenyl)imidazole

Compound purchased from a commercial supplier, namely Fluorochem.

Compound 150: 5-(4-chlorophenyl)isoxazole

Compound purchased from a commercial supplier, namely Key Organics.

Compound 151: 5-(4-chlorophenyl) oxazole

Compound purchased from a commercial supplier, namely Key Organics.

Compound 152: [3-(4-chlorophenyl)-1,2,4-oxadiazol-5-yl]methanamine

Compound purchased from a commercial supplier, namely Combi-Blocks.

Compound 153: 3-(4-chlorophenyl)-1,2,4-oxadiazol-5-amine

Compound purchased from a commercial supplier, namely Enamine.

Compound 154: 5-amino-3-(4-chlorophenyl)isoxazole

Compound purchased from a commercial supplier, namely Key Organics.

Compound 155: 6-(4-chlorophenyl)pyridazin-3-ol

Compound purchased from a commercial supplier, namely Life Chemicals.

Compound 156: 2-amino-5-(4-chlorophenyl)-1,3,4-oxadiazole

Compound purchased from a commercial supplier, namely Sigma Aldrich.

Compound 157: [5-(4-chlorophenyl)oxazol-2-yl]methanol

Compound purchased from a commercial supplier, namely Enamine.

Compound 158: [5-(4-chlorophenyl)-1,2,4-oxadiazol-3-yl]methanol

Compound purchased from a commercial supplier, namely Enamine.

Compound 159: [5-(4-chlorophenyl)-4-methyl-1,2,4-triazol-3-yl]methanol

Compound purchased from a commercial supplier, namely Enamine.

Compound 160: 4-(4-chlorophenyl)-1H-pyrrole-2-carboxylic acid

Compound purchased from a commercial supplier, namely Enamine.

Compound 161: 3-(4-chlorophenyl)-1-methyl-1H-pyrazol-5-ol

Compound purchased from a commercial supplier, namely Fluorochem.

Compound 162: (1-(4-chlorobenzyl)-1H-1,2,3-triazol-4-yl)methanol

Compound purchased from a commercial supplier, namely Key Organics.

Compound 163: (1-(4-chlorophenyl)-5-methyl-1H-1,2,3-triazol-4-yl)methanol

Compound purchased from a commercial supplier, namely Key Organics.

Compound 164: (3-(4-chlorophenyl)-1,2,4-oxadiazol-5-yl)methanol

Compound purchased from a commercial supplier, namely Key Organics.

Compound 165: (3-(4-chlorophenyl)isoxazol-5-yl)methanol

Compound purchased from a commercial supplier, namely Key Organics.

Compound 166: (5-(4-chlorophenyl)isoxazol-3-yl)methanol

Compound purchased from a commercial supplier, namely Key Organics.

Compound 167: (3-(4-chlorophenyl)isoxazol-5-yl)methanamine

Compound purchased from a commercial supplier, namely Key Organics.

Compound 168: 5-(4-chlorophenyl)-1,3,4-thiadiazol-2-amine

Compound purchased from a commercial supplier, namely Sigma Aldrich.

Compound 169: [5-(4-chlorophenyl)-1-methyl-pyrazol-3-yl]methanol

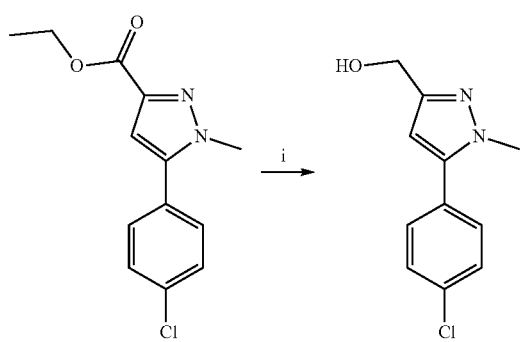

Reagents and conditions: i) Lithium aluminium hydride, tetrahydrofuran.

Step 1:
Lithium aluminium hydride (1 M in tetrahydrofuran, 0.53 mL, 0.53 mmol) was added dropwise to a solution of ethyl 5-(4-chlorophenyl)-1-methyl-1H-pyrazole-3-carboxylate (140 mg, 0.53 mmol) in tetrahydrofuran (5 mL) at 0° C. (external). The reaction mixture was stirred at 0° C. for 15 minutes, diluted with diethyl ether (5 mL), quenched with 0.3 mL of water, then 0.1 mL of 1 M NaOH. The reaction mixture was then warmed to room temperature, $Na_2SO_4$ (100 mg) was then added and the reaction mixture was stirred at room temperature for 30 minutes. The reaction mixture was then filtered, washed with methanol (20 mL) and the organics were then dried over anhydrous $Na_2SO_4$, filtered and concentrated under reduced pressure. Purification by column chromatography (0-10% methanol in dichloromethane) to gave [5-(4-chlorophenyl)-1-methyl-pyrazol-3-yl]methanol (75 mg, 0.34 mmol, 64%) as an off-white solid. LCMS: MS m/z 223.1 [M+H]$^+$; $^1$H NMR (600 MHz, DMSO) δ 7.57-7.53 (m, 4H), 6.35 (s, 1H), 5.01 (brs, 1H), 4.40 (s, 2H), 3.79 (s, 3H).

Compound 170: 3-(4-chlorophenyl)-1,2,4-oxadiazol-5-ol

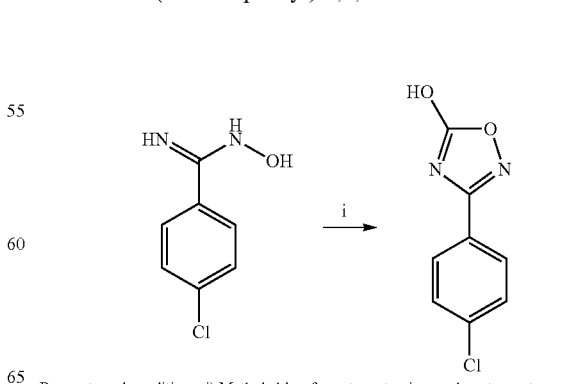

Reagents and conditions: i) Methyl chloroformate, potassium carbonate, acetone

Methyl chloroformate (0.11 mL, 1.47 mmol) was added dropwise to a suspension of 4-chloro-N-hydroxy-benzamidine (250 mg, 1.47 mmol) and potassium carbonate (200 mg, 1.47 mmol) at room temperature. The mixture was then heated to 60° C. for 5 hours, cooled to room temperature, dry-loaded onto reverse phase silica, then purified by reverse phase chromatography (0-100% acetonitrile in water, 0.1% formic acid modifier) to give 3-(4-chlorophenyl)-1,2,4-oxadiazol-5-ol (15 mg, 0.08 mmol, 5%) as a white solid. LCMS: MS m/z 195.0 [M−H]⁻; ¹H NMR (600 MHz, DMSO) δ 7.79-7.74 (m, 2H), 7.46-7.40 (m, 2H).

Compound 171: [5-(4-chlorophenyl)-1H-pyrazol-3-yl]methanol

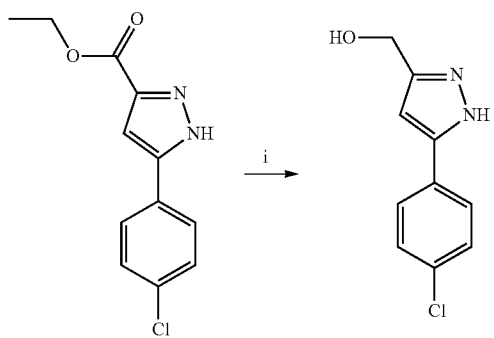

Reagents and conditions: i) Lithium aluminium hydride, tetrahydrofuran.

Lithium aluminium hydride (1 M in tetrahydrofuran, 1.6 mL, 1.6 mmol) was added dropwise to a solution of ethyl 5-(4-chlorophenyl)-1H-pyrazole-3-carboxylate (100 mg, 0.40 mmol) in tetrahydrofuran (5 mL) at 0° C. The reaction mixture was then warmed to room temperature, stirred for 15 minutes, re-cooled to 0° C. and then quenched with dropwise addition of saturated aqueous ammonium chloride (1 mL). The reaction mixture was then dry-loaded onto C18-silica and then purified via reverse phase chromatography (0-100% acetonitrile in water, 0.1% formic acid modifier) and the desired fractions were then concentrated to give [5-(4-chlorophenyl)-1H-pyrazol-3-yl]methanol (7 mg, 0.03 mmol, 8%). LCMS: MS m/z 209.1 [M+H]⁺; 1H NMR (600 MHz, MeOD) δ 7.80-7.58 (m, 2H), 7.41 (d, J=8.5 Hz, 2H), 6.62 (s, 1H), 4.65 (s, 2H).

Compound 229: 5-(4-chlorophenyl)-3-methyl-1,3,4-oxadiazol-2(3H)-one

Compound purchased from a commercial supplier, namely Sigma Aldrich.

TABLE 23

N-methyl-1-(5-phenyl-1,3,4-oxadiazol-2-yl)methanamine hydrochloride

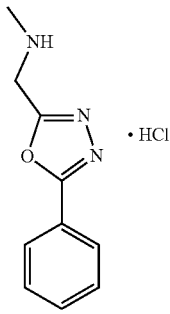

| Compound Number | IUPAC Name |
|---|---|
| 172 | N-methyl-1-(5-phenyl-1,3,4-oxadiazol-2-yl)methanamine hydrochloride |

Compound 172: N-methyl-1-(5-phenyl-1,3,4-oxadiazol-2-yl)methanamine hydrochloride Compound purchased from a commercial supplier, namely ChemBridge.

TABLE 24

2-[3-(2-pyridyl)-1H-1,2,4-triazol-5-yl]acetonitrile

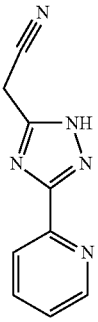

| Compound Number | IUPAC Name |
|---|---|
| 173 | 2-[3-(2-pyridyl)-1H-1,2,4-triazol-5-yl]acetonitrile |

Compound 173: 2-[3-(2-pyridyl)-1H-1,2,4-triazol-5-yl]acetonitrile

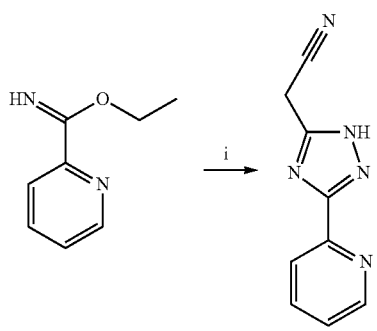

Reagents and conditions: i) Ethyl cyanoacetate, hydrazine monohydrate, ethanol

A 20 ml microwave tube with stirrer was charged with hydrazine monohydrate (48.6 μL, 1 mmol) and ethyl cyanoacetate (107 uL, 1 mmol). The two reagents were cooled to 0° C. and stirred until a white solid formed (5 minutes). A solution of ethyl pyridine-2-carboximidate (300 mg, 2 mmol) in ethanol (5 mL) was added. The vial was evacuated and back-filled with nitrogen (×3). The yellow solution was heated at 85° C. for 8 hours and then stirred at room temperature for 3 days. The reaction mixture was concentrated to dryness and then purified by column chromtography (0-5% methanol (1% Et$_3$N) in dichloromethane) to give 2-[3-(2-pyridyl)-1H-1,2,4-triazol-5-yl]acetonitrile (73 mg, 0.39 mmol, 40%) as an off-white solid. LCMS: MS m/z 186.1 [M+H]$^+$; $^1$H NMR (600 MHz, DMSO) δ 14.80 (s, 1H), 8.67-8.75 (m, 1H), 8.03-8.10 (m, 1H), 8.00 (apparent dt, J=1.7, 7.7 Hz, 1H), 7.55 (ddd, J=1.1, 4.8, 7.5 Hz, 1H), 3.32 (s, 2H).

TABLE 25

5-(2-pyridyl)-1H-1,2,4-triazol-3-ol

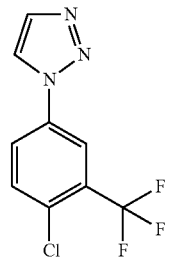 [SMILES: FC(F)(F)c1cc(-n2ccnn2)ccc1Cl]

| Compound Number | IUPAC Name |
|---|---|
| 174 | 5-(2-pyridyl)-1H-1,2,4-triazol-3-ol |

Compound 174: 5-(2-pyridyl)-1H-1,2,4-triazol-3-ol

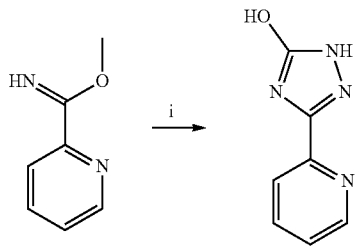

Reagents and conditions: i) tert-butyl carbazate, ethanol, 85° C.

Methyl picolinimidate (0.12 mL, 1 mmol) and tert-butyl carbazate (132 mg, 1 mmol), were dissolved in anhydrous ethanol (3 mL), then heated at 85° C. for 8 hours. The mixture was cooled to room temperature, concentrated under reduced pressure to give a white solid that was purified by column chromatography (0-10% methanol (1% Et$_3$N) in dichloromethane) to give 5-(2-pyridyl)-1H-1,2,4-triazol-3-ol (10 mg, 0.06 mmol, 6%). LCMS: MS m/z 163.1 [M+H]$^+$; $^1$H NMR (600 MHz, DMSO) δ 12.04 (s, 1H), 11.78 (s, 1H), 8.63 (td, J=1.3, 4.8 Hz, 1H), 7.88-7.96 (m, 2H), 7.44-7.50 (m, 1H).

TABLE 26

1-[4-chloro-3-(trifluoromethyl)phenyl]triazole

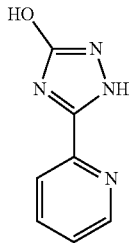

| Compound Number | IUPAC Name |
|---|---|
| 175 | 1-[4-chloro-3-(trifluoromethyl)phenyl]triazole |

Compound 175: 1-[4-chloro-3-(trifluoromethyl) phenyl]triazole

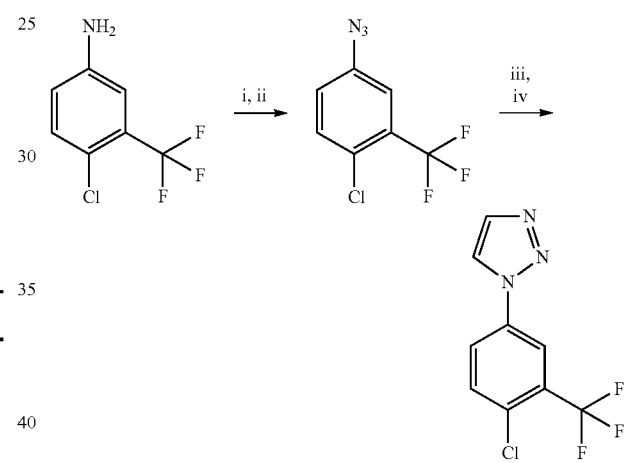

Reagents and conditions: i) Sodium nitrite, 37% aqueous hydrochloric acid, acetonitrile, water, room temperature; ii) sodium azide, 0° C.; iii) trimethylsilylacetylene, sodium L-ascorbate, potassium carbonate, copper(II) sulfate pentahydrate, tert-butanol, water; iv) tetrabutylammonium fluoride, tetrahydrofuran, methanol.

Step 1:

Aqueous hydrochloric acid (37%, 13.2 mL, 435.8 mmol) was added to a solution of 4-chloro-3-trifluoromethylaniline (1.32 g, 6.77 mmol) in water (3.75 mL) and acetonitrile (26.3 mL). The reaction mixture was stirred at room temperature for 2 minutes before portionwise addition of sodium nitrite (935 mg, 13.5 mmol). The mixture was then stirred for one hour, cooled to 0° C. and sodium azide (880 mg, 13.5 mmol) was added. The reaction mixture was then allowed to warm to room temperature over 1 hour, before stirring for an addition 2 hours. The reaction was diluted with water (30 mL), then extracted with diethyl ether (2×40 mL) to provide 4-azido-1-chloro-2-(trifluoromethyl)benzene as a stock solution (assumed 84.6 mM, 80 mL), which was used without further purification.

Step 2:

Water (5 mL) and tert-butanol (5 mL) were added to half of the solution of 4-azido-1-chloro-2-(trifluoromethyl)benzene (750 mg, 3.4 mmol) in diethyl ether (40 mL). The diethyl ether was then removed under reduced pressure at room temperature. Sodium L-ascorbate (134 mg, 0.68 mmol), potassium carbonate (935 mg, 6.77 mmol), copper (II) sulfate pentahydrate (85 mg, 0.34 mmol) and trimethylsilylacetylene (0.7 mL, 5.08 mmol), were then added. The reaction vessel was then sealed and the resultant suspension reaction mixture was heated at 60° C. for 16 hours. The organics were then removed under reduced pressure, then methanol (5 mL) and tetrabutylammonium fluoride (1 M in tetrahydrofuran, 3.4 mL, 3.40 mmol) were added and the mixture was then stirred at 50° C. for 16 hours. The reaction mixture was then concentrated under reduced pressure, taken up in 1 mL of dimethyl sulfoxide and purified by reverse phase chromatography (0-100% acetonitrile in water, 0.1% formic acid modifier). The desired fractions were then concentrated under reduced pressure, and the resultant brown solid was then recrystallized from diethyl ether to give 1-[4-chloro-3-(trifluoromethyl)phenyl]triazole (29 mg, 0.12 mmol, 3%) as an off white solid. LCMS: MS m/z 248.1 [M+H]⁺; ¹H NMR (600 MHz, DMSO) δ 9.05 (d, J=1.2 Hz, 1H), 8.39 (d, J=1.8 Hz, 1H), 8.18 (dd, J=8.7, 1.6 Hz, 1H), 8.11 (d, J=8.6 Hz, 1H), 8.06 (d, J=1.2 Hz, 1H).

TABLE 27

2-(3-chlorophenyl)-5-methoxy-1,3,4-oxadiazole

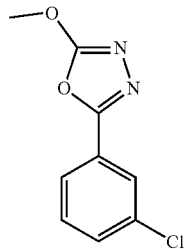

| Compound Number | IUPAC Name |
|---|---|
| 176 | 2-(3-chlorophenyl)-5-methoxy-1,3,4-oxadiazole |

Compound 176:
2-(3-chlorophenyl)-5-methoxy-1,3,4-oxadiazole

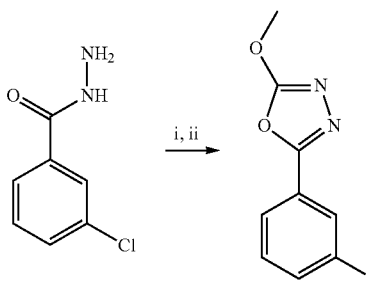

Reagents and conditions: i) Methyl chloroformate, sodium hydrogen carbonate, 1,4-dioxane, water; ii) trimethylamine, p-toluenesulfonyl chloride, dichloromethane.

Methyl chloroformate (0.22 mL, 2.78 mmol) was added to a solution of 3-chlorobenzohydrazide (396 mg, 2.32 mmol) and sodium hydrogen carbonate (584 mg, 6.96 mmol) in 1,4-dioxane (10 mL)/water (10 mL) at 0° C., and then stirred at that temperature for 1 hour. The mixture was diluted with ethyl acetate (50 mL), the organic phase was then dried over anhydrous Na₂SO₄, filtered and concentrated under reduced pressure. The resultant solid was then taken up in anhydrous dichloromethane (5 mL), p-toluenesulfonyl chloride (464 mg, 2.44 mmol), then triethylamine (0.81 mL, 5.80 mmol) were added and the mixture was stirred at room temperature for 16 hours. The mixture was then concentrated under reduced pressure, dissolved up in dimethyl sulfoxide (1 mL) and purified via reverse phase chromatography (0-100% acetonitrile in water, 0.1% formic acid modifier). The desired fractions were then concentrated under reduced pressure to give 2-(3-chlorophenyl)-5-methoxy-1,3,4-oxadiazole (31 mg, 0.15 mmol, 6%) as an off white solid. LCMS: MS m/z 211.1 [M+H]⁺; ¹H NMR (600 MHz, DMSO) δ 7.89-7.88 (m, 1H), 7.87-7.84 (m, 1H), 7.67 (ddd, J=8.1 Hz, 2.1 Hz, J=1.0 Hz, 1H), 7.61 (t, J=7.9 Hz, 1H), 4.19 (s, 3H).

TABLE 28

Substituted Phenyl Tetrazoles

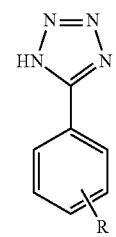

| Compound Number | R group | Generic route | IUPAC Name |
|---|---|---|---|
| 178 | 3,5-Me | 9 | 5-(3,5-dimethylphenyl)-1H-tetrazole |
| 212 | 3-CF₃, 4-Cl | 9 | 5-[4-chloro-3-(trifluoromethyl)phenyl]-1H-tetrazole |

Compound 178:
5-(3,5-dimethylphenyl)-1H-tetrazole

Following generic route 9, using 3,5-dimethylbenzonitrile, yield=10% (colourless gum). LCMS: MS m/z 175.1 [M+H]⁺; ¹H NMR (600 MHz, DMSO) δ 7.66 (apparent s, 2H), 7.23 (apparent s, 1H), 2.37 (s, 6H).

Compound 212: 5-[4-chloro-3-(trifluoromethyl)phenyl]-1H-tetrazole

Following generic route 9, using 2-chloro-5-cyanobenzotrifluoride, yield=33% (white solid). LCMS: MS m/z 249.0 [M+H]⁺; ¹H NMR (600 MHz, CDCl₃) δ 8.50 (d, J=1.7 Hz, 1H), 8.29 (dd, J=8.3, 1.7 Hz, 1H), 7.69 (d, J=8.3 Hz, 1H).

TABLE 29

1-[4-chloro-3-(trifluoromethyl)phenyl]-5-methyl-tetrazole

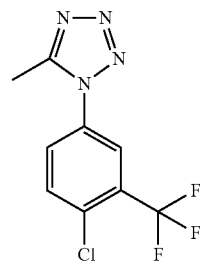 [SMILES: Cc1nnnn1-c1ccc(Cl)c(C(F)(F)F)c1]

| Compound Number | IUPAC Name |
|---|---|
| 182 | 1-[4-chloro-3-(trifluoromethyl)phenyl]-5-methyl-tetrazole |

Compound 182: 1-[4-chloro-3-(trifluoromethyl)phenyl]-5-methyl-tetrazole

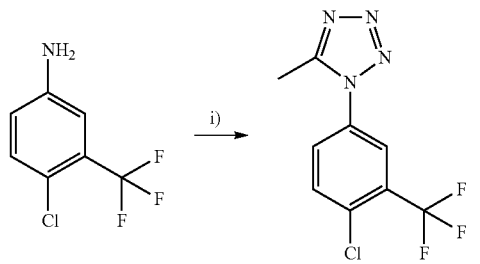

Reagents and conditions: i) Sodium azide, trimethyl orthoacetate, acetic acid, toluene.

To a suspension of 4-chloro-3-trifluoromethylaniline (150 mg, 0.77 mmol) in acetic acid (3 mL, 52 mmol) was added trimethyl orthoacetate (0.14 mL, 1.23 mmol) and sodium azide (75 mg, 1.15 mmol). The reaction mixture was heated to 65° C. under $N^2$ in a MW vial (turns into pale yellow solution) for 36 hours. The reaction mixture was concentrated under reduced pressure. The resulting residue was diluted with dichloromethane, washed with 1 M HCl and dried under vacuum. The residue was purified by passage through a SCX-2 cartridge, eluting with MeOH. The residue was further purified by column chromatography (0-0.5% MeOH in dichloromethane, long gradient) to give 1-[4-chloro-3-(trifluoromethyl)phenyl]-5-methyl-tetrazole (52.5 mg, 0.20 mmol, 26%) as a white solid. LCMS: MS m/z 263.0 [M+H]$^+$; $^1$H NMR (600 MHz, CDCl$_3$) δ 7.85 (d, J=3.7 Hz, 0.3H), 7.79 (m, 1H), 7.77 (d, J=8.6 Hz, 0.3H), 7.74 (dd, J=8.6, 2.3 Hz, 1H), 7.64 (dd, J=8.6, 2.7 Hz, 0.3H), 7.44 (d, J=8.6 Hz, 1H), 2.67 (s, 1H), 2.20 (s, 3H)-rotamers reported as seen.

TABLE 30

Substituted Phenyl tetrazoles

| Compound Number | R group | Generic route | IUPAC Name |
|---|---|---|---|
| 194 | 3,5-Me | 10 | 1-(3,5-dimethylphenyl)tetrazole |
| 213 | 3-CF$_3$ | 10 | 1-[3-(trifluoromethyl)phenyl]tetrazole |
| 214 | 3,4-Cl | 10 | 1-(3,4-dichlorophenyl)tetrazole |
| 215 | 3-CF$_3$, 4-Cl | 10 | 1-[4-chloro-3-(trifluoromethyl)phenyl]tetrazole |
| 216 | 4-Cl | 10 | 1-(4-chlorophenyl)tetrazole |
| 217 | 4-$^i$Pr | 10 | 1-(4-isopropylphenyl)tetrazole |

Compound 194: 1-(3,5-dimethylphenyl)tetrazole

Following generic route 10, using 3,5-dimethylaniline, yield=33% (white solid). LCMS: MS m/z 175.1 [M+H]$^+$; $^1$H NMR (600 MHz, CDCl$_3$) δ 8.94 (s, 1H), 7.31 (apparent s, 2H), 7.15 (m, 1H), 2.42 (s, 6H).

Compound 213: 1-[3-(trifluoromethyl)phenyl]tetrazole

Following generic route 10, using 3-(trifluoromethyl)aniline, yield=62% (white solid). LCMS: MS m/z 215.1 [M+H]$^+$; $^1$H NMR (600 MHz, CDCl$_3$) δ 9.08 (s, 1H), 8.01 (s, 1H), 7.96 (d, J=7.9 Hz, 1H), 7.82 (d, J=7.9 Hz, 1H), 7.77 (t, J=7.9 Hz, 1H).

Compound 214: 1-(3,4-dichlorophenyl)tetrazole

Following generic route 10, using 3,4-dichloroaniline, yield=87% (beige solid). LCMS: MS m/z 215.1 [M+H]$^+$; $^1$H NMR (600 MHz, CDCl$_3$) δ 9.00 (s, 1H), 7.89 (d, J=2.5 Hz, 1H), 7.69 (d, J=8.6 Hz, 1H), 7.60 (dd, J=8.6, 2.5 Hz, 1H).

Compound 215: 1-[4-chloro-3-(trifluoromethyl)phenyl]tetrazole

Following generic route 10, using 4-chloro-3-trifluoromethylaniline, yield=81% (white solid). LCMS: MS m/z 249.1 [M+H]$^+$; $^1$H NMR (700 MHz, CDCl$_3$) δ 9.07 (s, 1H), 8.08 (s, 1H), 7.90 (br d, J=8.5 Hz, 1H), 7.78 (d, J=8.5 Hz, 1H).

Compound 216: 1-(4-chlorophenyl)tetrazole

Following generic route 10, using 4-chloroaniline, yield=59% (off-white solid). LCMS: MS m/z 181.0 [M+H]$^+$; $^1$H NMR (700 MHz, CDCl$_3$) δ 8.98 (s, 1H), 7.68 (d, J=8.0 Hz, 2H), 7.58 (d, J=8.0 Hz, 2H).

Compound 217: 1-(4-isopropylphenyl)tetrazole

Following generic route 10, using 4-isopropylaniline, yield=59% (dark red solid). LCMS: MS m/z 189.1 [M+H]$^+$; $^1$H NMR (700 MHz, MeOD) δ 9.71 (s, 1H), 7.76 (d, J=8.2 Hz, 2H), 7.50 (d, J=8.2 Hz, 2H), 3.02 (m, 1H), 1.31 (s, 3H), 1.30 (s, 3H).

TABLE 31

5-[4-chloro-3-(trifluoromethyl)phenyl]-1,3,4-thiadiazol-2-ol

| Compound Number | IUPAC Name |
|---|---|
| 183 | 5-[4-chloro-3-(trifluoromethyl)phenyl]-1,3,4-thiadiazol-2-ol |

Compound 183: 5-[4-chloro-3-(trifluoromethyl)phenyl]-1,3,4-thiadiazol-2-ol

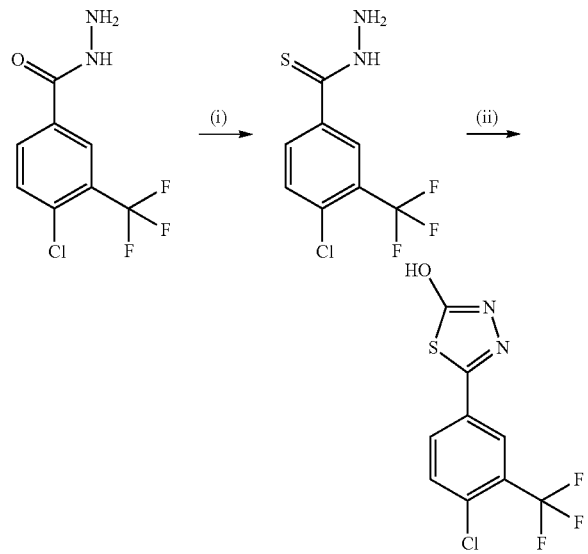

Reagents and conditions: i) Lawesson's reagent, toluene; ii) Generic route 4

Step 1:
To a suspension of 4-chloro-3-(trifluoromethyl)benzohydrazide (500 mg, 2.1 mmol) in toluene (10 mL) was added Lawesson's reagent (847 mg, 2.1 mmol). The mixture was heated to 110° C. overnight. The mixture was quenched by stirring with water (5 mL) at 50° C. for 10 minutes. The biphasic mixture was then concentrated under reduced pressure. The crude material was dissolved in a minimal quantity of dimethyl sulfoxide. Purification by reverse phase chromatography (0-100% acetonitrile in water, 0.1% formic acid modifier) gave 4-chloro-3-(trifluoromethyl)benzothiohydrazide as a yellow solid. LCMS: MS m/z 255.1 [M+H]$^+$.

Step 2:
Following generic route 4, using 4-chloro-3-(trifluoromethyl)benzothiohydrazide, to afford 5-[4-chloro-3-(trifluoromethyl)phenyl]-1,3,4-thiadiazol-2-ol (66 mg, 0.24 mmol, 40%) as a white solid. LCMS: MS m/z 279.0 [M−H]$^-$; $^1$H NMR (600 MHz, CDCl$_3$) δ 9.50 (s, 1H), 8.01 (d, J=2.1 Hz, 1H), 7.76 (dd, J=8.4, 2.1 Hz, 1H), 7.61 (d, J=8.4 Hz, 1H).

TABLE 32

5-[3-cyclopropyl-4-(trifluoromethyl)phenyl]-1,3,4-oxadiazole-2-thiol

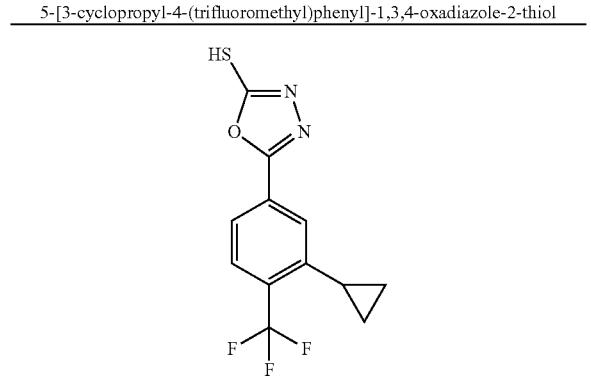

| Compound Number | IUPAC Name |
|---|---|
| 187 | 5-[3-cyclopropyl-4-(trifluoromethyl)phenyl]-1,3,4-oxadiazole-2-thiol |

Compound 187: 5-[3-cyclopropyl-4-(trifluoromethyl)phenyl]-1,3,4-oxadiazole-2-thiol

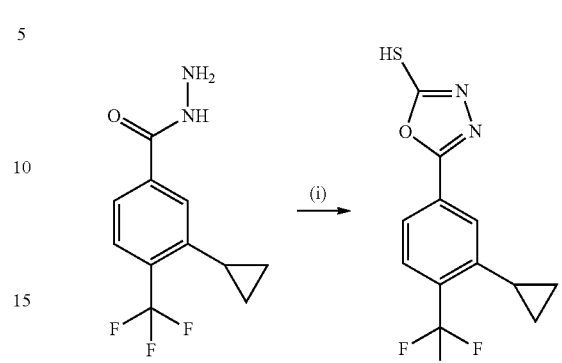

Reagents and conditions: i) C(S)Cl$_2$, N,N-diisopropylethylamine, dichloromethane.

A solution of thiophosgene (0.07 mL, 0.86 mmol) in dichloromethane (10 mL), was added dropwise to a solution of crude 3-cyclopropyl-4-(trifluoromethyl)benzohydrazide (200 mg, 0.82 mmol) and N,N-Diisopropylethylamine (0.29 mL, 1.64 mmol) in dichloromethane (10 mL) at 0° C. (external). The reaction was stirred at 0° C. for 20 minutes, then warmed to room temperature and stirred for a further 40 minutes. The reaction mixture was then diluted with dichloromethane, then cautiously diluted with saturated aqueous sodium bicarbonate. The organic phase was then dried over anhydrous MgSO$_4$, filtered and concentrated under reduced pressure. Purification by column chromatography (0-2% methanol in dichloromethane) gave 5-[3-cyclopropyl-4-(trifluoromethyl)phenyl]-1,3,4-oxadiazole-2-thiol (68 mg, 0.24 mmol, 29%) as a white solid. LCMS: MS m/z 285.1 [M−H]$^-$; $^1$H NMR (600 MHz, DMSO) δ 14.91 (s, 1H), 7.88 (d, J=8.3 Hz, 1H), 7.84 (d, J=8.3 Hz, 1H), 7.50 (s, 1H), 2.18 (m, 1H), 1.17-1.08 (m, 2H), 0.93-0.84 (m, 2H).

TABLE 33

2-[4-cyclopropyl-3-(trifluoromethyl)phenyl]-5-methyl-1,3,4-oxadiazole

| Compound Number | Generic route | IUPAC Name |
|---|---|---|
| 190 | 5 | 2-[4-cyclopropyl-3-(trifluoromethyl)phenyl]-5-methyl-1,3,4-oxadiazole |

Compound 190: 2-[4-cyclopropyl-3-(trifluoromethyl)phenyl]-5-methyl-1,3,4-oxadiazole Following generic route 5, using 4-cyclopropyl-3-(trifluoromethyl)benzohydrazide and trimethyl orthoacetate, yield=68% (white solid). LCMS: MS m/z 269.1 [M+H]⁺; ¹H NMR (600 MHz, DMSO) δ 8.13 (d, J=1.7 Hz, 1H), 8.10 (dd, J=8.3, 1.7 Hz, 1H), 7.35 (d, J=8.3 Hz, 1H), 2.59 (s, 3H), 2.22-2.13 (m, 1H), 1.18-1.11 (m, 2H), 0.95-0.89 (m, 2H).

TABLE 34

Heteroaryl substituted 1,3,4-oxadiazol-2-ols

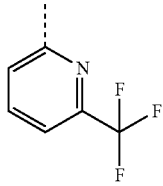

| Compound Number | R group | Generic route | IUPAC Name |
|---|---|---|---|
| 206 | 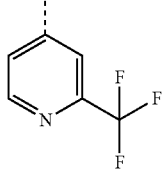 | 3 | 5-[6-(trifluoromethyl)-2-pyridyl]-1,3,4-oxadiazol-2-ol |
| 207 | 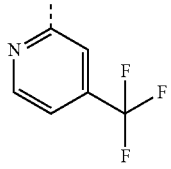 | 3 | 5-[2-(trifluoromethyl)-4-pyridyl]-1,3,4-oxadiazol-2-ol |
| 208 | 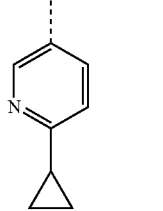 | 3 | 5-[4-(trifluoromethyl)-2-pyridyl]-1,3,4-oxadiazol-2-ol |
| 209 | 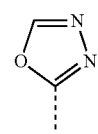 | 3 | 5-(6-cyclopropyl-3-pyridyl)-1,3,4-oxadiazol-2-ol |

Compound 206: 5-[6-(trifluoromethyl)-2-pyridyl]-1,3,4-oxadiazol-2-ol

Following generic route 3, using methyl 6-(trifluoromethyl)picolinate, yield=68% (white solid). LCMS: MS m/z 230.1 [M−H]⁻; ¹H NMR (400 MHz, DMSO) δ 12.95 (s, 1H), 8.29 (apparent t, J=7.9 Hz, 1H), 8.21 (d, J=7.8 Hz, 1H), 8.09 (dd, J=7.8, 0.8 Hz, 1H).

Compound 207: 5-[2-(trifluoromethyl)-4-pyridyl]-1,3,4-oxadiazol-2-ol

Following generic route 3, using methyl 2-(trifluoromethyl)isonicotinate, yield=51% (white solid). LCMS: MS m/z 230.1 [M−H]⁻; ¹H NMR (400 MHz, DMSO) δ 13.10 (s, 1H), 8.96 (d, J=5.1 Hz, 1H), 8.09 (s, 1H), 8.06 (dd, J=5.1, 1.2 Hz, 1H).

Compound 208: 5-[4-(trifluoromethyl)-2-pyridyl]-1,3,4-oxadiazol-2-ol

Following generic route 3, using methyl 4-(trifluoromethyl)picolinate, yield=65% (white solid). LCMS: MS m/z 232.1 [M+H]⁺; ¹H NMR (400 MHz, MeOD) δ 8.91 (d, J=5.1 Hz, 1H), 8.20-8.14 (m, 1H), 7.86-7.78 (m, 1H).

Compound 209: 5-(6-cyclopropyl-3-pyridyl)-1,3,4-oxadiazol-2-ol

Following generic route 3, using methyl 6-cyclopropylpyridine-3-carboxylate yield=8% (white solid). LCMS: MS m/z 204.1 [M+H]⁺; ¹H NMR (400 MHz, DMSO) δ 12.65 (s, 1H), 8.77 (dd, J=2.3, 0.5 Hz, 1H), 7.99 (dd, J=8.3, 2.3 Hz, 1H), 7.48 (dd, J=8.3, 0.7 Hz, 1H), 2.24-2.16 (m, 1H), 1.07-0.96 (m, 4H).

TABLE 35

Heteroaryl substituted 1,3,4-oxadiazoles

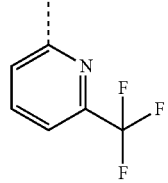

| Compound Number | R group | Generic route | IUPAC Name |
|---|---|---|---|
| 205 | 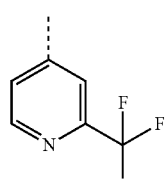 | 5 | 2-[4-(trifluoromethyl)-2-pyridyl]-1,3,4-oxadiazole |
| 221 | | 5 | 2-[6-(trifluoromethyl)-2-pyridyl]-1,3,4-oxadiazole |
| 222 | | 5 | 2-[2-(trifluoromethyl)-4-pyridyl]-1,3,4-oxadiazole |
| 226 | 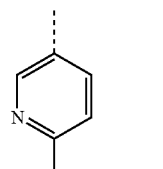 | 5 | 2-(6-cyclopropyl-3-pyridyl)-1,3,4-oxadiazole |

Compound 205: 2-[4-(trifluoromethyl)-2-pyridyl]-1,3,4-oxadiazole

Following generic route 5, using 4-(trifluoromethyl)pyridine-2-carbohydrazide yield=54% (colourless oil). LCMS: MS m/z 214.1 [M−H]⁻; ¹H NMR (400 MHz, MeOD) δ 9.18 (s, 1H), 9.02 (d, J=5.1 Hz, 1H), 8.51-8.47 (m, 1H), 7.96-7.91 (m, 1H).

Compound 221: 2-[6-(trifluoromethyl)-2-pyridyl]-1,3,4-oxadiazole

Following generic route 5, using 6-(trifluoromethyl)pyridine-2-carbohydrazide, yield=14% (white solid). LCMS: MS m/z 216.0 [M+H]⁺; ¹H NMR (400 MHz, DMSO) δ 9.49 (s, 1H), 8.50 (d, J=8.0 Hz, 1H), 8.38 (apparent t, J=7.9 Hz, 1H), 8.18 (dd, J=7.9, 0.8 Hz, 1H).

Compound 222: 2-[2-(trifluoromethyl)-4-pyridyl]-1,3,4-oxadiazole

Following generic route 5, using 4-(trifluoromethyl)pyridine-2-carbohydrazide yield=54% (white solid). LCMS: MS m/z 216.0 [M+H]⁺; ¹H NMR (400 MHz, MeOD) δ 9.18 (s, 1H), 9.02 (d, J=5.1 Hz, 1H), 8.51-8.47 (m, 1H), 7.96-7.91 (m, 1H).

Compound 226: 2-(6-cyclopropyl-3-pyridyl)-1,3,4-oxadiazole

Following generic route 5, using 6-cyclopropylpyridine-3-carbohydrazide, yield=33% (white solid). LCMS: MS m/z 188.1 [M+H]⁺, ¹H NMR (600 MHz, DMSO) δ 9.37 (s, 1H), 9.01 (dd, J=2.2, 0.7 Hz, 1H), 8.22 (dd, J=8.2, 2.2 Hz, 1H), 7.54 (dd, J=8.2, 0.8 Hz, 1H), 2.27-2.21 (m, 1H), 1.09-1.00 (m, 4H).

Further Examples

TABLE 36

O-Substituted 5-(2,4-dichloro-3-(trifluoromethyl)phenyl)-1,3,4-oxadiazol-2-ols

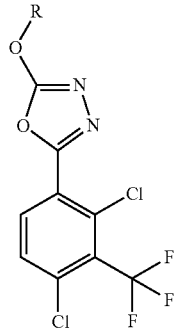

| Compound Number | R group | Generic route | IUPAC Name |
|---|---|---|---|
| 241 | CD₃ | 14 | 2-(2,4-dichloro-3-(trifluoromethyl)phenyl)-5-(methoxy-d3)-1,3,4-oxadiazole |
| 242 | Et | 14 | 2-(2,4-dichloro-3-(trifluoromethyl)phenyl)-5-ethoxy-1,3,4-oxadiazole |
| 243 | CH₃ | 14 | 2-(2,4-dichloro-3-(trifluoromethyl)phenyl)-5-methoxy-1,3,4-oxadiazole |

Compound 241: 2-(2,4-dichloro-3-(trifluoromethyl)phenyl)-5-(methoxy-d3)-1,3,4-oxadiazole Following generic route 14, using methanol-d4, yield=31% (white solid).
LCMS: MS m/z 316.0 [M+H]⁺; ¹H NMR (700 MHz, DMSO) δ 8.08 (dd, J=8.6, 0.6 Hz, 1H), 7.89 (dd, J=8.6, 0.7 Hz, 1H).

Compound 242: 2-(2,4-dichloro-3-(trifluoromethyl)phenyl)-5-ethoxy-1,3,4-oxadiazole Following generic route 14, using sodium ethanolate 21 wt. % in ethanol, yield=28% (white solid).
LCMS: MS m/z no mass ion; ¹H NMR (600 MHz, DMSO) δ 8.10 (dd, J=8.6, 0.6 Hz, 1H), 7.91 (dd, J=8.6, 0.7 Hz, 1H), 4.60 (q, J=7.1 Hz, 2H), 1.44 (dd, J=7.8, 6.4 Hz, 3H).

Compound 243: 2-(2,4-dichloro-3-(trifluoromethyl)phenyl)-5-methoxy-1,3,4-oxadiazole Following generic route 14, using sodium methoxide, yield=49% (white solid).
LCMS: MS m/z 315.0 [M+H]⁺; ¹H NMR (700 MHz, DMSO) δ 8.09 (d, J=8.5 Hz, 1H), 7.91 (d, J=8.6 Hz, 1H), 4.21 (s, 3H).

TABLE 37

N-Substituted 5-(2,4-dichloro-3-(trifluoromethyl)phenyl)-1,3,4-oxadiazol-2-ols

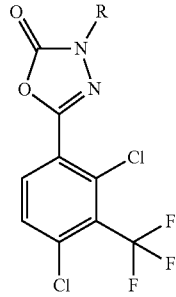

| Compound Number | R group | Generic route | IUPAC Name |
|---|---|---|---|
| 244 | CH₂CN | 17 | 2-(5-(2,4-dichloro-3-(trifluoromethyl)phenyl)-2-oxo-1,3,4-oxadiazol-3(2H)-yl)acetonitrile |
| 245 | CH₃ | 17 | 5-(2,4-dichloro-3-(trifluoromethyl)phenyl)-3-methyl-1,3,4-oxadiazol-2(3H)-one |

Compound 244: 2-(5-(2,4-dichloro-3-(trifluoromethyl)phenyl)-2-oxo-1,3,4-oxadiazol-3(2H)-yl)acetonitrile Following generic route 17, using chloroacetonitrile, yield=74% (white solid).
LCMS: MS m/z no mass ion; ¹H NMR (700 MHz, DMSO) δ 8.05 (dd, J=8.6, 0.5 Hz, 1H), 7.92 (dd, J=8.6, 0.6 Hz, 1H), 5.22 (s, 2H).

Compound 245: 5-(2,4-dichloro-3-(trifluoromethyl)phenyl)-3-methyl-1,3,4-oxadiazol-2(3H)-one Following generic route 17, using iodomethane, yield=81% (white solid).

LCMS: MS m/z no mass ion; $^1$H NMR (700 MHz, DMSO) δ 8.03 (dd, J=8.6, 0.6 Hz, 1H), 7.89 (dd, J=8.6, 0.7 Hz, 1H), 3.45 (s, 3H).

TABLE 38

N-Substituted 5-(2,4-dichloro-3-(trifluoromethyl)phenyl)-1,3,4-oxadiazol-2-amines

| Compound Number | R group | Salt | Generic route | IUPAC Name |
|---|---|---|---|---|
| 246 | ⁓N≡ (propargyl-like, see structure) | NH$_3$ | 16 | N-(5-(2,4-dichloro-3-(trifluoromethyl)phenyl)-1,3,4-oxadiazol-2-yl)cyanamide, ammonia salt |
| 247 | N,N-dimethyl | | 16 | 5-(2,4-dichloro-3-(trifluoromethyl)phenyl)-N,N-dimethyl-1,3,4-oxadiazol-2-amine |
| 248 | H | | — | 5-(2,4-dichloro-3-(trifluoromethyl)phenyl)-1,3,4-oxadiazol-2-amine |
| 249 | Me | | — | 5-(2,4-dichloro-3-(trifluoromethyl)phenyl)-N-methyl-1,3,4-oxadiazol-2-amine |

Compound 246: N-(5-(2,4-dichloro-3-(trifluoromethyl)phenyl)-1,3,4-oxadiazol-2-yl)cyanamide, Ammonia Salt Following generic route 16, using sodium hydrogen cyanamide, yield=33% (white solid).

LCMS: MS m/z 323.0 [M+H]$^+$; $^1$H NMR (700 MHz, DMSO) δ 7.99 (d, J=8.6 Hz, 1H), 7.79 (d, J=8.6 Hz, 1H), 7.08 (s, 4H).

Compound 247: 5-(2,4-dichloro-3-(trifluoromethyl)phenyl)-N,N-dimethyl-1,3,4-oxadiazol-2-amine Following generic route 16, using dimethylamine 2N in tetrahydrofuran, yield=92% (white solid).

LCMS: MS m/z 326.1 [M+H]$^+$; $^1$H NMR (700 MHz, DMSO) δ 8.10 (d, J=8.6 Hz, 1H), 7.86 (d, J=8.6 Hz, 1H), 3.08 (s, 6H).

Compound 248: 5-(2,4-dichloro-3-(trifluoromethyl)phenyl)-1,3,4-oxadiazol-2-amine

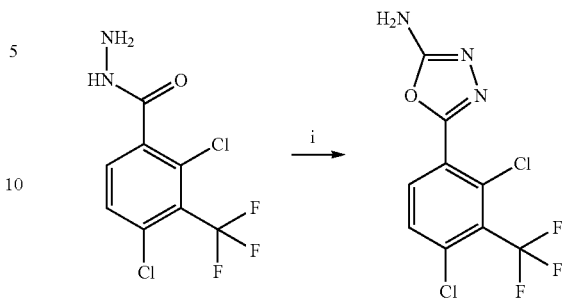

Reagents and conditions: i) Trimethylsilylisothiocyanate, 5N sodium hydroxide, 5% iodine in 10% potassium iodide, ethanol, reflux.

Step 1:
2,4-dichloro-3-(trifluoromethyl)benzohydrazide (100 mg, 0.37 mmol) and trimethylsilylisothiocyanate (0.05 mL, 0.37 mmol) in ethanol (5 mL) was refluxed for 4 hours. An additional trimethylsilylisothiocyanate (0.05 mL, 0.37 mmol) was added and the reaction was heated at reflux overnight. Sodium hydroxide 5N in water (0.37 mL, 1.83 mmol) was added resulting in the formation of a clear solution. To this 5% iodine in 10% potassium iodide solution was added dropwise with stirring until the colour of iodine persisted (approx. 3.5 mL added). The reaction mixture was refluxed for an additional 2 hours, cooled and poured on to ice-water. The solid was separated via Büchner filtration. The solid was dried under a continuous flow of air. $^1$H NMR showed residual impurities. The crude material was dissolved in the minimum volume of dimethyl sulfoxide and chromatographed via reverse phase (eluent 0-100% acetonitrile in water, 0.1% ammonium hydroxide modifier) to give 5-[2,4-dichloro-3-(trifluoromethyl)phenyl]-1,3,4-oxadiazol-2-amine (34 mg, 0.11 mmol, 31%) as a white solid.

LCMS: MS m/z 298.0 [M+H]$^+$; $^1$H NMR (700 MHz, DMSO) δ 8.02 (d, J=8.6 Hz, 1H), 7.86 (d, J=8.6 Hz, 1H), 7.45 (s, 2H).

Compound 249: 5-(2,4-dichloro-3-(trifluoromethyl)phenyl)-N-methyl-1,3,4-oxadiazol-2-amine

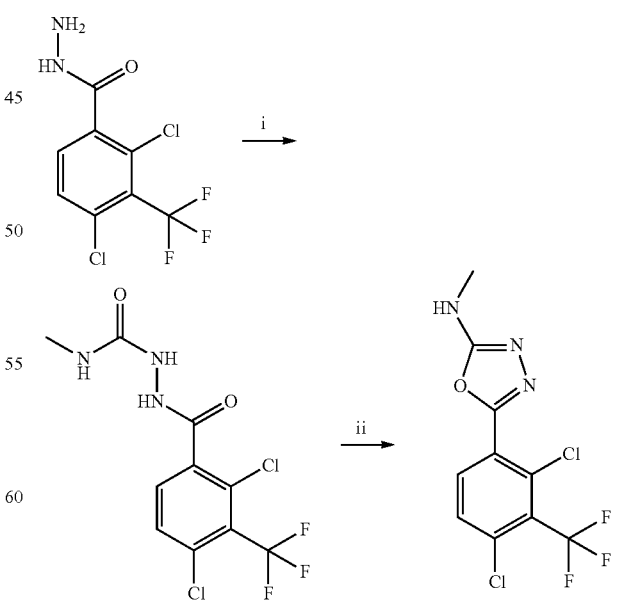

Reagents and conditions: i) N-Methylcarbamoyl chloride, N,N-diisopropylethylamine, acetonitrile; ii) N,N-diisopropylethylamine, para-toluenesulfonyl chloride, dichloromethane.

Step 1:

To a solution of 2,4-dichloro-3-(trifluoromethyl)benzohydrazide (100 mg, 0.37 mmol) in acetonitrile (2 mL) was added N,N-diisopropylethylamine (0.13 mL, 0.73 mmol) followed by N-methylcarbamoyl chloride (41 mg, 0.44 mmol). The reaction was stirred at room temperature overnight. After this time the reaction mixture was loaded directly on to a reverse phase cartridge (12 g, eluent 0-100% acetonitrile in water, 0.1% ammonium hydroxide modifier) to give 1-[[2,4-dichloro-3-(trifluoromethyl)benzoyl]amino]-3-methyl-urea (33 mg, 0.1 mmol, 27%) as an off-white solid.

LCMS: MS m/z 330.1 [M−H]⁻.

Step 2:

To a solution of 1-[[2,4-dichloro-3-(trifluoromethyl)benzoyl]amino]-3-methyl-urea (33 mg, 0.1 mmol) and N,N-diisopropylethylamine (0.09 mL, 0.5 mmol) in dichloromethane (2 mL) was added para-toluenesulfonyl chloride (57 mg, 0.3 mmol). The reaction was stirred at room temperature for 2 hours. After this time the reaction was concentrated under a continuous flow of air. The residue was dissolved in the minimum volume of DMSO and chromatographed via reverse phase (eluent 0-100% acetonitrile in water, 0.1% ammonium hydroxide modifier) to give 5-(2,4-dichloro-3-(trifluoromethyl)phenyl)-N-methyl-1,3,4-oxadiazol-2-amine (21 mg, 0.067 mmol, 67%) as a white solid.

LCMS: MS m/z 312.0 [M+H]⁺; ¹H NMR (700 MHz, DMSO) δ 8.02 (d, J=8.6 Hz, 1H), 7.85 (d, J=8.6 Hz, 1H), 7.84-7.81 (m, 1H), 2.87 (d, J=4.9 Hz, 3H).

TABLE 39

Substituted 5-phenyl-1,3,4-oxadiazol-2-ols

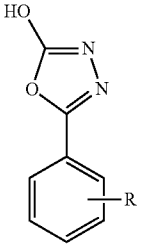

| Compound Number | R group | Generic route | IUPAC Name |
|---|---|---|---|
| 250 | 3-Cl, 4,5- | 4 | 5-(8-chlorochroman-6-yl)-1,3,4-oxadiazol-2-ol |
| 251 | 3,4- | 4 | 5-(chroman-6-yl)-1,3,4-oxadiazol-2-ol |
| 252 | 3-Cl, 4,5- | 4 | 5-(7-chloro-3,3-dimethyl-2,3-dihydrobenzofuran-5-yl)-1,3,4-oxadiazol-2-ol |
| 253 | 3,4- | 4 | 5-(3,3-dimethyl-2,3-dihydrobenzofuran-5-yl)-1,3,4-oxadiazol-2-ol |
| 254 | 3,4- | 4 | 5-(1'-methylspiro[cyclopropane-1,3'-indolin]-5'-yl)-1,3,4-oxadiazol-2-ol |

TABLE 39-continued

Substituted 5-phenyl-1,3,4-oxadiazol-2-ols

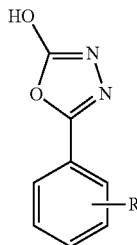

| Compound Number | R group | Generic route | IUPAC Name |
|---|---|---|---|
| 255 | 3,4- (structure) | 4 | 5-(4-methyl-3,4-dihydrospiro[benzo[b][1,4]oxazine-2,1'-cyclopropan]-7-yl)-1,3,4-oxadiazol-2-ol |
| 256 | 3,4- (structure) | 4 | 5-(1,4-dimethyl-1,2,3,4-tetrahydroquinoxalin-6-yl)-1,3,4-oxadiazol-2-ol |
| 257 | 3-Cl, 5-OCF$_3$ | 4 | 5-(3-chloro-5-(trifluoromethoxy)phenyl)-1,3,4-oxadiazol-2-ol |
| 258 | 3-CF$_3$, 4-Br | 4 | 5-(4-bromo-3-(trifluoromethyl)phenyl)-1,3,4-oxadiazol-2-ol |
| 259 | 3-pyrrolidine, 4-CF$_3$ | 15 | 5-(3-(pyrrolidin-1-yl)-4-(trifluoromethyl)phenyl)-1,3,4-oxadiazol-2-ol |
| 260 | 3-morpholine, 4-CF$_3$ | 15 | 5-(3-morpholino-4-(trifluoromethyl)phenyl)-1,3,4-oxadiazol-2-ol |
| 261 | 2-Cl, 3-CF$_3$, 4-Cl | 4 | 5-[2,4-dichloro-3-(trifluoromethyl)phenyl]-1,3,4-oxadiazol-2-ol |
| 262 | 2-CH$_3$, 3-CF$_3$ | 4 | 5-[2-methyl-3-(trifluoromethyl)phenyl]-1,3,4-oxadiazol-2-ol |
| 263 | 2-Cl, 3-CF$_3$ | 4 | 5-[2-chloro-3-(trifluoromethyl)phenyl]-1,3,4-oxadiazol-2-ol |
| 264 | 3-CF$_3$, 4-pyrrolidine | 4 | 5-[4-pyrrolidin-1-yl-3-(trifluoromethyl)phenyl]-1,3,4-oxadiazol-2-ol |
| 265 | 3-CF$_3$, 4-morpholine | 4 | 5-[4-morpholino-3-(trifluoromethyl)phenyl]-1,3,4-oxadiazol-2-ol |
| 266 | 3-CF$_3$, 4- (3,3-difluoroazetidin-1-yl) | 4 | 5-[4-(3,3-difluoroazetidin-1-yl)-3-(trifluoromethyl)phenyl]-1,3,4-oxadiazol-2-ol |
| 267 | 3-CF$_3$, 4- (3-fluoroazetidin-1-yl) | 4 | 5-[4-(3-fluoroazetidin-1-yl)-3-(trifluoromethyl)phenyl]-1,3,4-oxadiazol-2-ol |
| 268 | 2-CH$_3$, 5-CF$_3$ | 4 | 5-[2-methyl-5-(trifluoromethyl)phenyl]-1,3,4-oxadiazol-2-ol |

TABLE 39-continued

Substituted 5-phenyl-1,3,4-oxadiazol-2-ols

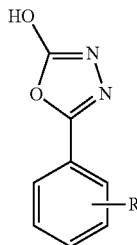

| Compound Number | R group | Generic route | IUPAC Name |
|---|---|---|---|
| 269 | 3,4- 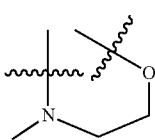 | 4 | 5-(4-methyl-2,3-dihydro-1,4-benzoxazin-7-yl)-1,3,4-oxadiazol-2-ol |

Compound 250:
5-(8-chlorochroman-6-yl)-1,3,4-oxadiazol-2-ol

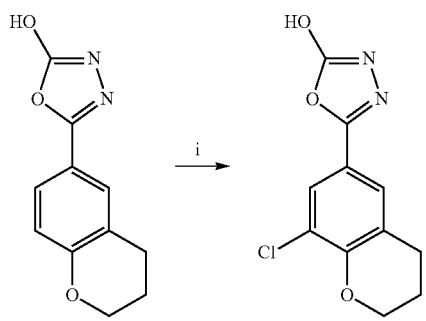

Reagents and conditions: i) N-Chlorosuccinimide, acetic acid

To a solution of 5-chroman-6-yl-1,3,4-oxadiazol-2-ol (80 mg, 0.37 mmol) in acetic acid (1 mL) was added N-chlorosuccinimide (64 mg, 0.48 mmol). The reaction was stirred at 25° C. for 2 hours. After this time the reaction was quenched with saturated aqueous sodium bicarbonate solution and extracted into ethyl acetate. The organics were combined, dried over anhydrous magnesium sulfate, filtered to remove the solids and concentrated under reduced pressure. The crude material was dissolved in to a minimum volume of dimethyl sulfoxide and purified via reverse phase column chromatography (0-100% acetonitrile in water, 0.1% formic acid modifier) to give 5-(8-chlorochroman-6-yl)-1,3,4-oxadiazol-2-ol yield=75% (white solid).

LCMS: MS m/z 251.1 [M–H]$^-$; $^1$H NMR (700 MHz, DMSO) δ 12.51 (s, 1H), 7.57 (s, 1H), 7.48 (s, 1H), 4.36-4.26 (m, 2H), 2.84 (t, J=6.3 Hz, 2H), 1.99-1.89 (m, 2H).

Compound 251:
5-(chroman-6-yl)-1,3,4-oxadiazol-2-ol

Following generic route 4, using chromane-6-carbohydrazide, yield=82% (white solid).

LCMS: MS m/z 217.2 [M–H]$^-$; $^1$H NMR (700 MHz, DMSO) δ 12.20 (s, 1H), 7.53-7.46 (m, 2H), 6.86 (d, J=8.4 Hz, 1H), 4.26-4.12 (m, 2H), 2.79 (t, J=6.3 Hz, 2H), 2.00-1.88 (m, 2H).

Compound 252: 5-(7-chloro-3,3-dimethyl-2,3-dihydrobenzofuran-5-yl)-1,3,4-oxadiazol-2-ol

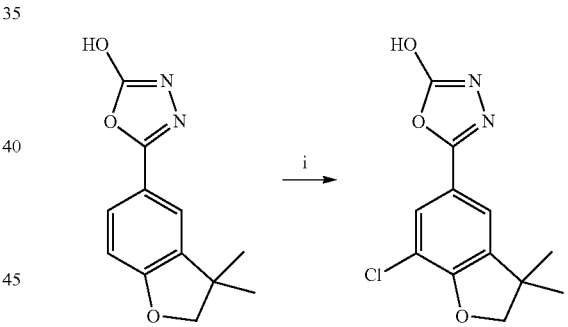

Reagents and conditions: i) N-Chlorosuccinimide, acetic acid

To a solution of 5-(3,3-dimethyl-2H-benzofuran-5-yl)-1,3,4-oxadiazol-2-ol (75 mg, 0.32 mmol) in acetic acid (1 mL) was added N-chlorosuccinimide (56 mg, 0.42 mmol). The reaction was stirred at 25° C. for 2 hours. After this time the reaction was quenched with saturated aqueous sodium bicarbonate solution and extracted into ethyl acetate. The organics were combined, dried over anhydrous magnesium sulfate, filtered to remove the solids and concentrated under reduced pressure. The crude material was dissolved in to a minimum volume of dimethyl sulfoxide and purified via reverse phase column chromatography (0-100% acetonitrile in water, 0.1% formic acid modifier) to give 5-(3,3-dimethyl-2H-benzofuran-5-yl)-1,3,4-oxadiazol-2-ol, yield=43% (white solid).

LCMS: MS m/z 265.1 [M–H]$^-$; $^1$H NMR (700 MHz, DMSO) δ 12.50 (s, 1H), 7.61 (d, J=1.6 Hz, 1H), 7.57 (d, J=1.6 Hz, 1H), 4.42 (s, 2H), 1.34 (s, 6H).

Compound 253: 5-(3,3-dimethyl-2,3-dihydrobenzofuran-5-yl)-1,3,4-oxadiazol-2-ol Following generic route 4, using 3,3-dimethyl-2H-benzofuran-5-carbohydrazide, yield=72% (white solid).
LCMS: MS m/z 231.1 [M−H]⁻; ¹H NMR (700 MHz, DMSO) δ 12.38 (s, 1H), 7.62 (d, J=1.4 Hz, 1H), 7.56 (dd, J=8.3, 1.6 Hz, 1H), 6.91 (d, J=8.4 Hz, 1H), 4.30 (s, 2H), 1.32 (s, 6H).

Compound 254: 5-(1'-methylspiro[cyclopropane-1,3'-indolin]-5'-yl)-1,3,4-oxadiazol-2-ol Following generic route 4, using methyl 1'-methylspiro[cyclopropane-1,3'-indoline]-5'-carboxylate, yield=10% (white solid).
LCMS: MS m/z 244.2 [M+H]⁺; ¹H NMR (600 MHz, DMSO) δ 12.19 (s, 1H), 7.41 (dd, J=8.2, 1.8 Hz, 1H), 6.92 (d, J=1.6 Hz, 1H), 6.52 (d, J=8.3 Hz, 1H), 3.48 (s, 2H), 2.83 (s, 3H), 1.04-0.96 (m, 4H).

Compound 255: 5-(4-methyl-3,4-dihydrospiro[benzo[b][1,4]oxazine-2,1'-cyclopropan]-7-yl)-1,3,4-oxadiazol-2-ol Following generic route 4, using 4-methylspiro[3H-1,4-benzoxazine-2,1'-cyclopropane]-7-carbohydrazide, yield=56% (white solid).
LCMS: MS m/z 260.1 [M+H]⁺; ¹H NMR (600 MHz, DMSO) δ 12.25 (s, 1H), 7.25 (dd, J=8.5, 2.0 Hz, 1H), 6.93 (d, J=2.0 Hz, 1H), 6.80 (d, J=8.6 Hz, 1H), 3.34 (s, 2H), 2.94 (s, 3H), 0.94 (q, J=5.7 Hz, 2H), 0.76 (q, J=5.7 Hz, 2H).

Compound 256: 5-(1,4-dimethyl-1,2,3,4-tetrahydroquinoxalin-6-yl)-1,3,4-oxadiazol-2-ol Following generic route 4, using 1,4-dimethyl-1,2,3,4-tetrahydroquinoxalin-6-carbohydrazide, yield=72% (white solid).
LCMS: MS m/z 247.2 [M+H]⁺; ¹H NMR (600 MHz, DMSO) δ 12.18 (s, 1H), 7.02 (dd, J=8.3, 2.0 Hz, 1H), 6.72 (d, J=1.9 Hz, 1H), 6.50 (d, J=8.4 Hz, 1H), 3.40 (dd, J=5.7, 4.1 Hz, 2H), 3.26 (dd, J=5.7, 4.1 Hz, 2H), 2.88 (s, 3H), 2.82 (s, 3H).

Compound 257: 5-(3-chloro-5-(trifluoromethoxy)phenyl)-1,3,4-oxadiazol-2-ol

Following generic route 4, using 3-chloro-5-(trifluoromethoxy)benzohydrazide, yield=82% (white solid).
LCMS: MS m/z 279.0 [M−H]⁻; ¹H NMR (600 MHz, DMSO) δ 12.82 (s, 1H), 7.83 (t, J=1.6 Hz, 1H), 7.81 (s, 1H), 7.69-7.66 (m, 1H).

Compound 258: 5-(4-bromo-3-(trifluoromethyl)phenyl)-1,3,4-oxadiazol-2-ol

Following generic route 4, using methyl 4-bromo-3-(trifluoromethyl)benzoate, yield=79% (white solid).
LCMS: MS m/z 307.0 [M−H]⁻; ¹H NMR (400 MHz, DMSO) δ 12.83 (s, 1H), 8.08 (d, J=8.4 Hz, 1H), 8.05 (d, J=2.0 Hz, 1H), 7.95 (dd, J=8.4, 2.0 Hz, 1H).

Compound 259: 5-(3-(pyrrolidin-1-yl)-4-(trifluoromethyl)phenyl)-1,3,4-oxadiazol-2-ol Following generic route 15, using pyrrolidine, yield=93% (white solid).
LCMS: MS m/z 300.0 [M+H]⁺; ¹H NMR (700 MHz, CDCl₃) δ 9.15 (br s, 1H), 7.65 (d, J=8.3 Hz, 1H), 7.36 (app s, 1H), 7.25 (d, J=8.3 Hz, 1H), 3.42-3.41 (m, 4H), 2.00-1.98 (m, 4H).

Compound 260: 5-(3-morpholino-4-(trifluoromethyl)phenyl)-1,3,4-oxadiazol-2-ol Following generic route 15, using morpholine, yield=81% (white solid).
LCMS: MS m/z 316.1 [M+H]⁺; ¹H NMR (700 MHz, CDCl₃) δ 9.55 (br s, 1H), 7.82 (s, 1H), 7.76 (d, J=8.1 Hz, 1H), 7.71 (d, J=8.1 Hz, 1H), 3.87 (app t, J=4.4 Hz, 4H), 2.99 (app t, J=4.4 Hz, 4H).

Compound 261: 5-[2,4-dichloro-3-(trifluoromethyl)phenyl]-1,3,4-oxadiazol-2-ol Following generic route 4, using 2,4-dichloro-3-(trifluoromethyl)benzoic acid, yield=24% (white solid).
LCMS: MS m/z 297.0 [M−H]⁻; ¹H NMR (600 MHz, CDCl₃) δ 9.04 (s, 1H), 7.82 (apparent dd, J=8.6, 0.6 Hz, 1H), 7.58 (apparent dd, J=8.6, 0.7 Hz, 1H).

Compound 262: 5-[2-methyl-3-(trifluoromethyl)phenyl]-1,3,4-oxadiazol-2-ol

Following generic route 4, using 2-methyl-3-(trifluoromethyl)benzohydrazide, yield=20% (white solid).
LCMS: MS m/z 243.1 [M−H]⁻; ¹H NMR (400 MHz, CDCl₃) δ 9.13 (s, 1H), 7.95 (d, J=7.9 Hz, 1H), 7.81 (d, J=7.9 Hz, 1H), 7.43 (apparent t, J=7.9 Hz, 1H), 2.71 (d, J=1.2 Hz, 3H).

Compound 263: 5-[2-chloro-3-(trifluoromethyl)phenyl]-1,3,4-oxadiazol-2-ol

Following generic route 4, using 2-chloro-3-(trifluoromethyl)benzohydrazide, yield=16% (white solid).
LCMS: MS m/z 263.0 [M−H]⁻; ¹H NMR (600 MHz, DMSO) δ 12.91 (s, 1H), 8.11 (dd, J=7.9, 1.4 Hz, 1H), 8.08 (dd, J=7.9, 1.4 Hz, 1H), 7.74 (apparent t, J=7.9 Hz, 1H).

Compound 264: 5-[4-pyrrolidin-1-yl-3-(trifluoromethyl)phenyl]-1,3,4-oxadiazol-2-ol Following generic route 4, using 4-pyrrolidin-1-yl-3-(trifluoromethyl)benzohydrazide, yield=9% (white solid).
LCMS: MS m/z 300.1 [M+H]⁺; ¹H NMR (600 MHz, DMSO) δ 12.39 (br s 1H), 7.85 (d, J=2.2 Hz, 1H), 7.75 (dd, J=9.0, 2.2 Hz, 1H), 7.10 (d, J=9.0 Hz, 1H), 3.42-3.38 (m, 4H), 1.94-1.92 (m, 4H).

Compound 265: 5-[4-morpholino-3-(trifluoromethyl)phenyl]-1,3,4-oxadiazol-2-ol Following generic route 4, using 4-morpholino-3-(trifluoromethyl)benzohydrazide, yield=9% (white solid).
LCMS: MS m/z 314.1 [M−H]⁻; ¹H NMR (400 MHz, MeOD) δ 8.09-7.99 (m, 2H), 7.59 (d, J=8.4 Hz, 1H), 3.85-3.75 (m, 4H), 3.04-2.94 (m, 4H).

Compound 266: 5-[4-(3,3-difluoroazetidin-1-yl)-3-(trifluoromethyl)phenyl]-1,3,4-oxadiazol-2-ol

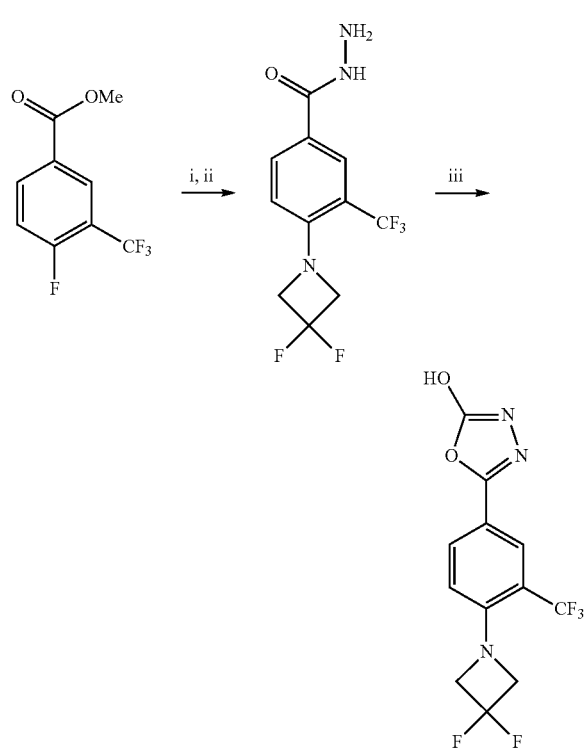

Reagents and conditions: i) N,N-Diisopropylethylamine, dimethyl sulfoxide, 3,3-difluoroazetidine hydrochloride; ii) toluene, ethanol, hydrazine, monohydrate; iii) generic route 4.

Step 1:

3,3-Difluoroazetidine hydrochloride (128 mg, 0.99 mmol), N,N-diisopropylethylamine (0.34 mL, 1.98 mmol) and methyl 4-fluoro-3-(trifluoromethyl)benzoate (200 mg, 0.90 mmol) were heated to 65° C. in dimethyl sulfoxide (1 mL) for 4 hours, by which time the starting material appeared to have been consumed by TLC.

Step 2:

The reaction mixture was then concentrated under reduced pressure and the crude residue was dissolved in toluene (1 mL) and ethanol (1 mL). Hydrazine monohydrate (0.17 mL, 0.90 mmol) was then added and the reaction mixture was heated at 65° C. for 16 hours, by which time the starting material appeared to have been consumed by TLC. The reaction mixture was then concentrated under reduced pressure and the crude residue was recrystallised from cyclohexane and diethyl ether to give crude 4-(3,3-difluoroazetidin-1-yl)-3-(trifluoromethyl)benzohydrazide (124 mg, 0.4200 mmol, 46.7% yield) as a yellow solid that was used without further purification.

Step 3:

Following generic route 4, using 4-(3,3-difluoroazetidin-1-yl)-3-(trifluoromethyl)benzohydrazide, yield=24% (white solid).

LCMS: MS m/z 320.0 [M−H]−; 1H NMR (600 MHz, DMSO) δ 12.47 (s, 1H), 7.87-7.82 (m, 2H), 6.84 (d, J=8.5 Hz, 1H), 4.54 (apparent t, J=12.2 Hz, 4H).

Compound 267: 5-[4-(3-fluoroazetidin-1-yl)-3-(trifluoromethyl)phenyl]-1,3,4-oxadiazol-2-ol

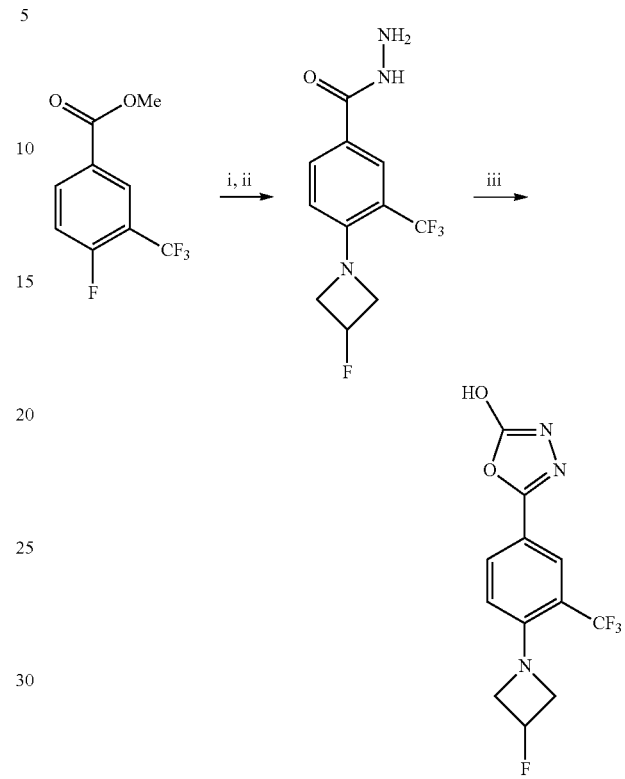

Reagents and conditions: i) N,N-Diisopropylethylamine, dimethyl sulfoxide, 3-fluoroazetidine hydrochloride; ii) toluene, ethanol, hydrazine monohydrate; iii) generic route 4.

Step 1:

3-Fluoroazetidine hydrochloride (110 mg, 0.99 mmol), N,N-diisopropylethylamine (0.34 mL, 1.98 mmol) and methyl 4-fluoro-3-(trifluoromethyl)benzoate (200 mg, 0.90 mmol) were heated to 65° C. in dimethyl sulfoxide (1 mL) for 4 hours, by which time the starting material appeared to have been consumed by TLC.

Step 2:

The reaction mixture was then concentrated under reduced pressure and the crude residue was dissolved in toluene (1 mL) and ethanol (1 mL). Hydrazine monohydrate (0.17 mL, 3.60 mmol) was then added and the reaction mixture was heated at 65° C. for 16 hours, by which time the starting material appeared to have been consumed by TLC. The reaction mixture was then concentrated under reduced pressure and the crude residue was recrystallised from cyclohexane and diethyl ether to give crude 4-(3-fluoroazetidin-1-yl)-3-(trifluoromethyl)benzohydrazide (82 mg, 0.30 mmol, 33% yield) as a yellow solid that was used without further purification.

Step 3:

Following generic route 4, using 4-(3-fluoroazetidin-1-yl)-3-(trifluoromethyl)benzohydrazide, yield=29% (white solid).

LCMS: MS m/z 302.1 [M−H]−; 1H NMR 1H NMR (400 MHz, MeOD) δ 7.93 (d, J=2.0 Hz, 1H), 7.83 (dd, J=8.8, 2.0 Hz, 1H), 6.69 (d, J=8.8 Hz, 1H), 5.42 (dtt, J=58.0, 5.9, 3.1 Hz, 1H), 4.53-4.38 (m, 2H), 4.27-4.14 (m, 2H).

Compound 268: 5-[2-methyl-5-(trifluoromethyl) phenyl]-1,3,4-oxadiazol-2-ol

Following generic route 4, using 2-methyl-5-(trifluoromethyl)benzoic acid, yield=3% (white solid).
LCMS: MS m/z 243.1 [M−H]⁻; ¹H NMR (400 MHz, DMSO) δ 12.75 (s, 1H), 7.94 (s, 1H), 7.82 (d, J=8.0 Hz, 1H), 7.65 (d, J=8.0 Hz, 1H), 2.62 (s, 3H).

Compound 269: 5-(4-methyl-2,3-dihydro-1,4-benzoxazin-7-yl)-1,3,4-oxadiazol-2-ol Following generic route 4, using 4-methyl-3, 4-dihydro-2H-1, 4-benzoxazine-7-carboxylic acid, yield=3% (white solid).
LCMS: MS m/z 234.1 [M+H]⁺; ¹H NMR (700 MHz, MeOD) δ 7.28 (dd, J=8.5, 2.0 Hz, 1H), 7.11 (d, J=2.0 Hz, 1H), 6.73 (d, J=8.5 Hz, 1H), 4.28-4.24 (m, 2H), 3.38-3.35 (m, 2H), 2.96 (s, 3H).

TABLE 40

Substituted ((phenyl)-1H-1,2,3-triazol-4-yl)methanols

| Compound Number | R group | Generic route | IUPAC Name |
|---|---|---|---|
| 270 | 3-OCF₃, 4-Cl | 2 | (1-(4-chloro-3-(trifluoromethoxy) phenyl)-1H-1,2,3-triazol-4-yl)methanol |
| 271 | 4-CF₃ | 19 | (1-(4-(trifluoromethyl)phenyl)-1H-1,2,3-triazol-4-yl)methanol |
| 272 | 4-F | 19 | (1-(4-fluorophenyl)-1H-1,2,3-triazol-4-yl)methanol |
| 273 | 2-F | 19 | (1-(2-fluorophenyl)-1H-1,2,3-triazol-4-yl)methanol |
| 274 | 3-F | 19 | (1-(3-fluorophenyl)-1H-1,2,3-triazol-4-yl)methanol |
| 275 | 3-CF₃ | 19 | (1-(3-(trifluoromethyl)phenyl)-1H-1,2,3-triazol-4-yl)methanol |
| 276 | 3-ᶜPr, 4-Cl | — | (1-(4-chloro-3-cyclopropylphenyl)-1H-1,2,3-triazol-4-yl)methanol |
| 277 | 2-Cl, 3-CF₃, 4-Cl | 21 | [1-[2,4-dichloro-3-(trifluoromethyl) phenyl]triazol-4-yl]methanol |

Compound 270: (1-(4-chloro-3-(trifluoromethoxy) phenyl)-1H-1,2,3-triazol-4-yl)methanol Following generic route 2, using 4-chloro-3-(trifluoromethoxy)aniline, yield=77% (white solid).
LCMS: MS m/z 294.1 [M+H]⁺; ¹H NMR (700 MHz, DMSO) δ 8.84 (s, 1H), 8.17 (d, J=1.1 Hz, 1H), 8.04 (dd, J=8.8, 2.5 Hz, 1H), 7.93 (d, J=8.8 Hz, 1H), 5.37 (t, J=5.6 Hz, 1H), 4.61 (d, J=5.5 Hz, 2H).

Compound 271: (1-(4-(trifluoromethyl)phenyl)-1H-1,2,3-triazol-4-yl)methanol

Following generic route 2, using 4-aminobenzotrifluoride, yield=65% (white solid).
LCMS: MS m/z 244.2 [M+H]⁺; ¹H NMR (700 MHz, DMSO) δ 8.84 (s, 1H), 8.17 (d, J=8.4 Hz, 2H), 7.97 (d, J=8.5 Hz, 2H), 5.38 (t, J=5.6 Hz, 1H), 4.63 (d, J=5.3 Hz, 2H).

Compound 272: (1-(4-fluorophenyl)-1H-1,2,3-triazol-4-yl)methanol

Following generic route 2, using 4-fluoroaniline, yield=32% (white solid).
LCMS: MS m/z 194.2 [M+H]⁺; ¹H NMR (700 MHz, DMSO) δ 8.65 (s, 1H), 7.97-7.88 (m, 2H), 7.47-7.36 (m, 2H), 5.32 (t, J=5.6 Hz, 1H), 4.60 (dd, J=5.6, 0.6 Hz, 2H).

Compound 273: (1-(2-fluorophenyl)-1H-1,2,3-triazol-4-yl)methanol

Following generic route 19, using 2-fluoroaniline, yield=3% (light brown oil).
LCMS: MS m/z 194.1 [M+H]⁺; ¹H NMR (400 MHz, MeOD) δ 8.31 (d, J=2.4 Hz, 1H), 7.89-7.77 (m, 1H), 7.63-7.51 (m, 1H), 7.47-7.35 (m, 2H), 4.80-4.78 (m, 2H).

Compound 274: (1-(3-fluorophenyl)-1H-1,2,3-triazol-4-yl)methanol

Following generic route 19, using 3-fluoroaniline, yield=3% (colourless oil).
LCMS: MS m/z 194.1 [M+H]⁺; ¹H NMR (500 MHz, MeOD) δ 8.50 (s, 1H), 7.73-7.68 (m, 2H), 7.63-7.57 (m, 1H), 7.25 (ddd, J=10.8, 5.3, 1.6 Hz, 1H), 4.76 (s, 2H).

Compound 275: (1-(3-(trifluoromethyl)phenyl)-1H-1,2,3-triazol-4-yl)methanol

Following generic route 19, using 3-(trifluoromethyl)aniline, yield=39% (tan solid).
LCMS: MS m/z 244.1 [M+H]⁺; ¹H NMR (700 MHz, DMSO) δ 8.88 (s, 1H), 8.33-8.16 (m, 2H), 7.87-7.76 (m, 2H), 5.37 (t, J=5.6 Hz, 1H), 4.63 (d, J=5.6, 0.6 Hz, 2H).

Compound 276: (1-(4-chloro-3-cyclopropylphenyl)-1H-1,2,3-triazol-4-yl)methanol

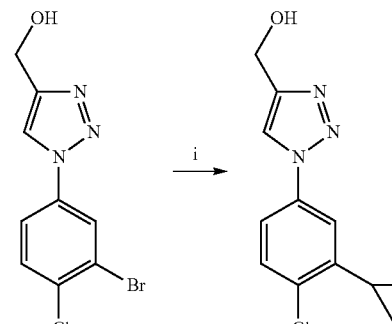

Reagents and conditions: i) Cyclopropylboronic acid MIDA ester, Pd(dppf)Cl₂·dichloromethane, 2 N aqueous sodium hydrogen carbonate, 1,4-dioxane, 130° C.

To a 20 mL microwave vial was added (1-(3-bromo-4-chlorophenyl)-1H-1,2,3-triazol-4-yl)methanol (500 mg, 1.73 mmol), cyclopropylboronic acid MIDA ester (683 mg, 3.47 mmol) and Pd(dppf)Cl₂·dichloromethane (141 mg, 0.17 mmol). The vial was sealed, evacuated and purged with argon 3 times, then 1,4-dioxane (6 mL) and disodium carbonate aqueous solution (2 N, 2.6 mL, 5.2 mmol). The vial was evacuated and purged with argon a further 3 times. The vial was placed on to a preheated aluminium heating block at 130° C. and stirred for 16 hours (solids dissolved upon heating). The contents of the vial were concentrated under reduced pressure. The crude material was suspended in methanol (50 mL), passed through a short silica plug then purified via reverse phase chromatography (0-100% acetonitrile in water, 0.1% formic acid modifier) to give [1-(4-chloro-3-cyclopropyl-phenyl)triazol-4-yl]methanol (8 mg, 0.03 mmol, 2% yield) as a glassy solid.

LCMS: MS m/z 250.2 [M+H]$^+$; $^1$H NMR (700 MHz, MeOD) δ 8.21 (s, 1H), 7.41-7.36 (m, 2H), 7.21-7.19 (m, 1H), 4.78 (d, J=0.6 Hz, 2H), 1.66 (tt, J=8.5, 5.3 Hz, 1H), 0.96-0.82 (m, 2H), 0.77-0.62 (m, 2H).

Compound 277: [1-[2,4-dichloro-3-(trifluoromethyl)phenyl]triazol-4-yl]methanol

Following generic route 21, using 2,4-dichloro-3-(trifluoromethyl)aniline and propargyl alcohol, yield=44% (white solid).

LCMS: MS m/z 312.0 [M+H]$^+$; $^1$H NMR (600 MHz, CDCl$_3$) δ 7.92 (t, J=0.6 Hz, 1H), 7.67-7.62 (m, 2H), 4.93 (t, J=7.3 Hz, 2H), 2.17 (t, J=6.0 Hz, 1H).

TABLE 41

Substituted (phenyl)-1,3,4-oxadiazoles

| Compound Number | R group | Generic route | IUPAC Name |
|---|---|---|---|
| 278 | 3,4- (3,3-dimethyl-2,3-dihydrobenzofuran-5-yl) | 5 | 2-(3,3-dimethyl-2,3-dihydrobenzofuran-5-yl)-1,3,4-oxadiazole |
| 279 | 3-CF$_3$, 4-morpholine | 18 | 4-(4-(1,3,4-oxadiazol-2-yl)-2-(trifluoromethyl)phenyl)morpholine |
| 280 | 3-CF$_3$, 4-pyrrolidine | 18 | 4-(4-(1,3,4-oxadiazol-2-yl)-2-(trifluoromethyl)phenyl)pyrrolidine |
| 281 | 3-pyrrolidine, 4-CF$_3$ | 18 | 2-(3-(pyrrolidin-1-yl)-4-(trifluoromethyl)phenyl)-1,3,4-oxadiazole |
| 282 | 3-(3-fluoroazetidin-1-yl), 4-CF$_3$ | 18 | 2-(3-(3-fluoroazetidin-1-yl)-4-(trifluoromethyl)phenyl)-1,3,4-oxadiazole |
| 283 | 3-CF$_3$, 4-(3-fluoroazetidin-1-yl) | 5 | 2-[4-(3-fluoroazetidin-1-yl)-3-(trifluoromethyl)phenyl]-1,3,4-oxadiazole |
| 284 | 3-CF$_3$, 4-(oxetan-3-yl) | 5 | 2-(4-(oxetan-3-yl)-3-(trifluoromethyl)phenyl)-1,3,4-oxadiazole |
| 311 | 2-Cl, 3CF$_3$, 2-Cl | 5 | 2-[2,4-dichloro-3-(trifluoromethyl)phenyl]-1,3,4-oxadiazole |
| 312 | 2-Cl, 3-CF$_3$ | 5 | 2-[2-chloro-3-(trifluoromethyl)phenyl]-1,3,4-oxadiazole |

Compound 278: 2-(3,3-dimethyl-2,3-dihydrobenzofuran-5-yl)-1,3,4-oxadiazole

Following generic route 5, using 3,3-dimethyl-2H-benzofuran-5-carbohydrazide, yield=65% (white solid).

LCMS: MS m/z 217.2 [M+H]$^+$; $^1$H NMR (700 MHz, DMSO) δ 9.24 (s, 1H), 7.85 (d, J=1.7 Hz, 1H), 7.80 (dd, J=8.3, 1.8 Hz, 1H), 6.97 (d, J=8.3 Hz, 1H), 4.33 (s, 2H), 1.34 (s, 6H).

Compound 279: 4-(4-(1,3,4-oxadiazol-2-yl)-2-(trifluoromethyl)phenyl)morpholine Following generic route 18, using 4-bromo-3-(trifluoromethyl)benzoic acid and morpholine, yield=68% (white solid).

LCMS: MS m/z 300.1 [M+H]$^+$; $^1$H NMR (600 MHz, CDCl$_3$) δ 8.48 (d, J=2.7 Hz, 1H), 8.34 (d, J=2.1 Hz, 1H), 8.24 (dd, J=8.5, 2.0 Hz, 1H), 7.43 (d, J=8.5 Hz, 1H), 3.90-3.81 (m, 4H), 3.06-3.00 (m, 4H).

Compound 280: 4-(4-(1,3,4-oxadiazol-2-yl)-2-(trifluoromethyl)phenyl)pyrrolidine Following generic route 18, using 4-bromo-3-(trifluoromethyl)benzoic acid and pyrrolidine, yield=72% (white solid).

LCMS: MS m/z 290.1 [M+H]$^+$; $^1$H NMR (700 MHz, CDCl$_3$) δ 8.31 (d, J=2.0 Hz, 1H), 8.17 (dd, J=8.4, 2.0 Hz, 1H), 7.31 (d, J=8.4 Hz, 1H), 3.93 (s, 3H), 3.85 (dd, J=5.4, 3.7 Hz, 4H), 3.04-3.00 (m, 4H).

Compound 281: 2-(3-(pyrrolidin-1-yl)-4-(trifluoromethyl)phenyl)-1,3,4-oxadiazole Following generic route 18, using 3-Bromo-4-(trifluoromethyl)benzoic acid and pyrrolidine, yield=86% (off-white solid).

LCMS: MS m/z 284.1 [M+H]$^+$; $^1$H NMR (700 MHz, CDCl$_3$) δ 8.48 (s, 1H), 7.70 (d, J=8.3 Hz, 1H), 7.67 (d, J=8.3 Hz, 1H), 7.43 (d, J=8.3 Hz, 1H), 3.46-3.44 (m, 4H), 2.01-1.99 (m, 4H).

Compound 282: 2-(3-(3-fluoroazetidin-1-yl)-4-(trifluoromethyl)phenyl)-1,3,4-oxadiazole Following generic route 18, using 3-bromo-4-(trifluoromethyl)benzoic acid and 3-fluoroazetidine hydrochloride, yield=28% (white solid).

LCMS: MS m/z 288.0 [M+H]$^+$; $^1$H NMR (600 MHz, CDCl$_3$) δ 8.50 (s, 1H), 7.66 (d, J=8.2 Hz, 1H), 7.45 (d, J=8.2 Hz, 1H), 7.22 (s, 1H), 5.41 (dm, J=57.5 Hz, 1H), 4.46-4.41 (m, 2H), 4.27-4.21 (m, 2H).

Compound 283: 2-[4-(3-fluoroazetidin-1-yl)-3-(trifluoromethyl)phenyl]-1,3,4-oxadiazole Following generic route 5, using 4-(3-fluoroazetidin-1-yl)-3-(trifluoromethyl)benzohydrazide, yield=2% (white solid).

LCMS: MS m/z 288.1 [M+H]$^+$; $^1$H NMR (400 MHz, MeOD) δ 8.93 (s, 1H), 8.18 (d, J=2.0 Hz, 1H), 8.05 (dd, J=8.8, 2.1 Hz, 1H), 6.74 (d, J=8.8 Hz, 1H), 5.44 (dtt, J=58.0, 6.0, 3.0 Hz, 1H), 4.56-4.43 (m, 2H), 4.31-4.18 (m, 2H).

Compound 284: 2-(4-(oxetan-3-yl)-3-(trifluoromethyl)phenyl)-1,3,4-oxadiazole

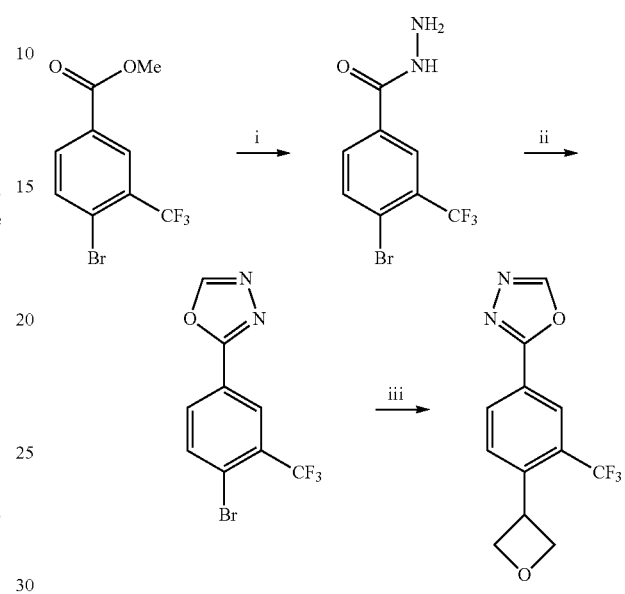

Reagents and conditions: i) Generic route 4; ii) generic route 5; Ir[dF(CF$_3$)ppy]$_2$(dtbbpy)PF$_6$, tris(trimethylsilyl)silane, NiCl$_2$•glyme, 4,4'-di-tert-butyl-2,2'-bipyridine, sodium carbonate, 1,2-dimethoxyethane, 3-bromooxetane.

Step 1:

Following generic route 4, using methyl 4-bromo-3-(trifluoromethyl)benzoate, yield=33% (white solid).

LCMS: MS m/z 282.9 [M+H]$^+$; $^1$H NMR (600 MHz, DMSO) δ 10.11 (s, 1H), 8.23 (s, 1H), 8.03-7.97 (m, 2H), 4.59 (s, 2H).

Step 2:

Following generic route 5, using 4-bromo-3-(trifluoromethyl)benzohydrazide, yield=81% (white solid).

LCMS: MS m/z 293.0 [M+H]$^+$; $^1$H NMR (700 MHz, CDCl$_3$) δ 8.53 (s, 1H), 8.38 (d, J=2.0 Hz, 1H), 8.10 (dd, J=8.3, 2.0 Hz, 1H), 7.90 (d, J=8.3 Hz, 1H).

Step 3:

To a 10 mL microwave vial under an atmosphere of air was added photocatalyst [4,4'-bis(1,1-dimethylethyl)-2,2'-bipyridine-N$^1$,N$^1$']bis[3,5-difluoro-2-[5-(trifluoromethyl)-2-pyridinyl-N]phenyl-C]iridium(III) hexafluorophosphate (2.2 mg, 1.9 μmol), 2-[4-bromo-3-(trifluoromethyl)phenyl]-1,3,4-oxadiazole (95 mg, 0.32 mmol), 3-bromooxetane (27 μL, 0.32 mmol), tris(trimethylsilyl)silane (99 μL, 0.32 mmol), disodium carbonate (69 mg, 0.65 mmol). A stirrer bar was then added and the vessel was sealed. The vessel was evacuated under vacuum, then back-filled with argon (process repeated three times), before addition of ethylene glycol dimethyl ether (2.5 mL). The mixture was then further deoxygenated by purging with argon for 10 minutes. To a separate microwave vial under an atmosphere of air, was added nickel (II) chloride ethylene glycol dimethyl ether complex (3.0 mg, 13 μmol) and 4,4'-di-tert-butyl-2,2'-dipyridyl (3.9 mg, 15 μmol). A stirrer bar was then added and the vessel was sealed. The vessel was evacuated under vacuum, then back-filled with argon (process repeated three times), before addition of ethylene glycol dimethyl ether (6 mL). The mixture was then further deoxygenated by sparging with argon for 5 minutes under stirring to ensure catalyst dissolved. The nickel (II) precatalyst solution (0.65 mL) was then added to the iridium photocatalyst solution. The mixture was then further deoxygenated by sparging with argon for 5 minutes. The vessel was then stirred at room temperature and irradiated with blue strip LED lights for 16 hours at room temperature. The reaction mixture was then concentrated under reduced pressure and purified by silica gel chromatography, eluting with 0-60% ethyl acetate in cyclohexane. The desired fractions were then concentrated under reduced pressure to give 2-[4-(oxetan-3-yl)-3-(trifluoromethyl)phenyl]-1,3,4-oxadiazole (7 mg, 0.03 mmol, 8% yield) as a clear colourless oil.

LCMS: MS m/z 271.1 [M+H]$^+$; $^1$H NMR (600 MHz, DMSO) δ 9.43 (s, 1H), 8.40 (dd, J=8.2, 1.7 Hz, 1H), 8.25 (d, J=1.7 Hz, 1H), 8.21 (d, J=8.2 Hz, 1H), 4.98 (dd, J=8.2, 6.1 Hz, 2H), 4.73 (apparent t, J=6.4 Hz, 2H), 4.67-4.61 (m, 1H).

Compound 311: 2-[2,4-dichloro-3-(trifluoromethyl)phenyl]-1,3,4-oxadiazole

Following generic route 5, using 2,4-dichloro-3-(trifluoromethyl)benzohydrazide, yield=39% (white solid).

LCMS: MS m/z 283.0 [M+H]$^+$; $^1$H NMR (600 MHz, CDCl$_3$) δ 8.60 (s, 1H), 7.96 (apparent dd, J=8.5, 0.6 Hz, 1H), 7.61 (apparent dd, J=8.5, 0.7 Hz, 1H).

Compound 312: 2-[2-chloro-3-(trifluoromethyl)phenyl]-1,3,4-oxadiazole

Following generic route 5, using 2-chloro-3-(trifluoromethyl)benzohydrazide, yield=10% (colourless oil).

LCMS: MS m/z 249.1[M+H]$^+$; $^1$H NMR (400 MHz, CDCl$_3$) δ 8.61 (s, 1H), 8.14 (dd, J=7.9, 1.3 Hz, 1H), 7.92 (dd, J=7.9, 1.3 Hz, 1H), 7.56 (apparent td, J=7.9, 0.7 Hz, 1H).

TABLE 42

Substituted (phenyl)-1H-1,2,3-triazoles

| Compound Number | R group | Generic route | IUPAC Name |
|---|---|---|---|
| 285 | 3-Cl, 4-Cl | 9 | 1-(3,4-dichlorophenyl)-1H-1,2,3-triazole |
| 286 | 3-CF$_3$, 4-pyrrolidine | 9 | 1-(4-(pyrrolidin-1-yl)-3-(trifluoromethyl)phenyl)-1H-1,2,3-triazole |
| 287 | 3-pyrrolidinyl, 4-CF$_3$ | 13 | 1-(3-(pyrrolidin-1-yl)-4-(trifluoromethyl)phenyl)-1H-1,2,3-triazole |
| 288 | 3-(3-fluoroazetidin-1-yl), 4-CF$_3$ | 13 | 1-(3-(3-fluoroazetidin-1-yl)-4-(trifluoromethyl)phenyl)-1H-1,2,3-triazole |
| 289 | 2-Cl, 3-CH$_2$OH, 4-Cl | — | [2,6-dichloro-3-(triazol-1-yl)phenyl]methanol |
| 290 | 2-Cl, 3-Cl, 4-Cl | 20 | 1-(2,3,4-trichlorophenyl)triazole |
| 291 | 2-Cl, 3-Cl, 5-Cl | 20 | 1-(2,3,5-trichlorophenyl)triazole |
| 292 | 3-Cl, 4-Cl, 5-Cl | 20 | 1-(3,4,5-trichlorophenyl)triazole |
| 293 | 2-Cl, 4-Cl, 5-Cl | 20 | 1-(2,4,5-trichlorophenyl)triazole |
| 294 | 2-Cl, 4-Cl, 5-CF$_3$ | 9 | 1-[2,4-dichloro-5-(trifluoromethyl)phenyl]triazole |
| 295 | 2-Cl, 3-CF$_3$, 4-Cl | — | 1[2,4-dichloro-3-(trifluoromethyl)phenyl]triazole |

Compound 285: 1-(3,4-dichlorophenyl)-1H-1,2,3-triazole

Following generic route 9, using 3,4-dichloroaniline, yield=55% (light yellow solid).

LCMS: MS m/z 214.1 [M+H]$^+$; $^1$H NMR (600 MHz, CDCl$_3$) δ 7.98 (d, J=1.1 Hz, 1H), 7.91 (dd, J=2.2, 0.6 Hz, 1H), 7.87 (d, J=1.1 Hz, 1H), 7.66-7.59 (m, 2H).

Compound 286: 1-(4-(pyrrolidin-1-yl)-3-(trifluoromethyl)phenyl)-1H-1,2,3-triazole

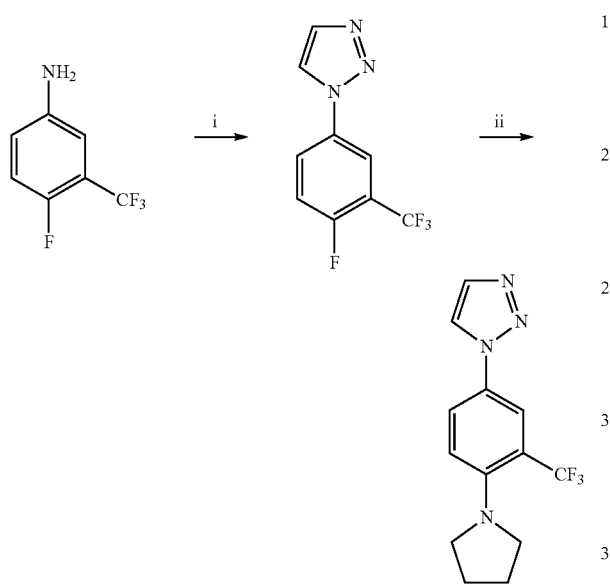

Reagents and conditions: i) Generic route 9; ii) pyrrolidine, N,N-diisopropylethylamine, dimethyl sulfoxide.

Step 1:
Following generic route 9, using 4-fluoro-3-(trifluoromethyl)aniline, to afford 1-(4-fluoro-3-(trifluoromethyl)phenyl)-1H-1,2,3-triazole (486 mg, 2.1 mmol, 38% yield over 2 steps) as an light orange solid.

Step 3:
To 10 mL microwave vial 1-(4-fluoro-3-(trifluoromethyl)phenyl)-1H-1,2,3-triazole (75 mg, 0.32 mmol) was added dimethyl sulfoxide (1 mL) followed by pyrrolidine (0.03 mL, 0.39 mmol) and N,N-diisopropylethylamine (0.08 mL, 0.49 mmol) and the reaction mixture was heated 140° C. for 2 hours. The reaction mixture was by reverse phase column chromatography (15-80% acetonitrile in water, 0.1% formic acid modifier). The desired fractions were concentrated to dryness under reduced pressure and gave a yellow oil. This was allowed to dry under reduced pressure at 45° C. overnight to give 1-[4-pyrrolidin-1-yl-3-(trifluoromethyl)phenyl]triazole (63 mg, 0.22 mmol, 69% yield).

LCMS: MS m/z 283.1 [M+H]$^+$; $^1$H NMR (700 MHz, CDCl$_3$) δ 7.89 (dd, J=19.2, 1.9 Hz, 2H), 7.83 (d, J=1.0 Hz, 1H), 7.70 (dd, J=9.1, 2.7 Hz, 1H), 7.01 (d, J=9.1 Hz, 1H), 3.44 (t, J=6.2 Hz, 4H), 2.02-1.98 (m, 4H).

Compound 287: 1-(3-(pyrrolidin-1-yl)-4-(trifluoromethyl)phenyl)-1H-1,2,3-triazole Following generic route 13, using azetidine-3-carbonitrile hydrochloride, yield=91% (colourless oil).

LCMS: MS m/z 294.1 [M+H]$^+$; $^1$H NMR (600 MHz, CDCl$_3$) δ 8.05 (d, J=1.1 Hz, 1H), 7.87 (d, J=1.1 Hz, 1H), 7.64 (d, J=8.4 Hz, 1H), 7.37 (d, J=1.4 Hz, 1H), 7.08 (dd, J=8.4, 1.4 Hz, 1H), 3.82 (app t, J=6.7 Hz, 2H), 3.61 (dd, J=5.4, 1.8 Hz, 2H), 3.42 (m, 1H).

Compound 288: 1-(3-(3-fluoroazetidin-1-yl)-4-(trifluoromethyl)phenyl)-1H-1,2,3-triazole Following generic route 13, using 3-fluoroazetidine hydrochloride, yield=60%.

LCMS: MS m/z 287.1 [M+H]$^+$; $^1$H NMR (600 MHz, CDCl$_3$) δ 8.01 (d, J=1.1 Hz, 1H), 7.86 (d, J=1.1 Hz, 1H), 7.65 (app d, J=9.2 Hz, 1H), 7.03-7.01 (m, 2H), 5.14 (d, J=57.5 Hz, 1H), 4.47-4.41 (m, 2H), 4.28-4.22 (m, 2H).

Compound 289: [2,6-dichloro-3-(triazol-1-yl)phenyl]methanol

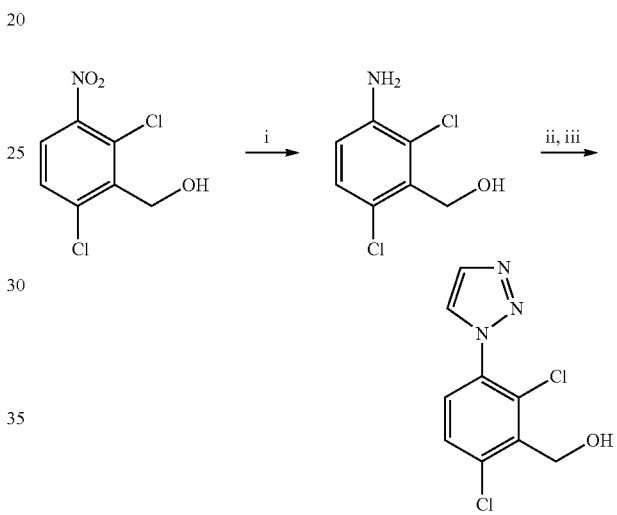

Reagents and conditions: i) Iron, acetic acid; ii) sodium nitrite, trifluoroacetic acid, sodium azide, water, iii) copper(II)sulfate pentahydrate, sodium L-ascorbate, tert-butanol, trimethylsilylacetylene, water.

Step 1:
Iron (25.1 g, 450.4 mmol) was added to a solution of 2,6-dichloro-3-nitrobenzyl alcohol (10 g, 45 mmol) in acetic acid (250 mL) in a 250 mL round bottomed flask fitted with a condenser at room temperature in 5 portions over 10 min, without stirring.

The mixture was gently warmed to 25° C. and left to stand for 2 hours. The mixture was heated at 30° C. for 2 hours, then 40° C. for 1 hour. The mixture was cooled to room temperature, diluted with 100 mL ethyl acetate, and filtered through Celite®, then washed with further ethyl acetate (100 mL). The filtrate was concentrated under reduced pressure to give a dark brown viscous oil. The material was suspended in dichloromethane, passed through a short silica plug, washing with ethyl acetate to remove residual iron impurities. The crude material was concentrated under reduced pressure to give (3-amino-2,6-dichloro-phenyl)methanol (21.2 g, assumed quantitative, 45 mmol, maximum 41% purity based on major quantities of inorganics) as a pale pink solid, which was used without further purification LCMS: MS m/z 192.1 [M+H]$^+$.

Step 2:
Sodium nitrite (3.7 g, 54 mmol) was added to a solution of (3-amino-2,6-dichloro-phenyl)methanol (21.2 g, 45 mmol) in trifluoroacetic acid (70 mL, 90.1 mmol) at 0° C.

over a period of 30 minutes. The reaction mixture was then allowed to warm to room temperature for 1.5 hours, before the mixture was then re-cooled to 0° C.

A solution of sodium azide (3.2 g, 49.5 mmol) in water (20 mL) was then added dropwise over 30 minutes, the reaction mixture was then allowed to warm to room temperature over 16 hours. The mixture was basified to pH 8-9 by dropwise addition of 5N aqueous sodium hydroxide. The reaction mixture was then was diluted with t-butanol (70 mL), to provide a solution of crude azide, which was used without further purification.

Step 3:

Copper(II)sulfate pentahydrate (2.25 g, 9.01 mmol), sodium L-ascorbate (3.6 mg, 18 mmol), water (70 mL), then trimethylsilylacetylene (4.4 g, 45 mmol) were added to the solution from step 2. The reaction vessel was stirred at 50° C. for 16 hours, after this time the reaction was diluted with brine, then extracted with ethyl acetate.

The organic phase was then dried over anhydrous magnesium sulfate, filtered and concentrated under reduced pressure. Purification via silica gel chromatography, eluting with 0-60% ethyl acetate in cyclohexane gave [2,6-dichloro-3-(triazol-1-yl)phenyl]methanol (2.2 g, 9.01 mmol, 20% yield) as a tan solid. LCMS: MS m/z 244.1 [M+H]+; 1H NMR (700 MHz, DMSO) δ 8.55 (d, J=1.1 Hz, 1H), 7.98 (d, J=1.1 Hz, 1H), 7.71 (d, J=8.5 Hz, 1H), 7.64 (d, J=8.5 Hz, 1H), 5.43 (t, J=5.3 Hz, 1H), 4.78 (d, J=5.3 Hz, 2H).

Compound 290: 1-(2,3,4-trichlorophenyl)triazole

Following generic route 20, using 2,3,4-trichloroaniline, yield=72% (off-white solid).

LCMS: MS m/z 248.0 [M+H]+; 1H NMR (400 MHz, DMSO) δ 8.62 (d, J=1.2 Hz, 1H), 8.02 (d, J=1.2 Hz, 1H), 7.93 (d, J=8.7 Hz, 1H), 7.75 (d, J=8.7 Hz, 1H).

Compound 291: 1-(2,3,5-trichlorophenyl)triazole

Following generic route 20, using 2,3,5-trichloroaniline, yield=9% (tan solid).

LCMS: MS m/z 248.1 [M+H]+; 1H NMR (600 MHz, DMSO) δ 8.63 (d, J=1.2 Hz, 1H), 8.18 (d, J=2.4 Hz, 1H), 8.02 (d, J=1.2 Hz, 1H), 7.96 (d, J=2.4 Hz, 1H).

Compound 292: 1-(3,4,5-trichlorophenyl)triazole

Following generic route 20, using 3,4,5-trichloroaniline, yield=11% (off-white solid).

LCMS: MS m/z 248.0 [M+H]+; 1H NMR (600 MHz, DMSO) δ 8.97 (d, J=1.2 Hz, 1H), 8.32 (s, 2H), 8.04 (d, J=1.2 Hz, 1H).

Compound 293: 1-(2,4,5-trichlorophenyl)triazole

Following generic route 20, using 2,4,5-trichloroaniline, yield=37% (tan solid).

LCMS: MS m/z 248.1 [M+H]+; 1H NMR (600 MHz, DMSO) δ 8.60 (d, J=1.1 Hz, 1H), 8.25 (s, 1H), 8.16 (s, 1H), 8.01 (d, J=1.1 Hz, 1H).

Compound 294: 1-[2,4-dichloro-5-(trifluoromethyl)phenyl]triazole

Following generic route 9, using 2,4-dichloro-5-(trifluoromethyl)aniline, yield=9% (off-white solid) LCMS: MS m/z 282.1 [M+H]+; 1H NMR (600 MHz, DMSO) δ 8.64 (d, J=1.2 Hz, 1H), 8.37 (s, 1H), 8.25 (s, 1H), 8.03 (d, J=1.2 Hz, 1H).

Compound 295: 1-[2,4-dichloro-3-(trifluoromethyl)phenyl]triazole

Reagents and conditions: ii) Sodium nitrite, acetonitrile, hydrochloric acid, sodium azide, water, iii) copper(II)sulfate pentahydrate, sodium L-ascorbate, tert-butanol, potassium carbonate, trimethylsilylacetylene, methanol, water.

Step 1:

2,4-Dichloro-3-(trifluoromethyl)aniline (200 mg, 0.87 mmol) was dissolved in water (0.5 mL) and acetonitrile (3 mL). Aqueous 37% hydrochloric acid (9.8 mL, 43.6 mmol) was added and the solution stirred vigorously at room temperature for 10 minutes. Sodium nitrite (120 mg, 1.75 mmol) was then added portion-wise and the solution stirred for an additional 1 hour. The solution was cooled to 0° C. and then sodium azide (114 mg, 1.75 mmol) was added. After 1 hour, the solution was diluted with water then extracted with diethyl ether. 2-Methyl-2-propanol (2 mL) was added and the organic layer was cautiously concentrated under reduced pressure to around 2 mL and the resulting solution of azide in tert-butyl alcohol taken through to the next step without further purification.

Step 2:

The solution from step 1 was added copper(II)sulfate pentahydrate (44 mg, 0.17 mmol), trimethylsilylacetylene (0.04 mL, 0.37 mmol), potassium carbonate (121 mg, 0.87 mmol), water (2 mL) and methanol (1 mL). The reaction was stirred at 60° C. overnight, cooled to room temperature, then 2N aqueous sodium hydroxide (2 mL) was added, and stirred for a further 2 hours. The mixture was then cautiously concentrated to remove the volatile organics then extracted with dichloromethane. The organics were separated, dried over sodium sulfate and concentrated under reduced pressure. The crude material was purified by silica gel chromatography, eluting with 0-5% methanol in dichloromethane. The desired fractions were then concentrated under reduced pressure to give 1-[2,4-dichloro-3-(trifluoromethyl)phenyl]triazole (43 mg, 0.15 mmol, 41% yield) as an off-white solid.

LCMS: MS m/z 282.1 [M+H]+; 1H NMR (400 MHz, DMSO) δ 8.61 (d, J=1.2 Hz, 1H), 8.06-7.94 (m, 3H).

Compound 296: (5-(4-chloro-3-(trifluoromethyl) phenyl)-1,3,4-oxadiazol-2-yl)methanol

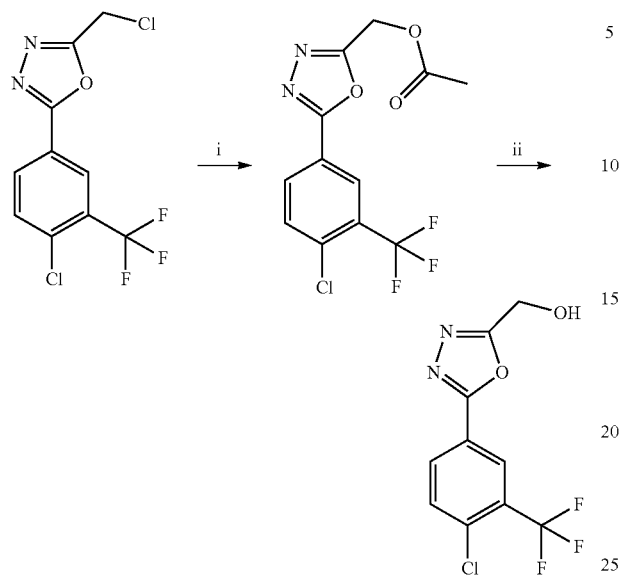

Reagents and conditions: (i) Sodium acetate, acetonitrile, 80° C. (ii) potassium carbonate, methanol.

To a solution of 2-(chloromethyl)-5-[4-chloro-3-(trifluoromethyl)phenyl]-1,3,4-oxadiazole (300 mg, 1 mmol) in acetonitrile (6 mL) was added sodium acetate (166 mg, 2 mmol). The reaction was heated at 80° C. for 18 hours. The cooled mixture was concentrated under reduced pressure and the residue was partitioned between water and ethyl acetate. The organic phase was washed with brine, dried over anhydrous magnesium sulfate and concentrated under reduced pressure. The residual oil was dissolved in methanol (6 mL), and potassium carbonate (279 mg, 2 mmol) and water (1 mL). The mixture was stirred at room temperature for 2 hours and then concentrated under reduced pressure. The residue was partitioned between ethyl acetate and water. The organics were washed with water (×1) and brine (×1), dried over anhydrous magnesium sulfate, filtered and adsorbed on to silica. Purification by column chromatography (0-10% methanol in dichloromethane) gave (5-(4-chloro-3-(trifluoromethyl)phenyl)-1,3,4-oxadiazol-2-yl) methanol (46 mg, 0.17 mmol, 16%) as a white solid.

LCMS: MS m/z 279.0 [M+H]$^+$; $^1$H NMR (700 MHz, DMSO) δ 8.29 (d, J=1.9 Hz, 1H), 8.27 (dd, J=8.4, 2.0 Hz, 1H), 7.98 (d, J=8.4 Hz, 1H), 6.00 (t, J=6.3 Hz, 1H), 4.73 (d, J=6.3 Hz, 2H).

Compound 298: 1-(2,4-dichloro-3-(trifluoromethyl) phenyl)-1H-tetrazole

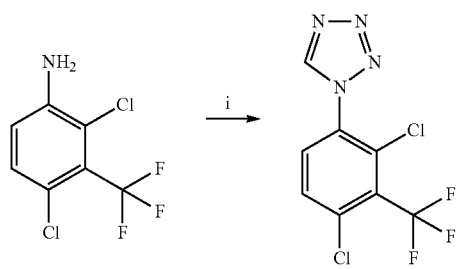

Reagents and conditions: i) Trimethyl orthoformate, sodium azide, acetic acid.

To a solution of 2,4-dichloro-3-(trifluoromethyl)aniline (0.26 mL, 1.09 mmol) in acetic acid (2.5 mL, 43.7 mmol) was added trimethyl orthoformate (0.39 mL, 3.26 mmol) and sodium azide (219 mg, 3.37 mmol). The reaction mixture was heated to 100° C. under a nitrogen atmosphere for 90 minutes, behind a blast shield. The reaction mixture was concentrated under reduced pressure (ca. 1 mL solvent remaining), water (30 mL) was then added to the resultant residue and a white crystalline solid precipitated. The white solid was collected by filtration, washed with water (ca. 10 mL) and dried in a vacuum oven overnight to give 1-[2,4-dichloro-3-(trifluoromethyl)phenyl]tetrazole (31 mg, 0.11 mmol, 10% yield) as a white crystalline solid.

LCMS: MS m/z 283.0 [M+H]+; $^1$H NMR (700 MHz, DMSO) δ 9.90 (s, 1H), 8.15 (apparent dd, J=8.7, 0.5 Hz, 1H), 8.06 (apparent dd, J=8.7, 0.5 Hz, 1H).

Compound 299: 2-(2,4-dichloro-3-(trifluoromethyl) phenyl)-5-methyl-1,3,4-oxadiazole

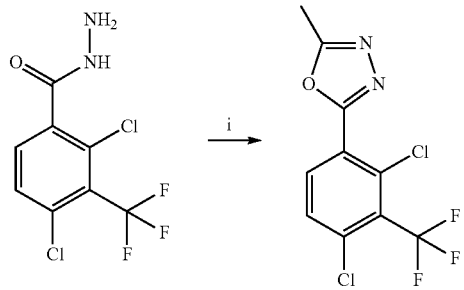

Reagents and conditions: i) Trimethyl orthoacetate, para-toluenesulfonic acid monohydrate para-Toluenesulfonic acid monohydrate (9 mg, 0.05 mmol) was added cautiously to a 10 mL microwave vial containing trimethyl orthoacetate (2.5 mL, 20.5 mmol) and 2,4-dichloro-3-(trifluoromethyl)benzohydrazide (250 mg, 0.92 mmol) under a nitrogen atmosphere and then cautiously warmed to 130° C., and the mixture was then stirred at that temperature for 6 hours. The mixture was then cooled to room temperature, and then cautiously transferred to a beaker containing saturated aqueous sodium hydrogen carbonate (20 mL). The mixture was then diluted with ethyl acetate (50 ml), the organics were separated, dried over sodium sulfate and concentrated under reduced pressure. The crude material was purified by silica gel chromatography, eluting with 20-30% ethyl acetate in cyclohexane. The desired fractions were concentrated under reduced pressure to give 2-[2,4-dichloro-3-(trifluoromethyl)phenyl]-5-methyl-1,3,4-oxadiazole (90 mg, 0.30 mmol, 33% yield) as a white solid.

LCMS: MS m/z 297.0 [M+H]$^+$; $^1$H NMR (700 MHz, DMSO) δ 8.13 (apparent dd, J=8.6, 0.6 Hz, 1H), 7.93 (apparent dd, J=8.6, 0.7 Hz, 1H), 2.62 (s, 3H).

Compound 300: 4-(2,4-dichloro-3-(trifluoromethyl)phenyl)-4H-1,2,4-triazole

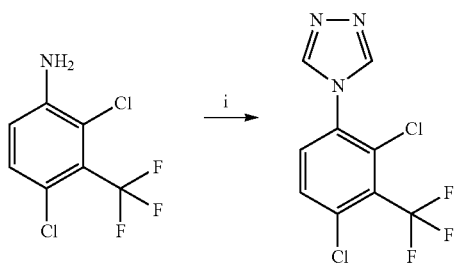

Reagents and conditions: i) Chlorotrimethylsilane, 1,2-diformylhydrazine, triethylamine, pyridine.

Chlorotrimethylsilane (1.9 mL, 15 mmol) was added dropwise to a solution of 2,4-dichloro-3-(trifluoromethyl) aniline (230 mg, 1 mmol), 1,2-diformylhydrazine (264 mg, 3 mmol) and triethylamine (1 mL, 7 mmol) in pyridine (9 mL, 111 mmol) at 0° C. The reaction mixture was then heated to 115° C. for 2.5 hours, (thick white slurry started to stir and become less viscous and pink after ~1 h), then further heated to 130° C. for 20 hours. The reaction mixture was cooled to room temperature, water (2 mL) was added then the mixture was concentrated under reduced pressure. The crude material was purified by reverse phase chromatography (0-100% acetonitrile in water, 0.1% ammonium hydroxide modifier) and the desired fractions were concentrated under reduced pressure to give 4-[2,4-dichloro-3-(trifluoromethyl)phenyl]-1,2,4-triazole (140 mg, 0.5 mmol, 50% yield) as a tan solid. LCMS: MS m/z 282.1 [M+H]$^+$; $^1$H NMR (500 MHz, DMSO) δ 8.86 (s, 2H), 8.00 (d, J=8.7 Hz, 1H), 7.96 (d, J=8.7 Hz, 1H).

Compound 301: 1-(2,4-dichloro-3-(trifluoromethyl)phenyl)-4-methyl-1H-1,2,3-triazole

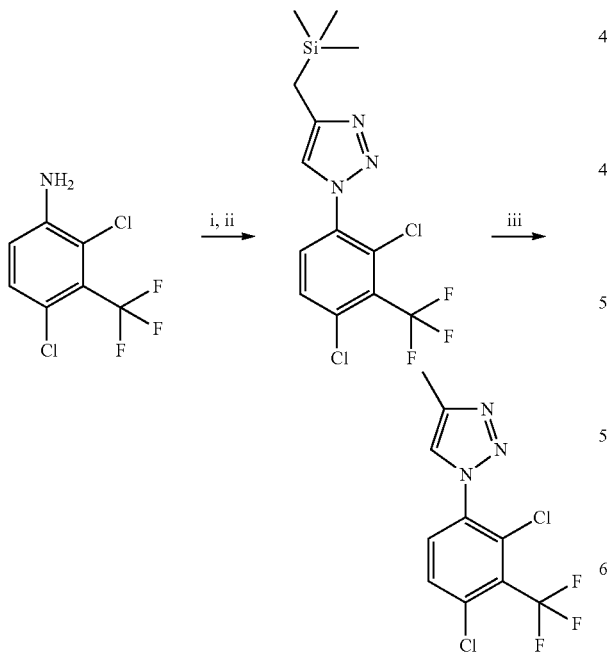

Reagents and conditions: i) Sodium nitrite, trifluoroacetic acid, water, sodium nitrite ii) tert-butanol, methanol, water, sodium L-ascorbate, trimethyl(propargyl)silane, copper(II) sulfate pentahydrate iii) tetrahydrofuran, water, tetrabutylammonium fluoride hydrate.

Step 1:
Sodium nitrite (180 mg, 2.61 mmol) was added portionwise to a solution of 2,4-dichloro-3-(trifluoromethyl)aniline (500 mg, 2.17 mmol) in trifluoroacetic acid (5 mL, 4.35 mmol) at 0° C. over a period of 30 minutes. The reaction mixture was then allowed to warm to room temperature for 1.5 hours, water (100 μL) was added and the mixture was then re-cooled to 0° C. Sodium azide (155 mg, 2.39 mmol) was added portionwise over 30 minutes, the reaction mixture was then allowed to warm to room temperature over 1 hour. The mixture was basified to pH 8-9 by dropwise addition of saturated aqueous sodium bicarbonate, and extracted with ethyl acetate.

The organic phase was dried over anhydrous magnesium sulfate, filtered, tert-butanol (5 mL) was added and the mixture was cautiously concentrated under reduced pressure at 25° C., to remove the ethyl acetate.

Step 2:
Methanol (5 mL), water (5 mL), sodium L-ascorbate (172 mg, 0.9 mmol), trimethyl(propargyl)silane (244 mg, 2.2 mmol), and copper(II) sulfate pentahydrate (109 mg, 0.43 mg) were added to the solution of crude azide from step one.

The reaction vessel was stirred at 50° C. for 16 hours, after this time the reaction was diluted with water, extracted with ethyl acetate and the organic phase was washed with water and brine. The crude material was then suspended in methanol (15 mL), before addition of potassium carbonate (3.05 g, 21.7 mmol) and the mixture was heated at reflux overnight. The mixture was taken to pH 7 by addition of 1N aqueous hydrochloric acid, extracted with ethyl acetate and the organics were separated, dried over sodium sulfate and concentrated under reduced pressure.

Step 3:
The crude material was suspended in tetrahydrofuran (10 mL) and a solution of tetrabutylammonium fluoride hydrate (1.22 g, 4.35 mmol) in water (0.5 mL) was added and the mixture was stirred at room temperature overnight. The mixture was extracted with ethyl acetate, the organics were separated, dried over sodium sulfate and concentrated under reduced pressure.

The crude material was purified by silica gel chromatography, eluting with 0-30% ethyl acetate in cyclohexane to give 1-[2,4-dichloro-3-(trifluoromethyl)phenyl]-4-methyltriazole (12 mg, 0.04 mmol, 2% yield) as an off-white solid. LCMS: MS m/z 296.0 [M+H]$^+$; $^1$H NMR (700 MHz, CDCl$_3$) δ 7.67 (d, J=0.8 Hz, 1H), 7.64 (d, J=8.6 Hz, 1H), 7.61 (d, J=8.6 Hz, 1H), 2.47 (d, J=0.8 Hz, 3H).

Compound 302: 3-[1-[4-chloro-3-(trifluoromethyl)phenyl]triazol-4-yl]propan-1-ol

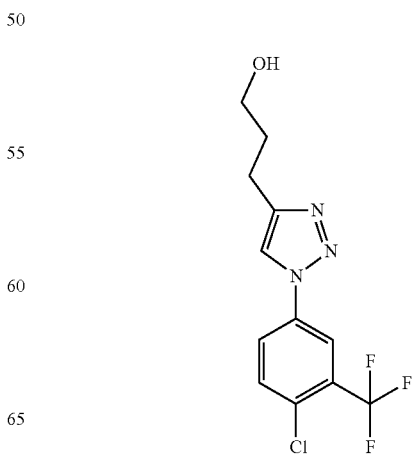

Following generic route 20, using 4-chloro-3-trifluoromethylaniline and 4-pentyn-1-ol, yield=52% (off-white solid).

LCMS: MS m/z 306.0 [M+H]$^+$; $^1$H NMR (400 MHz, CDCl$_3$) δ 8.01-7.92 (d, J=1.9 Hz, 1H), 7.87-7.82 (m, 2H), 7.79-7.73 (m, 1H), 3.76 (t, J=6.0 Hz, 2H), 2.94 (t, J=7.4 Hz, 2H), 2.07-1.97 (m, 2H).

Compound 303: 2-[1-[4-chloro-3-(trifluoromethyl)phenyl]triazol-4-yl]ethanol

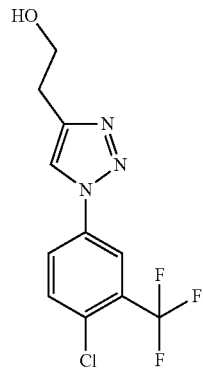 [SMILES: OCCc1cn(-c2ccc(Cl)c(C(F)(F)F)c2)nn1]

Following generic route 20, using 4-chloro-3-trifluoromethylaniline and 3-butyn-1-ol, yield=41% (off-white solid).

LCMS: MS m/z 292.0 [M+H]$^+$; $^1$H NMR (400 MHz, CDCl$_3$) δ 7.97 (d, J=2.0 Hz, 1H), 7.93 (s, 1H), 7.85 (d, J=8.6 Hz, 1H), 7.79-7.74 (m, 1H), 4.03 (broad s, 2H), 3.07 (dd, J=8.6, 3.0 Hz, 2H), 2.29 (broad s, 1H).

Compound 304: 1-[2,4-dichloro-3-(trifluoromethyl)phenyl]triazole-4-carboxylic acid

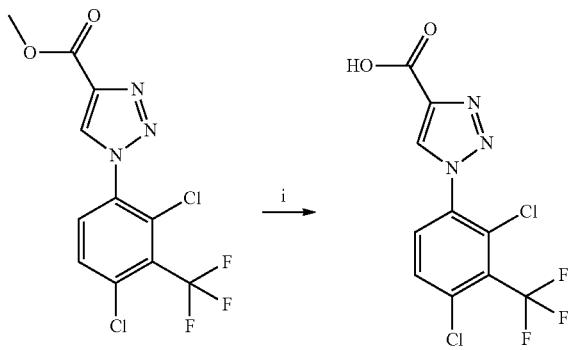

Reagents and conditions: i) Sodium hydroxide, water, methanol.

Aqueous sodium hydroxide (1M, 2.7 mL, 2.7 mmol) was added to a solution of methyl 1-[2,4-dichloro-3-(trifluoromethyl)phenyl]triazole-4-carboxylate (450 mg, 1.32 mmol) in methanol (30 mL) and the mixture was stirred at room temperature for 1 hour. The mixture was then acidified with to pH 3 with 1M hydrochloric acid and extracted with ethyl acetate. The organics were washed with brine, dried over magnesium sulfate then concentrated under reduced pressure to give 1-[2,4-dichloro-3-(trifluoromethyl)phenyl]triazole-4-carboxylic acid (410 mg, 1.26 mmol, 95% yield) as an off white solid.

LCMS: MS m/z 325.9 [M+H]$^+$; $^1$H NMR (600 MHz, DMSO) δ 13.43 (s, 1H), 9.16 (s, 1H), 8.10 (apparent dd, J=8.7, 0.5 Hz, 1H), 8.02 (apparent dd, J=8.7, 0.6 Hz, 1H).

Compound 305: 1-[1-[2,4-dichloro-3-(trifluoromethyl)phenyl]triazol-4-yl]propan-2-ol

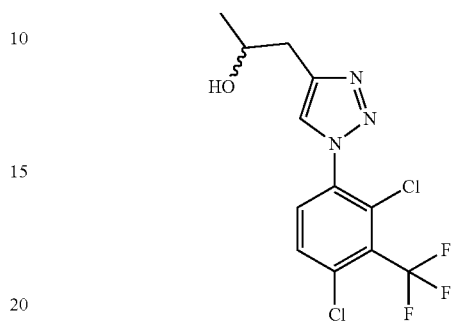

Following generic route 2, using 2,4-dichloro-3-(trifluoromethyl)aniline and 4-pentyn-2-ol, yield=37% (waxy solid).

LCMS: MS m/z 340.1 [M+H]$^+$; $^1$H NMR (600 MHz, CDCl$_3$) δ 8.01 (s, 1H), 7.67 (d, J=8.8 Hz, 1H), 7.63 (d, J=8.4 Hz, 1H), 4.42 (brs, 1H), 3.14-2.32 (m, 3H), 1.51-1.36 (m, 3H).

Compound 306: 4-[2,4-dichloro-3-(trifluoromethyl)phenyl]-1H-triazole

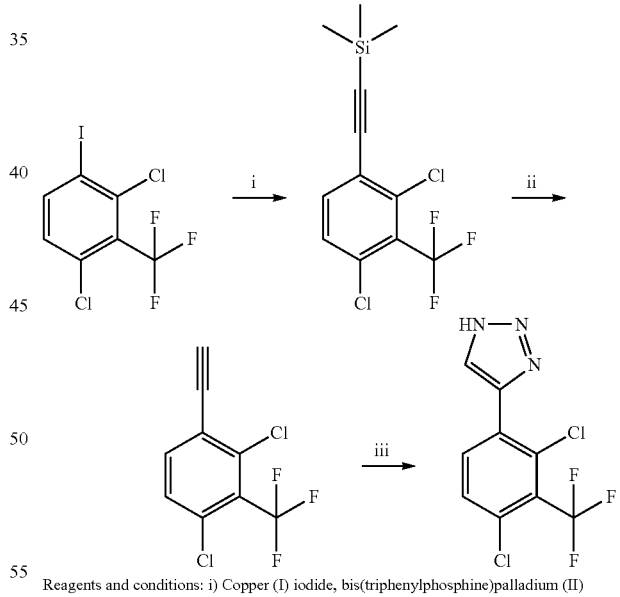

Reagents and conditions: i) Copper (I) iodide, bis(triphenylphosphine)palladium (II) dichloride, tetrahydrofuran, trimethylamine; ii) potassium carbonate, methanol; iii) copper (I) iodide, N,N-dimethylformamide, methanol, azidotrimethylsilane Step 1:

1,3-Dichloro-4-iodo-2-(trifluoromethyl)benzene (530 mg, 1.55 mmol), copper (I) iodide (18 mg, 0.09 mmol) and bis(triphenylphosphine)palladium (II) dichloride (33 mg, 0.05 mmol) were dissolved in tetrahydrofuran (5 mL) under an argon atmosphere. Triethylamine (1.7 mL, 12 mmol) was then added and the reaction was sparged argon for 15 min, before heating to 60° C. overnight. The reaction mixture was cooled to room temperature, diluted in dichloromethane then washed with brine, before further extraction with dichloromethane. The organics were then dried over magnesium sulfate and concentrated under reduced pressure and the resultant oil was purified by silica gel chromatography, eluting with 100% cyclohexane, to give 2-[2,4-dichloro-3-(trifluoromethyl)phenyl]ethynyl-trimethyl-silane (305 mg, 0.98 mmol, 63% yield).

$^1$H NMR (600 MHz, CDCl$_3$) δ 7.54 (apparent dd, J=8.5, 0.5 Hz, 1H), 7.35 (apparent dd, J=8.5, 0.6 Hz, 1H), 0.28 (s, 9H).

Step 2:

Potassium carbonate (266 mg, 1.93 mmol) was added to a solution of 2-[2,4-dichloro-3-(trifluoromethyl)phenyl] ethynyl-trimethyl-silane (300 mg, 0.96 mmol) in methanol (5 mL) and the mixture was stirred at room temperature for 16 hours. Water (30 mL) was added to dissolve solid potassium carbonate and the organics removed under reduced pressure before the material was extracted with dichloromethane and concentrated under reduced pressure (100 mbar) to give 1,3-dichloro-4-ethynyl-2-(trifluoromethyl)benzene (190 mg, 0.84 mmol, 87%).

Step 3:

Copper (I) iodide (8 mg, 0.04 mmol), 1-chloro-4-ethynyl-2-(trifluoromethyl)benzene (190 mg, 0.84 mmol) were dissolved in anhydrous N,N-dimethylformamide (1 mL) and anhydrous methanol (0.5 mL) under an atmosphere of nitrogen. Azidotrimethylsilane (0.1 mL, 0.73 mmol) was added to this dropwise. The mixture was then heated to 100° C. for 3 hours, the reaction was cooled to room temperature, diluted in ethyl acetate, washed with 5% aqueous lithium chloride, water then brine. The organics were then dried over magnesium sulfate and concentrated under reduced pressure, then purified by reverse phase chromatography (0-100% acetonitrile in water, 0.1% formic acid modifier) to give 4-[2,4-dichloro-3-(trifluoromethyl)phenyl]-1H-triazole (22 mg, 0.08 mmol, 9% yield) as an off-white solid.

LCMS: MS m/z 282.0 [M+H]$^+$; $^1$H NMR (700 MHz, CDCl$_3$) δ 8.25 (s, 1H), 7.97 (d, J=8.5 Hz, 1H), 7.53 (d, J=8.5 Hz, 1H).

Compound 307: 3,5-dichloro-2-(triazol-1-yl)-4-(trifluoromethyl)pyridine

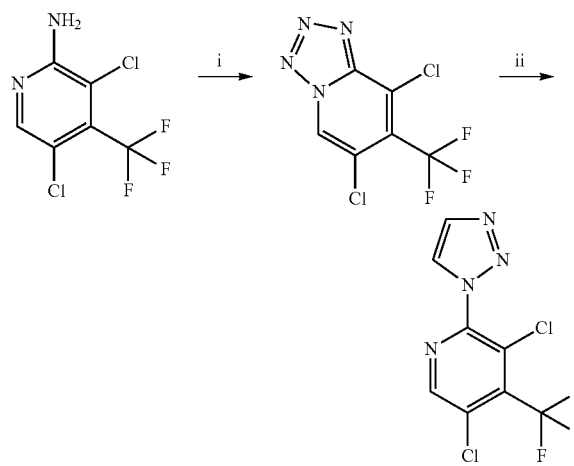

Reagents and conditions: i) Hydrazine monohydrate, ethanol, 1N hydrochloric acid, sodium nitrite, water; ii) sodium hydroxide, water, tert-butanol, sodium L-ascorbate, copper (II) sulfate pentahydrate.

Step 1:

Hydrazine monohydrate (0.06 mL, 1.2 mmol) was added to a solution of 2,3,5-trichloro-4-trifluoromethyl pyridine (200 mg, 0.80 mmol) in ethanol (0.5 mL) and warmed to 85° C. over 4 hours. The reaction mixture was concentrated under reduced pressure, and the resultant solid was suspended in 1N aqueous hydrochloric acid (10 mL, 10 mmol). The mixture was then cooled to 0° C.*(external), before a solution of sodium nitrite (110 mg, 1.6 mmol) in water (0.5 mL) was added over 30 minutes.

Step 2:

The mixture was stirred for a further 30 minutes before cautious addition of 5N sodium hydroxide to adjust the pH to 8-9. Water (2 mL) and tert-butanol (2 mL) then sodium L-ascorbate (159 mg, 0.8 mmol) and copper (II) sulfate pentahydrate (20 mg, 0.08 mmol) were added and the mixture was heated to 40° C. overnight. The mixture was then cooled to room temperature, extracted with ethyl acetate, and the organics were then dried over sodium sulfate and concentrated under reduced pressure. The crude material was purified by reverse phase chromatography (0-100% acetonitrile in water, 0.1% formic acid modifier). The desired fractions were then concentrated under reduced pressure to give 3,5-dichloro-2-(triazol-1-yl)-4-(trifluoromethyl)pyridine (5 mg, 0.02 mmol, 2% yield) as a white solid. LCMS: MS m/z 283.0 [M+H]$^+$; $^1$H NMR (700 MHz, CDCl$_3$) δ 8.66 (apparent d, J=0.6 Hz, 1H), 8.08 (d, J=1.2 Hz, 1H), 7.90 (d, J=1.2 Hz, 1H).

Compound 308: 4,5-dideuterio-1-[2,4-dichloro-3-(trifluoromethyl)phenyl]triazole

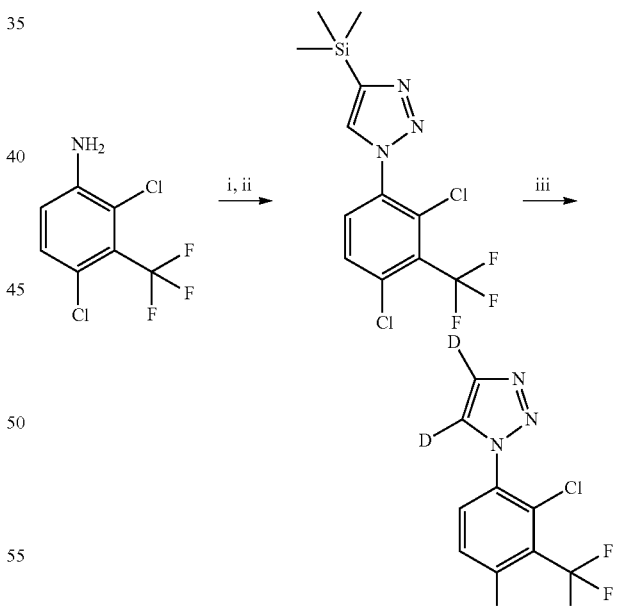

Reagents and conditions: i) Sodium nitrite, trifluoroacetic acid, water, sodium azide; ii) tert-butanol, copper(II)sulfate pentahydrate, sodium L-ascorbate, trimethylsilylacetylene, watert; iii) potassium carbonate, d4-methanol.

Step 1:

Sodium nitrite (360 mg, 5.22 mmol) was added to a solution of 2,4-dichloro-3-(trifluoromethyl)aniline (1 g, 4.35 mmol) in trifluoroacetic acid (10 mL, 8.7 mmol) at 0° C. over a period of 30 minutes. The reaction mixture was then allowed to warm to room temperature for 90 minutes, water (1 mL) was then added and the mixture was then re-cooled to 0° C. Sodium azide (310 mg, 4.78 mmol) was then added over 30 minutes, then the reaction mixture was allowed to warm to room temperature over 1 hour. The mixture was basified to pH 8-9 by dropwise addition of saturated aqueous sodium bicarbonate, then extracted with dichloromethane. The organic phase was diluted with tert-butanol (10 mL) and the dichloromethane was cautiously removed under reduced pressure at 25° C., to provide a solution of crude azide, which was used without further purification.

Step 2:

Copper(II) sulfate pentahydrate (217 mg, 0.87 mmol), Sodium L-ascorbate (345 mg, 1.74 mmol), water (10 mL), then trimethylsilylacetylene (0.6 mL, 4.35 mmol) were added to the solution from step 1. The reaction mixture was stirred at room temperature for 16 hours, after this time the reaction was diluted with water, extracted with ethyl acetate and the organic phase was washed with water and brine. The organic phase was then dried over anhydrous magnesium sulfate, filtered and concentrated under reduced pressure. Purification by silica gel chromatography eluting with 0-30% ethyl acetate in cyclohexane gave [1-[2,4-dichloro-3-(trifluoromethyl)phenyl]triazol-4-yl]-trimethyl-silane (390 mg, 1.1 mmol, 25% yield) as an oily solid.

$^1$H NMR (400 MHz, DMSO) δ 8.62 (s, 1H), 8.01 (d, J=8.8 Hz, 1H), 7.96 (d, J=8.8 Hz, 1H), 0.33 (s, 9H).

Step 3:

1-[2,4-Dichloro-3-(trifluoromethyl)phenyl]triazol-4-yl]-trimethyl-silane (100 mg, 0.28 mmol) and potassium carbonate (117 mg, 0.85 mmol) were dried for 2 hours under vacuum (0.5 mbar, room temperature), before addition of >99% d4-methanol (5 mL) was added under an argon atmosphere. The mixture was then stirred at room temperature for 3 days before addition of d2-water (5 mL) to dissolve all the carbonate, before the vessel was quickly transferred to rotary evaporator and the organics were removed under reduced pressure. The vessel was quickly sealed before addition of alumina treated anhydrous dichloromethane. After stirring for 15 minutes the organic layer was then removed via syringe and concentrated to a crude oil, which was purified via silica gel chromatography, eluting with 0-30% ethyl acetate in cyclohexane. The fractions were then concentrated under reduced pressure to give 4,5-dideuterio-1-[2,4-dichloro-3-(trifluoromethyl)phenyl] triazole (60 mg, 0.1901 mmol, 67.3% yield, >90% d2-isotope) as a white solid.

LCMS: MS m/z 284.2 [M+H]$^+$; $^1$H NMR (400 MHz, DMSO) δ 7.99 (apparent dd, J=8.7, 0.6 Hz, 1H), 7.72 (apparent dd, J=8.7, 0.6 Hz, 1H).

Biochemical Notum Enzymatic Activity Assay

An Echo liquid handler was used to acoustically dispense 500 nL of compounds into dry Greiner 384-well plates (catalog #781076), followed by 25 µL of 2 µM trisodium 8-octanoyloxypyrene-1,3,6-trisulfonate (OPTS, Sigma #74875) solution in 50 mM Tris, 5 mM CaCl$_2$), 0.5 mM MgCl$_2$, pH 7.4 assay buffer, and 25 µL of 2.38 nM notum carboxyesterase enzyme solution in the same buffer to every well in the assay plate. After 1 hour incubation at room temperature, fluorescence was measured on a PheraSTAR FSX microplate reader with an excitation wavelength of 485 nm and emission wavelength of 520 nm.

Dose-Response Curve Analysis

Plate layout and measured fluorescence values were input into Dotmatics Studies data management tool. After implementing Quality Control with a cut-off of Z prime values higher than 0.5, compound IC$_{50}$ values were estimated and compared between technical replicates. Final potency values implied an n≥2 with IC$_{50}$ within 0.5-2× between replicates.

Results

| Compound Number | IC$_{50}$ (µM) |
| --- | --- |
| 3 | 1.28 |
| 4 | 37.3 |
| 5 | 0.810 |
| 6 | 44.6 |
| 7 | 6.77 |
| 8 | 7.2 |
| 9 | 0.0935 |
| 12 | 52.5 |
| 13 | 1.72 |
| 15 | 86.1 |
| 17 | 5.69 |
| 18 | >10 |
| 19 | 0.484 |
| 20 | 39.1 |
| 21 | 9.49 |
| 25 | 36.8 |
| 26 | 25.5 |
| 27 | 3.03 |
| 29 | 15.2 |
| 30 | 6.61 |
| 31 | 8.82 |
| 36 | 44.6 |
| 38 | 37.5 |
| 39 | 4.87 |
| 40 | >10 |
| 41 | >10 |
| 42 | 19.5 |
| 43 | 5.04 |
| 44 | 74.5 |
| 46 | 18.5 |
| 47 | 49.5 |
| 48 | 85.9 |
| 49 | 0.008 |
| 50 | 0.0194 |
| 51 | 1.36 |
| 52 | 3.27 |
| 53 | 16.7 |
| 54 | 17.7 |
| 55 | 5.1 |
| 56 | 23.0 |
| 57 | 34.2 |
| 58 | 0.97 |
| 59 | 13.8 |
| 60 | 0.995 |
| 62 | 7.96 |
| 63 | 1.75 |
| 64 | 4.0 |
| 65 | 0.336 |
| 66 | 0.528 |
| 67 | 0.0201 |
| 68 | 0.0143 |
| 69 | 0.923 |
| 70 | 0.185 |
| 71 | 0.359 |
| 73 | 0.019 |
| 74 | 0.100 |
| 75 | 0.730 |
| 76 | 0.128 |
| 77 | 0.152 |
| 78 | 0.127 |
| 79 | 0.036 |
| 80 | 1.14 |
| 81 | 0.069 |
| 83 | 0.084 |
| 84 | 1.84 |
| 85 | 0.177 |
| 86 | 0.0227 |
| 87 | 0.0317 |
| 88 | 0.0459 |
| 89 | 0.235 |
| 90 | 0.834 |
| 91 | 0.241 |
| 92 | 0.399 |

-continued

| Compound Number | IC$_{50}$ (μM) |
|---|---|
| 93 | 0.0201 |
| 94 | 3.28 |
| 95 | 0.745 |
| 96 | 0.243 |
| 97 | 0.0191 |
| 98 | 13.8 |
| 99 | 0.0778 |
| 100 | 0.428 |
| 101 | 0.0326 |
| 102 | 0.768 |
| 103 | 0.777 |
| 104 | 0.385 |
| 105 | 0.727 |
| 106 | 12.9 |
| 107 | 2.51 |
| 108 | 1.74 |
| 109 | 11.1 |
| 110 | 0.425 |
| 111 | 29.1 |
| 113 | 4.08 |
| 114 | 10.7 |
| 115 | 0.629 |
| 116 | 2.03 |
| 117 | 0.555 |
| 118 | 10.7 |
| 121 | 0.0130 |
| 122 | 0.0946 |
| 124 | 13.0 |
| 125 | 61 |
| 126 | 0.726 |
| 127 | 5.95 |
| 129 | 0.378 |
| 130 | 0.596 |
| 132 | 18.8 |
| 134 | 19.4 |
| 137 | 33.0 |
| 140 | 2.94 |
| 141 | 70.6 |
| 143 | 11.6 |
| 144 | 6.94 |
| 145 | 3.47 |
| 147 | 15.2 |
| 149 | 5.16 |
| 150 | 1.10 |
| 151 | 5.74 |
| 152 | 43.1 |
| 156 | 11.9 |
| 157 | 17 |
| 158 | 35.8 |
| 160 | 21 |
| 162 | 68.5 |
| 163 | 41.9 |
| 164 | 64.6 |
| 165 | 19.2 |
| 166 | 3.95 |
| 167 | 70.2 |
| 168 | 8.29 |
| 171 | >10 |
| 175 | 0.0993 |
| 176 | 5.36 |
| 179 | 0.0103 |
| 180 | 0.0344 |
| 181 | 0.257 |
| 182 | 1.17 |
| 183 | 0.0354 |
| 184 | 0.129 |
| 185 | 1.23 |
| 186 | 0.450 |
| 187 | 0.426 |
| 188 | 24.7 |
| 189 | 0.0316 |
| 190 | 0.0887 |
| 191 | 0.0307 |
| 192 | 0.012 |
| 193 | 0.0421 |
| 194 | 3.22 |

-continued

| Compound Number | IC$_{50}$ (μM) |
|---|---|
| 195 | 0.0491 |
| 196 | 0.0166 |
| 197 | 0.0499 |
| 198 | 1.76 |
| 199 | 2.71 |
| 201 | 15.7 |
| 202 | 0.334 |
| 203 | 5.38 |
| 204 | 0.201 |
| 206 | >23.1 |
| 209 | 43.5 |
| 210 | 0.923 |
| 211 | 0.433 |
| 212 | 21 |
| 213 | 4.87 |
| 214 | 1.56 |
| 215 | 0.457 |
| 216 | 26.9 |
| 217 | 21.4 |
| 218 | 3.26 |
| 219 | 1.02 |
| 220 | 0.824 |
| 221 | 82.5 |
| 222 | 8.05 |
| 223 | 0.754 |
| 224 | 3.54 |
| 225 | 1.16 |
| 226 | 42.2 |
| 227 | 0.221 |
| 228 | 0.155 |
| 229 | 26.1 |
| 230 | 37.4 |
| 231 | 0.0672 |
| 232 | 3.94 |
| 233 | 1.74 |
| 236 | 14.1 |
| 237 | 49.6 |
| 241 | 0.0036 |
| 242 | 0.0043 |
| 243 | 0.0058 |
| 244 | 0.4106 |
| 245 | 0.067 |
| 246 | 0.0073 |
| 247 | 0.4393 |
| 248 | 0.0119 |
| 249 | 0.0319 |
| 250 | 0.0129 |
| 251 | 0.2022 |
| 252 | 0.0203 |
| 253 | 0.1115 |
| 254 | 0.0706 |
| 255 | 0.3756 |
| 256 | 0.1874 |
| 257 | 0.847 |
| 258 | 0.012 |
| 259 | 0.0271 |
| 260 | 0.3356 |
| 261 | 0.0057 |
| 262 | 0.0367 |
| 263 | 0.3283 |
| 264 | 0.0314 |
| 265 | 0.131 |
| 266 | 0.0651 |
| 267 | 0.0247 |
| 268 | 1.36 |
| 269 | 1.51 |
| 270 | 0.6969 |
| 271 | 8.7 |
| 273 | 63.6 |
| 275 | 2.23 |
| 276 | 1.06 |
| 277 | 0.0096 |
| 278 | 0.5273 |
| 279 | 0.0843 |
| 280 | 0.4047 |
| 281 | 0.1547 |

-continued

| Compound Number | IC$_{50}$ (μM) |
|---|---|
| 282 | 0.1914 |
| 283 | 0.0661 |
| 284 | 4.05 |
| 285 | 0.4567 |
| 286 | 0.862 |
| 287 | 0.3393 |
| 288 | 0.2481 |
| 289 | 0.5556 |
| 290 | 0.0167 |
| 291 | 0.6118 |
| 292 | 0.046 |
| 293 | 0.2833 |
| 294 | 0.3883 |
| 295 | 0.0061 |
| 296 | 0.1405 |
| 298 | 0.136 |
| 299 | 0.027 |
| 300 | 1.31 |
| 301 | 0.108 |
| 302 | 7.51 |
| 303 | 0.149 |
| 304 | 0.0303 |
| 305 | 1.32 |
| 306 | 0.0029 |
| 307 | 0.0081 |
| 308 | 0.0044 |
| 309 | 0.107 |
| 310 | 1.83 |
| 311 | 0.003 |
| 312 | 0.125 |

STATEMENTS OF INVENTION

1. A compound for use in the treatment of a disease ameliorated by the inhibition of Notum of formula (I):

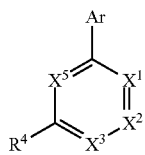

(I)

where Ar is $C_5$ heteroaryl or a $C_6$ N-containing heteroaryl, optionally substituted by a group selected from
a) OH, SH, NH$_2$, OMe, SMe, NHMe, NMe$_2$, OEt, NHCN, Me;
b) CN, CO$_2$H;
c) SO$_2$Me, SO$_3^-$Na$^+$;
d) CH$_2$Q$^1$, where Q$^1$ is selected from OH, OMe, Cl, CN, NHCOMe, SO$_3$H, NR$^{N1}$R$^{N2}$, where R$^{N1}$ and R$^{N2}$ are either H or Me;
e) C$_{2-3}$ alkyl substituted by OH;
where a N-ring heteroatom may additional bear a methyl group; and
X$^1$ is selected from CR$^1$ and N;
X$^2$ is selected from CR$^2$ and N;
X$^3$ is selected from CR$^3$ and N;
X$^5$ is selected from CR$^5$ and N, where only 1 of X$^1$, X$^2$, X$^3$ and X$^5$ may be N;
R$^1$, R$^2$, R$^3$, R$^4$ and R$^5$ (if present) are independently selected from:
i) H;
ii) halo;
iii) C$_{1-4}$ alkyl, optionally substituted by one or more F atoms;
iv) C$_{3-6}$ cycloalkyl, with an optional O ring atom;
v) CN, NMe$_2$, NO$_2$;
vi) O—C$_{1-4}$ alkyl, optionally substituted by one or more F atoms;
vii) OCH$_2$Q$^2$, where Q$^2$ is selected from C$_{3-6}$ cycloalkyl and phenyl;
viii) CH$_2$OH;
ix) NR$^{N6}$R$^{N7}$, where R$^{N6}$ and R$^{N7}$ together form a C$_{4-6}$ heterocyclyl group optionally substituted with 1 to 2 groups selected from halo, C$_{1-3}$ alkyl, cyano and oxetanyl;
or two adjacent groups of R$^1$ to R$^4$ together form a group -Q$^3$-(CR$^C{}_2$)$_n$-Q$^4$-, where Q$^3$ is selected from NR$^{N3}$ and O, where R$^{N3}$ is selected from H, C$_{1-3}$ alkyl, cyclopropylmethyl and COMe; Q$^4$ is NR$^{N4}$, O or a single bond, where R$^{N4}$ is selected from H, C$_{1-3}$ alkyl, cyclopropylmethyl and COMe; each R$^C$ is independently H, F or Me or two R$^C$ which are attached to the same atom can be linked together to form a C$_{3-5}$ cycloalkyl; and n is 1, 2 or 3; or two adjacent groups of R$^1$ to R$^5$ form a fused benzene or C$_{5-6}$ heteroaromatic ring with the phenyl group, which itself is optionally substituted by a C$_{1-2}$ alkyl group.

2. A compound for use according to statement 1, wherein Ar is selected from:

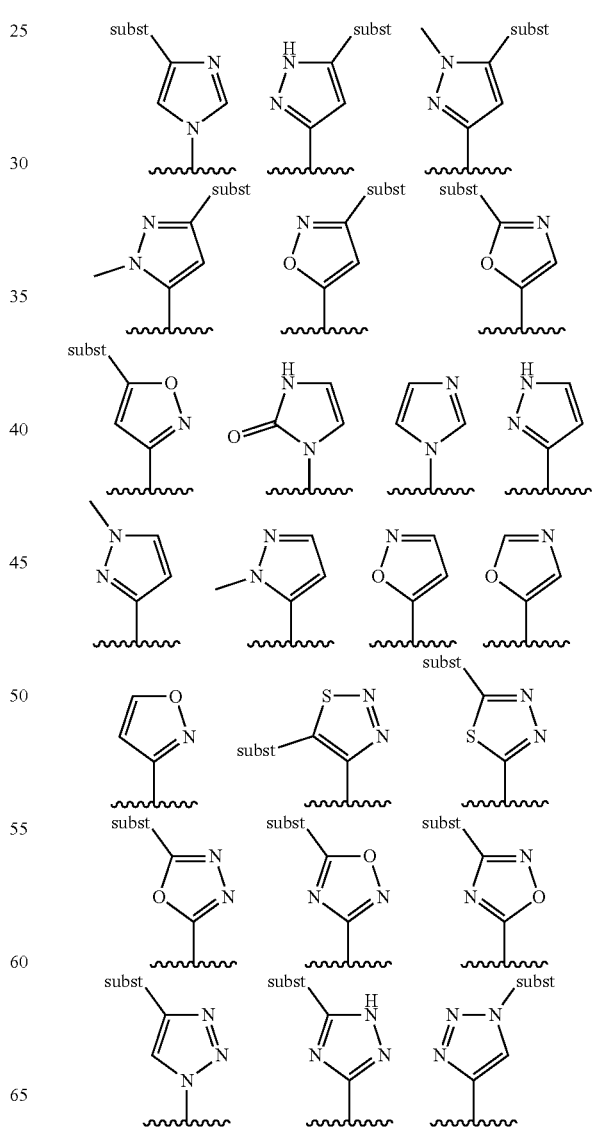

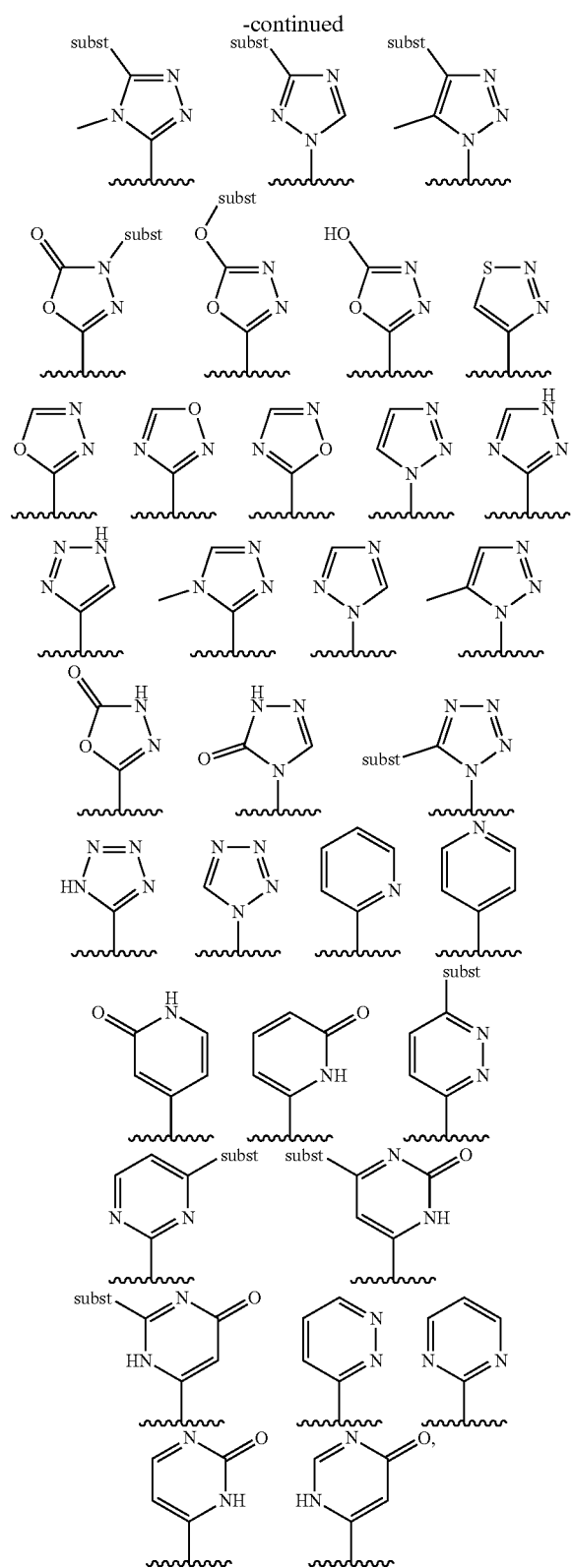
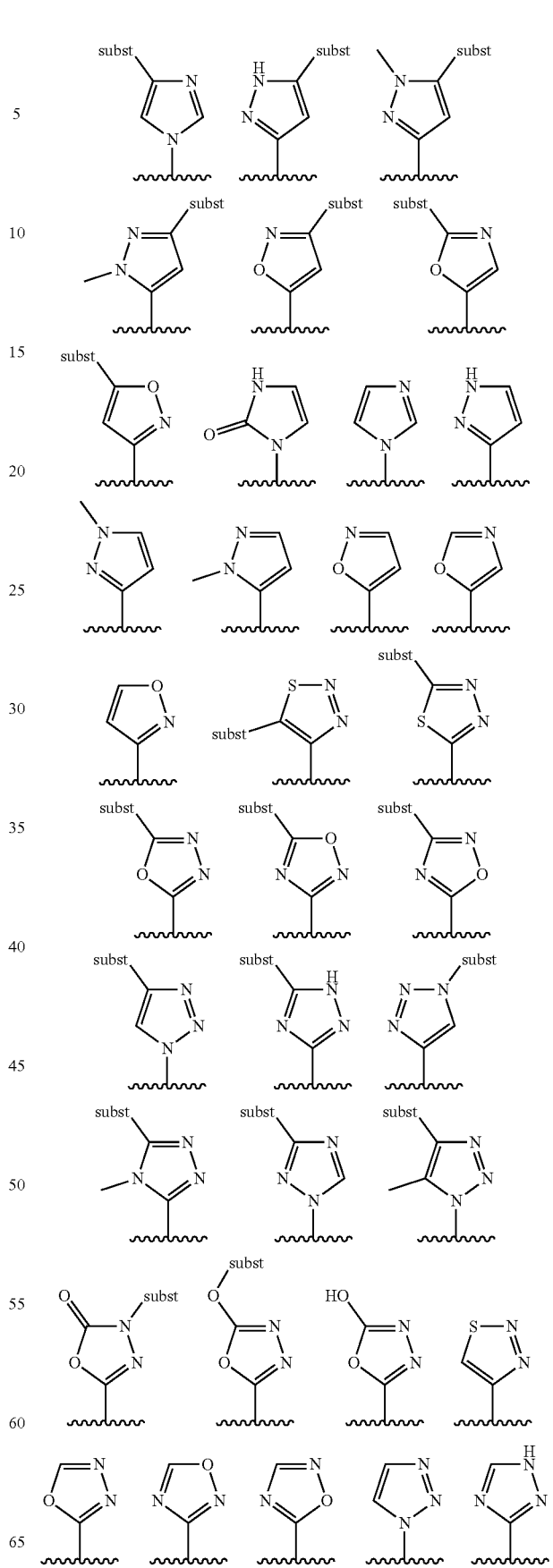
where subst represents the optional substituent.
3. A compound for use according to statement 1, wherein Ar is C₅ heteroaryl, with an optional substituent.
4. A compound for use according to statement 3, wherein Ar is selected from:

-continued

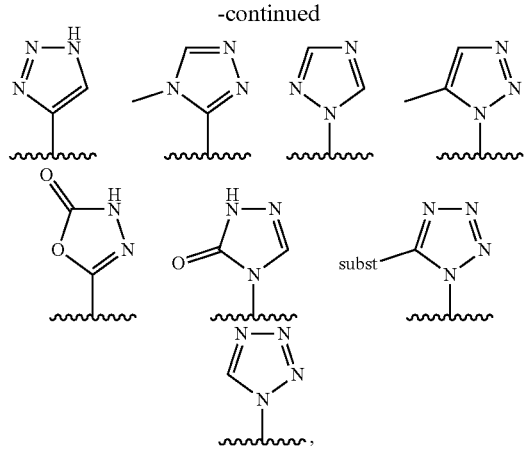

where subst represents the optional substituent.

5. A compound for use according to statement 4, wherein Ar is selected from:

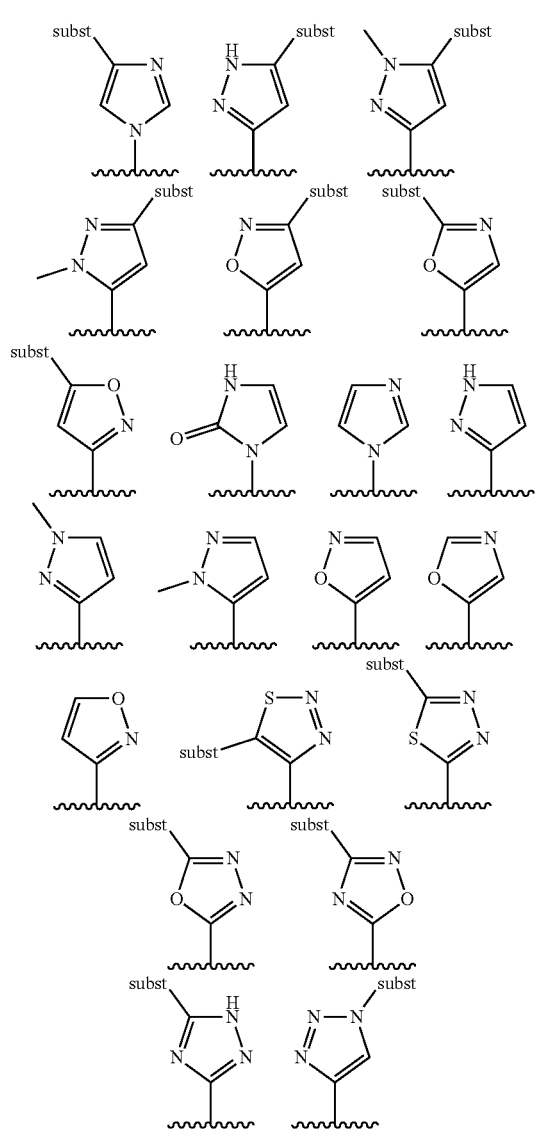

-continued

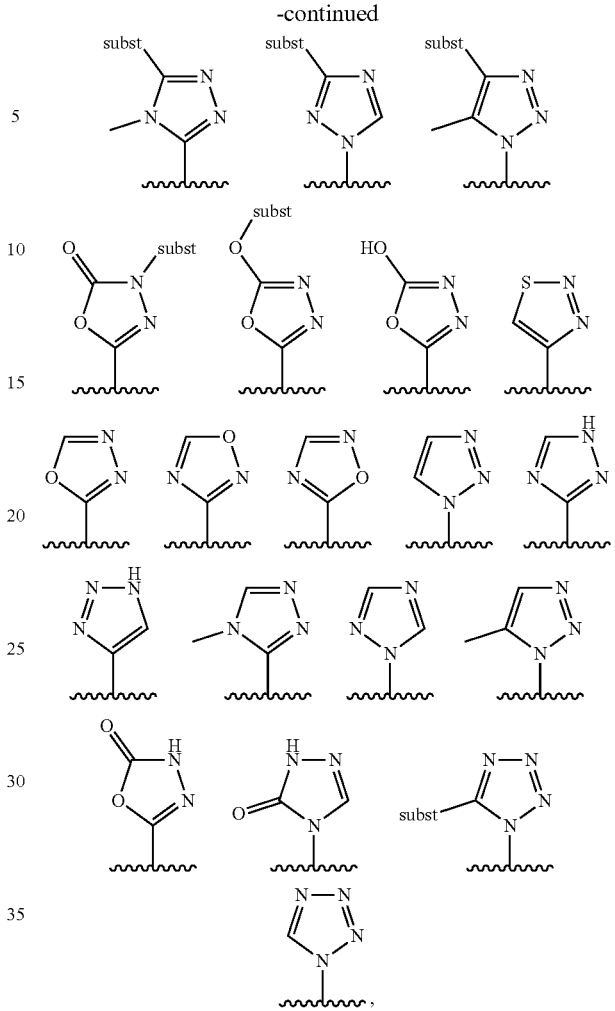

where subst represents the optional substituent.

6. A compound for use according to statement 5, wherein Ar is selected from:

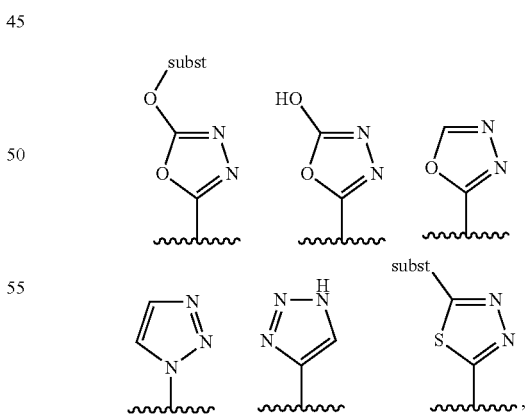

where subst represents the optional substituent.

7. A compound for use according to statement 3, wherein there is one heteroatom in the ring.

8. A compound for use according to statement 3, wherein Ar is:

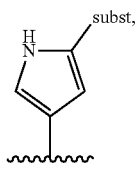

where subst represents the optional substituent.

9. A compound for use according to statement 3, wherein there are two heteroatoms in the ring.

10. A compound for use according to statement 9, wherein Ar is selected from:

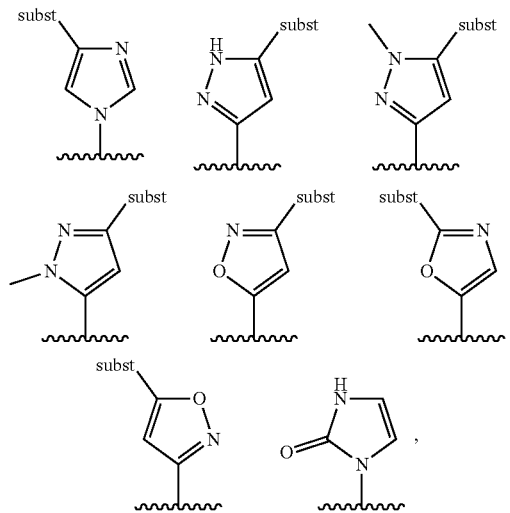

where subst represents the optional substituent.

11. A compound for use according to statement 3, wherein there are three heteroatoms in the ring.

12. A compound for use according to statement 11 wherein Ar is selected from:

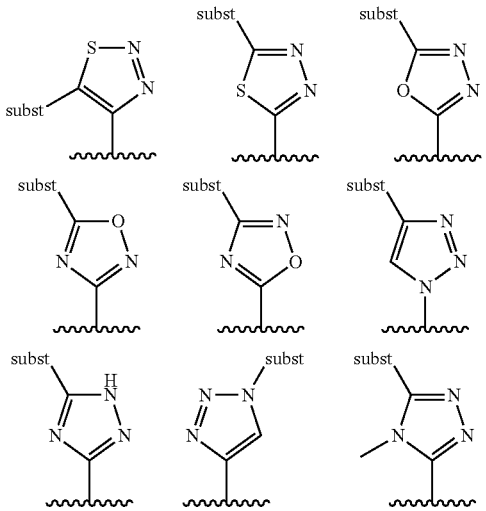

-continued

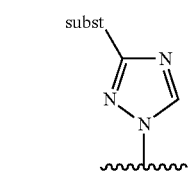

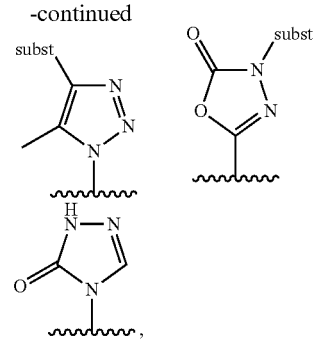

where subst represents the optional substituent.

13. A compound for use according to statement 3, wherein there are four heteroatoms in the ring.

14. A compound for use according to statement 13, wherein Ar is selected from:

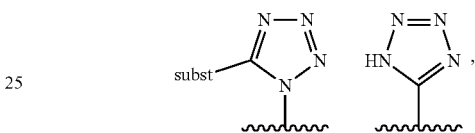

where subst represents the optional substituent.

15. A compound for use according to statement 12, wherein Ar is selected from:

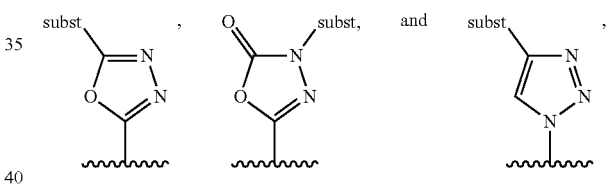

where subst represents the optional substituent.

16. A compound for use according to statement 15, wherein Ar is:

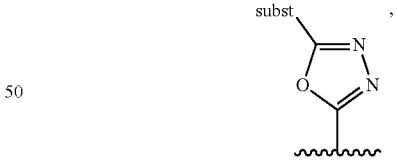

where subst represents the optional substituent.

17. A compound for use according to statement 15, wherein Ar is:

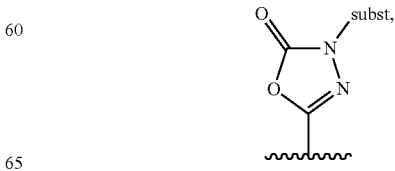

where subst represents the optional substituent.

18. A compound for use according to statement 15, wherein Ar is:

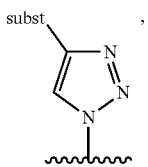

where subst represents the optional substituent.

19. A compound for use according to statement 1, wherein Ar is $C_6$ N-containing heteroaryl, with an optional substituent.

20. A compound for use according to statement 19, wherein there is one heteroatom in the ring.

21. A compound for use according to statement 20, wherein Ar is selected from:

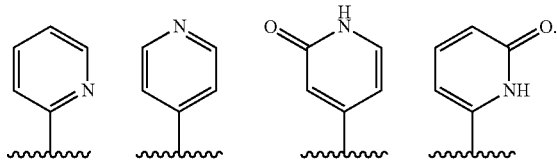

22. A compound for use according to statement 19, wherein there are two heteroatoms in the ring.

23. A compound for use according to statement 22, wherein Ar is selected from:

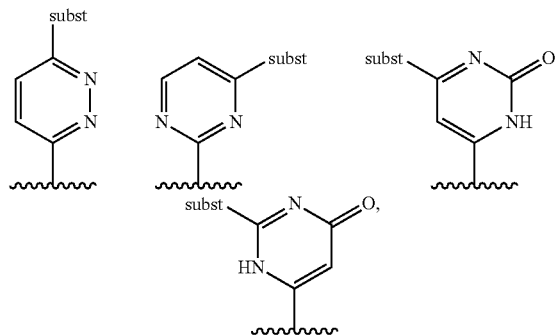

where subst represents the optional substituent.

24. A compound for use according to statement 19, wherein Ar is selected from:

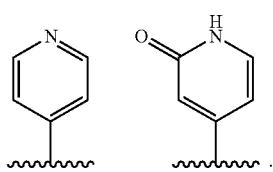

25. A compound for use according to statement 24, wherein Ar is:

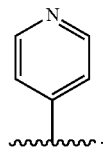

26. A compound for use according to any one of statements 1 to 25, wherein the substituent on Ar is selected from OH, SH, $NH_2$, OMe, SMe, NHMe, $NMe_2$, OEt, NHCN and Me.

27. A compound for use according to any one of statements 1 to 25, wherein the substituent on Ar is selected from OH, SH, $NH_2$, OMe and SMe.

28. A compound for use according to any one of statements 1 to 25, wherein the substituent on Ar is selected from OH, $NH_2$, OMe, SMe, NHMe, $NMe_2$, OEt, NHCN and Me.

29. A compound for use according to any one of statements 1 to 25, wherein the substituent on Ar is selected from OH, $NH_2$, OMe and SMe.

30. A compound for use according to statement 26, wherein the substituent is OH.

31. A compound for use according to statement 26, wherein the substituent is SH.

32. A compound for use according to statement 26, wherein the substituent is $NH_2$.

33. A compound for use according to statement 26, wherein the substituent is OMe.

34. A compound for use according to statement 26, wherein the substituent is SMe.

35. A compound for use according to statement 26, wherein the substituent is NHMe.

36. A compound for use according to statement 26, wherein the substituent is $NMe_2$.

37. A compound for use according to statement 26, wherein the substituent is OEt.

38. A compound for use according to statement 26, wherein the substituent is NHCN.

39. A compound for use according to statement 26, wherein the substituent is Me.

40. A compound for use according to any one of statements 1 to 25, wherein the substituent on Ar is selected from CN and $CO_2H$.

41. A compound for use according to statement 40, wherein the substituent is CN.

42. A compound for use according to statement 40, wherein the substituent is $CO_2H$.

43. A compound for use according to any one of statements 1 to 25, wherein the substituent on Ar is selected from $SO_2Me$ and $SO_3^-Na^+$.

44. A compound for use according to statement 43, wherein the substituent is $SO_2Me$.

45. A compound for use according to statement 43, wherein the substituent is $SO_3^-Na^+$.

46. A compound for use according to any one of statements 1 to 25, wherein the substituent on Ar is selected from $CH_2Q^1$, where $Q^1$ is selected from OH, OMe, Cl, NHCOMe, $SO_3H$ and $NR^{N1}R^{N2}$, where $R^{N1}$ and $R^{N2}$ are either H or Me, CN.

47. A compound for use according to statement 46, wherein the substituent is selected from $CH_2OH$, $CH_2OMe$, $CH_2Cl$, $CH_2NH_2$, $CH_2NHMe$, $CH_2NMe_2$, $CH_2CN$, $CH_2NHCOMe$ and $CH_2SO_3H$.

48. A compound for use according to statement 47, wherein the substituent is $CH_2OH$.

49. A compound for use according to any one of statements 1 to 25, wherein the substituent on Ar is selected from $C_{2-3}$ alkyl substituted by OH.

50. A compound for use according to statement 49, wherein the substituent is $C(CH_3)_2OH$ or $CH(CH_3)OH$.

51. A compound for use according to any one of statements 1 to 25, wherein there is no substituent on Ar.

52. A compound for use according to any one of statements 1 to 51, wherein none of $X^1$, $X^2$, $X^3$ and $X^5$ are N.

53. A compound for use according to any one of statements 1 to 51, wherein one of $X^1$, $X^2$, $X^3$ and $X^5$ is N.

54. A compound for use according to statement 53, wherein $X^1$ is N.

55. A compound for use according to statement 53, wherein $X^2$ is N.

56. A compound for use according to statement 53, wherein $X^3$ is N.

57. A compound for use according to statement 53, wherein $X^5$ is N.

58. A compound for use according to any of statements 1 to 52, wherein $X^5$ is CH.

59. A compound for use according to any one of statements 1 to 58, wherein $R^1$ to $R^5$ (if present) are all H.

60. A compound for use according to any one of statements 1 to 58, wherein one of $R^1$ to $R^5$ (if present) is not H.

61. A compound for use according to any one of statements 1 to 58, wherein two of $R^1$ to $R^5$ (if present) are not H.

62. A compound for use according to any one of statements 1 to 58, wherein three of $R^1$ to $R^5$ (if present) are not H.

63. A compound for use according to any one of statements 1 to 58 and 60 to 62, wherein at least one of those of $R^1$ to $R^5$ which are not H is halo.

64. A compound for use according to statement 63, wherein the halo group is selected from Cl and F.

65. A compound for use according to any one of statements 1 to 58 and 60 to 62, wherein at least one of those of $R^1$ to $R^5$ which are not H is 01-4 alkyl, optionally substituted by one or more F atoms.

66. A compound for use according to statement 65, wherein the $C_{1-4}$ alkyl group is selected from methyl, ethyl, iso-propyl and tert-butyl.

67. A compound for use according to statement 65, wherein the $C_{1-4}$ alkyl group substituted by F atoms is selected from $CF_3$ and $CF_2H$.

68. A compound for use according to any one of statements 1 to 58 and 60 to 62, wherein at least one of those of $R^1$ to $R^5$ which are not H is $C_{3-6}$ cycloalkyl, which group may have an O ring atom.

69. A compound for use according to statement 68, wherein the $C_{3-6}$ cycloalkyl is selected from cyclopropyl, cyclopentyl and cyclohexyl.

70. A compound for use according to statement 68, wherein the $C_{3-6}$ cycloalkyl with an O ring atom is oxetanyl.

71. A compound for use according to any one of statements 1 to 58 and 60 to 62, wherein at least one of those of $R^1$ to $R^5$ which are not H is selected from CN, $NMe_2$ and $NO_2$.

72. A compound for use according to statement 71, wherein the group is CN.

73. A compound for use according to statement 71, wherein the group is $NMe_2$.

74. A compound for use according to statement 71, wherein the group is $NO_2$.

75. A compound for use according to any one of statements 1 to 58 and 60 to 62, wherein at least one of those of $R^1$ to $R^5$ which are not H is O—$C_{1-4}$ alkyl, optionally substituted by one or more F atoms.

76. A compound for use according to statement 75, wherein the O—$C_{1-4}$ alkyl group is selected from methoxy, ethoxy and propyloxy.

77. A compound for use according to statement 75, wherein the O—$C_{1-4}$ alkyl group is $OCF_3$.

78. A compound for use according to any one of statements 1 to 58 and 60 to 62, wherein at least one of those of $R^1$ to $R^5$ which are not H is $OCH_2Q^2$, where $Q^2$ is selected from $C_{3-6}$ cycloalkyl and phenyl.

79. A compound for use according to statement 78, wherein the $OCH_2Q^2$ group is $OCH_2$-cyclopropyl.

80. A compound for use according to statement 78, wherein the $OCH_2Q^2$ group is $OCH_2Ph$.

81. A compound for use according to any one of statements 1 to 58 and 60 to 62, wherein at least one of those of $R^1$ to $R^5$ which are not H is $CH_2OH$.

82. A compound for use according to any one of statements 1 to 58 and 60 to 62, wherein at least one of those of $R^1$ to $R^5$ which are not H is $NR^{N6}R^{N7}$, where $R^{N6}$ and $R^{N7}$ together form a $C_{4-6}$heterocyclyl group optionally substituted with 1 to 2 groups selected from halo, $C_{1-3}$ alkyl, cyano and oxetanyl.

83. A compound for use according to statement 82, wherein the $C_{4-6}$heterocyclyl group is selected from azetidinyl, pyrrolidinyl, piperidinyl and morpholinyl.

84. A compound for use according to statement 82, wherein the $C_{4-6}$heterocyclyl group is selected from fluoroazetidinyl and difluoroazetidinyl.

85. A compound for use according to statement 82, wherein the $C_{4-6}$heterocyclyl group is pyrrolidinyl.

86. A compound for use according to statement 82, wherein the $C_{4-6}$heterocyclyl group is morpholinyl.

87. A compound for use according to any one of statements 1 to 58 and 61 to 62, wherein two adjacent groups of $R^1$ to $R^5$ together form a group -$Q^3$-$(CR^C_2)_n$-$Q^4$-, where $Q^3$ is selected from $NR^{N3}$ and O, where $R^{N3}$ is selected from H, $C_{1-3}$ alkyl, cyclopropylmethyl and COMe; $Q^4$ is $NR^{N4}$, O or a single bond, where $R^{N4}$ is selected from H, $C_{1-3}$ alkyl, cyclopropylmethyl and COMe each $R^C$ is independently H, F or Me or two $R^C$ which are attached to the same atom can be linked together to form a $C_{3-5}$ cycloalkyl; and n is 1, 2 or 3.

88. A compound for use according to statement 87, where $Q^3$ is $NR^{N3}$; $Q^4$ is a single bond, each $R^C$ is independently H, F or Me; and n is 1 or 2.

89. A compound for use according to statement 88, wherein $R^{N3}$ is H.

90. A compound for use according to statement 88, wherein $R^{N3}$ is $C_{1-3}$ alkyl, for example methyl or iso-propyl.

91. A compound for use according to statement 88, wherein $R^{N3}$ is cyclopropylmethyl.

92. A compound for use according to statement 88, wherein $R^{N3}$ is COMe.

93. A compound for use according to any one of statements 89 to 92, wherein each $R^C$ is H.

94. A compound for use according to statement 88, wherein two adjacent groups of $R^1$ to $R^5$ together form a group selected from —$NHC_2H_4$—; —$NMeC_2H_4$—; —$N(COMe)C_2H_4$—; and —N-iPr-$C_2H_4$—.

95. A compound for use according to statement 87, where $Q^3$ is O, and $Q^4$ is O and, each $R^C$ is independently H, F or Me; and n is 1 or 2.

96. A compound for use according to statement 95, wherein each $R^C$ is selected from H and F.

97. A compound for use according to statement 95, wherein two adjacent groups of $R^1$ to $R^4$ together form a group selected from —OCH$_2$O—; —OCF$_2$O—; and —OC$_2$H$_4$O—.

98. A compound for use according to any one of statements 1 to 58 and 61 to 62, wherein two adjacent groups of $R^1$ to $R^5$ form a fused benzene with the phenyl group, which itself is optionally substituted by a $C_{1-2}$ alkyl group.

99. A compound for use according to any one of statements 1 to 58 and 61 to 62, wherein two adjacent groups of $R^1$ to $R^5$ form a fused $C_{5-6}$ heteroaromatic ring with the phenyl group, which itself is optionally substituted by a $C_{1-2}$ alkyl group.

100. A compound for use according to statement 99, wherein the fused ring is a $C_5$ heteroaromatic ring.

101. A compound for use according to statement 100, wherein the fused ring is imadazoline.

102. A compound for use according to statement 99, wherein the fused ring is a $C_6$ heteroaromatic ring.

103. A compound for use according to statement 102, wherein the fused ring is selected from pyridine or piperazine.

104. A compound for use according to any one of statements 87 to 103, wherein the two adjacent groups are $R^1$ and $R^2$.

105. A compound for use according to any one of statements 87 to 103, wherein the two adjacent groups are $R^2$ and $R^3$.

106. A compound for use according to any one of statements 87 to 103, wherein the two adjacent groups are $R^3$ and $R^4$.

107. A compound for use according to any one of statements 87 to 103, wherein the two adjacent groups are $R^4$ and $R^5$.

108. A compound for use according to any one of statements 1 to 58, wherein two of $R^1$ to $R^5$ are both Cl.

109. A compound for use according to any one of statements 1 to 58, wherein two of $R^1$ to $R^5$ are both F.

110. A compound for use according to any one of statements 1 to 58, wherein two of $R^1$ to $R^5$ are both Me.

111. A compound for use according to any one of statements 1 to 58, wherein two of $R^1$ to $R^5$ are both CF$_3$.

112. A compound for use according to any one of statements 1 to 58, wherein one of $R^1$ to $R^5$ is Cl and another is selected from CF$_3$; OCF$_3$; CN; OMe; and Br.

113. A compound for use according to statement 112, wherein one of $R^1$ to $R^5$ is Cl and another is CF$_3$.

114. A compound for use according to any one of statements 1 to 58, wherein one of $R^1$ to $R^5$ is CF$_3$ and another is selected from Cl, Me and cyclo-propyl.

115. A compound for use according to any one of statements 108 to 114, wherein the substituents are in the 3,4; 2,3; or 2,4 positions.

116. A compound for use according to statement 115, wherein the substituents are in the 3,4 positions.

117. A compound for use according to any one of statements 1 to 58, wherein three of $R^1$ to $R^5$ are not H, and the substituents are OH and two F groups.

118. A compound for use according to statement 117, wherein the substituents are 2-OH, 3,5-F.

119. A compound according to any one of statements 1 to 58, wherein three of $R^1$ to $R^5$ are not H, and the substituents are CF$_3$ and two Cl groups.

120. A compound according to statement 119, wherein the substituents are 2-Cl, 3-CF$_3$ and 4-Cl.

121. A compound for use according to any of statements 1 to 120, wherein the method of therapy is for treating a disease or disorder selected from neurodegenerative disorders, central nervous system disorders, proliferative disorders, bone disorders, liver disorders, hair disorders, metabolic disorders, metabolic complications.

122. A compound for use according to statement 121, wherein the disease or disorder is a neurodegenerative disorder.

123. A compound for use according to statement 122, wherein the neurodegenerative disorder is selected from Alzheimer's disease, multiple sclerosis, vascular dementia, small vessel disease, Ataxia-telangiectasia, Baggio-Yoshinari syndrome, neuronal ceroid lipofuscinoses such as Batten disease or Kufs disease, Corticobasal degeneration, Corticobasal syndrome, Prion disease such as Creutzfeldt-Jakob disease, Fatal insomnia, Huntington's disease, Refsum disease, Kufor-Rakeb syndrome, Machado-Joseph disease, Motor Neurone disease, Niemann-Pick disease, Parkinson's disease, Pontocerebellar hypoplasia, Sandhoff disease, Shy-Drager syndrome, Spinocerebellar ataxia, Spinal muscular atrophy, Tabes dorsalis, and Tay-Sachs disease.

124. A compound for use according to statement 123, wherein the neurodegenerative disease is Alzheimer's disease.

125. A compound for use according to statement 121, wherein the disease or disorder is a central nervous system disorder.

126. A compound for use according to statement 125, wherein the central nervous system disorder is selected from stroke, ischemia and traumatic brain damage.

127. A compound for use according to statement 121, wherein the disease or disorder is a proliferative disorder.

128. A compound for use according to statement 127, wherein the proliferative disorder is selected from colorectal cancer, hepatocellular carcinoma, melanoma, breast cancer, triple-negative breast cancer, gastrointestinal cancer, leukaemia, and lymphoma.

129. A compound for use according to statement 121, wherein the disease or disorder is a bone disorder.

130. A compound for use according to statement 129, wherein the bone disorder is selected from osteoporosis, osteoporosis-pseudoglioma syndrome, sclerosteosis, van Buchem's disease, and osteopenia.

131. A compound for use according to statement 121, wherein the disease or disorder is a liver disorder.

132. A compound for use according to statement 131, wherein the liver disorder is selected from liver fibrosis, liver cirrhosis, non-alcoholic steatohepatitis, alcoholic liver disease, cholangiopathies, Primary Sclerosing Cholangitis (PSC), Focal nodular hyperplasia, Polycystic liver disease (PCLD), hepatocellular adenomas, hepatocellular cancers, and hepatoblastomas.

133. A compound for use according to statement 121, wherein the disease or disorder is a hair disorder.

134. A compound for use according to statement 133, wherein the hair disorder is selected from alopecia and hypertrichosis, wherein alopecia includes male-pattern hair loss, female-pattern hair loss, alopecia areata, and telogen effluvium.

135. A compound for use according to statement 121, wherein the disease or disorder is a metabolic disorder.

136. A compound for use according to statement 135, wherein the metabolic disorder is selected from Type 2 diabetes, insulin resistance, metabolic syndrome, obesity, cachexia, Prader-Willi Syndrome, and Anorexia Nervosa.

137. A compound as defined in any one of statements 1 to 120, for use in a method of therapy.

138. A pharmaceutical composition comprising a compound as defined in any one of statements 1 to 120, and a pharmaceutically acceptable excipient.

139. A pharmaceutical composition according to statement 138, for use in a method of therapy, wherein the method of therapy is for treating a disease or disorder as defined in any one of statements 122 to 137.

140. A compound as defined in any one of statements 1 to 120, wherein:

(i) Ar is

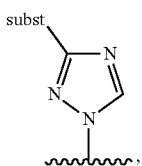

where subst represents the optional substituent;

(ii) Ar is

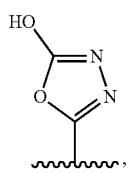

and:
a. at least 2 of $R^1$ to $R^5$ are not H and one of $R^1$ to $R^5$ is not Me; and $R^1$, $R^2$, $R^3$, $R^4$ and $R^5$ (if present) are independently selected from:
 i) H;
 ii) $C_{3-6}$ cycloalkyl, with an optional O ring atom;
 ii) CN, $NMe_2$, $NO_2$;
 iv) $OCH_2Q^2$, where $Q^2$ is selected from $C_{3-6}$ cycloalkyl and phenyl;
 v) $CH_2OH$;
 vi) $NR^{N6}R^{N7}$, where $R^{N6}$ and $R^{N7}$ together form a $C_{4-6}$ heterocyclyl group optionally substituted with 1 to 2 groups selected from halo, $C_{1-3}$ alkyl, cyano and oxetanyl;
 or two adjacent groups of $R^1$ to $R^4$ together form a group $-Q^3-(CR^C{}_2)_n-Q^4-$, where $Q^3$ is selected from $NR^{N3}$ and O, where $R^{N3}$ is selected from H, $C_{1-3}$ alkyl, cyclopropylmethyl and COMe; $Q^4$ is $NR^{N4}$, O or a single bond, where $R^{N4}$ is selected from H, $C_{1-3}$ alkyl, cyclopropylmethyl and COMe; each $R^C$ is independently H, F or Me or two $R^C$ which are attached to the same atom can be linked together to form a $C_{3-5}$ cycloalkyl; and n is 1, 2 or 3;
 or two adjacent groups of $R^1$ to $R^5$ form a fused benzene or $C_{5-6}$ heteroaromatic ring with the phenyl group, which itself is optionally substituted by a $C_{1-2}$ alkyl group;
b. at least 1 of $R^1$ to $R^4$ (if present) is $C_{3-6}$ cycloalkyl;
c. two adjacent groups of $R^1$ to $R^4$ together form a group $-Q^3-(CH_2)_n-Q^4-$, where $Q^3$ is selected from $NR^{N3}$ and O, where $R^{N3}$ is selected from H, Me and COMe; $Q^4$ is a single bond; and n is 1 or 2;

(iii) Ar is

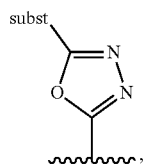

subst is selected from:
 a) H;
 b) $NH_2$, SH, OMe, SMe;
 c) CN, $CO_2H$, COmorph;
 d) $SO_2Me$;
 e) $C_{2-3}$ alkyl substituted by OH;
 and at least 2 of $R^1$ to $R^4$ are not H;

(iv) Ar is

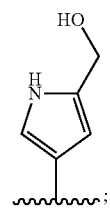 [SMILES: *c1c[nH]c(CO)c1]

or
(v) Ar is

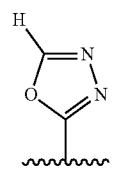

and $R^3$ is iPr;

(vi)

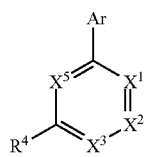

is

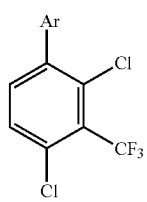

and Ar is a $C_5$ heteroaryl group.

141. A compound according to statement 140, wherein the compound is selected from:
   5-(4-chloro-3-(trifluoromethyl)phenyl)-1,3,4-oxadiazol-2-ol (67);
   5-[4-chloro-3-(trifluoromethyl)phenyl]-1,3,4-thiadiazol-2-ol (183);
   5-(1-methylindolin-5-yl)-1,3,4-oxadiazol-2-ol (81);
   2-[4-chloro-3-(trifluoromethyl)phenyl]-1,3,4-oxadiazole (196);
   1-[4-chloro-3-(trifluoromethyl)phenyl]triazole (175);
   5-(7-chloro-1,3,3-trimethyl-indolin-5-yl)-1,3,4-oxadiazol-2-ol (179);
   4-[2,4-dichloro-3-(trifluoromethyl)phenyl]-1H-triazole (306);
   2-(2,4-dichloro-3-(trifluoromethyl)phenyl)-5-(methoxy-d3)-1,3,4-oxadiazole (241);
   2-(2,4-dichloro-3-(trifluoromethyl)phenyl)-5-ethoxy-1,3,4-oxadiazole (242);
   4,5-dideuterio-1-[2,4-dichloro-3-(trifluoromethyl)phenyl]triazole (308);
   5-[2,4-dichloro-3-(trifluoromethyl)phenyl]-1,3,4-oxadiazol-2-ol (261);
   2-(2,4-dichloro-3-(trifluoromethyl)phenyl)-5-methoxy-1,3,4-oxadiazole (243);
   1-[2,4-dichloro-3-(trifluoromethyl)phenyl]triazole (295);
   N-(5-(2,4-dichloro-3-(trifluoromethyl)phenyl)-1,3,4-oxadiazol-2-yl)cyanamide, ammonia salt (246); and
   3,5-dichloro-2-(triazol-1-yl)-4-(trifluoromethyl)pyridine (307).

142. A compound according to statement 141, wherein the compound is selected from:
   4-[2,4-dichloro-3-(trifluoromethyl)phenyl]-1H-triazole (306);
   2-(2,4-dichloro-3-(trifluoromethyl)phenyl)-5-(methoxy-d3)-1,3,4-oxadiazole (241);
   2-(2,4-dichloro-3-(trifluoromethyl)phenyl)-5-ethoxy-1,3,4-oxadiazole (242);
   4,5-dideuterio-1-[2,4-dichloro-3-(trifluoromethyl)phenyl]triazole (308);
   5-[2,4-dichloro-3-(trifluoromethyl)phenyl]-1,3,4-oxadiazol-2-ol (261);
   2-(2,4-dichloro-3-(trifluoromethyl)phenyl)-5-methoxy-1,3,4-oxadiazole (243);
   1-[2,4-dichloro-3-(trifluoromethyl)phenyl]triazole (295);
   N-(5-(2,4-dichloro-3-(trifluoromethyl)phenyl)-1,3,4-oxadiazol-2-yl)cyanamide, ammonia salt (246); and
   3,5-dichloro-2-(triazol-1-yl)-4-(trifluoromethyl)pyridine (307).

143. A compound according to statement 142, wherein the compound is
   4-[2,4-dichloro-3-(trifluoromethyl)phenyl]-1H-triazole (306).

144. A compound according to statement 142, wherein the compound is
   2-(2,4-dichloro-3-(trifluoromethyl)phenyl)-5-(methoxy-d3)-1,3,4-oxadiazole (241).

145. A compound according to statement 142, wherein the compound is
   2-(2,4-dichloro-3-(trifluoromethyl)phenyl)-5-ethoxy-1,3,4-oxadiazole (242).

146. A compound according to statement 142, wherein the compound is
   4,5-dideuterio-1-[2,4-dichloro-3-(trifluoromethyl)phenyl]triazole (308).

147. A compound according to statement 142, wherein the compound is
   5-[2,4-dichloro-3-(trifluoromethyl)phenyl]-1,3,4-oxadiazol-2-ol (261).

148. A compound according to statement 142, wherein the compound is
   2-(2,4-dichloro-3-(trifluoromethyl)phenyl)-5-methoxy-1,3,4-oxadiazole (243).

149. A compound according to statement 142, wherein the compound is
   1-[2,4-dichloro-3-(trifluoromethyl)phenyl]triazole (295).

150. A compound according to statement 142, wherein the compound is
   N-(5-(2,4-dichloro-3-(trifluoromethyl)phenyl)-1,3,4-oxadiazol-2-yl)cyanamide, ammonia salt (246).

151. A compound according to statement 142, wherein the compound is 3,5-dichloro-2-(triazol-1-yl)-4-(trifluoromethyl)pyridine (307).

The invention claimed is:
1. A compound of formula (I):

$$\text{(I)}$$

where Ar is $C_5$ heteroaryl, optionally substituted by a group selected from
a) OH, SH, $NH_2$, OMe, SMe, NHMe, $NMe_2$, OEt, NHCN, Me;
b) CN, $CO_2H$;
c) $SO_2Me$, $SO_3^-Na^+$;
d) $CH_2Q^1$, where $Q^1$ is selected from OH, OMe, Cl, CN, NHCOMe, $SO_3H$, $NR^{N1}R^{N2}$, where $R^{N1}$ and $R^{N2}$ are either H or Me;
e) $C_{2-3}$ alkyl substituted by OH;
where a N-ring heteroatom may additional bear a methyl group; and
$X^1$ is $CR^1$;
$X^2$ is $CR^2$;
$X^3$ is $CR^3$;
$X^5$ is $CR^5$;
two of $R^1$, $R^2$, $R^3$, $R^4$ and $R^5$ are H, two of $R^1$, $R^2$, $R^3$, $R^4$ and $R^5$ are Cl and one of $R^1$, $R^2$, $R^3$, $R^4$ and $R^5$ is $CF_3$.

2. A compound according to claim 1, wherein Ar is selected from:

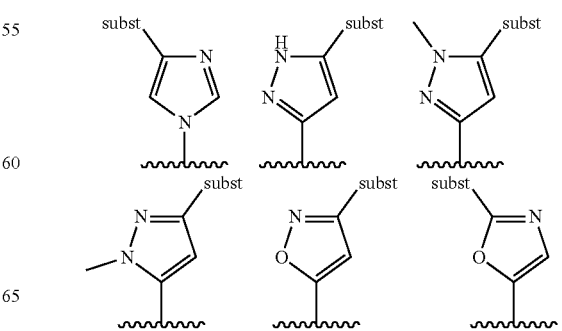

where subst represents the substituent.

3. A compound according to claim 2, wherein Ar is selected from:

where subst represents the substituent.

4. A compound according to claim 1, wherein there are three heteroatoms in the ring.

5. A compound according to claim 1, wherein the substituent is selected from OH, OMe, OEt and NHCN.

6. A compound according to claim 5, wherein the substituent is OH.

7. A compound according to claim 1, wherein the substituent is $CH_2OH$.

8. A compound according to claim 1, wherein there is no substituent on Ar.

9. A compound according to claim 1, wherein $R^2$ is Cl, $R^3$ is $CF_3$ and $R^4$ is Cl.

10. A pharmaceutical composition comprising a compound of claim 1, and a pharmaceutically acceptable excipient.

11. A compound according to claim 1, wherein:
(i) Ar is where subst represents the optional substituent;
(ii) Ar is and:
a. at least 2 of $R^1$ to $R^5$ are not H and one of $R^1$ to $R^5$ is not Me; and
$R^1$, $R^2$, $R^3$, $R^4$ and $R^5$ (if present) are independently selected from:
i) H;
ii) $C_{3-6}$ cycloalkyl, with an optional O ring atom;
ii) CN, $NMe_2$, $NO_2$;
iv) $OCH_2Q^2$, where $Q^2$ is selected from $C_{3-6}$ cycloalkyl and phenyl;
v) $CH_2OH$;
vi) $NR^{N6}R^{N7}$, where $R^{N6}$ and $R^{N7}$ together form a $C_{4-6}$heterocyclyl group optionally substituted with 1 to 2 groups selected from halo, $C_{1-3}$ alkyl, cyano and oxetanyl;
or two adjacent groups of $R^1$ to $R^4$ together form a group $-Q^3-(CR^C_2)n-Q^4-$, where $Q^3$ is selected from $NR^{N3}$ and O, where $R^{N3}$ is selected from H, $C_{1-3}$ alkyl, cyclopropylmethyl and COMe; $Q^4$ is $NR^{N4}$, O or a single bond, where $R^{N4}$ is selected from H, $C_{1-3}$ alkyl, cyclopropylmethyl and COMe; each $R^C$ is independently H, F or Me or two $R^c$ which are attached to the same atom can be linked together to form a $C_{3-5}$cycloalkyl; and n is 1, 2 or 3;
or two adjacent groups of $R^1$ to $R^5$ form a fused benzene or $C_{5-6}$ heteroaromatic ring with the phenyl group, which itself is optionally substituted by a $C_{1-2}$ alkyl group;
b. at least 1 of $R^1$ to $R^4$ (if present) is $C_{3-6}$ cycloalkyl;
c. two adjacent groups of $R^1$ to $R^4$ together form a group $-Q^3-(CH_2)_n-Q^4-$, where $Q^3$ is selected from $NR^{N3}$ and O, where $R^{N3}$ is selected from H, Me and COMe; $Q^4$ is a single bond; and n is 1 or 2;
(iii) Ar is

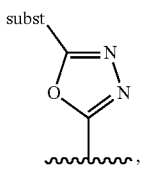

subst is selected from:
a) H;
b) $NH_2$, SH, OMe, SMe;
c) CN, $CO_2H$, COmorph;
d) $SO_2Me$;
e) $C_{2-3}$ alkyl substituted by OH;
and at least 2 of $R^1$ to $R^4$ are not H;

(iv) Ar is

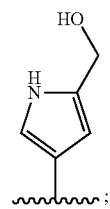 [SMILES: *c1c[nH]c(CO)c1]

or
(v) Ar is

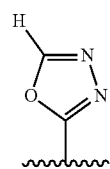 [SMILES: *c1nnco1]

and $R^3$ is iPr.

12. A compound according to claim 1, wherein the compound is selected from:
4-[2,4-dichloro-3-(trifluoromethyl)phenyl]-1H-triazole (306);
2-(2,4-dichloro-3-(trifluoromethyl)phenyl)-5-(methoxy-d3)-1,3,4-oxadiazole (241);
2-(2,4-dichloro-3-(trifluoromethyl)phenyl)-5-ethoxy-1,3,4-oxadiazole (242);
4,5-dideuterio-1-[2,4-dichloro-3-(trifluoromethyl)phenyl]triazole (308);
5-[2,4-dichloro-3-(trifluoromethyl)phenyl]-1,3,4-oxadiazol-2-ol (261);
2-(2,4-dichloro-3-(trifluoromethyl)phenyl)-5-methoxy-1,3,4-oxadiazole (243);
1-[2,4-dichloro-3-(trifluoromethyl)phenyl]triazole (295); and
N-(5-(2,4-dichloro-3-(trifluoromethyl)phenyl)-1,3,4-oxadiazol-2-yl)cyanamide, ammonia salt (246).

13. A compound: 1-[2,4-dichloro-3-(trifluoromethyl)phenyl]triazole (295).

14. A method of treatment of a disease or disorder ameliorated by the inhibition of Notum, comprising administering to a patient in need of treatment, a compound as defined in claim 1.

15. A method according to claim 14, wherein the disease or disorder is a neurodegenerative disorder or a central nervous system disorder.

16. A method according to claim 14, wherein the disease or disorder is a neurodegenerative disease, and the neurodegenerative disease is Alzheimer's disease.

* * * * *